(12) United States Patent
Nobles et al.

(10) Patent No.: US 11,197,661 B2
(45) Date of Patent: Dec. 14, 2021

(54) DEVICE FOR APPLYING A KNOT TO A SUTURE

(71) Applicant: Scarab Technology Services, LLC, St. Thomas, VI (US)

(72) Inventors: Anthony A. Nobles, Fountain Valley, CA (US); Benjamin G. Brosch, Mission Viejo, CA (US); Steven E. Decker, Anaheim, CA (US); Michael J. Mullen, Kingston (GB)

(73) Assignee: Scarab Technology Services, LLC, St. Thomas, VI (US)

( * ) Notice: Subject to any disclaimer, the term of this patent is extended or adjusted under 35 U.S.C. 154(b) by 361 days.

(21) Appl. No.: 16/161,610

(22) Filed: Oct. 16, 2018

(65) Prior Publication Data
US 2019/0150903 A1 May 23, 2019

Related U.S. Application Data

(60) Continuation of application No. 14/850,210, filed on Sep. 10, 2015, now Pat. No. 10,182,802, which is a
(Continued)

(51) Int. Cl.
*A61B 17/00* (2006.01)
*A61B 17/04* (2006.01)

(52) U.S. Cl.
CPC ...... *A61B 17/0057* (2013.01); *A61B 17/0469* (2013.01); *A61B 17/0482* (2013.01);
(Continued)

(58) Field of Classification Search
CPC ............ A61B 17/0401; A61B 17/0467; A61B 17/0469; A61B 17/0487; A61B 2017/0474; A61B 2017/0475
See application file for complete search history.

(56) References Cited

U.S. PATENT DOCUMENTS

| 118,683 A | 9/1871 | Bruce |
| 1,064,307 A | 6/1913 | Fleming |

(Continued)

FOREIGN PATENT DOCUMENTS

| AU | 2003212025 | 8/2003 |
| AU | 2006251579 | 11/2006 |

(Continued)

OTHER PUBLICATIONS

Advances in Vascular Surgery, by John S. Najarian, M.D. and John p. Delaney, M.D., copyright 1983 by Year Book Publishers, Inc. at pp. 94,95,96, and 224.

(Continued)

*Primary Examiner* — Todd J Scherbel
(74) *Attorney, Agent, or Firm* — Knobbe, Martens, Olson & Bear LLP

(57) ABSTRACT

Methods and apparatuses are disclosed for closing a patent foramen ovale. Some of the disclosed apparatuses include an elongate body having a proximal end and a distal end, with first and second suture clasp arms adapted to hold end portions of a suture when in an extended position. A first suture catch mechanism is slidably housed in the elongate body and moves in a proximal-to-distal direction to engage the suture end held by the first suture clasp arm, and a second suture catch mechanism is slidably housed in the elongate body and moves in a distal-to-proximal direction to suture end held by the second suture clasp arm. The first suture clasp arm can be positioned around the septum primum to deliver a suture thereto, and the second suture clasp arm can be positioned around the septum secundum to deliver a suture thereto.

17 Claims, 97 Drawing Sheets

Related U.S. Application Data division of application No. 13/761,683, filed on Feb. 7, 2013, now Pat. No. 9,131,938, which is a continuation of application No. 13/552,849, filed on Jul. 19, 2012, now Pat. No. 8,372,089, which is a division of application No. 12/057,304, filed on Mar. 27, 2008, now Pat. No. 8,246,636.

(60) Provisional application No. 60/908,946, filed on Mar. 29, 2007, provisional application No. 60/981,468, filed on Oct. 19, 2007.

(52) U.S. Cl.
CPC .............. *A61B 2017/00243* (2013.01); *A61B 2017/00575* (2013.01); *A61B 2017/00623* (2013.01); *A61B 2017/047* (2013.01); *A61B 2017/0472* (2013.01)

(56) References Cited

U.S. PATENT DOCUMENTS

| | | |
|---|---|---|
| 1,593,347 A | 7/1926 | Nardi |
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,601,564 A | 6/1952 | Smith |
| 2,637,290 A | 5/1953 | Sigoda |
| 2,738,790 A | 3/1956 | Todt, Sr. et al. |
| 2,741,225 A | 4/1956 | Fink |
| 2,741,226 A | 4/1956 | Dietrich et al. |
| 2,748,748 A | 6/1956 | Lovejoy |
| 2,790,422 A | 4/1957 | Grumbach |
| 2,849,002 A | 8/1958 | Oddo |
| 2,945,460 A | 7/1960 | Kagiyama |
| 2,959,172 A | 11/1960 | Held |
| 2,988,055 A | 6/1961 | Platt |
| 3,098,467 A | 7/1963 | Nagele, Jr. |
| 3,107,654 A | 10/1963 | Fehrenback |
| 3,241,554 A | 3/1966 | Coanda |
| 3,260,242 A | 7/1966 | Liguori |
| 3,262,427 A | 7/1966 | Von Arx |
| 3,292,627 A | 12/1966 | Harautuneian |
| 3,294,068 A | 12/1966 | Hechtle |
| 3,301,221 A | 1/1967 | Von Arx |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 3,989,389 A | 11/1976 | Hashimoto et al. |
| 4,022,535 A | 5/1977 | Ritter |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,168,708 A | 9/1979 | Lepley et al. |
| 4,204,541 A | 5/1980 | Kapitanov |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,641,652 A | 2/1987 | Hutterer et al. |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,904,238 A | 2/1990 | Williams |
| 4,923,461 A | 5/1990 | Caspari et al. |
| 4,926,860 A | 5/1990 | Slice et al. |
| 4,932,956 A | 6/1990 | Reddy et al. |
| 4,935,027 A | 6/1990 | Yoon |
| 4,946,463 A | 8/1990 | Wright |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,988,339 A | 1/1991 | Vadher |
| 4,994,070 A | 2/1991 | Waters |
| 5,002,531 A | 3/1991 | Bonzel |
| 5,021,059 A | 6/1991 | Kensey et al. |
| 5,037,428 A | 8/1991 | Picha et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,108,421 A | 4/1992 | Fowler |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,152,769 A | 10/1992 | Baber |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,171,259 A | 12/1992 | Inoue |
| 5,176,691 A | 1/1993 | Pierce |
| 5,192,301 A | 3/1993 | Kamiya et al. |
| 5,196,025 A | 3/1993 | Ranalletta et al. |
| 5,201,760 A | 4/1993 | West |
| 5,222,508 A | 6/1993 | Contarini |
| 5,222,941 A | 6/1993 | Don Michael |
| 5,222,974 A | 6/1993 | Kensey et al. |

(56) References Cited

U.S. PATENT DOCUMENTS

| | | |
|---|---|---|
| 5,224,948 A | 7/1993 | Abe et al. |
| 5,236,443 A | 8/1993 | Sontag |
| 5,242,459 A | 9/1993 | Buelna |
| 5,254,126 A | 10/1993 | Filipi et al. |
| 5,269,791 A | 12/1993 | Mayzels et al. |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,323,789 A | 6/1994 | Berggren et al. |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,387,221 A | 2/1995 | Bisgaard |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,568 A | 12/1995 | Scott |
| 5,474,572 A | 12/1995 | Burst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,503,634 A | 4/1996 | Christy |
| 5,507,754 A | 4/1996 | Green et al. |
| 5,507,755 A | 4/1996 | Gresl et al. |
| 5,507,757 A | 4/1996 | Sauer et al. |
| 5,514,159 A | 5/1996 | Matula et al. |
| 5,520,609 A | 5/1996 | Moll et al. |
| 5,520,702 A | 5/1996 | Sauer et al. |
| 5,520,703 A | 5/1996 | Essig et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,618 A * | 8/1996 | Fleenor .............. A61B 17/0469 112/169 |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,685 A | 10/1996 | Mollenauer et al. |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,571,167 A | 11/1996 | Maginot |
| 5,573,540 A | 11/1996 | Yoon |
| 5,578,044 A | 11/1996 | Gordon et al. |
| 5,584,803 A | 12/1996 | Stevens et al. |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,662,664 A | 9/1997 | Gordon et al. |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Ambrosio |
| 5,700,273 A | 12/1997 | Buelna et al. |
| 5,700,276 A | 12/1997 | Benecke |
| 5,700,277 A | 12/1997 | Nash et al. |
| 5,707,379 A | 1/1998 | Fleenor et al. |
| 5,709,693 A | 1/1998 | Taylor |
| 5,713,910 A | 2/1998 | Gordon et al. |
| 5,716,329 A | 2/1998 | Dieter |
| 5,720,757 A | 2/1998 | Hathaway et al. |
| 5,722,983 A | 3/1998 | Weegen |
| 5,728,109 A | 3/1998 | Schulze et al. |
| 5,728,133 A | 3/1998 | Kontos |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |

(56) References Cited

U.S. PATENT DOCUMENTS

| | | |
|---|---|---|
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,836,956 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,868,764 A | 2/1999 | Rosengart |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,924,424 A | 7/1999 | Stevens et al. |
| 5,925,054 A | 7/1999 | Taylor et al. |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,947,919 A | 9/1999 | Krueger et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,042,601 A | 3/2000 | Smith |
| 6,048,351 A | 4/2000 | Gordon et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,276 A | 6/2000 | Kontos |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,165,196 A | 12/2000 | Stack et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,482,171 B1 | 11/2002 | Corvi et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,695,859 B1 | 2/2004 | Golden et al. |
| 6,712,831 B1 | 3/2004 | Kaplan et al. |
| 6,716,243 B1 | 4/2004 | Colvin et al. |
| 6,726,651 B1 | 4/2004 | Robinson et al. |
| 6,733,509 B2 * | 5/2004 | Nobles ............... A61B 17/0467 606/138 |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,887,249 B1 | 5/2005 | Houser et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 6,964,668 B2 | 11/2005 | Modesitt et al. |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |

(56) References Cited

U.S. PATENT DOCUMENTS

| | | |
|---|---|---|
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,197,510 B2 | 6/2012 | Nobles |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,709,020 B2 | 4/2014 | Nobles |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,758,223 B2 | 9/2020 | Nobles et al. |
| 10,828,022 B2 | 11/2020 | Nobles et al. |
| 2001/0021854 A1 | 9/2001 | Donnez et al. |
| 2001/0031973 A1 | 10/2001 | Nobles et al. |
| 2001/0049492 A1 | 12/2001 | Frazier et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0087178 A1 | 7/2002 | Nobles et al. |
| 2002/0096183 A1 | 7/2002 | Stevens et al. |
| 2002/0111653 A1 | 8/2002 | Foerster |
| 2002/0128598 A1 | 9/2002 | Nobles |
| 2002/0128684 A1 | 9/2002 | Foerster |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0149448 A1 | 8/2003 | Foerster et al. |
| 2003/0167062 A1 | 9/2003 | Gambale et al. |
| 2003/0171760 A1 | 9/2003 | Gambale |
| 2003/0181926 A1 | 9/2003 | Dana et al. |
| 2003/0195539 A1 | 10/2003 | Attinger et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0068273 A1 | 4/2004 | Fariss et al. |
| 2004/0093031 A1 | 5/2004 | Burkhart et al. |
| 2004/0097968 A1 | 5/2004 | Sikikhman et al. |
| 2004/0102797 A1 | 5/2004 | Golden et al. |
| 2004/0098050 A1 | 8/2004 | Foerster et al. |
| 2004/0153116 A1 | 8/2004 | Nobles |
| 2004/0210238 A1 | 10/2004 | Nobles et al. |
| 2004/0236356 A1 | 11/2004 | Rioux et al. |
| 2004/0260298 A1 | 12/2004 | Kaiseer et al. |
| 2005/0033319 A1 | 2/2005 | Gambale et al. |
| 2005/0033361 A1 | 2/2005 | Galdonik et al. |
| 2005/0070923 A1 | 3/2005 | McIntosh |
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0240226 A1 | 10/2005 | Foerster et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2005/0288688 A1 | 12/2005 | Sakamoto et al. |
| 2005/0288690 A1 | 12/2005 | Bourque et al. |
| 2006/0047314 A1 | 3/2006 | Green |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0271074 A1 | 11/2006 | Ewers et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0005081 A1* | 1/2007 | Findlay, III ........ A61B 17/0467 606/148 |
| 2007/0010829 A1 | 1/2007 | Nobles et al. |
| 2007/0032798 A1 | 2/2007 | Pantages et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0234729 A1 | 9/2008 | Page et al. |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |

(56) References Cited

U.S. PATENT DOCUMENTS

| | | |
|---|---|---|
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0238001 A1 | 9/2013 | Nobles et al. |
| 2013/0261645 A1 | 10/2013 | Nobles et al. |
| 2013/0324800 A1 | 12/2013 | Cahill |
| 2014/0163585 A1 | 6/2014 | Nobles et al. |
| 2014/0303654 A1 | 10/2014 | Nobles et al. |
| 2014/0309670 A1 | 10/2014 | Bakos et al. |
| 2014/0379006 A1 | 12/2014 | Sutherland et al. |
| 2015/0359531 A1 | 12/2015 | Sauer |
| 2017/0035425 A1 | 2/2017 | Fegelman et al. |
| 2017/0049451 A1 | 2/2017 | Hausen |
| 2017/0128059 A1 | 5/2017 | Coe et al. |

FOREIGN PATENT DOCUMENTS

| | | |
|---|---|---|
| AU | 2006262498 | 1/2007 |
| CA | 2323084 | 12/2006 |
| CN | 1654016 A | 8/2005 |
| CN | 101027001 | 8/2007 |
| CN | 101242785 A | 8/2008 |
| CN | 101495049 | 12/2010 |
| CN | 101257852 | 8/2011 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0 983 026 | 3/2002 |
| EP | 1 196 093 | 4/2002 |
| EP | 0 941 698 | 5/2005 |
| EP | 0 870 486 | 11/2005 |
| EP | 0 983 027 | 12/2005 |
| EP | 1 804 677 | 7/2007 |
| EP | 1 852 071 | 11/2007 |
| EP | 1 570 790 | 11/2008 |
| EP | 1 987 779 | 11/2008 |
| EP | 2 011 441 | 1/2009 |
| EP | 2 572 649 | 3/2013 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2002-500531 | 1/2002 |
| JP | 2003-139113 A2 | 5/2003 |
| JP | 2003-225241 A | 8/2003 |
| JP | 2005-534419 | 11/2005 |
| JP | 2007-503870 | 3/2007 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/25254 | 5/1999 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |

OTHER PUBLICATIONS

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 By B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, by Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

*Sutura, Inc.* v. *Abbott Laboratories, et al.* Civil Action No. 2:06CV-536 (TJW), Sworn Declaration of Dr. John R. Crew, M.D., Dated Sep. 4, 2001.

Techniques in Vascular Surgery, by Denton A. Cooley, MD. and Don C. Wukasch, MD., copyright 1979 by WB. Saunders Co., at pp. 38,57,86,134,156, and 184.

The problem: Closing wounds in deep areas during laparoscopic operations The solution: REMA Medizintechnik GmbH (no date).

Vascular Access, Principles and Practice, 3rd edition, by Samuel Eric Wilson, MD., copyright 1996, 1988,1980 by Mosby-Year Book, Inc., pp. 89 and 159.

Vascular and Endovascular Surgery, by Jonathan D. Beard and Peter Gainers, copyright 1998 by W. B. Saunders Co., Ltd, p. 414.

Vascular Surgery, 3rd edition, vol. 1, by Robert B. Rutherford, MD., copyright 1989, 1984, 1976 by W. B.SaundersCo., at pp. 347, 348, 354, 594, 607, 622, 675, 677, 680, 698, 700, 721, 727, 735, and 829.

Vascular Surgery, 4th edition by Robert B. Rutherford, MD., copyright 1995,1989,1976, by W.B. Saunders Co., vol. 1, at pp. 400-404, 661, and A.

(56) References Cited

OTHER PUBLICATIONS

Vascular Surgery, 4th edition, by Robert B. Rutherford, M.D., copyright 1995, 1989, 1984, 1976 by W. B. Saunders Co., vol. 2, at pp. 1318,1363,1426,1564, and 1580.
Vascular Surgery, by Robert B. Rutherford, M.D. copyright1977 by WB. Saunders Co., at pp. 334 and 817.
International Search Report and Written Opinion of PCT/US08/58519, dated Aug. 29, 2008.
Japanese Office Action dated Oct. 15, 2014, re JP Application No. 2013-230232.
Japanese Office Action dated Oct. 30, 2012 for Japanese Patent Application No. 2010-501228.
Cardio Medical Solutions, Inc. brochure titled: "Baladi Inverter for Clamp less Surgery"—Undated.

* cited by examiner

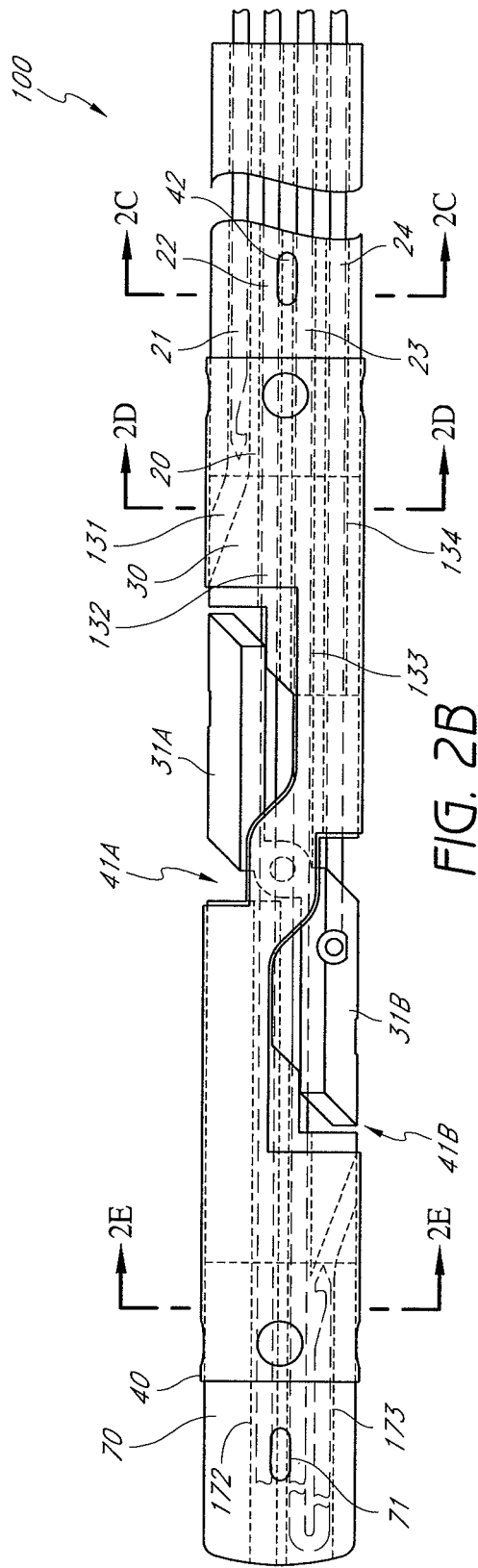
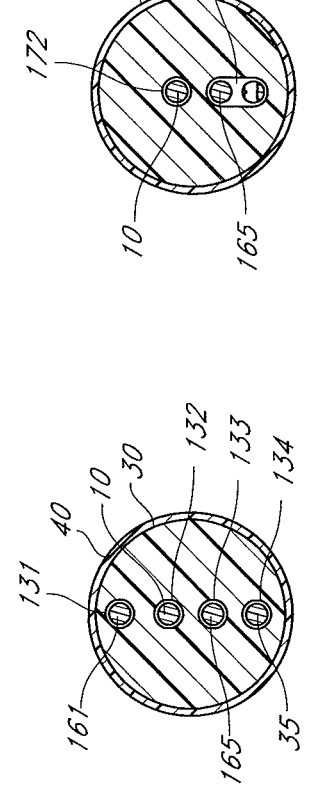
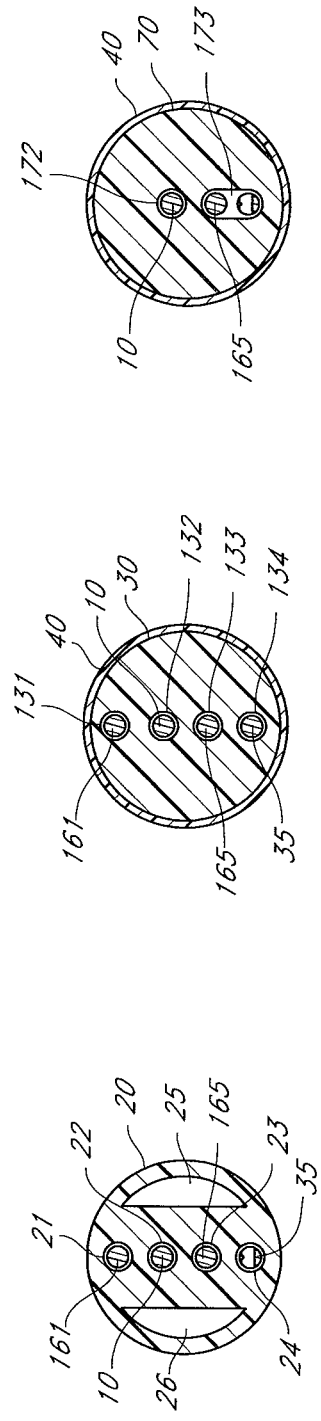

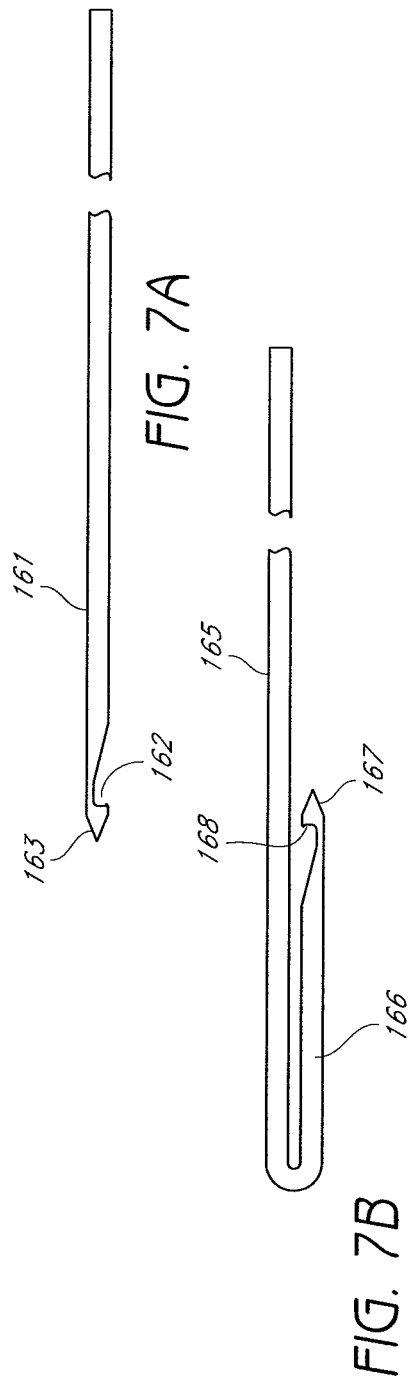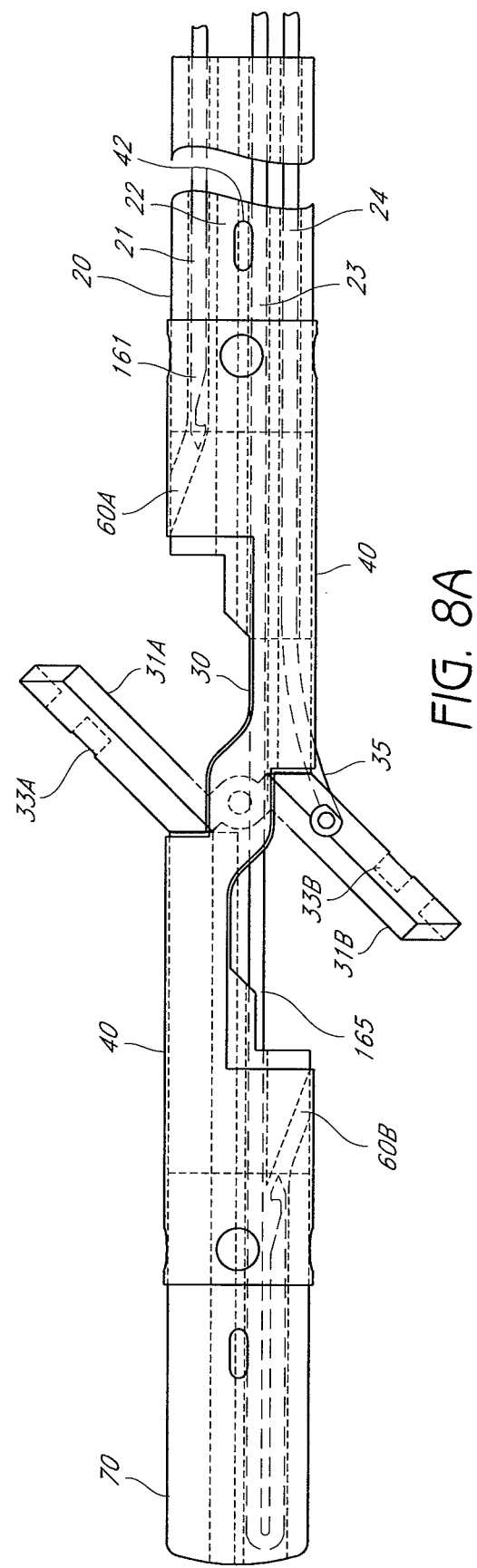

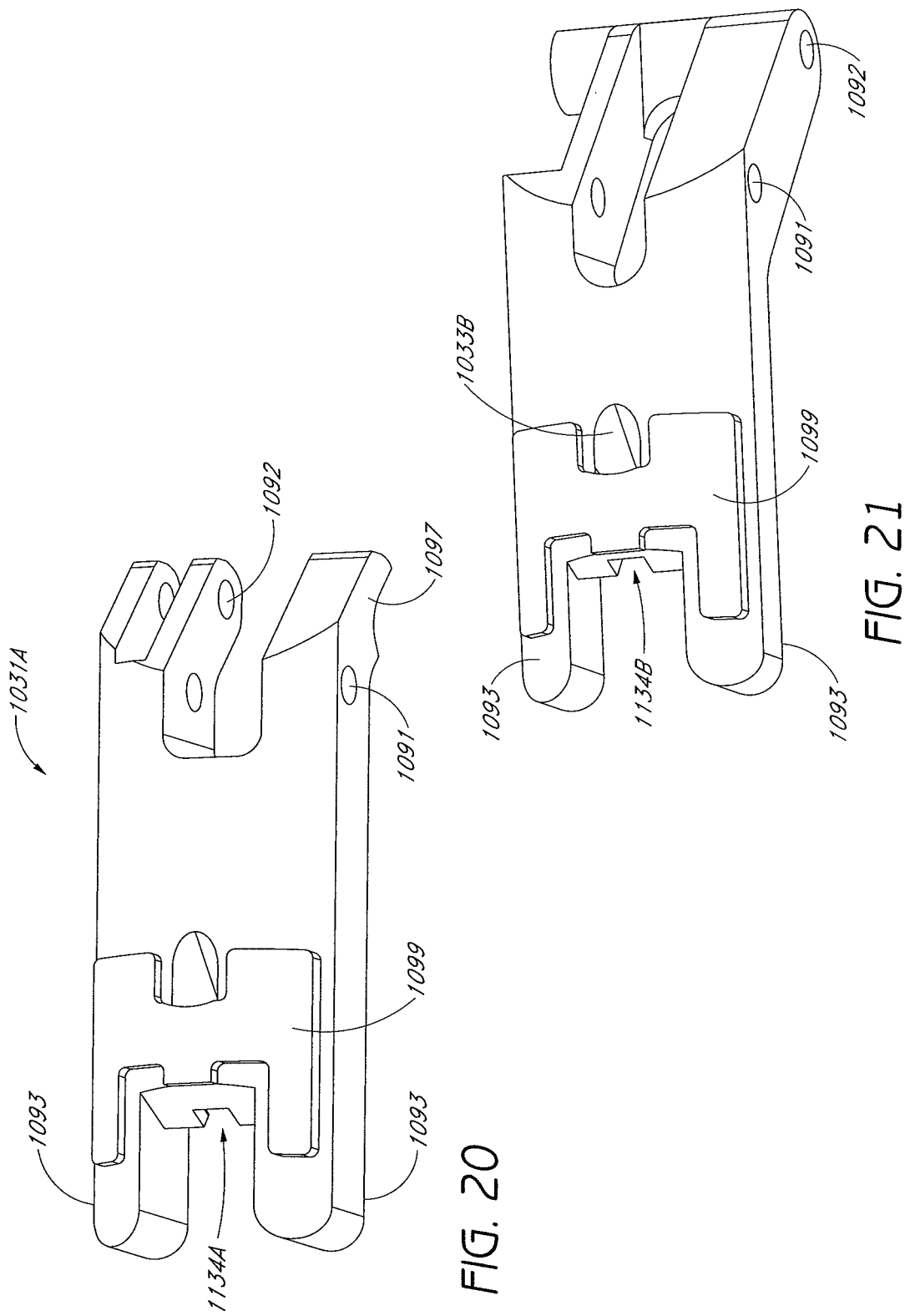

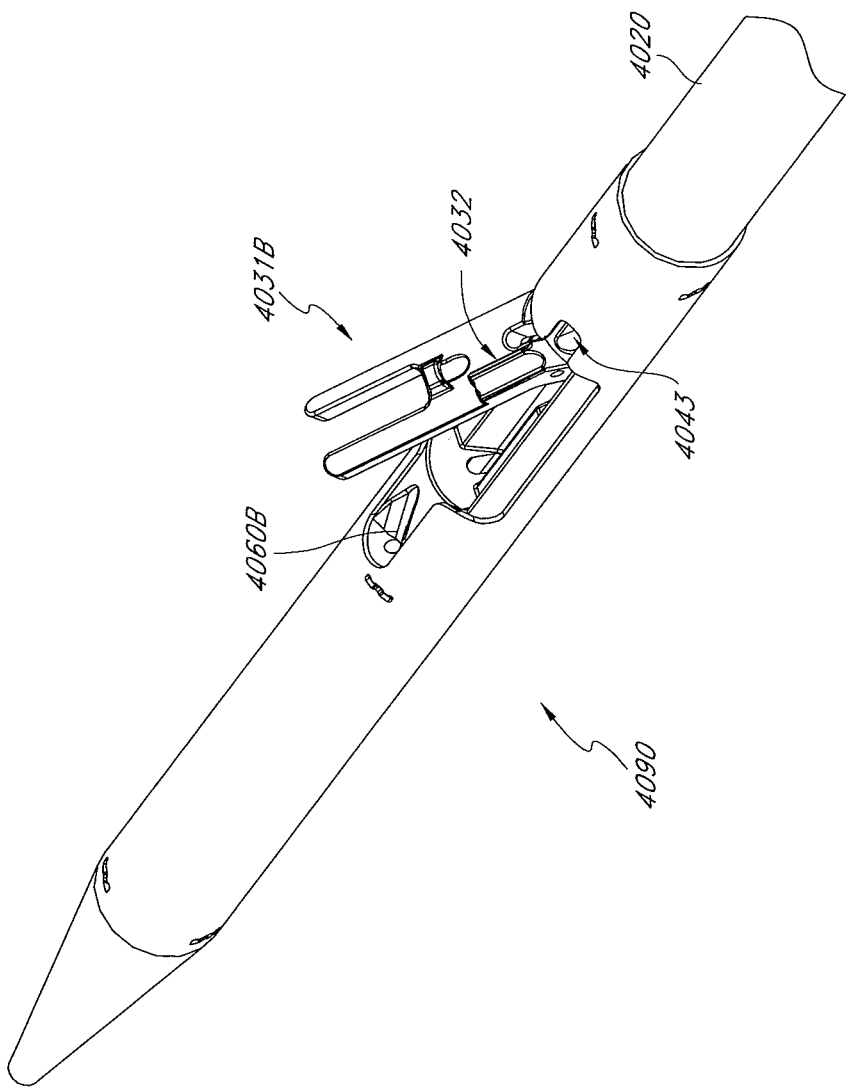

DEVICE FOR APPLYING A KNOT TO A SUTURE

CROSS-REFERENCE TO RELATED APPLICATIONS

This application is a continuation of U.S. application Ser. No. 13/552,849, filed Jul. 19, 2012, now U.S. Pat. No. 8,372,089, issued Feb. 12, 2013, which is a divisional application of U.S. application Ser. No. 12/057,304, filed Mar. 27, 2008, which claims the benefit of U.S. Provisional Application No. 60/908,946, filed Mar. 29, 2007, and U.S. Provisional Application No. 60/981,468, filed Oct. 19, 2007, the entirety of all of which are hereby incorporated by reference.

BACKGROUND OF THE INVENTIONS

Field of the Invention

Embodiments of the present inventions relate to suturing devices and methods. Specifically, preferred embodiments of the present inventions relate to suturing devices and methods for suturing a patent foramen ovale.

Description of the Related Art

Health practitioners frequently use sutures to close various openings such as cuts, punctures, and incisions in various places in the human body. Because of their importance and frequent use, several types of sutures and devices for their implantation and extraction have been developed. These devices include needles having various shapes and sizes as well as devices for inserting and removing staples. Generally, sutures are convenient to use and function properly to hold openings in biological tissue closed thereby aiding in blood clotting, healing, and prevention of scaring. However, there are some circumstances under which it is not feasible to use conventional sutures and suturing methods to close an opening. Some of these circumstances occur with incisions in arterial walls, or other internal bodily tissues. Here, catheter based devices and procedures have been suggested to close such openings.

For example, during development of a fetus in utero, blood is generally oxygenated by the mother's placenta, not the fetus' developing lungs. Most of the fetus' circulation is shunted away from the lungs through specialized vessels or foramens, such as the foramen ovale. The foramen ovale is a flaplike opening between the atrial septa primum and secundum which serves as a physiologic conduit for right to left shunting between the atria. Typically, once the pulmonary circulation is established after birth, left atrial pressure increases, resulting in the fusing of the septum primum and septum secundum and thus the closure of the foramen ovale. Occasionally, however, these foramen fail to close and create hemodynamic problems, which may ultimately prove fatal unless treated. A foramen ovale which does not seal is defined a patent foramen ovale, or PFO.

To close such PFOs, open surgery may be performed to ligate and close the defect. Such procedures are obviously highly invasive and pose substantial morbidity and mortality risks. Alternatively, catheter-based procedures have been suggested which involve introducing expandable structures through the patent foramen ovale to attempt to secure the tissue surrounding the patent foramen ovale, thereby blocking and sealing the patent foramen ovale. However, these structures involve support structures which may fail during the life of the patient and/or become dislodged, thereby re-opening the patent foramen ovale and possibly releasing the structure within the patient's heart. Thus, it would be advantageous to provide a simple, closure device and procedure for sealing a patent foramen ovale.

SUMMARY OF THE INVENTIONS

Embodiments of the present inventions address the above problems by providing a suturing device and method for suturing biological tissue, such as, for example, an organ or blood vessel. The device is particularly well suited to suture a patent foramen ovale.

One embodiment relates to a suturing device comprising an elongate body and at least one arm, more preferably first and second arms. Each of said arms has a suture mounting portion which mounts an end portion of a suture. The arms are mounted on the elongate body such that said suture mounting portions are movable away from said body to a first position and towards said body to a second position. The suturing device further comprises at least one needle, and preferably first and second needles, each of said needles having a distal end. Each of said needles is mounted such that the distal end of the needle is movable from a position adjacent said elongate body to a position away from said body, and towards the suture mounting portion of one of the arms when in said first position, wherein the respective distal ends of the first and second needles engage respective end portions of said suture. The suturing apparatus further comprises an actuator which drives the needles.

In one embodiment, a suturing apparatus comprises an elongate body having a proximal end and a distal end. A first suture clasp arm is adapted to hold an end portion of a suture, the first suture clasp arm being extendable from the body from a retracted position to an extended position. A second suture clasp arm is adapted to hold an end portion of a suture, the second suture clasp arm being extendable from the body from a retracted position to an extended position. A first suture catch mechanism is slidably housed in the elongate body, the first suture catch mechanism being moveable in a proximal to distal direction to engage a distal end of the first suture catch mechanism with the suture end held by the first suture clasp arm when the first suture clasp arm is in the extended position. A second suture catch mechanism is slidably housed in the elongate body, the second suture catch mechanism being moveable in a distal to proximal direction to engage a distal end of the first suture catch mechanism with the suture end held by the second suture clasp arm when the second suture clasp arm is in the extended position.

In another embodiment, a suturing apparatus for suturing a patent foramen ovale comprises an elongate body having a proximal end and a distal end configured to be delivered percutaneously into the patent foramen ovale. At least a first suture clasp arm is adapted to hold a first suture end portion. The first suture clasp arm is extendable from said body from a retracted position to an extended position and configured to be placed around one of the septum primum and septum secundum of the patent foramen ovale. At least a first suture catch mechanism is slidably housed in said elongate body. The first suture catch mechanism is movable through one of the septum primum and septum secundum of the patent foramen ovale to engage a distal end of the first suture catch mechanism with the first suture end portion held by the first suture clasp arm when the first suture clasp arm is in the extended position.

In another embodiment, a system for suturing a patent foramen ovale comprises a first suturing apparatus and a second suturing apparatus. The first suturing apparatus comprises a first elongate body having a proximal end and a distal end, a first suture clasp arm adapted to hold a first suture end portion, and a first suture catch mechanism slidably housed in said elongate body. The first suture clasp arm is extendable from said body from a retracted position to an extended position and configured to be placed around the septum primum of the patent foramen ovale. The first suture catch mechanism is moveable in a proximal to distal direction through the septum primum of the patent foramen ovale to engage a distal end of the first suture catch mechanism with the first suture end portion held by the first suture clasp arm when the first suture clasp arm is in the extended position. The second suturing apparatus comprises a second elongate body having a proximal end and a distal end, a second suture clasp arm adapted to hold a second suture end portion, and a second suture catch mechanism slidably housed in said elongate body. The second suture clasp arm is extendable from said body from a retracted position to an extended position and configured to be placed around the septum secundum of the patent foramen ovale. The second suture catch mechanism is moveable in a distal-to-proximal direction through the septum secundum of the patent foramen ovale to engage a distal end of the second suture catch mechanism with the second suture end portion held by the second suture clasp arm when the second suture clasp arm is in the extended position.

In another embodiment, a suturing apparatus for suturing a patent foramen ovale comprises an elongate body having a proximal end and a distal end, a first suture clasp arm, a second suture clasp arm, a first suture catch mechanism, and a second suture catch mechanism. The first suture clasp arm is adapted to hold a first suture end portion. The first suture clasp arm is extendable from said body from a retracted position to an extended position and configured to be placed around the septum primum of the patent foramen ovale. The second suture clasp arm is adapted to hold a second suture end portion. The second suture clasp arm is extendable from said body from a retracted position to an extended position and configured to be placed around the septum secundum of the patent foramen ovale. The first suture catch mechanism is slidably housed in said elongate body. The first suture catch mechanism is moveable in a proximal-to-distal direction through the septum primum of the patent foramen ovale to engage a distal end of the first suture catch mechanism with the first suture end portion held by the first suture clasp arm when the first suture clasp arm is in the extended position. The second suture catch mechanism is slidably housed in said elongate body. The second suture catch mechanism is moveable in a distal-to-proximal direction through the septum secundum of the patent foramen ovale to engage a distal end of the first suture catch mechanism with the second suture end portion held by the second suture clasp arm when the second suture clasp arm is in the extended position.

In another embodiment, a method of closing a patent foramen ovale having a septum primum and a septum secundum is provided. An elongate body is advanced into a tunnel of a patent foramen ovale. A first suture clasp arm is extended from the elongate body from a retracted position to an extended position, the first suture clasp arm holding an end portion of a suture. The first suture clasp arm is positioned around one of the septum primum and the septum secundum. A first needle positioned in the elongate body is advanced outwardly from the body through tissue of one of the septum primum and septum secundum and into engagement with the suture end held in the first suture clasp arm. The first needle is retracted into the elongate body with the suture end carried by the first needle. A second suture clasp arm is extended from the elongate body from a retracted position to an extended position, the second suture clasp arm holding an end portion of a suture. The second suture clasp arm is positioned around the other of the septum primum and the septum secundum. A second needle positioned in the elongate body is advanced outwardly from the body through tissue of the other of the septum primum and septum secundum and into engagement with the suture end held in the second suture clasp arm. The second needle is retracted into the elongate body with the suture end carried by the second needle. The elongate body is withdrawn from the tunnel of the patent foramen ovale. The septum primum and the septum secundum are drawn closed.

In another embodiment, a method of closing a patent foramen ovale having a septum primum and a septum secundum is provided. A first suture clasp arm is positioned around one of the septum primum and the septum secundum. The first suture clasp arm holds a first suture end portion. A first needle is advanced through tissue of one of the septum primum and septum secundum and into engagement with the first suture end portion held in the first suture clasp arm. The first needle is retracted through tissue of one of the septum primum and septum secundum with the first suture end portion carried by the first needle. A second suture clasp arm is positioned around the other of the septum primum and the septum secundum. The second suture clasp arm holds a second suture end portion. A second needle is advanced through tissue of the other of the septum primum and septum secundum and into engagement with the second suture end portion held in the second suture clasp arm. The second needle is retracted through tissue of the other of the septum primum and septum secundum with the second suture end portion. The septum primum and the septum secundum are drawn closed.

In another embodiment, a method of closing a patent foramen ovale having a septum primum and a septum secundum is provided. A first elongate body is advanced into a tunnel of a patent foramen ovale. A first suture clasp arm is extended from the first elongate body from a retracted position to an extended position. The first suture clasp arm holds a first suture end portion. The first suture clasp arm is positioned around one of the septum primum and the septum secundum. A first needle positioned in the elongate body is advanced outwardly from the body through tissue of one of the septum primum and septum secundum and into engagement with the first suture end portion held in the first suture clasp arm. The first needle is retracted into the first elongate body with the first suture end portion carried by the first needle. The first elongate body is withdrawn from the tunnel of the patent foramen ovale. A second elongate body is advanced near the tunnel of a patent foramen ovale. A second suture clasp arm is extended from the second elongate body from a retracted position to an extended position. The second suture clasp arm holds a second suture end portion. The second suture clasp arm is positioned around the other of the septum primum and the septum secundum. A second needle positioned in the second elongate body is advanced outwardly from the body through tissue of the other of the septum primum and septum secundum and into engagement with the second suture end portion held in the second suture clasp arm. The second needle is retracted into the second elongate body with the second suture end portion carried by the second needle. The second elongate body is withdrawn from the tunnel of the patent foramen ovale. The septum primum and the septum secundum are drawn closed.

BRIEF DESCRIPTION OF THE DRAWINGS

FIG. 2B illustrates a side view of the distal end of the suturing device of FIG. 2A.

FIG. 2C illustrates a cross-sectional view of the elongate tubular member of an embodiment of the suturing device taken along the line 2C-2C of FIG. 2B.

FIG. 2D illustrates a cross-sectional view of the spreader assembly of an embodiment of the suturing device taken along the line 2D-2D of FIG. 2B.

FIG. 2E illustrates a cross-sectional view of the distal tip of an embodiment of the suturing device taken along the line 2E-2E of FIG. 2B.

FIG. 7A is a side view of an embodiment of a suture catch mechanism for engaging the proximal suture clasp arm.

FIG. 7B is a side view of an embodiment of a suture catch mechanism for engaging the distal suture clasp arm.

FIG. 8A is a side view of an embodiment of the suturing device illustrating the proximal and distal suture catch mechanisms in a stored position.

FIG. 10I is a schematic representation as in FIG. 10H showing the suture portions positioned through the septum secundum and septum primum following withdrawal of the suturing device.

FIG. 12I is a schematic representation of the suturing device of FIG. 12A showing the proximal needle retracted from the septum primum.

FIG. 20 illustrates a perspective view of a suture clasp arm.

FIG. 21 illustrates a perspective view of a suture clasp arm.

FIG. 29I is a schematic representation as in FIG. 29H showing the suture portions positioned through the septum secundum and septum primum, and the suturing device being withdrawn.

FIG. 38 is a perspective view of a distal end of a second suturing device of the system of FIG. 36.

FIG. 39I is a schematic representation as in FIG. 39H showing the suture portions positioned through the septum secundum and septum primum, and the second suturing device being withdrawn.

DETAILED DESCRIPTION OF THE PREFERRED EMBODIMENTS

Embodiments of the present invention provide suturing devices and methods for closing an opening in biological tissue, a body lumen, hollow organ or other body cavity. The suturing devices and their methods use are useful in a variety of procedures, such as treating (closing) wounds and naturally or surgically created apertures or passageways. For example, the suturing devices may be used to seal an opening in the heart wall such as an atrial septal defect, a patent ductus arteriosis or a patent foramen ovale. In addition, the suturing devices may be used to close or reduce a variety of other tissue openings, lumens, hollow organs or natural or surgically created passageways in the body. Also, the suturing devices may be used to suture prosthetics, synthetic materials, or implantable devices in the body. For example, the devices may be used to suture pledget within the body.

Figure 1:
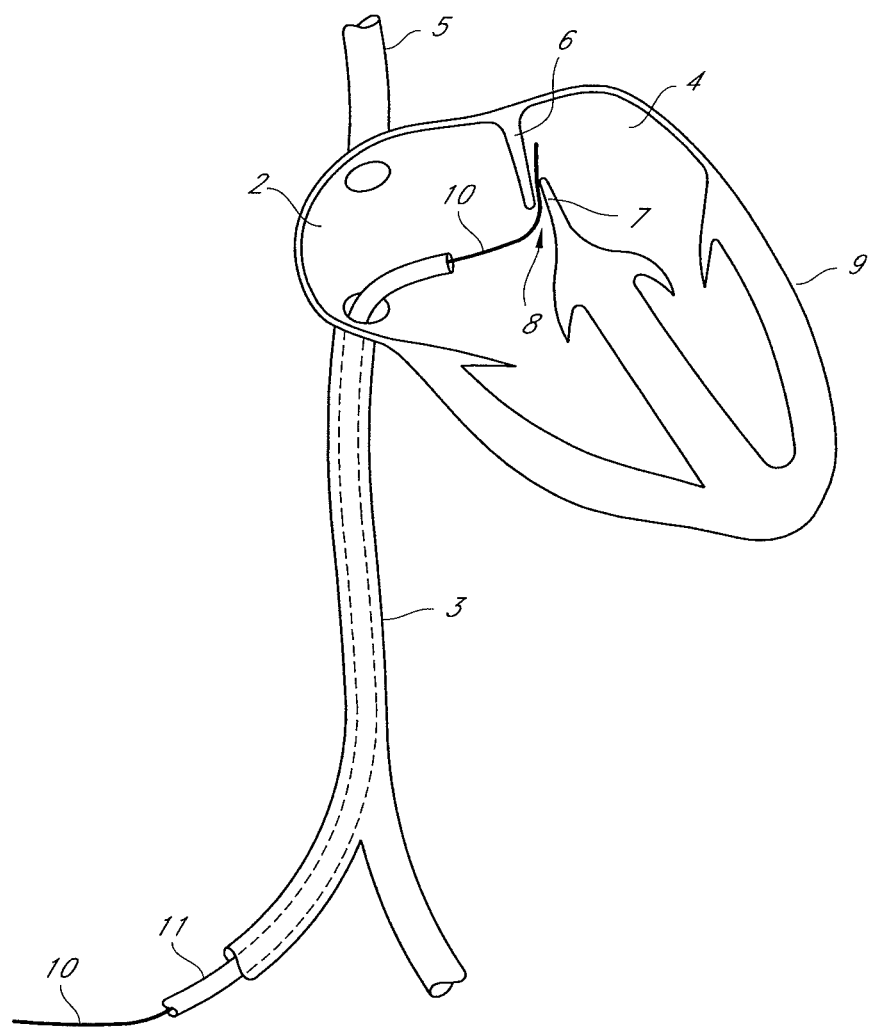
FIG. 1 illustrates a method of providing access to an exemplifying use environment, such as a patent foramen ovale.

FIG. 1 illustrates one embodiment in an exemplifying use environment for closing a patent foramen ovale (PFO). Adaption of the devices and methods disclosed herein for closing a PFO may also be made with respect to procedures for closing other bodily tissue openings, lumens, hollow organs or natural or surgically created passageways and procedures for suturing prosthetics, synthetic materials, or implantable devices in the body. As depicted by FIG. 1, a guidewire 10 is advanced into the right atrium 2 of the heart 9 through the inferior vena cava 3. It is anticipated that the heart may be accessed through any of a variety of pathways, such as through the inferior vena cava 3 via a femoral access site, through the superior vena cava 5 via the subclavian or jugular veins, or any other venous or arterial access sites. The guidewire 10 can then be further positioned in the tunnel or opening of the patent foramen 8 ovale between the septum primum 7 and septum secundum 6. With the guidewire 10 in place, the physician can insert a sheath 11 to the right atrium. This sheath 11 is typically a single lumen catheter with a valve on its proximal end. The valve is used to prevent extraneous bleed back or to introduce medication into the patient's body. The sheath 11 can be placed at or near the tunnel of a patent foramen ovale 8. The suturing device 100, described further below, can then be advanced to the PFO 8 through the lumen of the sheath 11. In an alternative embodiment, the suturing device 100 can be advanced over the guidewire 10 and positioned in the opening of the patent foramen ovale 8 without the need to insert an introducer 11. Other methods of accessing the PFO or other bodily locations.

Figure 2A:
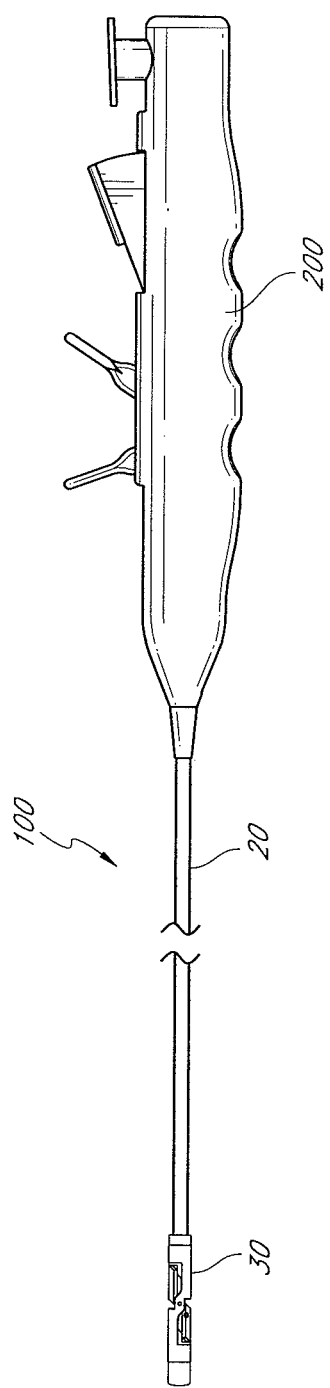
FIG. 2A illustrates a side view of one embodiment of a suturing device.

FIG. 2A shows one embodiment of the suturing device 100 for suturing an opening in a vessel wall and other biological tissue. While the device will be described in reference to suturing an opening in the heart wall such as a patent foramen ovale (PFO), the device could be used to close other openings in the heart wall, such as a patent ductus arteriosus (PDA) or an atrial septal defect (ASD), other puncture wounds in bodily tissue, or the like, or to perform other procedures as described above. The suturing device 100 comprises an elongated tubular member 20 having a spreader assembly 30 (shown in FIG. 2B) connected to the distal end of the elongated tubular member 20 for positioning in the opening of the PFO. A handle 200 is provided at the proximal end of the tubular member 20. The axial length and flexibility of the elongated tubular member 20 is sufficient to percutaneously access the patient's vasculature and advance the elongate tubular member 20 through the venous system to the patient's heart with the proximal end of the device remaining outside the patient's body. However, the length of the device may vary depending upon the intended access point and pathway to the heart. For example, for a femoral access point and pathway via the inferior vena cava, the axial length of the elongate tubular member 20 can be between about 70-120 cm, alternatively between about 80-100 cm, alternatively about 90 cm.

As shown in more detail in FIG. 2C, the elongate tubular member 20 has a plurality of lumens extending along the axial length. The multi-lumen elongate tubular member 20 can be manufactured in accordance with any of a variety of techniques known to those skilled in the art. For example, in some embodiments, the elongate tubular member 20 can be formed from a multi-lumen extruded plastic tubing, such as a polyester, polyethelyne, polymide, nylon or any other suitable material known to those skilled in the art. The elongate tubular member 20 comprises four central lumens 21, 22, 23 and 24 vertically stacked along a central axis of the elongate tubular member 20. In some embodiments, the central lumens may be surrounded by two semicircular or D-shaped lumens 25 and 26 extending axially on opposite sides of the elongate tubular member 20. In some embodiments, as will be discussed below in more detail, the central lumens 21, 22, 23, and 24 will be used to provide access through the elongate tubular member 20 for a guidewire, to provide access for an actuating rod connected to the suture clasp arms, and to house one or more suture catch mechanisms or needles. The semi-circular shaped lumens 25 and 26 can be used to deliver one or more sutures to the distal end of the elongate tubular member 20.

The spreader assembly 30 is bonded, or otherwise joined, to the distal end of the elongated tubular member 20, for example with epoxy or any other suitable technique known to those skilled in the art. Alternatively, the spreader assembly may be integral with the elongate tubular member 20 As shown in FIG. 2D, the spreader assembly comprises central lumens 131, 132, 133 and 134 vertically stacked along a central longitudinal axis of the spreader assembly 30. When the spreader 30 and the elongate tubular member are properly connected, the central lumens 21, 22, 23 and 24 of the elongate tubular member 20 and the central lumens 131, 132, 133 and 134 of the spreader assembly 30 are preferably substantially aligned to provide continuous passageways through the elongate tubular member 20 and spreader assembly 30. A metal casing, or bullet, 40, having a length greater than the length of the spreader 30 and an inner diameter substantially the same as the outer diameter of the spreader assembly 30 and elongate tubular member 20 is placed over the connection between the elongate tubular member 20 and the spreader assembly 30 to maintain the proper alignment of the internal lumens of the elongate tubular member 20 and spreader assembly 30. The bullet comprises openings 41A and 41B located on the opposite sidewalls of the bullet 40 for allowing the release and deployment of suture clasp arms housed within the spreader assembly 30. Accordingly, the openings 41A and 41B are sized and shaped to permit the suture clasp arms to fully extend from the spreader assembly 30.

In some embodiments, the bullet 40 has a length such that when the proximal end of the bullet is positioned over the connection between the spreader assembly 30 and the elongate tubular member 20, its distal end extends beyond the distal end of the spreader assembly 30. A distal tip 70 which may be rounded or atraumatic can be bonded or adhered to the distal end of the spreader assembly 30, for example with epoxy or any other suitable technique known to those skilled in the art. As shown in FIG. 2E, the distal tip can have at least one central lumen 172 that is axially aligned with a central lumen 132 of the spreader 30 and a central lumen 22 of elongate tubular member 20 for providing a continuous passageway through the entire length of suturing device 100, for example for a guidewire. In addition, the distal tip 70 may have one or more additional lumens 173 that can be aligned with lumens in the spreader assembly 30 and elongate tubular member 20 to provide additional continuous passageways, for example for housing a suture catch mechanism. Here, as discussed above, the outer diameter of the distal tip is substantially the same size as the inner diameter of the bullet 40 such that when the distal end of the bullet 40 is positioned over the connection between the distal tip 70 and the spreader assembly 30, the bullet maintains the proper alignment of the internal lumens of the distal tip 70 and spreader assembly 30.

As shown in FIG. 2B, a pair of suture clasp arms 31A and B are housed in recesses 41A and 41B in the central portion of the spreader assembly 30. During storage and delivery of the suturing device, the suture clasp arms 31A and 31B are situated parallel to the longitudinal axis of the suturing device such that the outer walls of the suture clasp arms do not extend beyond the outer diameter of the spreader assembly 30. After insertion and positioning of the suturing device at the PFO or other opening, the arms 31A and B can be deployed to the position shown in FIG. 3. To deploy the suture clasp arms, the suture clasp arms 31A and B are connected to an actuating rod 35 which extends through the passageway formed by lumen 134 in the spreader assembly and central lumen 24 in the elongate tubular member 20. For example, in certain embodiments, the proximal suture clasp arm 31A and the distal suture clasp arm 31B may be manufactured as a single component, or alternately fixedly connected at a central connection point. Here, the distal end of the actuating arm 35 may be connected to the distal suture clasp arm 31B, offset from the middle, or central connection point, of the suture clasp arms such that proximal retraction of the actuating arm 35 will pull on the distal suture clasp arm 31B creating a counterclockwise torquing force on the suture clasp arms which will cause both suture clasp arms 31A and B to flip out from the spreader assembly 30.

When deployed, the suture clasp arms 31A and B extend from the suturing device 100 in opposite directions along the longitudinal axis of the device. Preferably, the arms 31A and 31B form an acute angle with the longitudinal axis of the spreader. In some embodiments, a first arm 31A extends outward toward the proximal end of the spreader assembly 30 at an angle of between about 35-55.degree., alternatively about 40-50.degree., alternatively about 45.degree. with respect to the longitudinal axis of the spreader assembly 30, while the second arm 31B extends outward toward the distal end of the spreader assembly 30 at the same angle as the first arm 31A with respect to the longitudinal axis of the spreader assembly 30.

Figure 3:
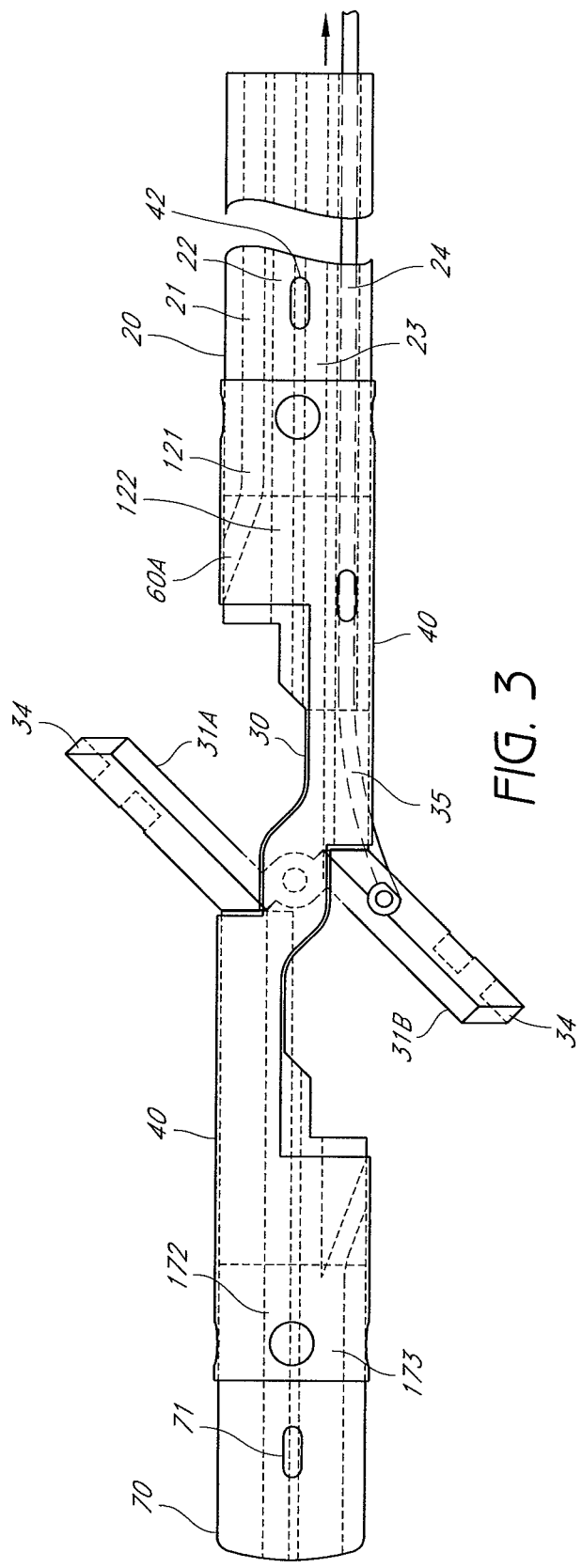
FIG. 3 illustrates a side view of an embodiment of the suturing device with the suture clasp arms deployed.

As shown in FIG. 3, the suture clasp arms 31A and 31B may be deployed simultaneously to extend equally in opposite directions with respect to the suturing device. In some embodiments, the suture clasp arms 31A and B can be independently actuated to be individually deployed depending upon the location of the tissue portion to be sutured. However, in some embodiments, it may be advantageous to simultaneously deploy both suture clasp arms 31A and B, even though only one of the suture clasp arms will be engaged at that location. For example in closing a PFO, the suturing device will first be positioned with respect to a first tissue portion to be sutured and then moved to a second position for suturing a second tissue portion. However, the second suture clasp arm 31B can still be deployed at the first location to provide mechanical support and stabilization for positioning the first suture clasp arm 31A proximal to the first tissue portion. For example, as shown in FIG. 10B, when closing a PFO, the suturing device 100 is first positioned such that suture clasp arm 31A extends around the septum primum 7 such that suture portion 52A may be engaged and pulled though the septum primum 7 to draw it toward the septum secundum 6. Here, the non-engaged suture clasp arm 31B is still extended toward and contacts the septum secundum 6 which pushes the suturing device 100 toward the septum primum 7 thereby assisting in placement of the suture clasp arm 31A around the septum primum 7 and stabilizing the suturing device 100 during deployment of the suture catch mechanism to engage the suture.

Figure 5:
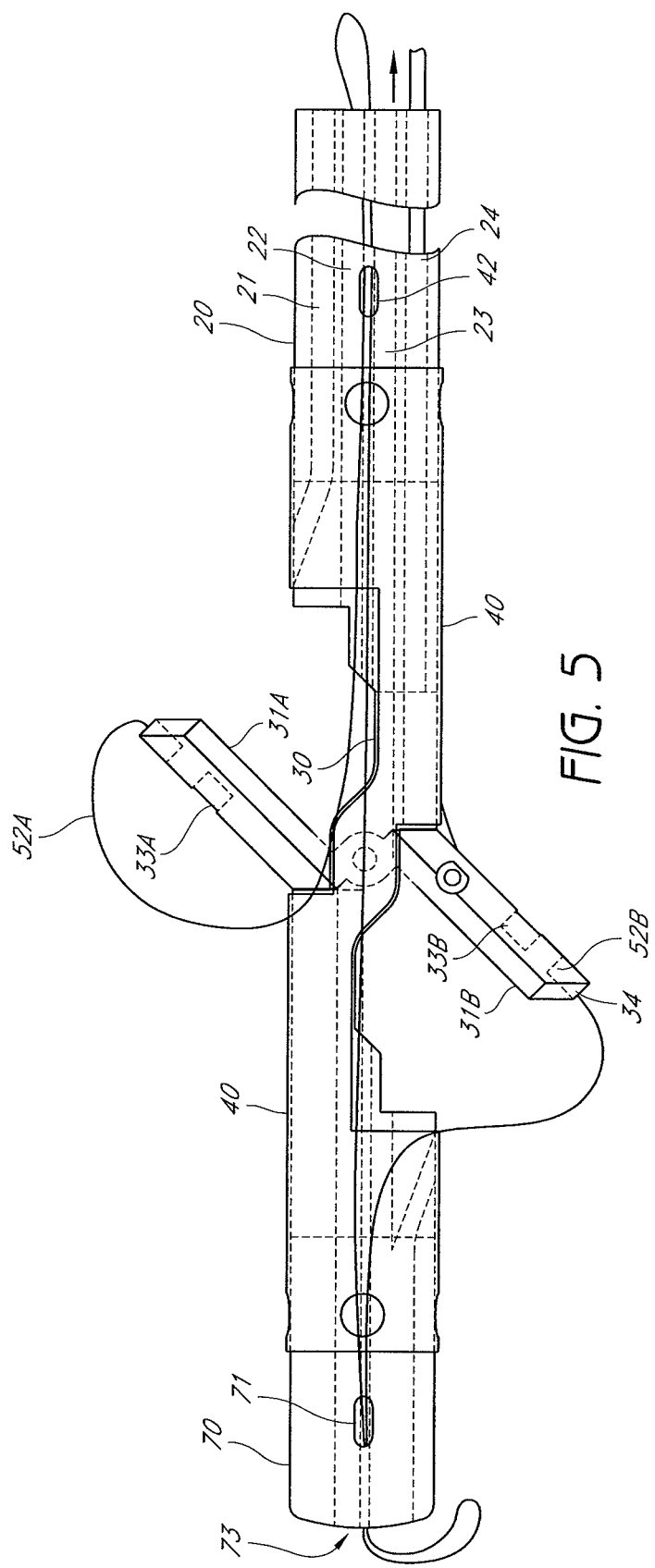
FIG. 5 is a side view of an embodiment of the suturing device showing suture portions positioned in the suture clasp arms.

As shown in FIG. 5, each of the suture clasp arms 31A, 31B has a suture clasp 33 for receiving and holding a suture 50. The suture clasp 33 can be a circular opening with a diameter sized to securely receive and hold a loop of suture 50. For example, as described in U.S. Pat. No. 6,562,052, the entirety of which is hereby incorporated by reference, the suture can comprise a length of suture 50 having a loop formed at each end of the suture. Other details regarding the apparatuses and methods of suturing devices that may be utilized with the embodiments disclosed throughout this specification are also found in U.S. Pat. No. 6,562,052 and are hereby incorporated by reference. The diameter of the suture loops and the inner diameter of the suture clasp 33 are preferably substantially the same such that the suture loops can be securely positioned in the suture clasp 33 during deployment of the suture clasp arms. The suture clasp 33 is advantageously angled such that when the suture clasp arm is deployed at an angle, the suture clasp 33 will hold the suture loop perpendicular to the path of the suture catch mechanism. In some embodiments, the suture clasp arm 31 can have a tab or slot 34 located on the distal end of the suture clasp arm 31 for guiding the suture loop into the suture catch 33 at the proper angle.

In use, as shown in FIG. 5, the suture 50 can be housed in one of the outer D-shaped, or suture, lumens 25, 26 of the elongate tubular member 20. The suture lumen 26 has a port or opening 42 on the distal end of the elongate tubular member 20. The suture 50 can be advanced through the opening 42 such that the suture ends, or end portions 52A and 52B, extend outside of the suturing device 100. One of the suture end portions 52A may extend from the opening 42 to the suture clasp arm 31A. The other suture end portion 52B may extend along the length of the bullet and into a side opening 71 in the distal tip 70. The suture portion 52B may extend out of a distal opening 73 in the distal tip, and then loop back into the opening 73. The suture end portion 52B then extends through side opening 71 to the suture clasp arm 31B.

The suture ends are positioned in the suture clasps 33A and 33B of the suture clasp arms 31A and 31B and held securely there until they are engaged and removed by a suture catch mechanism. As discussed above, the suture clasp arms 31A and 31B comprise slots 34A and 34B to guide the suture into the suture clasps 33 at the proper angle and assist in maintaining the suture loops in the suture clasp until they are engaged by the suture catch mechanisms. When the suture catch mechanism engages the loops of the suture ends, the suture loops will slide out of the suture clasp 33 and be released by the suture clasp arm 31.

Figure 4A:
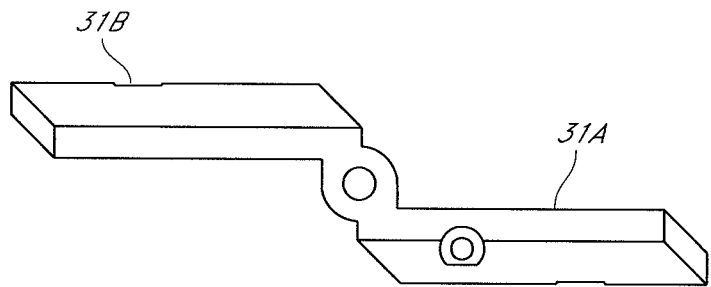
FIG. 4A illustrates a perspective view of the suture clasp arms.
Figure 4B:
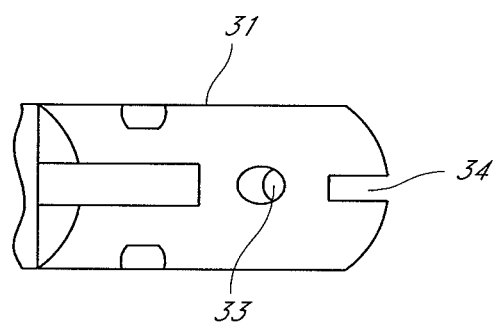
FIG. 4B illustrates a top plan view of an embodiment of a suture clasp arm having one suture clasp.
Figure 4C:
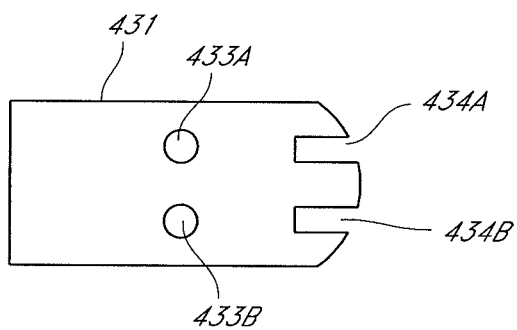
FIG. 4C illustrates a top plan view of an alternative embodiment of a suture clasp arm having two suture clasps.

In some embodiments, the suture clasp arms 31A and 31B may further comprise additional suture clasp(s) for holding additional suture portions. For example, in an alternative embodiment, shown in FIG. 4C, each suture clasp arm can be configured to deploy two sutures from the suturing device to a particular location for suturing a single tissue portion. Here, each suture clasp arm 431 has two suture clasps 433A and 433B for receiving two different suture portions 150 and 151. In addition, in some embodiments, each suture clasp arm can further include two slots 434A and 434B for guiding the suture portions 150 and 151 into the suture clasps 433A and 433B.

Figure 6A:
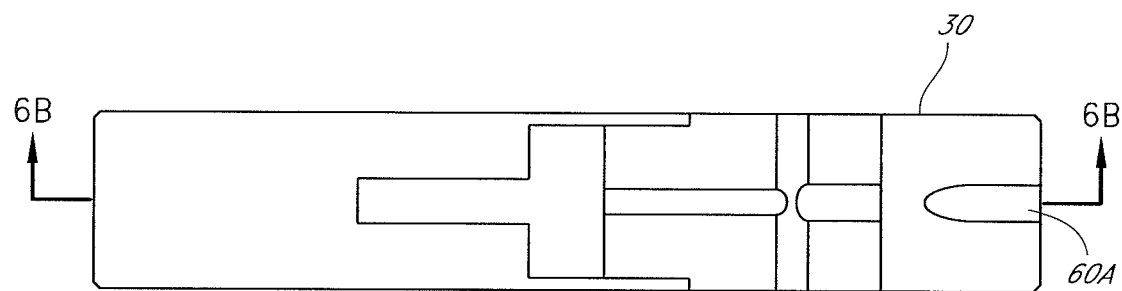
FIG. 6A illustrates a top plan view of an embodiment of a spreader assembly showing a needle guide.
Figure 6B:
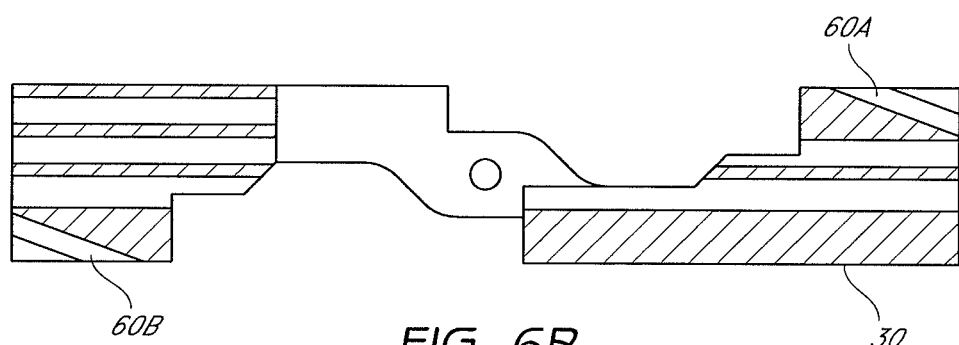
FIG. 6B illustrates a cross-sectional view of an embodiment of a spreader assembly showing proximal and distal needle guides.

As shown in more detail in FIGS. 6A-B, the spreader assembly 30 includes a plurality of needle guides 60A and 60B for guiding a plurality of suture catch mechanisms, such as a needle or other penetrating mechanism, towards the deployed suture clasp(s). In one embodiment, the spreader assembly 30 may comprise two needle guides 60A and 60B located on the distal and proximal ends of the spreader assembly for guiding two needles toward proximally and distally deployed suture arms 31A and 31B depicted in FIG. 3. Each of the needle guides 60A and 60B comprises an angled groove or channel in the sidewall of the spreader assembly 30 such that it will deflect a suture catch mechanism, or needle, exiting the suture assembly 30 along a path that intercepts the suture clasps 33A and 33B of the suture clasp arms when the suture clasp arms 31A and 31B are in a deployed position. For example, in some embodiments, the suture arms 31A and 31B may be sized such that a groove having an angle of between about 10-35.degree., alternatively about 15-25.degree., alternatively about 19.degree. with respect to the longitudinal axis of the spreader assembly will spread the needles to the proper angle to engage the suture loops in the deployed suture clasps 33. In use, the proximal needle guide 60A is aligned with lumen 131 of the spreader assembly and lumen 21 of the elongate tubular member such that when a suture catch mechanism is advanced through the passageway formed by lumens 131 and 21, the distal end of the needle will be deflected by the needle guide 60A towards the deployed suture clasp arm 31A. Likewise, distal needle guide 60B is aligned with lumen 173 of the distal tip such that when the distal tip of a needle housed in lumen 173 is extended towards suture clasp arm 31B, the needle will be deflected toward the suture clasp 33.

In some embodiments, as depicted in FIG. 7A, the suture catch mechanism 161 which is configured for engaging the suture clasp arm 31A extending toward the proximal end of the spreader assembly 30 comprises an elongate, straight needle 161. As shown in FIG. 7A, the needle 161 has a sharp, distal tip 163 for penetrating a tissue portion positioned between the suturing device and the deployed suture clasp arm 31A and a notch or groove 162 on the distal tip 162 for engaging the loop of suture portion 52A held by suture clasp 33. The notch or groove 162 is shaped or angled upward in order to grasp and dislodge the loop from the suture clasp 33 and retain the suture portion 52A against the groove 162 as the needle is pulled back through the suture clasp 33 and tissue portion and retracted back into the suturing device 100.

As shown in FIG. 7B, suture catch mechanism 165, which is configured to engage a suture clasp arm 31B extending towards the distal end of the spreader assembly 30 comprises an elongate needle 165 having a distal portion 166 bent approximately 180 degrees such that a portion of the needle is turned back upon itself. The turned portion 166 of the needle 165 has a length sufficient to extend from the spreader assembly 30 and engage the suture clasp 33B on suture clasp arm 31B when suture clasp arm 31B is in a fully deployed position. Similar to elongate, straight needle 161, the turned back portion 166 has a sharp distal tip 167 for penetrating a tissue portion positioned between the suturing device and the deployed suture clasp arm 31B and a notch or groove 168 on the distal tip 167 for engaging a loop of suture help by suture clasp arm 31B. The notch or groove 168 on the needle is configured to grasp and retain the loop of suture portion 52B from the suture catch 33B as the turned portion 166 of the needle 165 (FIG. 8B) is conveyed through the tissue portion and retracted back into the groove 173 (FIGS. 8B and 8C) of the distal tip 70 of the suturing device 10.

The needles 161 and 165 are flexible and are preferably made of a material with shape memory, such as nickel titanium or NITINOL. Alternatively, the needles 161 and 165 may be comprised of spring steel, surgical stainless steel or any variation thereof.

In use, as shown in FIG. 8A, the needles 161 and 165 can be housed within a central passageway formed by lumens within the elongate tubular member, spreader assembly and distal tip. Here, suture catch mechanism 161 is slidably housed in the passageway formed by the central lumens 21 of the elongate tubular member 20 and central lumen 131 of the spreader assembly while suture catch mechanism 165 is slidably housed in the passageway formed by central lumen 23 of the elongate tubular member, central lumen 133 of the spreader assembly and lumen 173 of the distal tip 70.

Figure 8B:
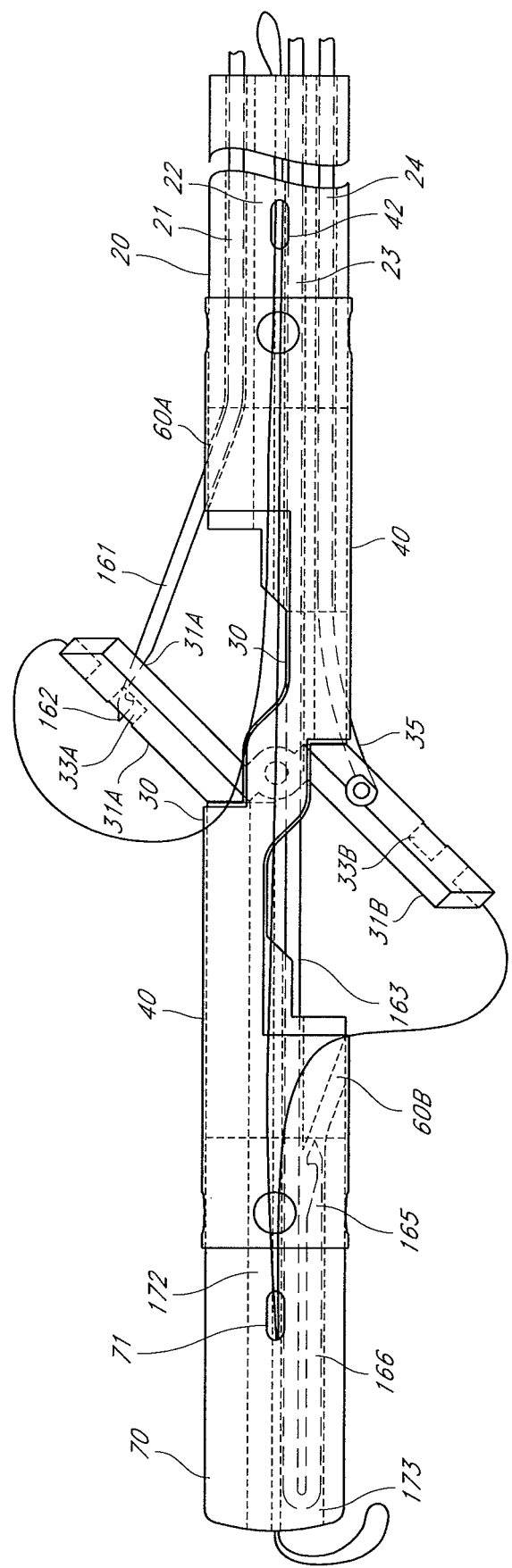
FIG. 8B is a side view of an embodiment of the suturing device illustrating the proximal suture catch mechanism in a deployed position.

As shown in FIG. 8B, for suture arm 31A extending outward toward the proximal end of the spreader assembly 30, the proximal end of the needle guide 60A is aligned with a lumen 131 (see FIG. 2B) extending though the spreader assembly 30 such that when needle 161, or other suture catch mechanism, is advanced through the passageway formed by central lumen 21 in the elongate tubular member 20 and central lumen 131 in the spreader assembly 30, the distal end of the needle will exit the suturing device through central lumen 131 and be advanced along the groove of the needle guide 60A. The needle guide 60A then deflects the distal end of needle 161 outward along the angle of the groove to penetrate suture clasp 33A on the suture clasp arm 31A and engage the suture portion 52A held by the suture clasp 33A. Once the needle 161 has engaged the suture portion 52A, the needle 161 may be retracted back into central lumen 131 along with the suture portion 52A held by groove 162 on the distal end of needle 161. (See FIG. 8C.)

Figure 8C:
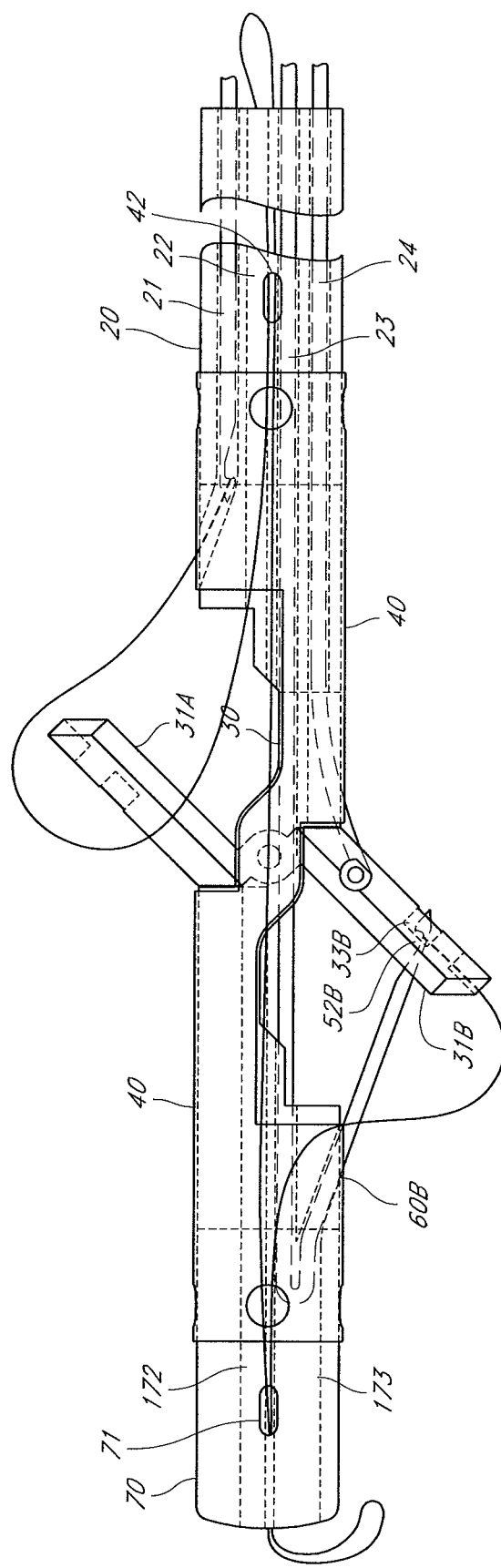
FIG. 8C is a side view of an embodiment of the suturing device illustrating the distal suture catch mechanism in a deployed position.

As shown in FIG. 8C, for suture arm 31B, extending outward toward the distal end of the spreader assembly in a deployed position, the distal end of needle guide 60B is aligned with a lumen 173 in the distal tip of the suturing device. Here, before insertion, the needle 165 has been advanced through central lumen 123 in the elongate tubular member beyond the spreader assembly 30 and positioned a slot or cavity 173 within the distal tip 70 of the suturing device that has been aligned with the central lumen 123 of the elongate tubular member. The cavity 173 has a diameter sized to receive the distal end of the needle 165, including the turned portion 166. The turned portion 166 is positioned in cavity 173 such that the distal tip 167 is aligned with the needle guide 60B located on the distal end of the spreader assembly 30. Thus, in use, when the proximal end of the needle 165 is pulled back through the central lumen 123 of the elongate tubular member 20, the turned portion 166 of the needle will be advanced along the groove of the needle guide 60B and deflected outward along the angle path of the groove to penetrate the deployed suture clasp 33B on the suture clasp arm 31B and engage suture portion 52B held therein. Once the needle 165 has engaged the suture portion 52B, the proximal end of the needle 165 may then be pushed forward through the central lumen 123 of the elongate tubular member which will cause the bent portion 166 of the needle to be retracted along needle guide 60B into cavity 173 along with the suture portion 52B held by the groove 168 on the distal end of the needle 165.

In some embodiments, as discussed above, the suture catch assembly can comprise two suture catch mechanisms, or needles housed on opposite sides of the elongate tubular member 20 for engaging the two suture clasp arms. The needles may be independently actuated such that the needles may be independently deployed. In an alternative embodiment, the suture catch assembly may comprise four needles, for example two needles housed on each side of the elongate tubular member for engaging multiple suture portions in each of the suture clasp arms. Here, each of the needles may be independently actuated or alternatively both needles for engaging a single suture clasp arm may be jointly actuated such that they are deployed at the same time.

Figure 9A:
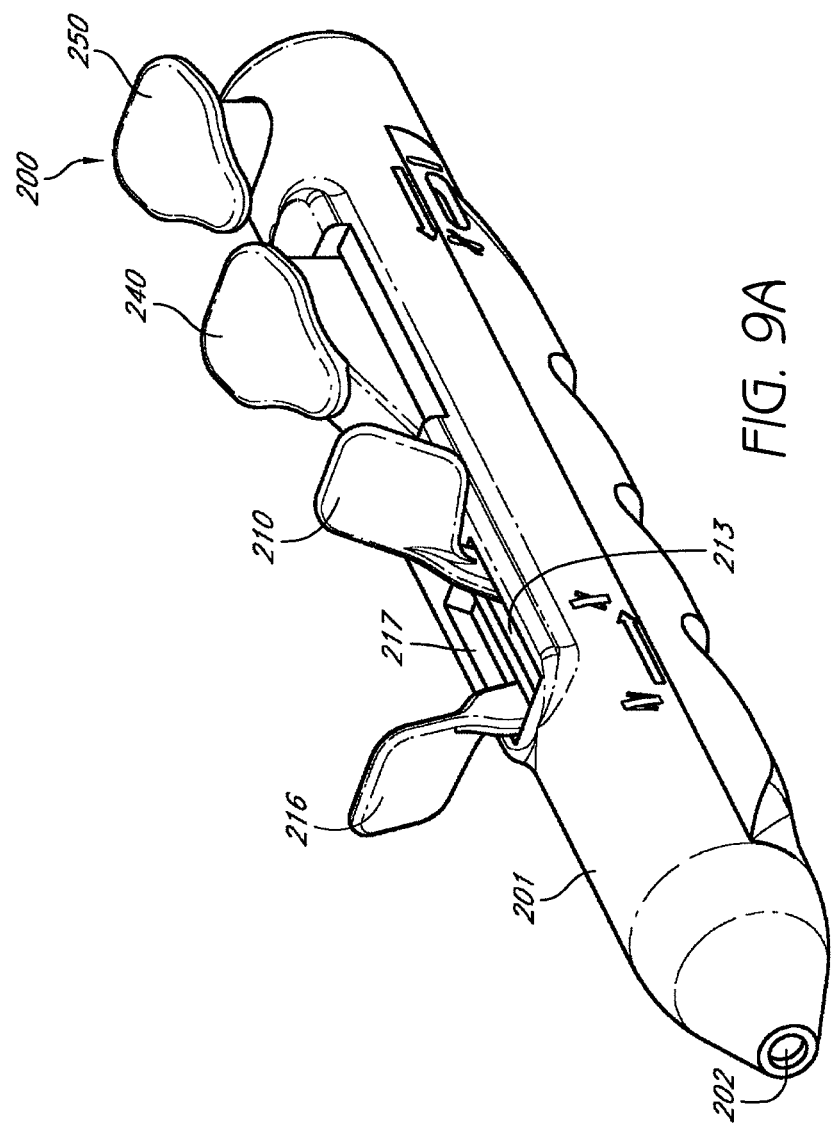
FIG. 9A is a perspective view of one embodiment of a handle of the suturing device.
Figure 9B:
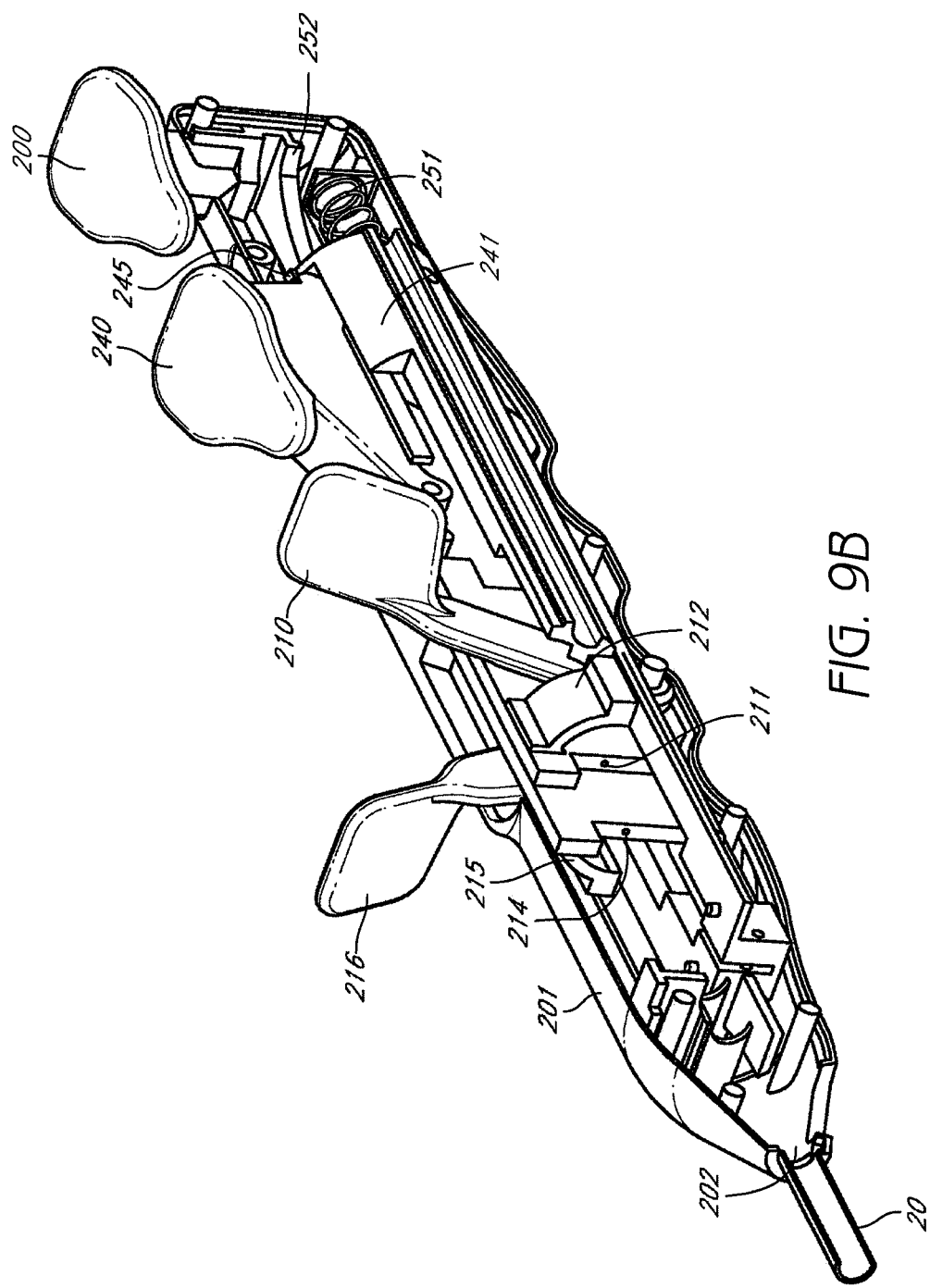
FIG. 9B is a perspective view of the handle of FIG. 9A, with a portion of the housing removed.

Referring now to FIGS. 9A-9B, the proximal end of the needles 161 and 165 extend through the central lumens 21 and 23 of the elongate tubular member and terminate at a connection to actuating levers 210 and 216 on the suturing device handle 200. The handle 200 includes a housing 201 which is attached to the proximal end of the elongate tubular member 20. The housing 201 has an aperture 202 providing a passageway between the handle 200 and the multiple lumens of the elongate tubular member 20. One or more levers or buttons 210, 216, 240 and 250 may extend from the housing 201. The levers or buttons 210, 216, 240 and 250 can be connected to actuating rods or mechanisms for deploying and/or retracting the suture clasp arms and suture catch mechanisms moveably housed in the suturing device.

With reference to FIGS. 9A-9B, in some embodiments, the handle 200 can have two actuating levers 210 and 216 for deploying and retracting the suture catch mechanisms such as needles 161 and 165 of the suturing device. For example, in one embodiment, the proximal end of needle 165 extends from the proximal end of central lumen 23 in the elongate tubular member through opening 202 into the handle 200 and is inserted into an opening 211 in a lever needle holder 212. The needle 165 may be securely connected to opening 211 in the lever needle holder 212 by friction fit in the opening 211, by bonding with epoxy, or any other suitable technique know to those in the art. The lever needle holder 212 is permanently connected to a needle deployment lever 210 extending from the handle housing 201, such that in use, when the physician pushes the lever forward or pulls the lever back, the needle deployment lever 210 will advance or retract the needle holder 212 longitudinally along an axis of the handle 200 and thus advance or retract the attached needle 163 longitudinally within the lumen 23 of the elongate tubular member 20. The housing 200 comprises a fixed length opening 213 surrounding the needle lever 210 which provides a limit to the distance the needle 163 can be advanced or retracted by limiting the distance over which the lever 210 can be pushed or pulled. In general, the axial length of the opening 213 should be sufficient to permit the turned distal end of the needle 163 to be extended from a pre-deployment position within the suturing device 100 to engage the distal suture clasp arm 31A in a fully deployed position, as discussed above. However, limiting the distance the needle can be deployed may advantageously prevent the needle from being advanced too far and potentially puncturing adjacent tissue.

The proximal end of needle 161 is likewise configured to extend through central lumen 21 of the elongate tubular member 20 and is inserted into an opening 214 in a lever needle holder 215. The lever needle holder 215 is permanently connected to a second needle deployment lever 216 extending from the handle housing 201, such that in use, when the physician pushes the lever forward or pulls the lever 216 back, the needle deployment lever 216 will advance or retract the needle holder 215 and thus advance or retract the attached needle 161. The housing 201 comprises a fixed length opening 217 surrounding the needle lever 216 which provides a limit to the distance the needle 161 can be advanced or retracted by limiting the distance over which the lever 216 can be pushed or pulled. In general, the axial length of the opening 217 should be sufficient to permit the distal end of the needle 161 to be extended from a pre-deployment position within the elongate tubular member 20 to engage the proximal suture clasp arm 31A in a fully deployed position, as discussed above.

Deployment of the suture claps arms 31A and 31B can be performed by depressing a button 240 located on the handle 200. The button 240 may be connected to an arm puller mechanism 241 which is configured to be extended and retracted along a longitudinal axis of the handle 200, which is operably connected to actuating rod 35. For example, in some embodiments, the arm puller mechanism may have a slot configured to receive the proximal end of the actuating rod 35.

The actuating rod 35 extends through central lumen 24 of the elongate tubular member 20 and is connected to the suture clasp arms 31 such that proximal retraction of the actuating rod 35 causes the suture clasp arms 31A and B to extend from the spreader assembly 30. For example, as discussed above, in some embodiments, the actuating rod 35 can be connected to the distal suture clasp arm 31B at a location that causes the suture clasp arms 31A and 31B to swing out from the spreader assembly 30 in a counter-clockwise direction. In use, when button 240 is depressed, the arm pull mechanism 241 is pulled back against spring 251 causing the actuating rod 35 to be retracted though central lumen 24, thus deploying the suture clasp arms. When button 240 has been completely depressed, the button 240 engages a lip 245 of the arm puller mechanism 241 and maintains the arm puller mechanism 241 in a locked, retracted position compressing spring 251. A second button 250 is located on handle 200, proximal to button 240. Button 250 has a lever 252 extending within the housing 201 which is configured to engage an edge of button 240 and raise the button 240 from lip 245 of the arm puller mechanism. Once the arm puller mechanism 241 has been released, spring 251 may expand to an uncompressed state, thereby pushing the arm puller mechanism 241 forward. Forward motion of the arm puller mechanism advances the attached actuating rod 135 which transmits a clockwise rotational force to the suture clasp arms causing the suture clasp arms to be retracted within the spreader assembly 30. Further details of actuation mechanisms as well as other devices and methods that may incorporated with the embodiments described throughout this specification are described in U.S. Patent Publication No. 2006-0069397 A1, published Mar. 30, 2006, the entirety of which is hereby incorporated by reference.

Figure 10A:
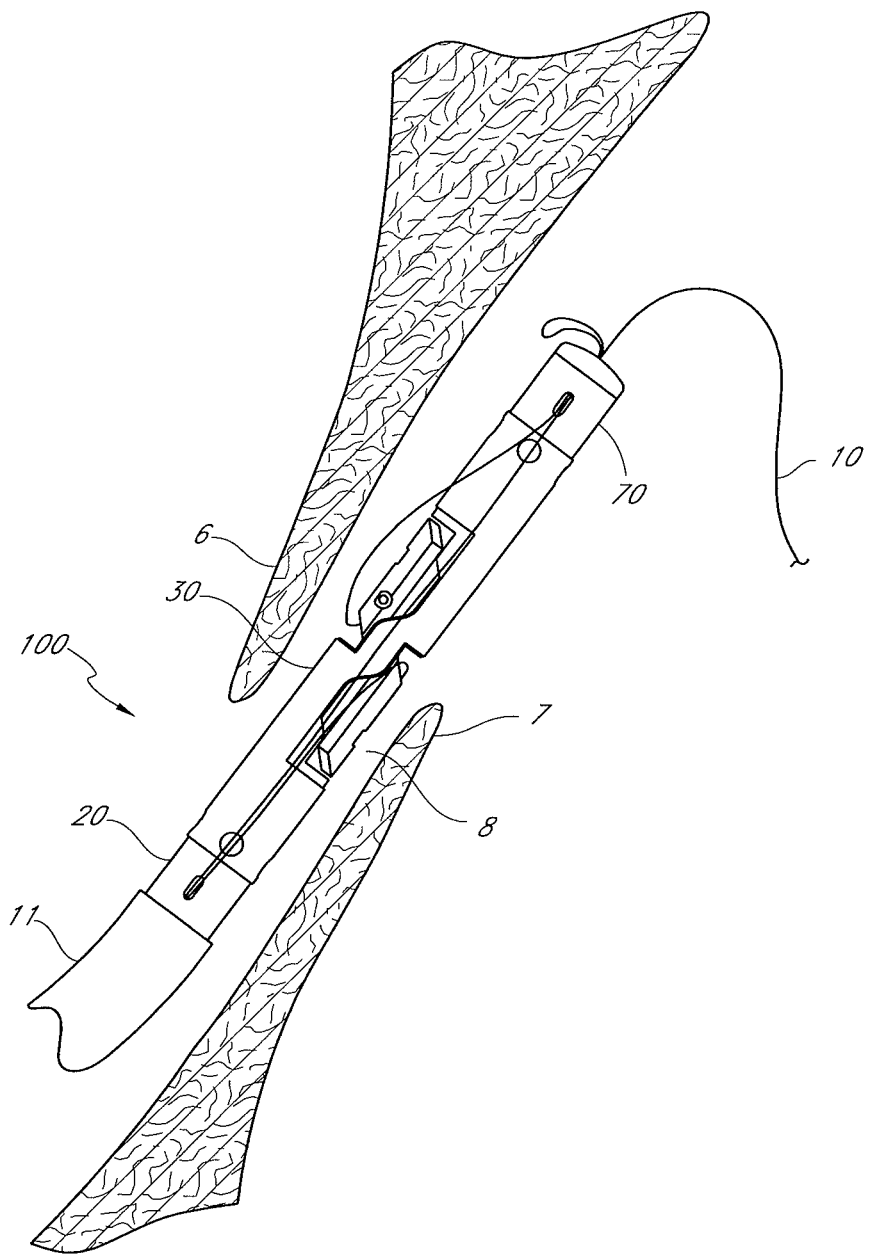
FIG. 10A is a schematic representation an embodiment of the suturing device deployed in a PFO.
Figure 10B:
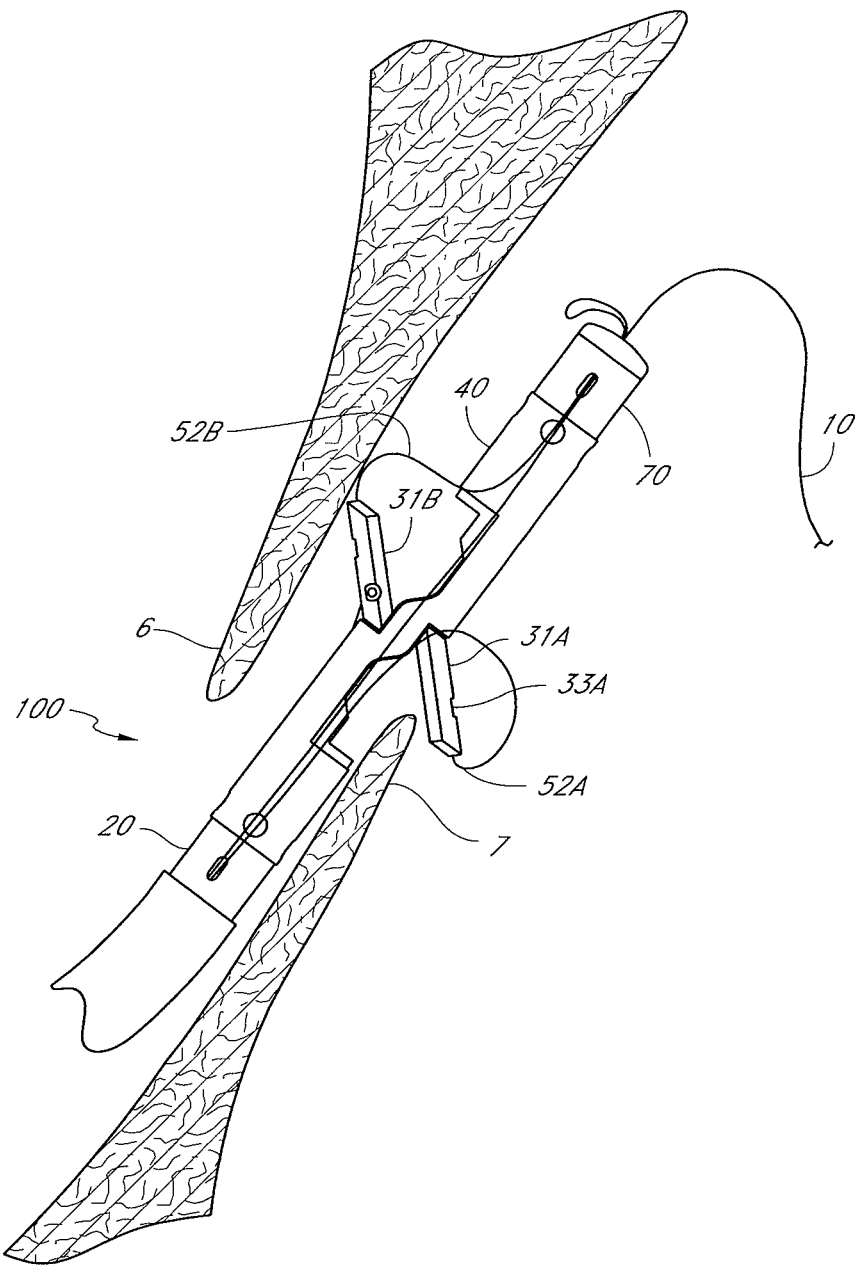
FIG. 10B is a schematic representation as in FIG. 10A with the proximal suture clasp arm positioned around the septum primum.

The operation of the device 100, described above, according to one embodiment is illustrated in sequence in FIGS. 10A-10L in conjunction with a procedure for closing a patent foramen ovale (PFO) in a patient's heart. As shown in FIG. 10A, the distal end of a suturing device 100 is advanced through a venous access, such as the inferior vena cava, into the patient's left atrium and positioned in the tunnel 8 of the PFO between the septum primum 7 and the septum secundum 6. The suturing device 100 may be advanced over a guidewire 10 or alternatively delivered through a catheter introducer sheath 11 using techniques which are known in the art.

The suturing device 100 is initially positioned with the distal tip extending beyond the tunnel of the PFO, such that the spreader assembly 30, and thus the suture clasp deployment arms are adjacent the tip of the secundum primum 7. As shown in FIG. 10B, the suture clasp arms 31A and 31B may then deployed from the spreader assembly such that the proximal suture clasp arm 31A extends around the tip of the secundum primum 7. The suture clasp arm 31A holds a suture portion 52A extending from opening 42 (FIG. 2B) on the suturing device in suture clasp 33A such that the suture portion is positioned on the opposite side of the secundum primum 7 relative to the suturing device 100. The distal suture clasp arm 31B is also extended from the spreader assembly and abuts the septum secundum 6, causing the suturing device 100 and proximal suture clasp arm 31A to be pushed toward the septum primum, thus assisting to properly position the proximal suture clasp arm 31A adjacent to the septum primum 7.

Figure 10C:
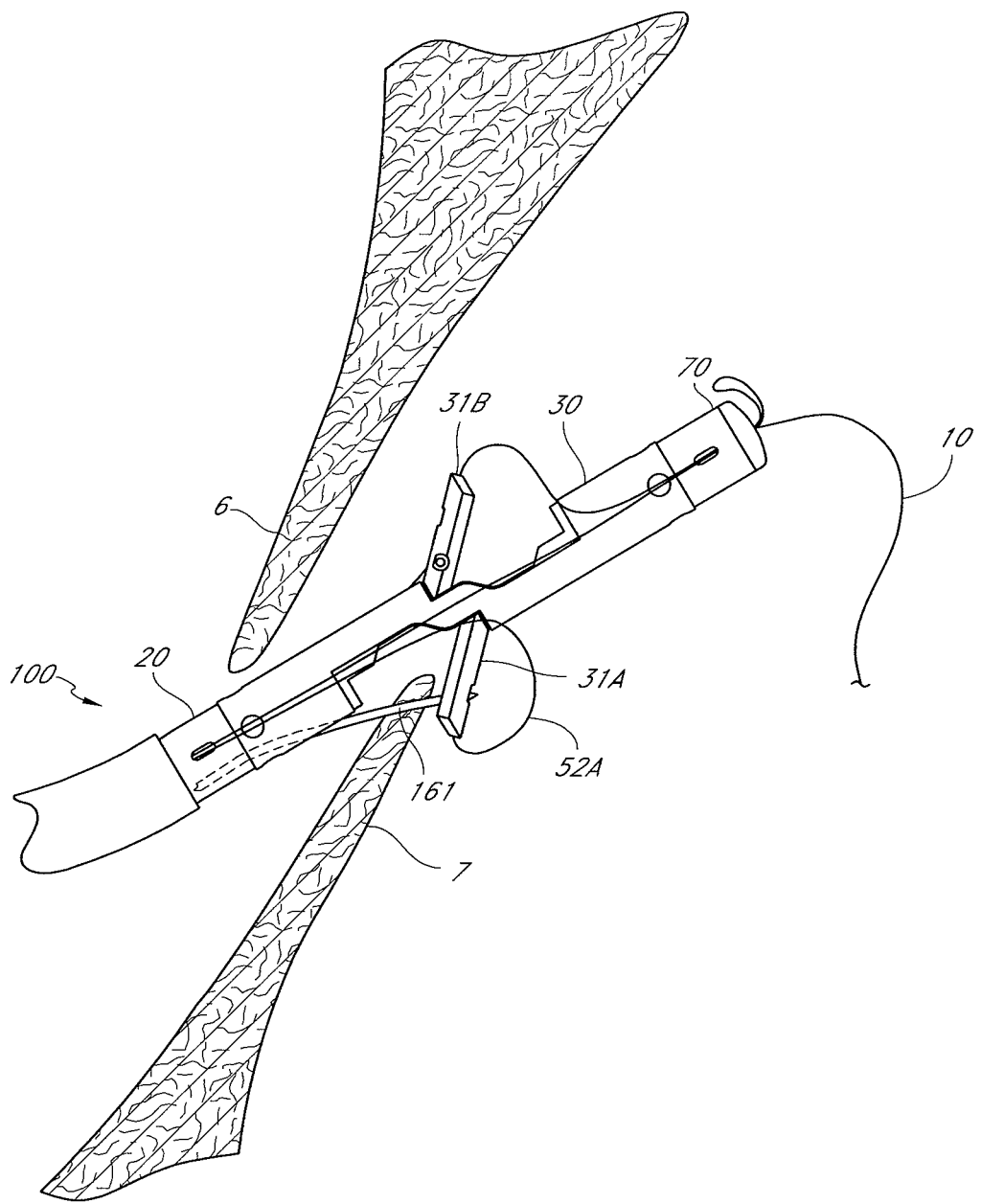
FIG. 10C is a schematic representation as in FIG. 10B showing the proximal needle engaging the proximal suture clasp arm.

Once the suture clasp arm 31A has been properly positioned around the septum primum 7, needle 161 may be deployed from the suturing device 100 to penetrate the septum primum 7 and engage the suture clasp arm positioned on the opposite side of the septum primum 7, as shown in FIG. 10C. As discussed above, the needle 161 is advanced through a passageway in the suturing device and deflected by needle guide 60A along an angle that intersects the deployed suture clasp arm 31A as it exits the suturing device 100. The needle has a sharp distal tip which penetrates the tissue of the septum primum and engages suture clasp 33A located on the tip of the suture clasp arm 31A. The needle is initially advanced through the suture clasp 33A which holds a suture portion 52A. When the needle is advanced through the suture clasp 33A, a groove on the needle tip engages the suture portion 52A.

Figure 10D:
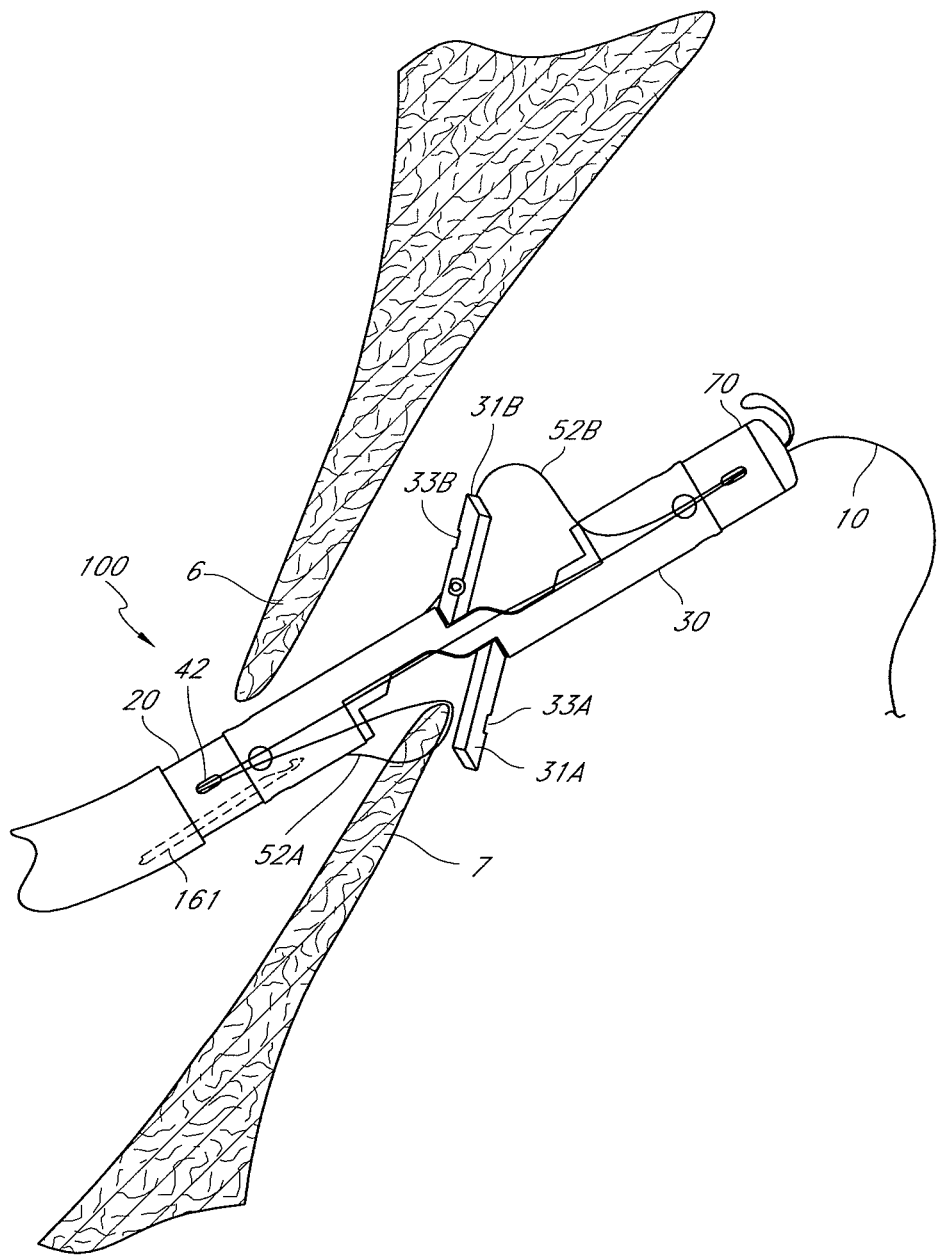
FIG. 10D is a schematic representation as in FIG. 10C showing the proximal needle and suture portion retracted through the septum primum.

As shown in FIG. 10D, once the suture loop has been engaged, the needle 161 and engaged suture portion 52A are then retracted through the tissue of the septum primum 7 and into the needle passageway of the suturing device 100. Once the suture has been engaged and pulled through the tissue of the septum primum, the suture clasp arms 31A and B may then be closed and the device may be repositioned such that the spreader assembly 30 and suture clasp arms 31A and B are adjacent the tip of the septum secundum 6. Alternatively, the suture clasp arms may remain extended.

Figure 10E:
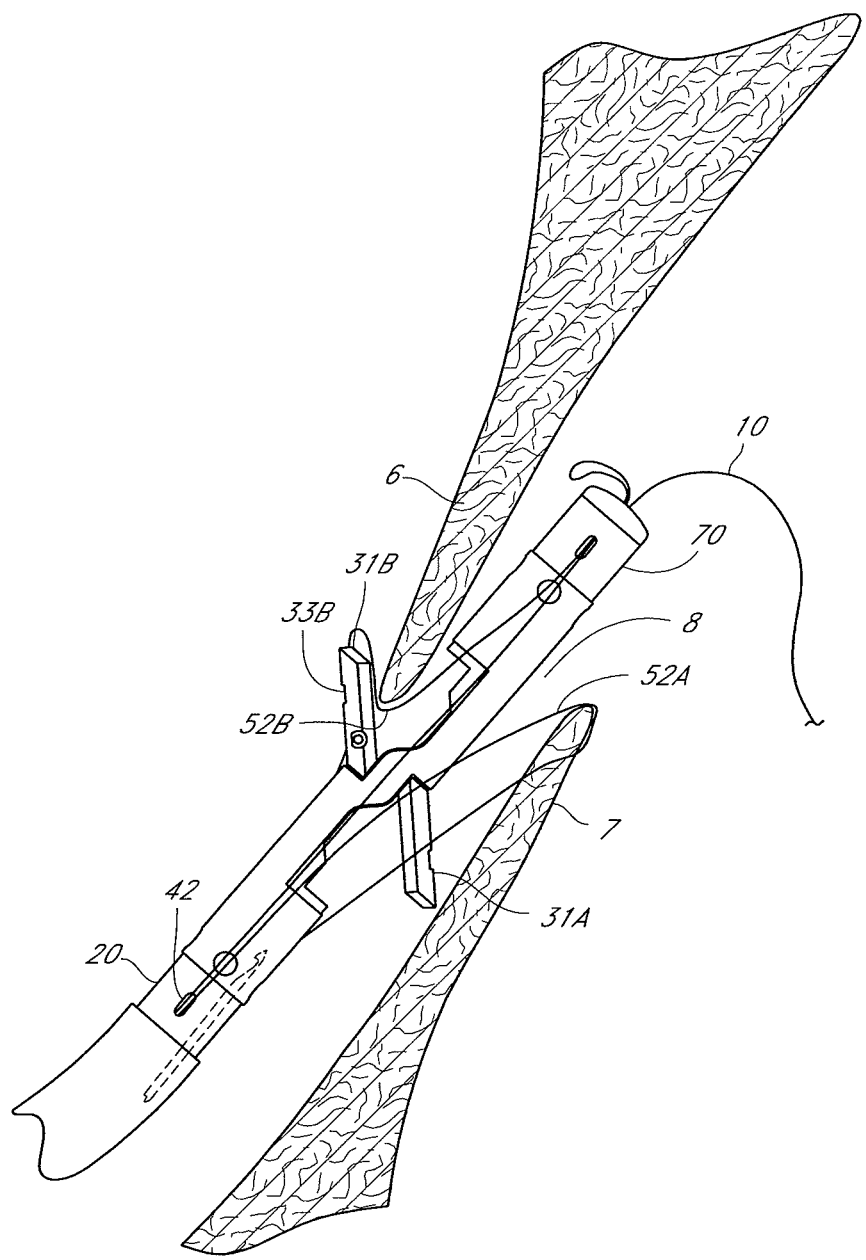
FIG. 10E is a schematic representation as in FIG. 10D with the distal suture clasp arm positioned around the septum secundum.

As shown in FIG. 10E, the suturing device is withdrawn proximally through the tunnel of the PFO 8 until the suture clasp arms can be deployed such that the distal suture clasp arm 31B extends around the tip of the septum secundum 6. The suture clasp arm 31B holds a suture portion 52B extending from opening 42 on the suturing device 100 in suture clasp 33B such that the suture portion 52b is positioned on the opposite side of the septum secundum 6 relative to the PFO 8 and the suturing device 100. The proximal suture clasp arm 31A is also extended from the spreader assembly and abuts the septum primum 7, causing the suturing device 100 and distal suture clasp arm 31B to be pushed toward the septum secundum 6, thus assisting to properly position the distal suture clasp arm 31B around the septum secundum 6.

Figure 10F:
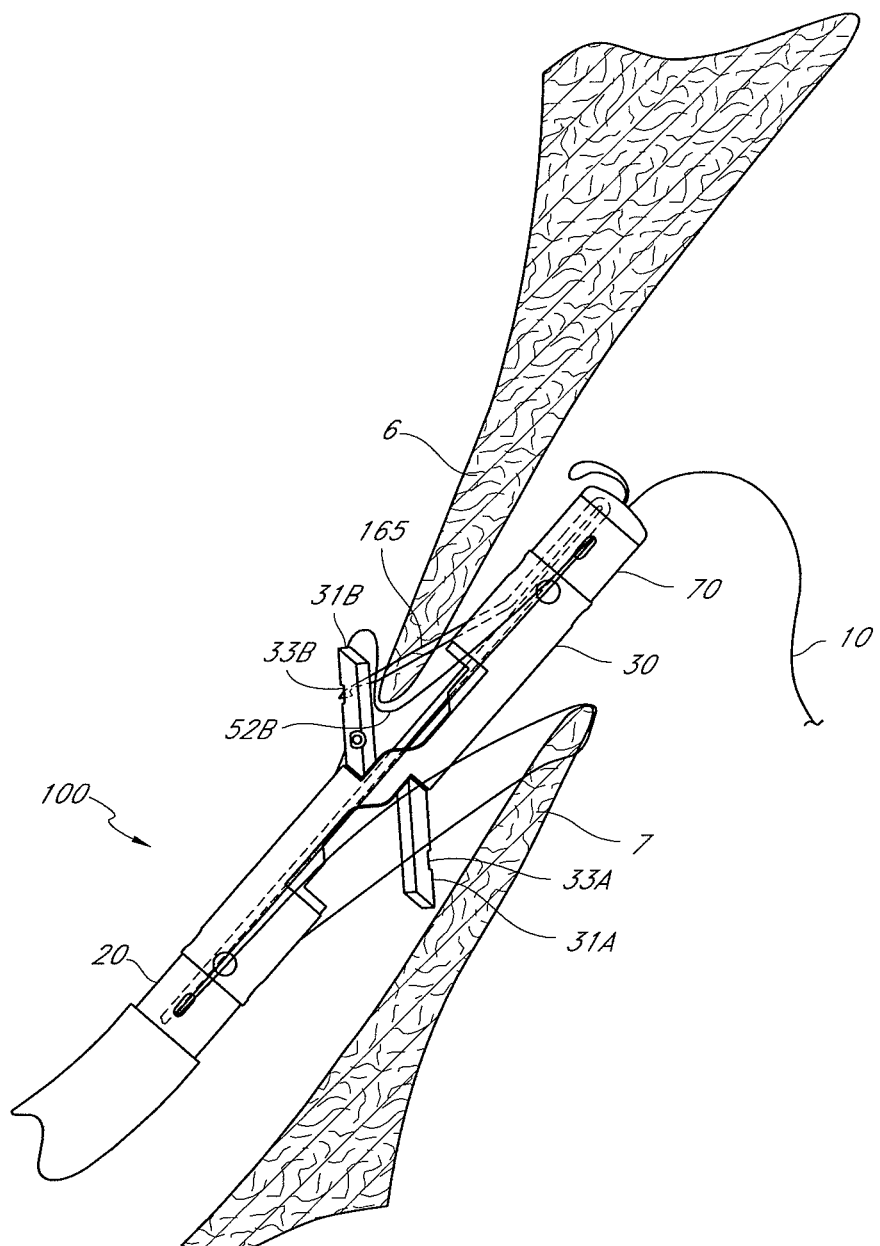
FIG. 10F is a schematic representation as in FIG. 10E showing the distal needle engaging the distal suture clasp arm.

Once the suture clasp arm 31B and suture portion 52B have been properly positioned around the septum secundum 6, a needle 165 may be deployed from the distal end of the suturing device 100 to penetrate the septum secundum 6 and engage the suture portion 52B. As shown in FIG. 10F, the tip of the needle 165 is advanced from a location distal the suture clasp arms 31A and 31B through the tissue of the septum secundum 6 towards deployed suture clasp arm 31B. As discussed above with respect to FIGS. 8A-8C, the needle 165 comprises a turned portion 166, such that the turned portion 166 will be advanced toward the deployed suture arm 31B, as shown, when the proximal portion of the needle 165 is pulled proximally through the suturing device 100. As the turned portion of the needle 166 is advanced from the suturing device 100, the turned portion 166 is deflected outward by a needle guide 60B along an angle that intersects the suture clasp 33B located on the tip of deployed suture arm 31B. The needle 165 has a sharp distal tip which penetrates the tissue of the septum secundum 6 and engages suture clasp 33B located on the tip of the suture clasp arm 31B. The needle 165 is initially advanced through the suture clasp 33B which holds a portion of suture 52b. When the needle 166 is advanced through the suture clasp 33B, a groove on the needle tip engages the suture portion 52b.

Figure 10G:
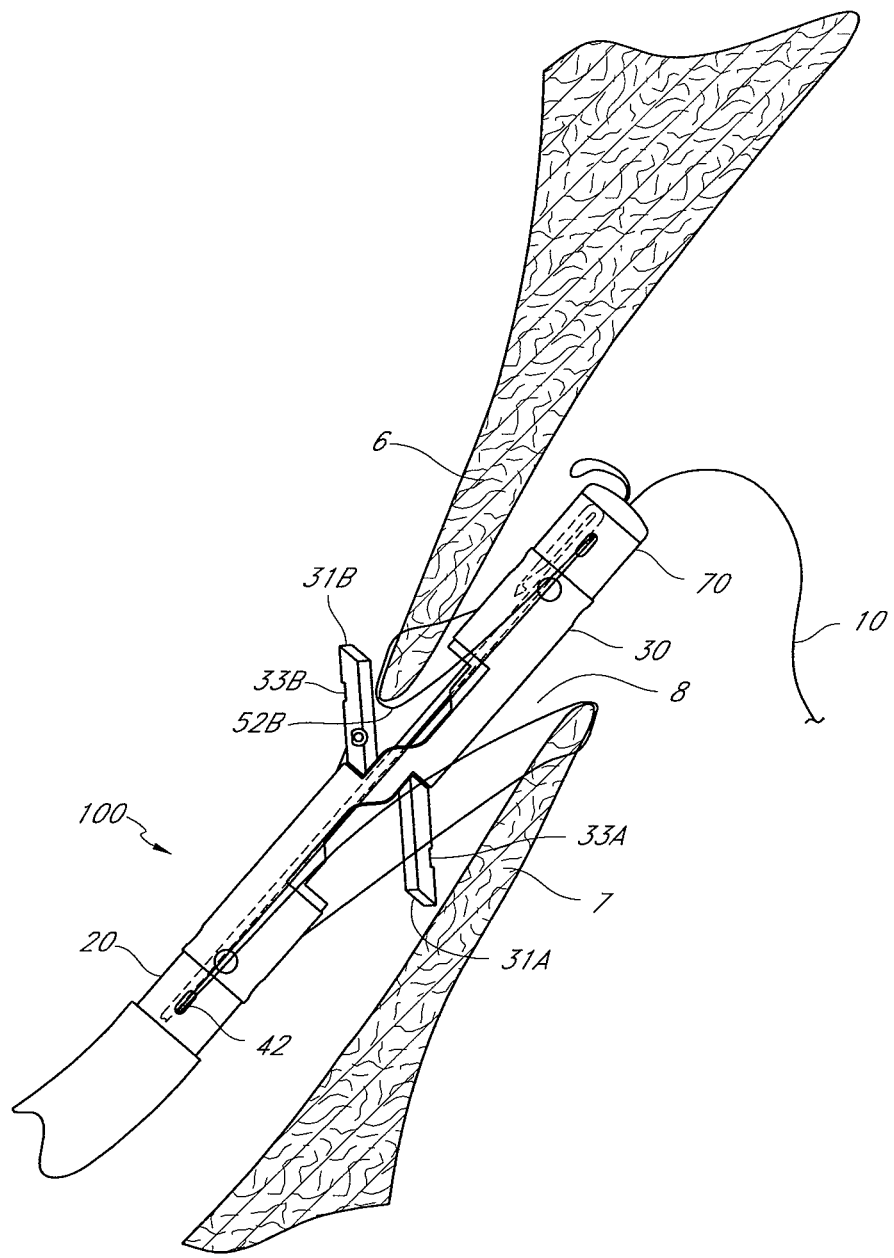
FIG. 10G is a schematic representation as in FIG. 10F following retraction of the distal needle and suture portion through the septum secundum.
Figure 10H:
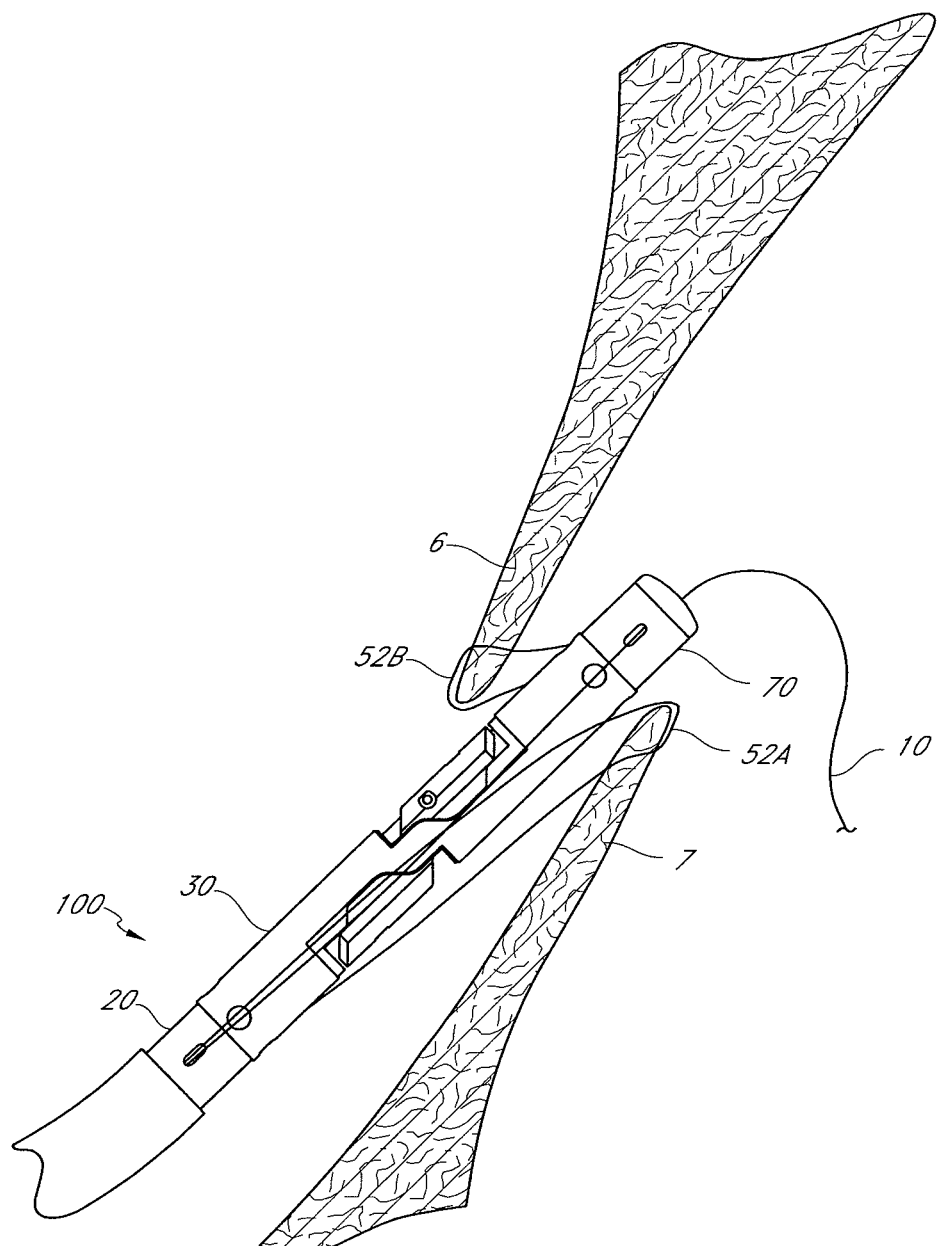
FIG. 10H is a schematic representation as in FIG. 10G showing the suture portions positioned through the septum secundum and septum primum, and the suturing device being withdrawn.
Figure 101:
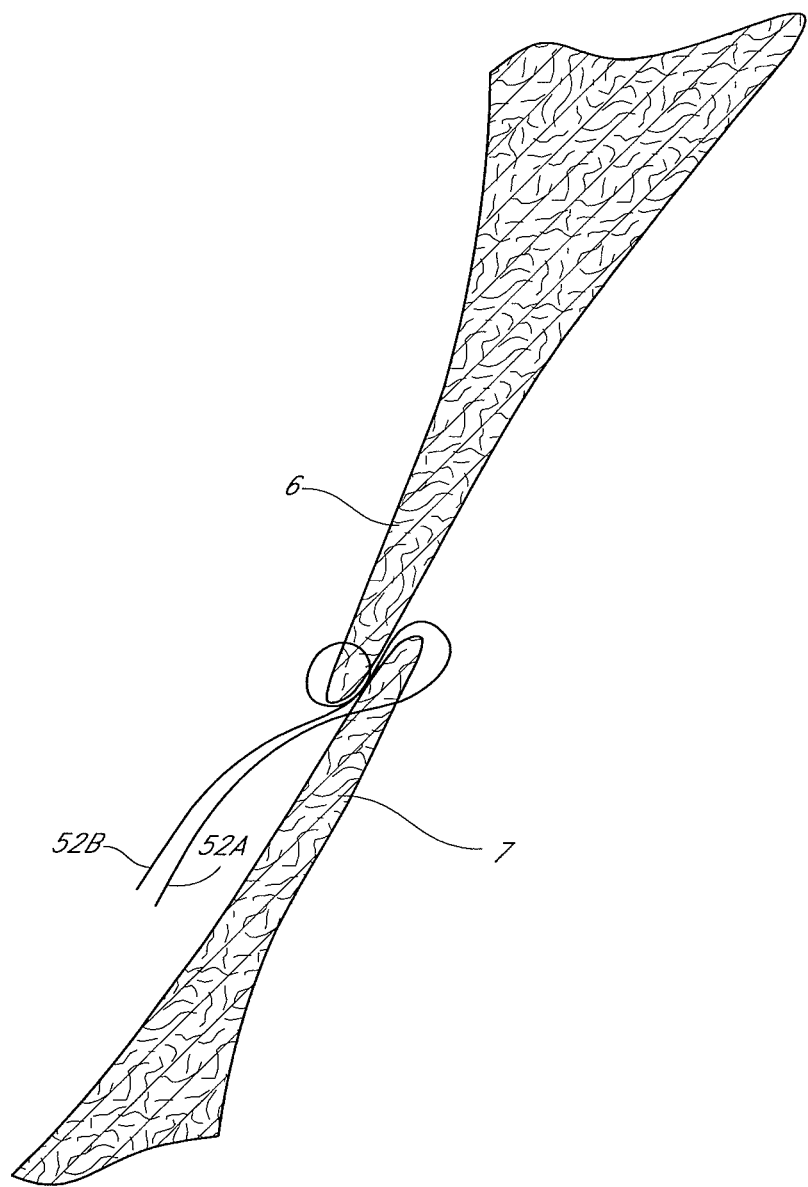

As shown in FIG. 10G, once the suture portion 52B has been engaged, the needle 165 and engaged suture portion 52B are then retracted through the tissue of the septum secundum 6 and into a cavity on the distal tip 70 of the suturing device 100. Once the suture portion 52B has been engaged and pulled through the tissue of the septum secundum, the suture clasp arms 31A and B may then be closed and the suturing device may be withdrawn from the patient's heart. As shown in FIG. 10H, suture portion 52A has been positioned through the septum primum 7 while suture portion 52B has been positioned through the septum secundum. After the suturing device 100 has been withdrawn, the suture portions 52A and 52B will extend proximally from the PFO tunnel 8. These suture end portions can then be pulled tight as shown in FIG. 10I to draw the septum secundum 6 and septum primum 7 towards one another and close the PFO.

Figure 10J:
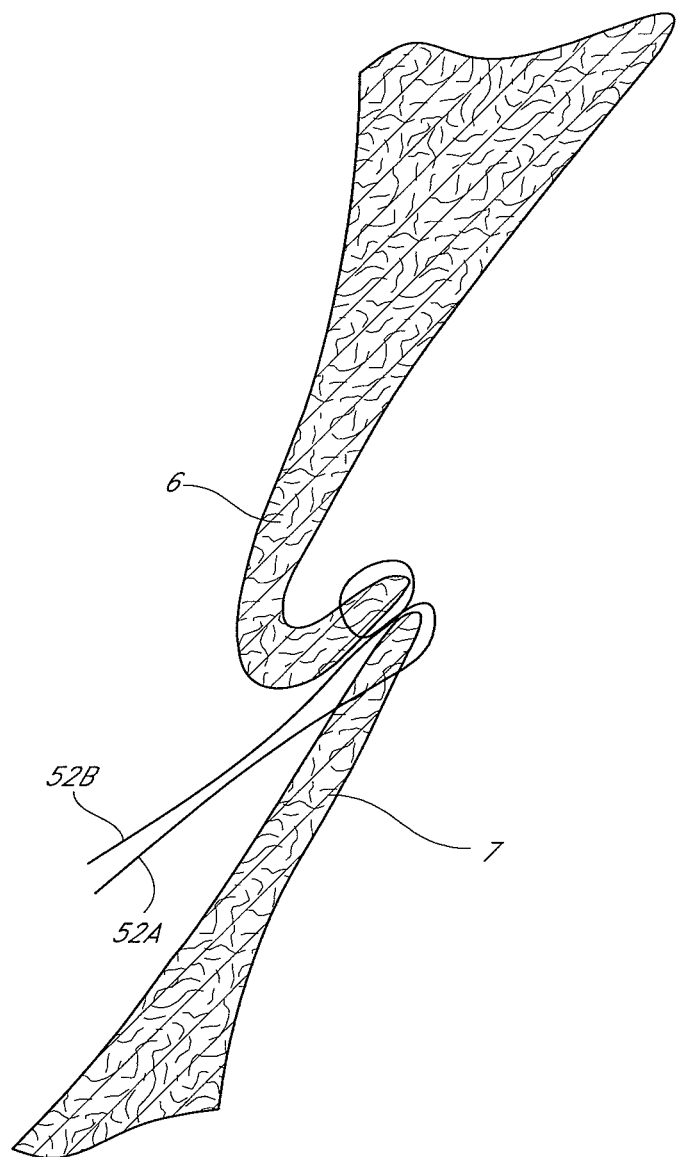
FIG. 10J is a schematic representation of an alternative embodiment showing the suture portions positioned through the septum secundum and septum primum following withdrawal of the suturing device.
Figure 10K:
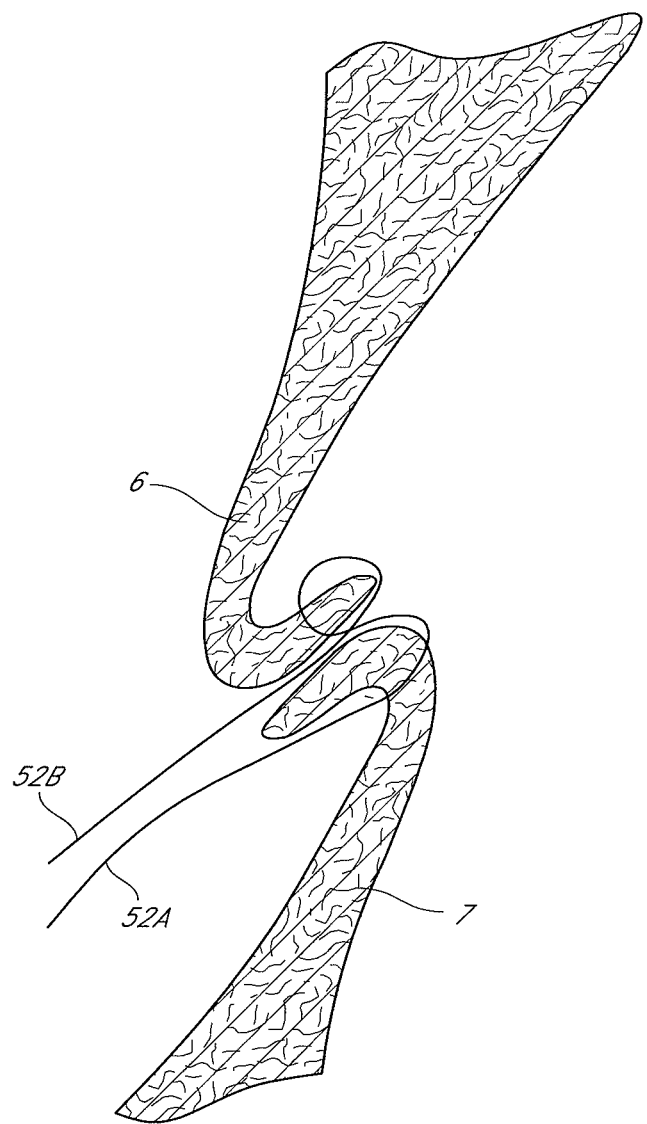
FIG. 10K is a schematic representation of an alternative embodiment showing the suture portions positioned through the septum secundum and septum primum following withdrawal of the suturing device.

FIG. 10J shows an alternative configuration for the septum primum and the septum secundum after the suture end portions are pulled tight to close the PFO. In FIG. 10J, the flap of the septum secundum 6 turns or folds so that the tips of both the septum primum and septum secundum extend in the same direction. FIG. 10K illustrates an alternative embodiment where the flap of the septum primum turns or folds so that the tip of the septum primum extends in the opposite direction compared to the tip of the septum secundum.

Figure 10L:
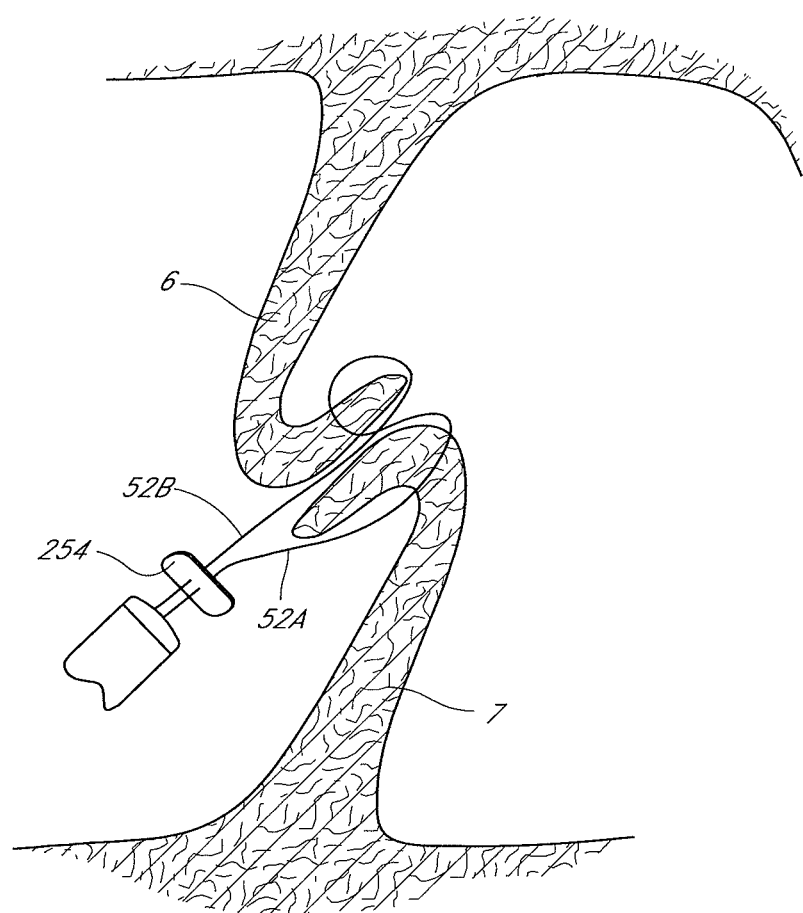
FIG. 10L is a schematic representation of a patch being delivered to the PFO.

With the suture portions 52A and 52B extending away from the PFO, a knot may be applied to the PFO to close the PFO. For example, a device for applying a knot may be used, such as described in U.S. Patent Publication No. 2007-0010829 A1, published Jan. 11, 2007, the entirety of which is hereby incorporated by reference. FIG. 10L illustrates another embodiment in which a patch 254 may be applied and may be delivered over the suture portions 52A and 52B to the PFO. Further details regarding delivery of a patch, as well as other devices, structures and methods that may be incorporated with the above or below embodiments, may be found in U.S. Pat. Nos. 5,860,990, 6,117,144, and 6,562,052, the entirety of each which is hereby incorporated by reference.

Figure 11A:
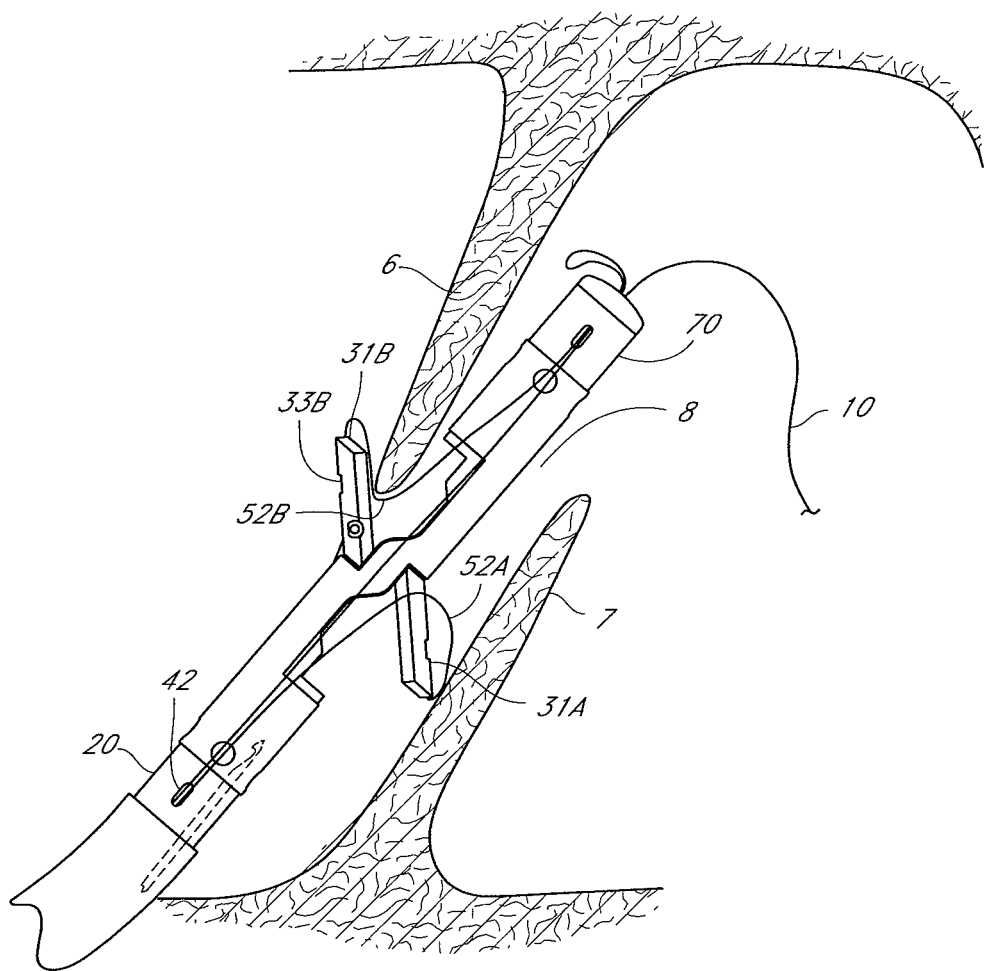
FIG. 11A is a schematic representation of an alternative embodiment showing a suturing device with the distal clasp arm positioned around the septum secundum.
Figure 11B:
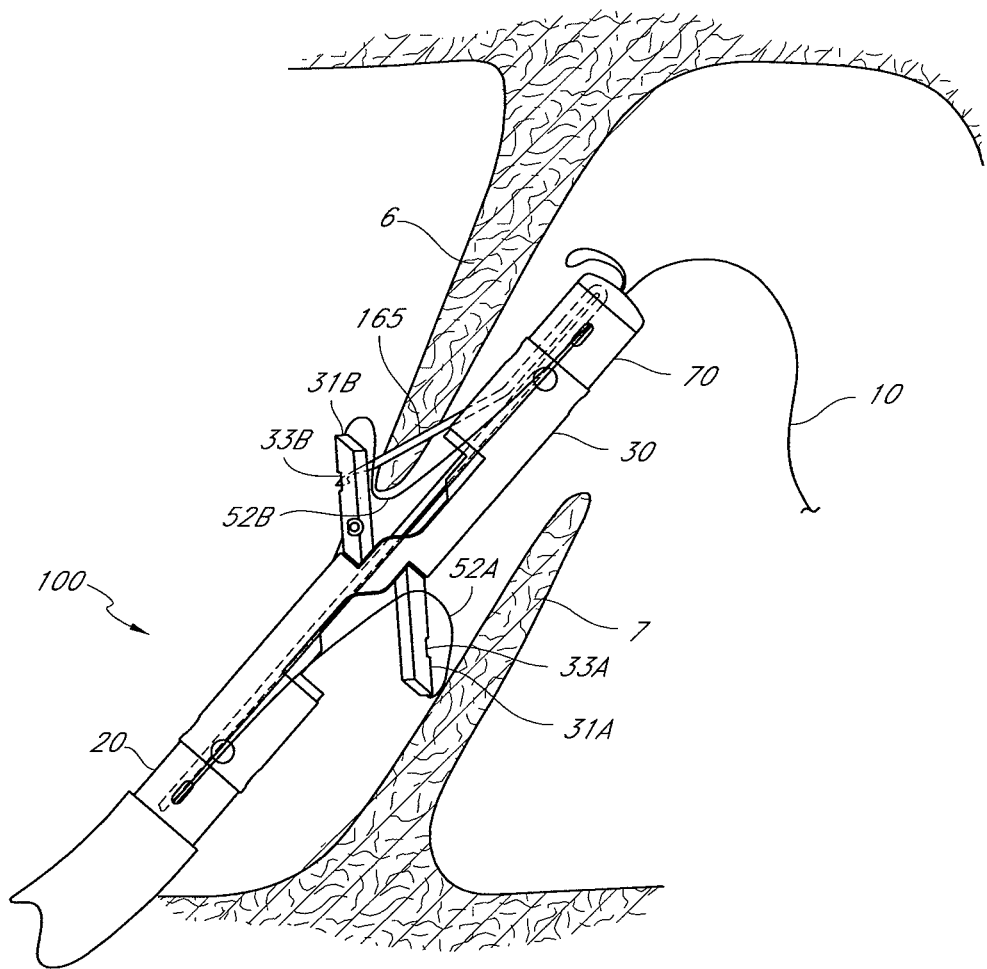
FIG. 11B is a schematic representation showing the suturing device of FIG. 11A with the distal needle engaging the distal suture clasp arm.
Figure 11C:
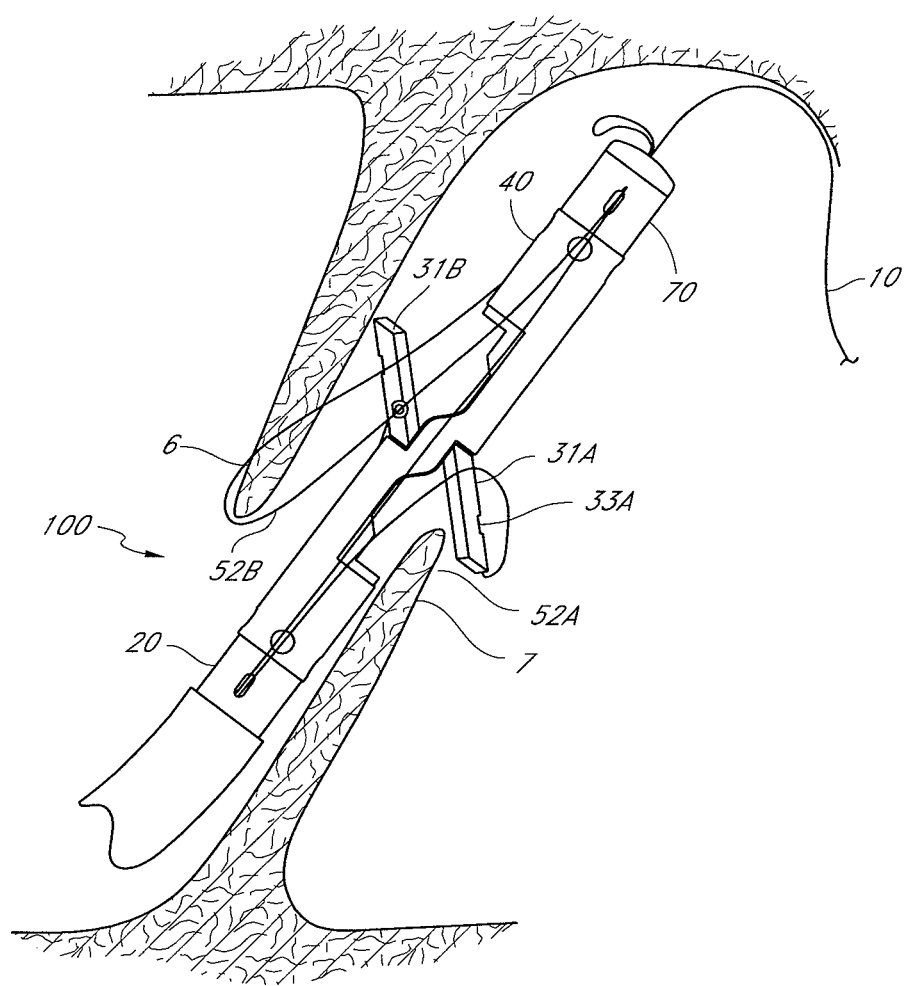
FIG. 11C is a schematic representation showing the suturing device of FIG. 11A with the proximal clasp arm positioned around the septum primum.
Figure 11D:
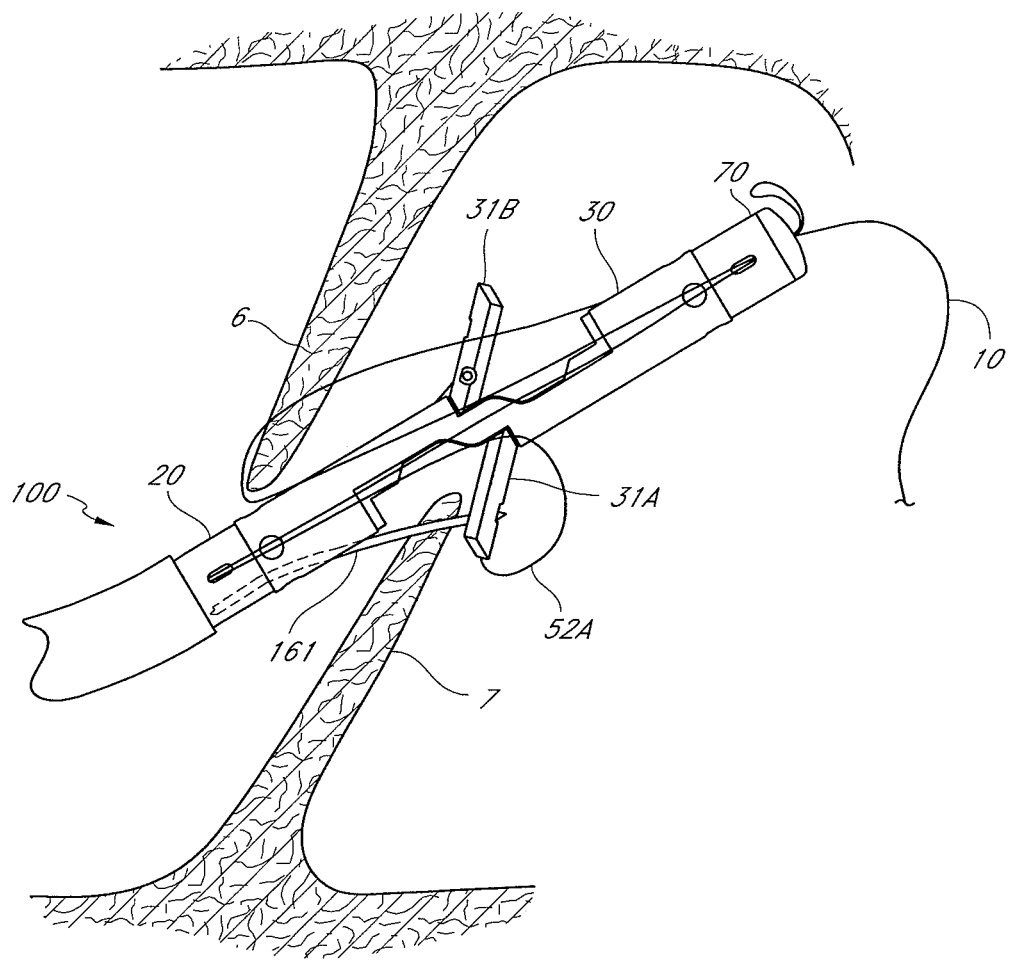
FIG. 11D is a schematic representation showing the suturing device of FIG. 11A with the proximal needle engaging the proximal suture clasp arm.
Figure 11E:
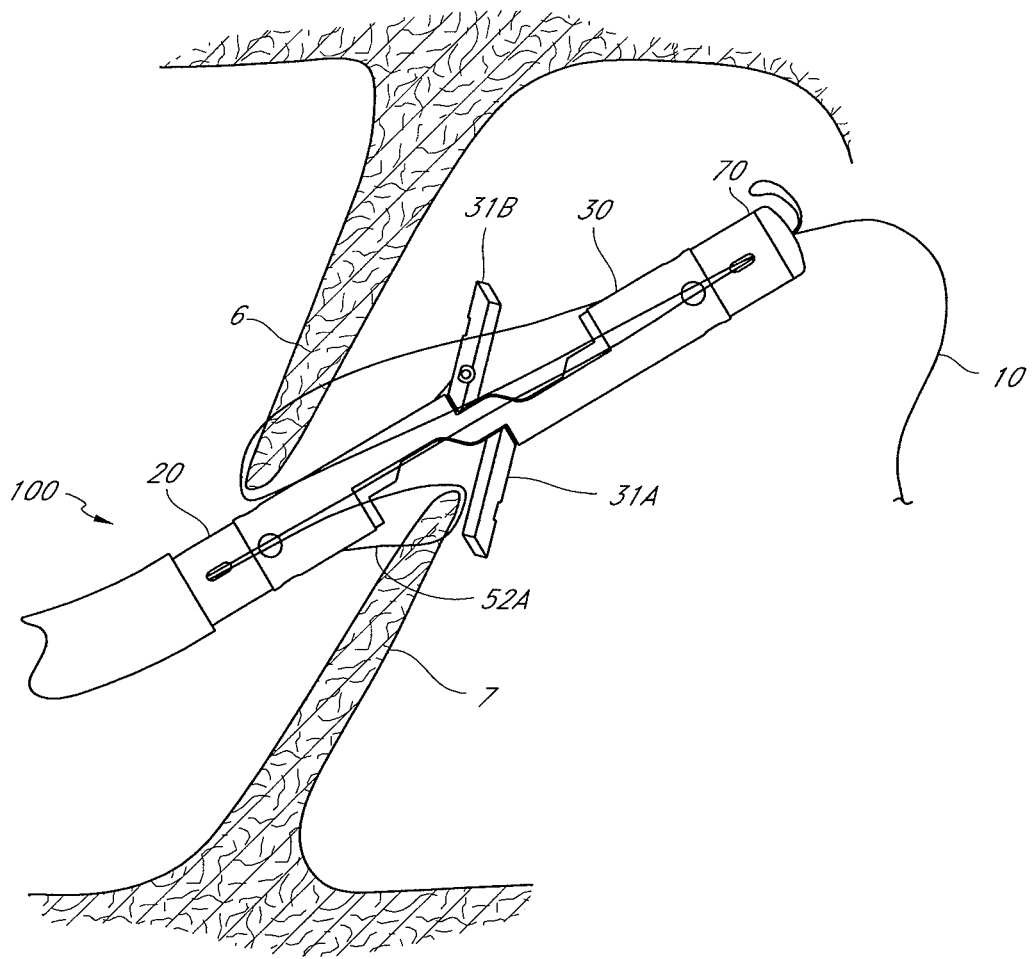
FIG. 11E is a schematic representation showing the suture portions deployed following the steps of FIGS. 11A-11D.

FIGS. 11A-11E illustrate an alternative sequence for delivering suture to close a PFO. In FIG. 11A, the extended suture clasp arm 31B is first positioned around the septum secundum 6, and as shown in FIG. 11B, the needle 165 is advanced proximally through tissue of the septum secundum to engage the suture portion 52B. The needle is withdrawn from the septum secundum 6, carrying the suture portion 52B with it, into the elongate body. In FIG. 11C, the extended suture clasp arm 31A is then positioned around the septum primum 7, and as shown in FIG. 11D, the needle 161 pierces the tissue of the septum primum to engage suture portion 52A in suture clasp arm 31A. As shown in FIG. 11E, the needle 161 is retracted, carrying the suture portion 52A into the elongate body. The suturing device 100 can then be withdrawn from the PFO, and the PFO can be closed as described above.

Figure 12A:
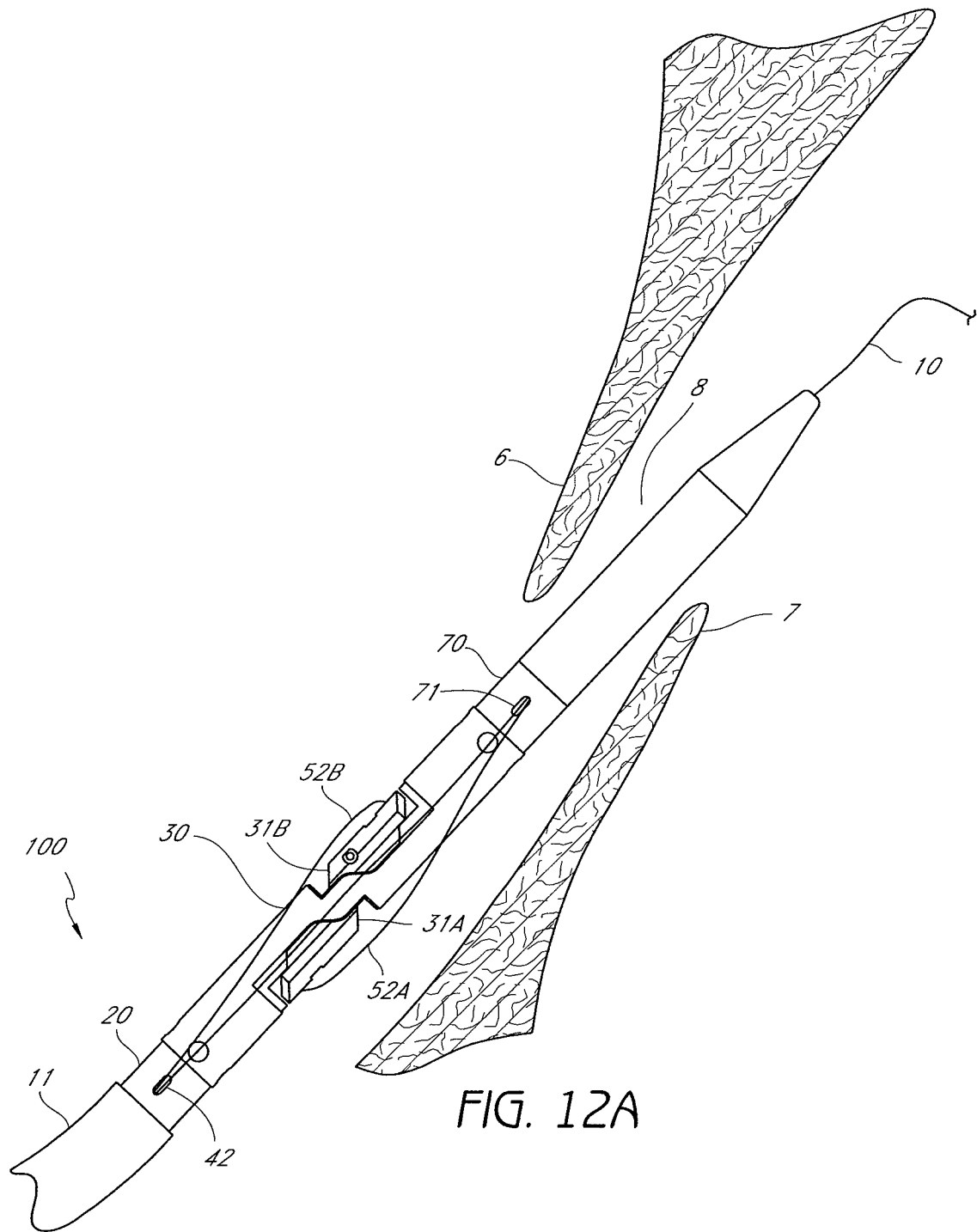
FIG. 12A is a schematic representation of an alternative embodiment of a suturing device being delivered through a tunnel of the PFO.

FIGS. 12A-12L illustrate another embodiment of a suturing device 100 used for closing the PFO. The suturing device 100 is similar to the suturing devices described above, except that the distal tip 70 of the suturing device may comprise an elongated distal tip that assists in navigating the device over the guidewire 10 and through the tunnel of the PFO. As illustrated in FIG. 12A, the suture portions 52A, 52B may exit the port or opening 42, with suture portion 52B extending to the distal suture clasp arm 31B, and the suture portion 52A extending into port 71 before returning proximally to the proximal suture clasp arm 31A. The suturing device 100 may be delivered over the guidewire 10 to the PFO as described above, and as illustrated in FIG. 12A, may be positioned with the spreader assembly 30 located proximal to the PFO tunnel 8.

Figure 12B:
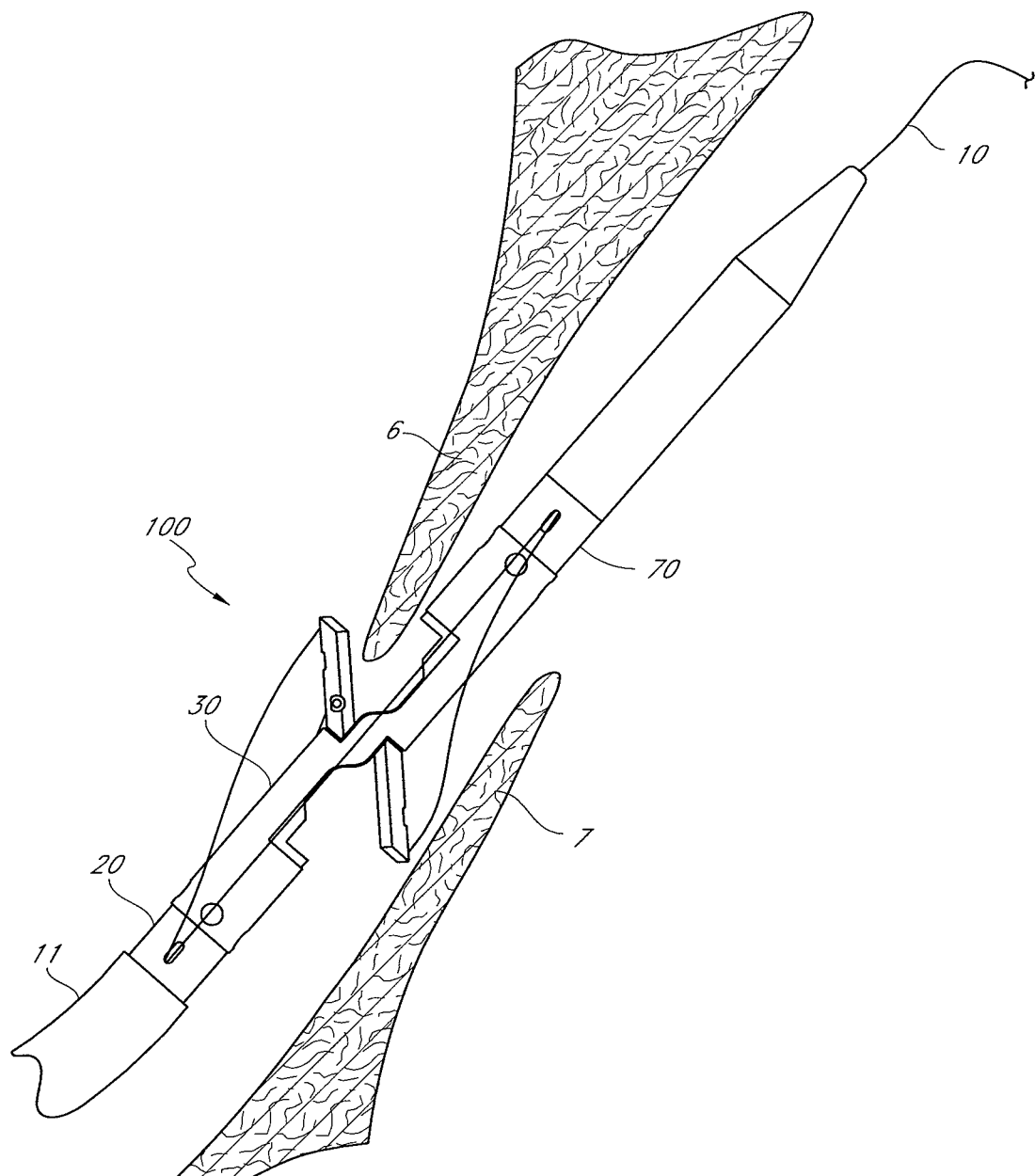
FIG. 12B is a schematic representation of the suturing device of FIG. 12A showing a distal suture clasp arm engaging the septum secundum.
Figure 12C:
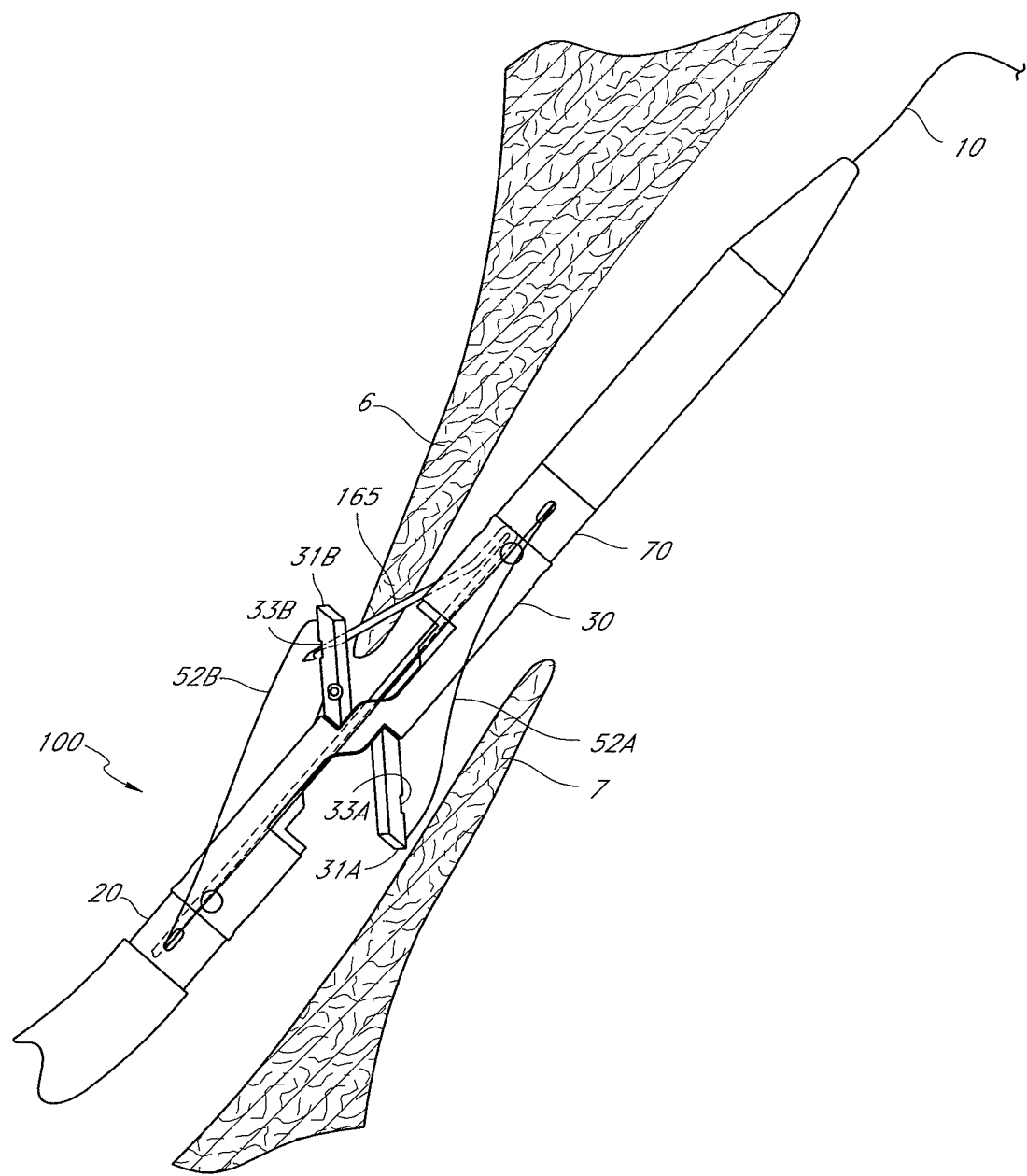
FIG. 12C is a schematic representation of the suturing device of FIG. 12A showing the distal needle engaging the distal suture clasp arm.
Figure 12D:
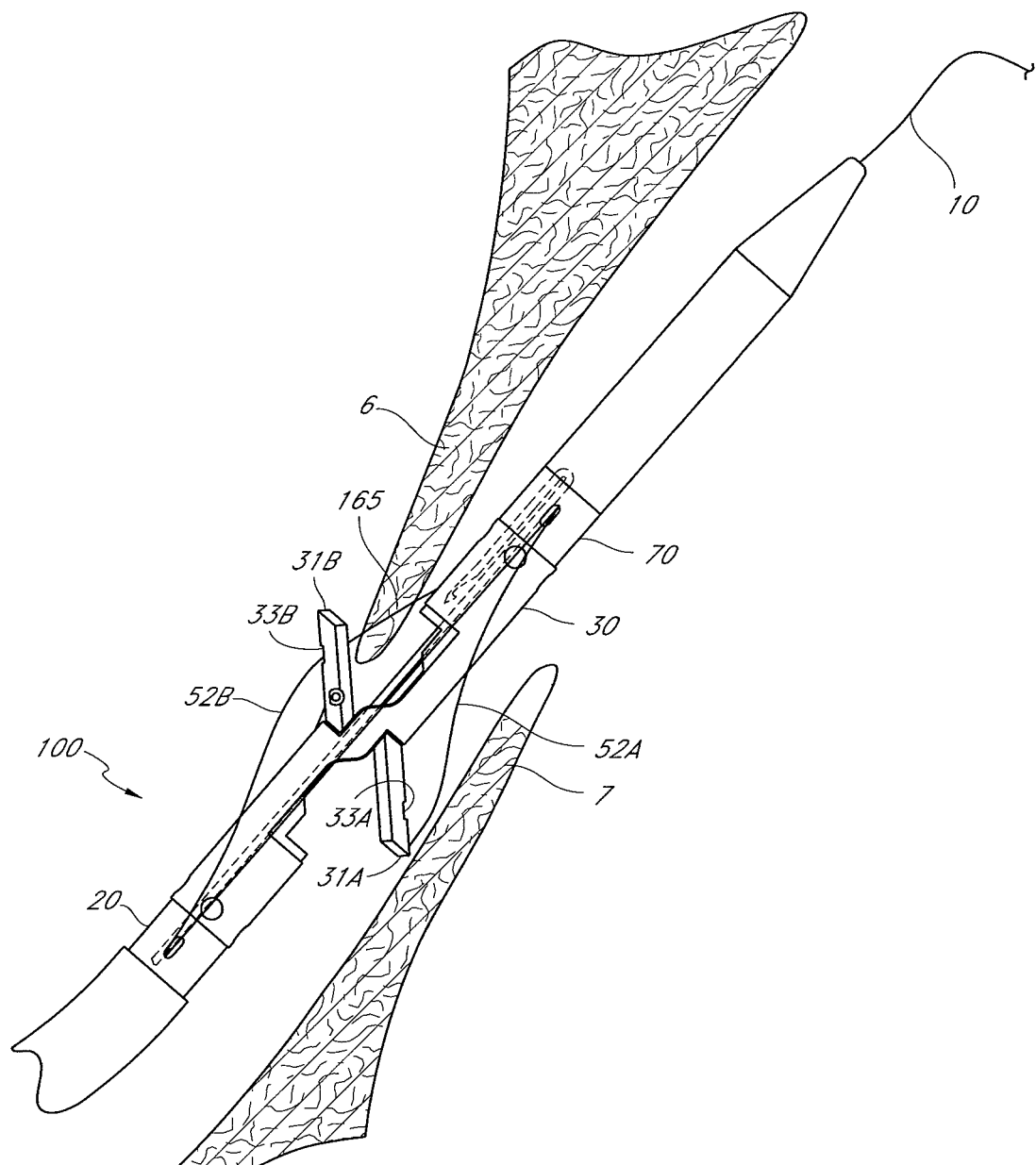
FIG. 12D is a schematic representation of the suturing device of FIG. 12A showing the distal needle retracted from the septum secundum.

As shown in FIG. 12B, the suture clasp arms 31A and 31B may be deployed from the spreader assembly 30. The spreader assembly 30 may be spaced away from the PFO prior to deployment of the suture clasp arms, to allow the arms room to deploy. The suturing device 100 may then be advanced such that the distal suture clasp arm 31B engages or is positioned adjacent the septum secundum 6. The suture clasp arm 31B holds suture portion 52B extending from opening 42 on the suturing device. As shown in FIG. 12C, needle 165 may then be deployed from the suturing device, passing through tissue of the septum secundum into engagement with suture portion 52B carried by the suture clasp arm 31B. Retraction of the needle 165, as shown in FIG. 12D, carries the suture portion 52B through the tissue of the septum secundum 6 and into the body of the suturing device 100.

Figure 12E:
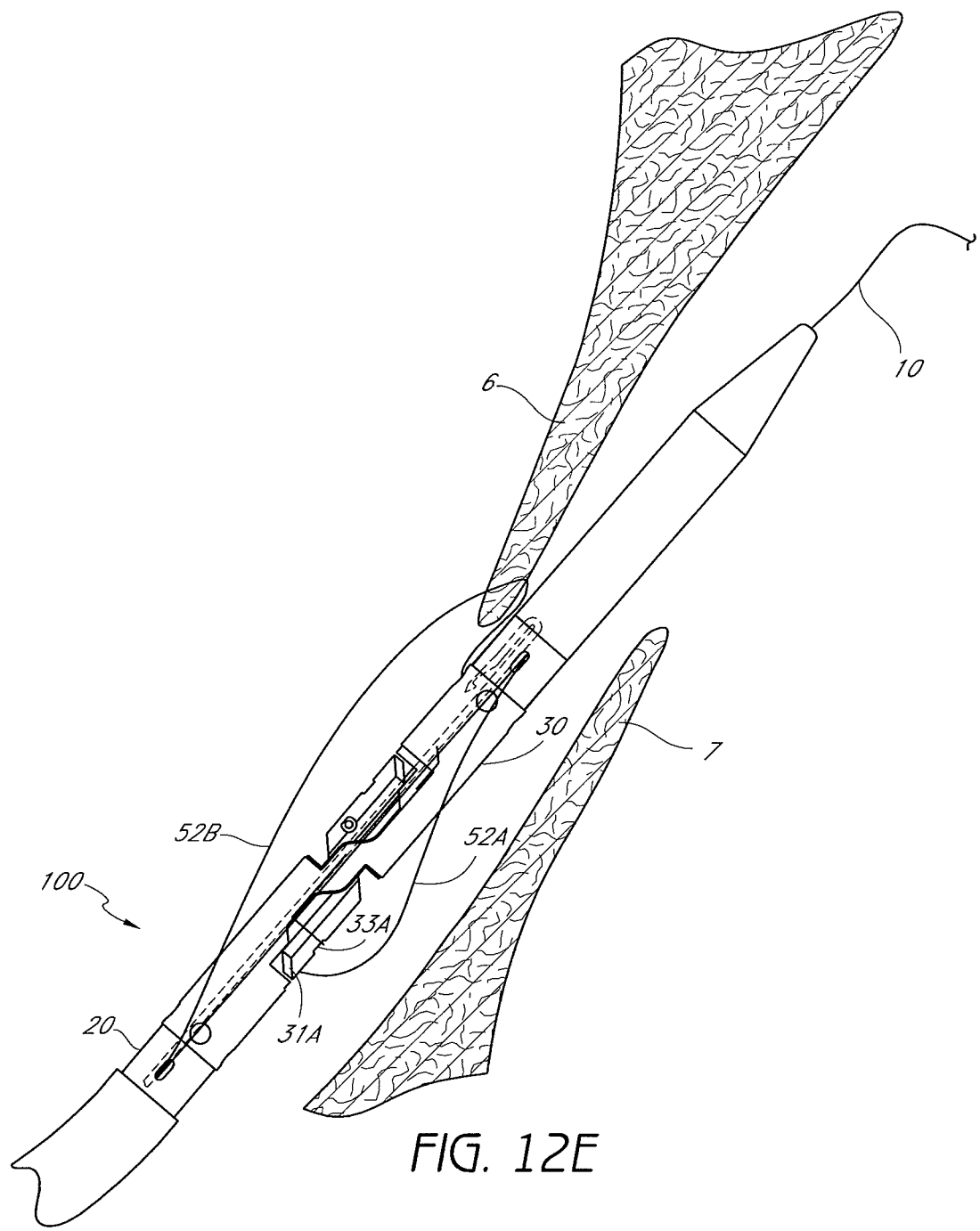
FIG. 12E is a schematic representation of the suturing device of FIG. 12A showing the suturing device partially withdrawn from the tunnel of the PFO and the suture clasp arms retracted into the device.
Figure 12F:
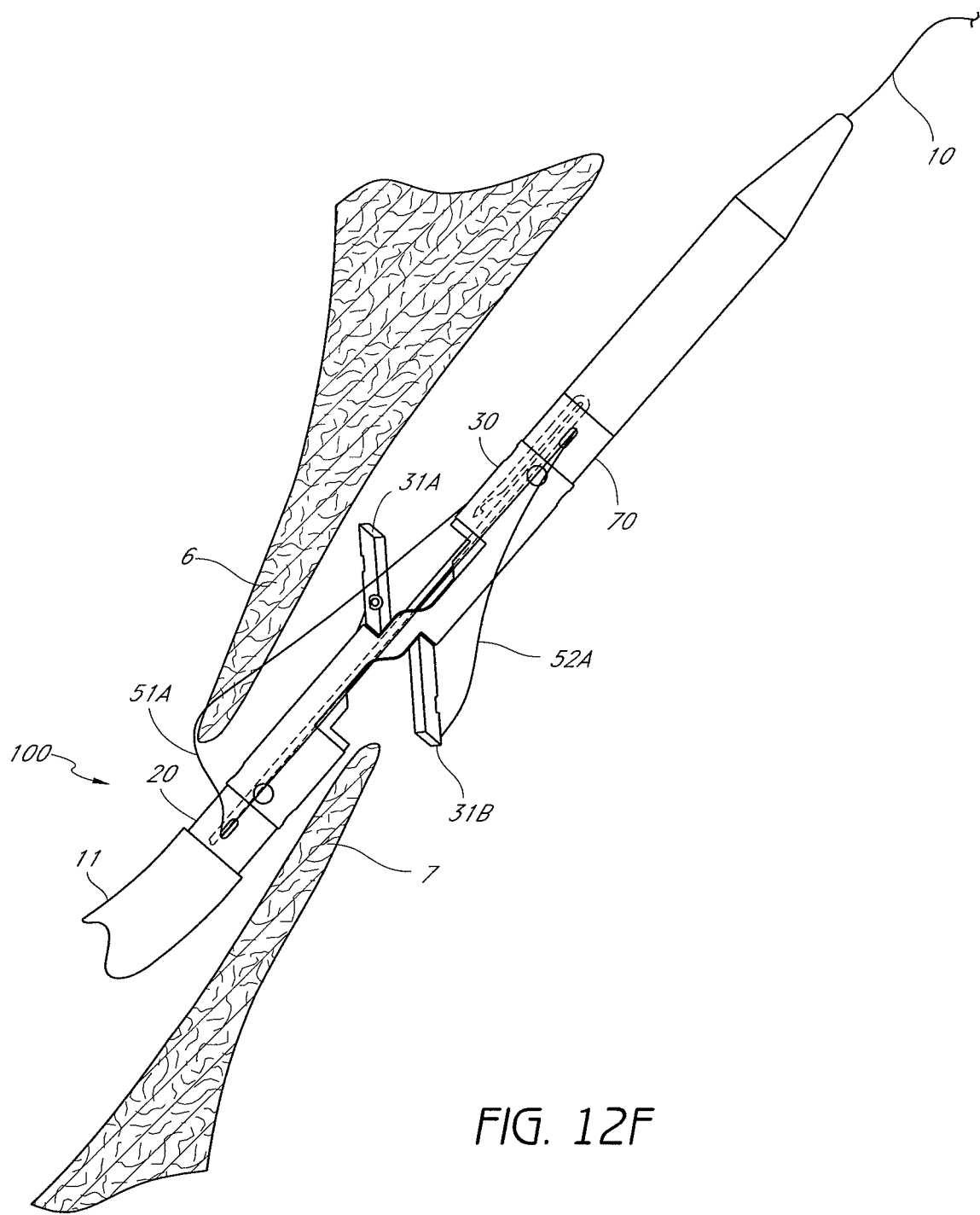
FIG. 12F is a schematic representation of the suturing device of FIG. 12A showing the suturing device advanced further into the left atrium with the proximal and distal suture clasp arms extended from the suturing device.
Figure 12G:
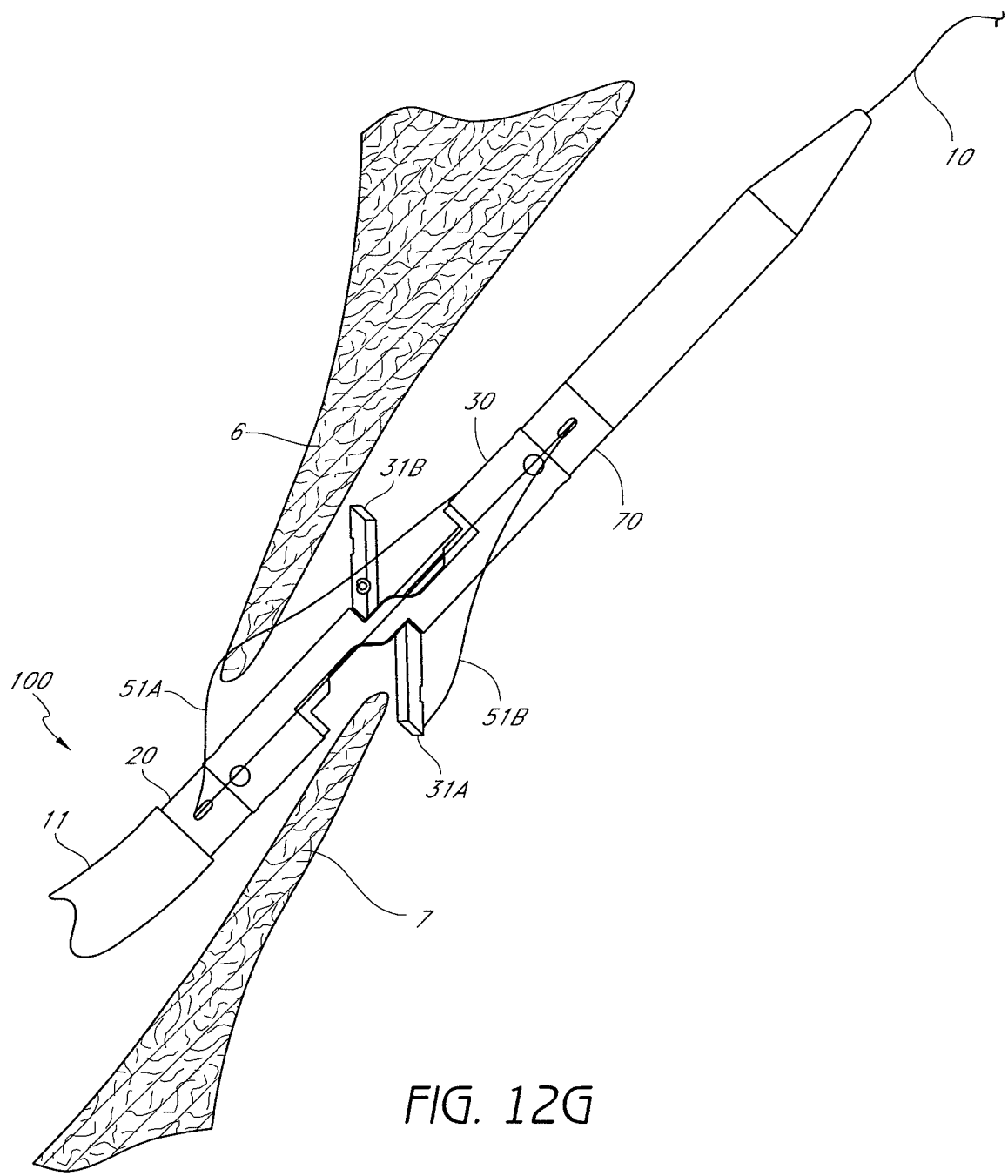
FIG. 12G is a schematic representation of the suturing device of FIG. 12A showing a proximal suture clasp arm engaging the septum primum.
Figure 12H:
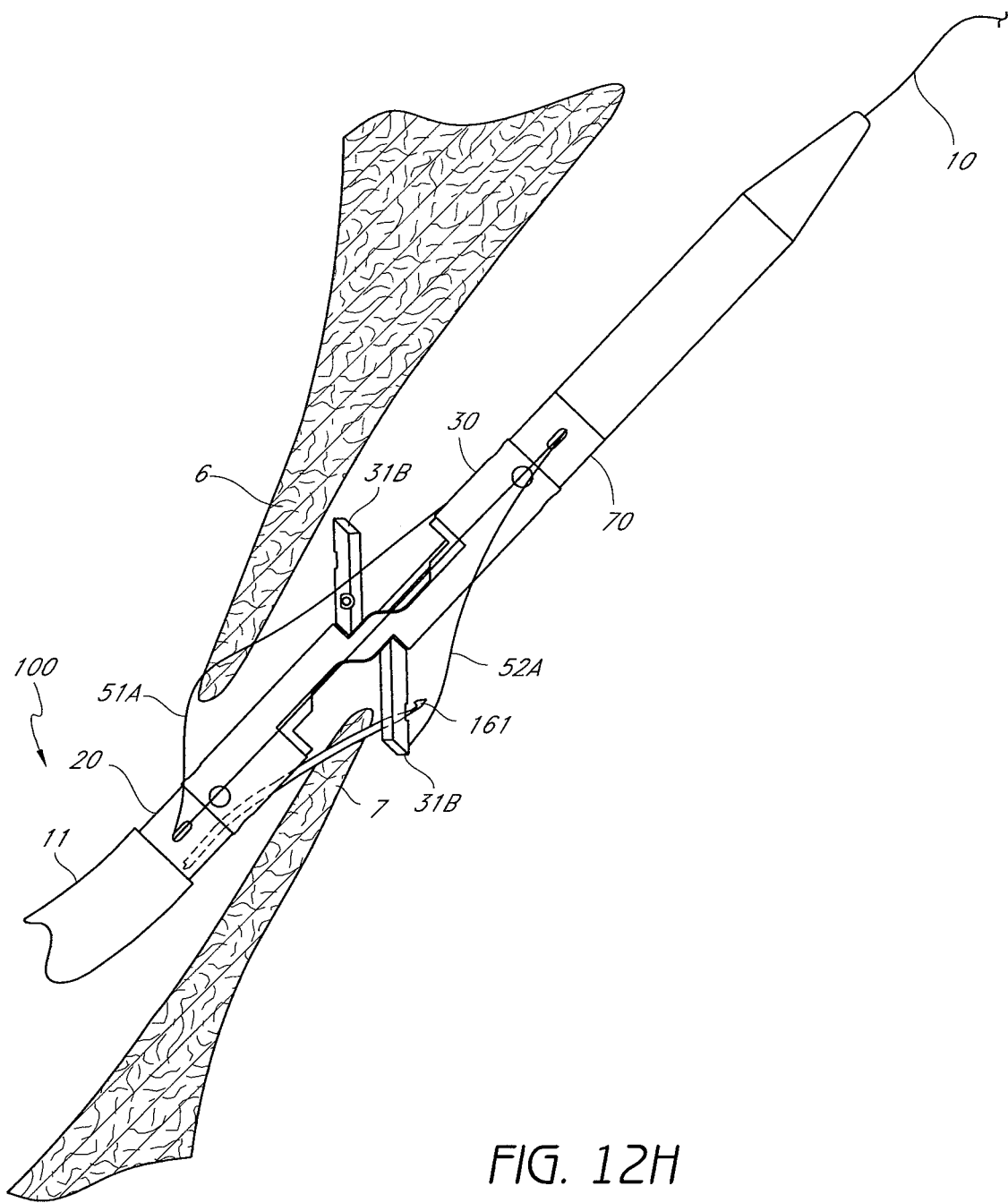
FIG. 12H is a schematic representation of the suturing device of FIG. 12A showing the proximal needle engaging the proximal suture clasp arm.
Figure 121:
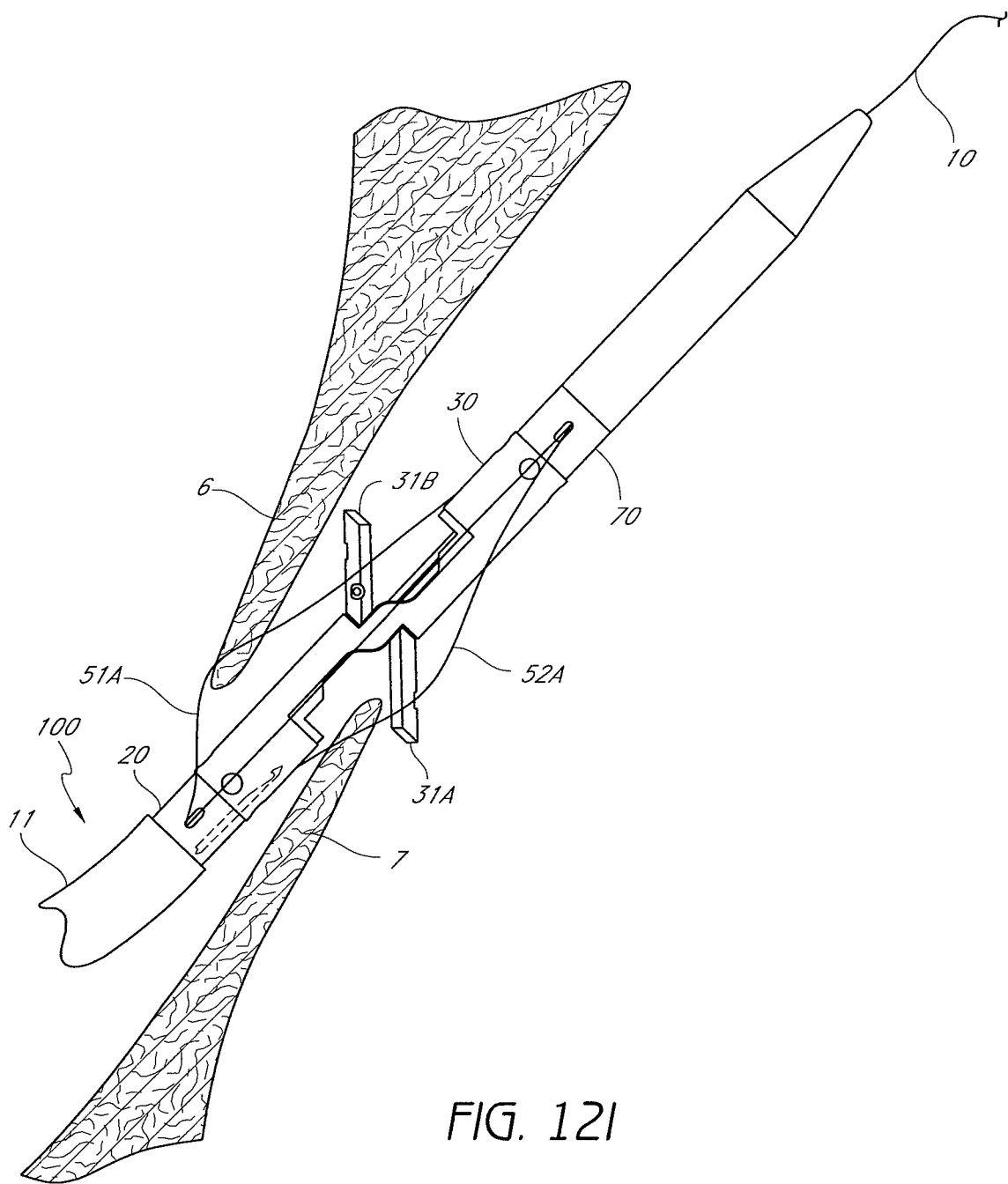

With the first suture portion 52B extending through tissue of the septum secundum, the suturing device may be partially withdrawn from the tunnel of the PFO and the suture clasp arms 31A and 31B may be retracted back into the suturing device, as shown in FIG. 12E. While in this low profile configuration, the suturing device can then be advanced further through the tunnel of the PFO into the left atrium, and the suture clasp arms 31A and 31B can be deployed once they are positioned past the tunnel of the PFO, as shown in FIG. 12F. FIG. 12G shows the suturing device 100 partially retracted to cause the proximal suture clasp arm 31A to engage or be positioned around or adjacent the septum primum 7. As shown in FIG. 12H, needle 161 can then be advanced from the suturing device, through tissue of the septum primum 7, and into engagement with the suture portion 52A carried by the suture clasp arm 31A. Retraction of the needle 161 back into the suturing device, as shown in FIG. 12I, carries the suture portion 52A through tissue of the septum primum 7.

Figure 12J:
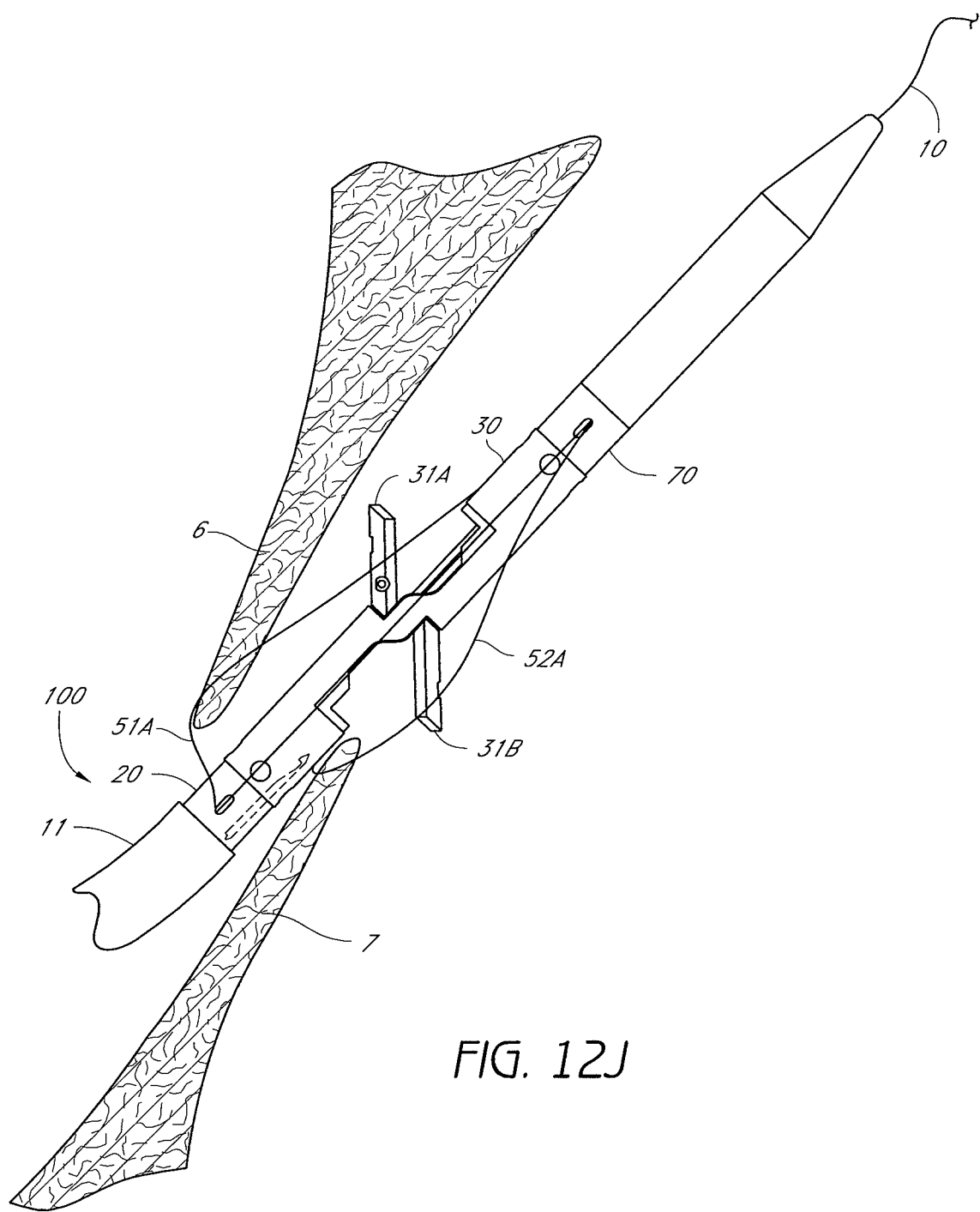
FIG. 12J is a schematic representation of the suturing device of FIG. 12A showing the suturing device advanced further into the left atrium.
Figure 12K:
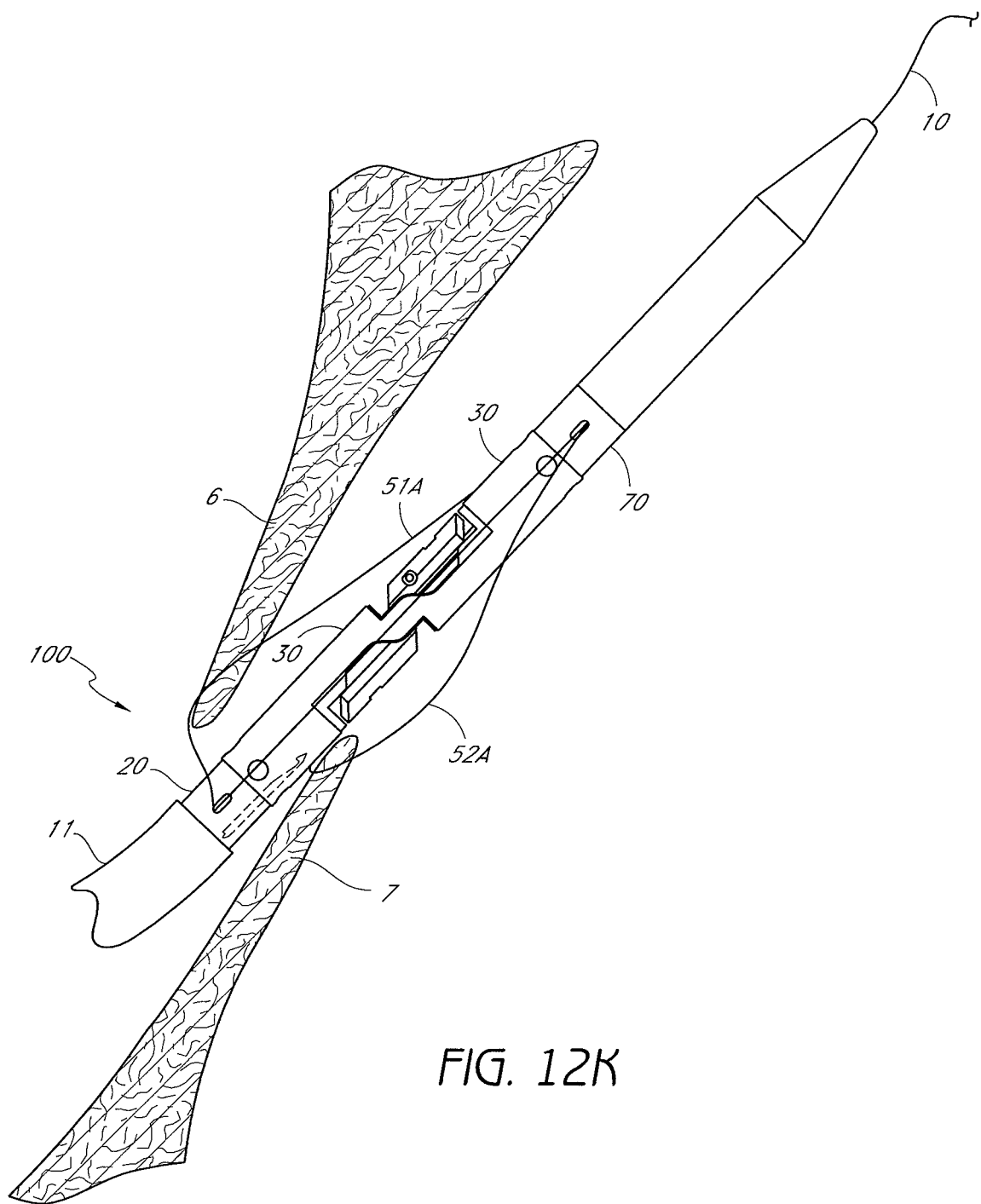
FIG. 12K is a schematic representation of the suturing device of FIG. 12A showing the suture clasp arms retracted into the suturing device.
Figure 12L:
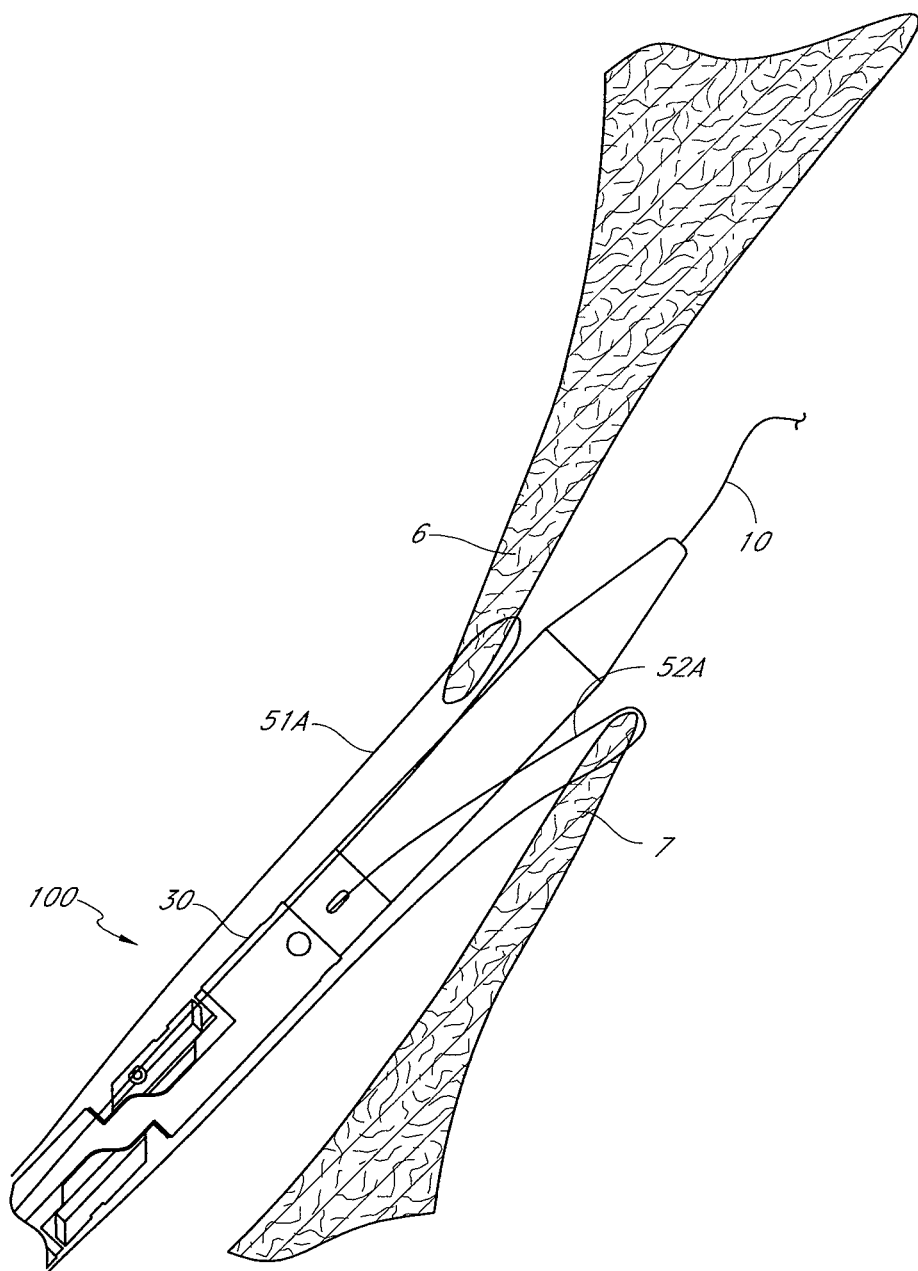
FIG. 12L is a schematic representation of the suturing device of FIG. 12A showing the suturing device being withdrawn from the PFO.

FIG. 12J illustrates the suturing device advanced further into the left atrium to allow the suture clasp arms 31A and 31B room to close before withdrawal of the device. With the arms closed or retracted, as shown in FIG. 12K, the suturing device 100 can be withdrawn from the tunnel of the PFO, as shown in FIG. 12L. The PFO may be closed using the suture portions 52A and 52B according to methods hereinbefore described.

Figure 13:
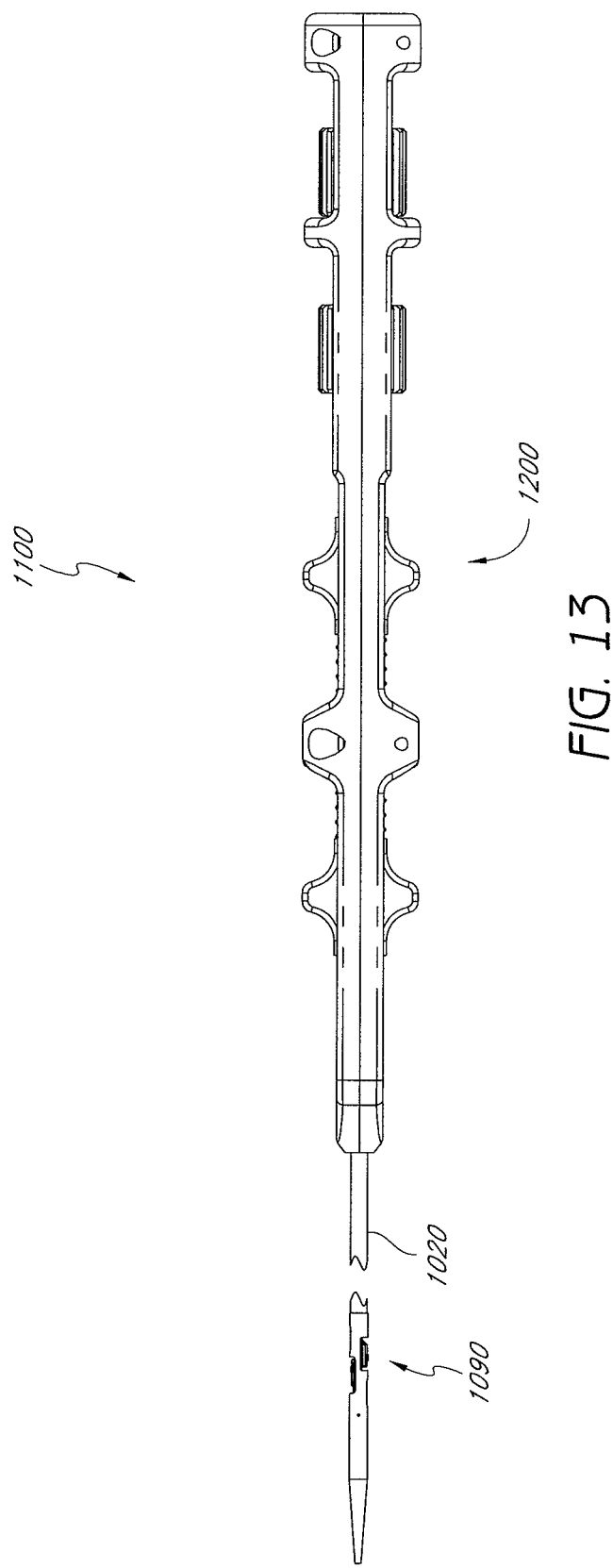
FIG. 13 illustrates a side view of one embodiment of a suturing device.

FIG. 13 shows a suturing device 1100 for suturing an opening in a vessel wall or other biological tissue. While the device will be described in reference to suturing an opening in the heart wall, such as a patent foramen ovale (PFO), the device 1100, like the device 100, could be used to close other openings in the heart wall, such as a patent ductus arteriosus (PDA) or an atrial septal defect (ASD), other openings in bodily tissue, or the like. The device 1100 could also be used to suture adjacent biological structures or any other time it may be desired to apply a suture to a biological structure, or to perform other procedures as described above with respect to the device 100.

Figure 14:
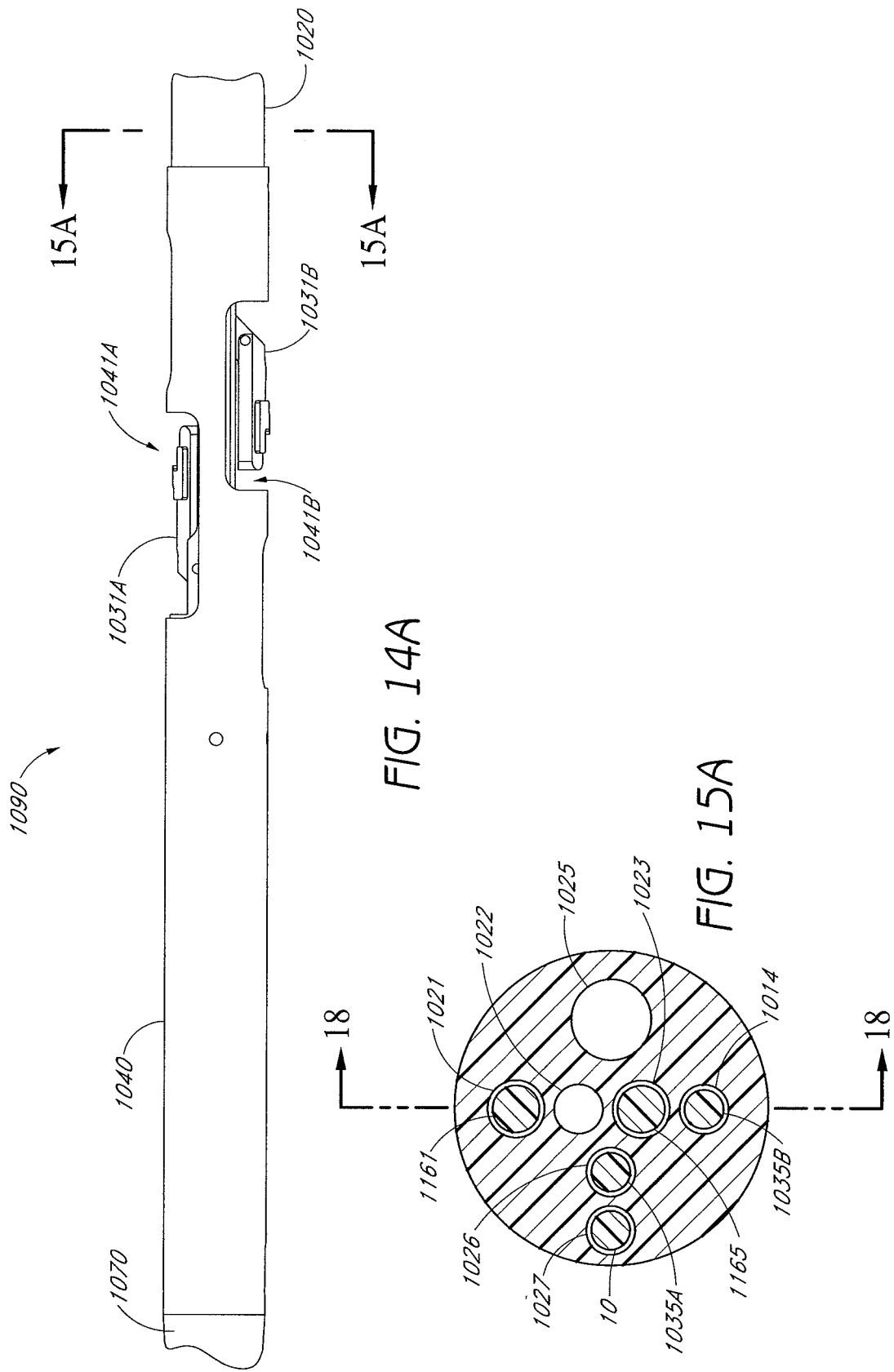
FIG. 14A illustrates a side view of the distal end of the suturing device of FIG. 13.
FIG. 14B illustrates a side view of a distal end of a suturing device of one embodiment.
Figure 19:
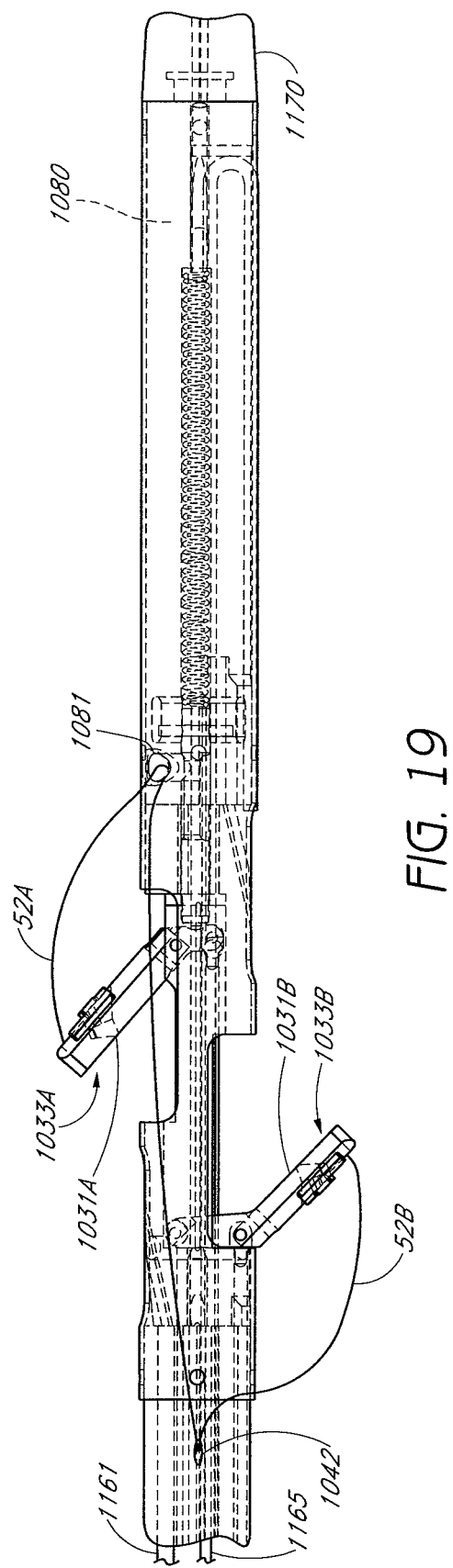
FIG. 19 illustrates a side view of an embodiment of the suturing device with the suture clasp arms deployed and various internal features shown in phantom.

The suturing device 1100 comprises an elongate tubular member 1020 having a spreader assembly 1090, shown in greater detail in FIGS. 14A and 19, connected to the distal end of the elongate tubular member 1020 for positioning in the opening of the PFO. A handle 1200 is provided at the proximal end of the tubular member 1020. The elongate tubular member 1020 can be similar to the elongate tubular member 20 in some respects. For example, as shown in more detail in FIG. 15A, the elongate tubular member 1020 has a plurality of lumens 1021, 1022, 1023 and 1024 extending along the axial length of the member 1020 in a generally stacked arrangment. Also, the elongate tubular member 1020 can have similar dimensions to the elongate tubular member 20. Additionally, the member 1020 can be manufactured by similar techniques and from similar materials to the member 20.

The elongate tubular member 1020 can differ from the elongate tubular member 20 in some respects. For example, in addition to the lumens 1021, 1022, 1023 and 1024 arranged generally across a diameter of the elongate tubular member 1020, the elongate tubular member 1020 may additionally comprise a one or more lumens, such as lumens 1025, 1026, and 1027 that are shown in FIG. 15A as extending axially within elongate tubular member 1020 on either side of the lumens 1021, 1022, 1023 and 1024.

In some embodiments, as will be discussed below in more detail, the lumens 1021, 1022, 1023, 1024, 1025, 1026 and 1027 can be used to provide access through the elongate tubular member 1020 for a guidewire, to provide access for one or more actuating rods connected to suture clasp arms, to house one or more suture catch mechanisms or needles, and to deliver one or more sutures to the distal end of the elongate tubular member 1020. Some embodiments may also employ these lumens, or include further lumens, for injection of die, housing an additional guidewire, or to facilitate molding of the elongate tubular member.

Figure 15:
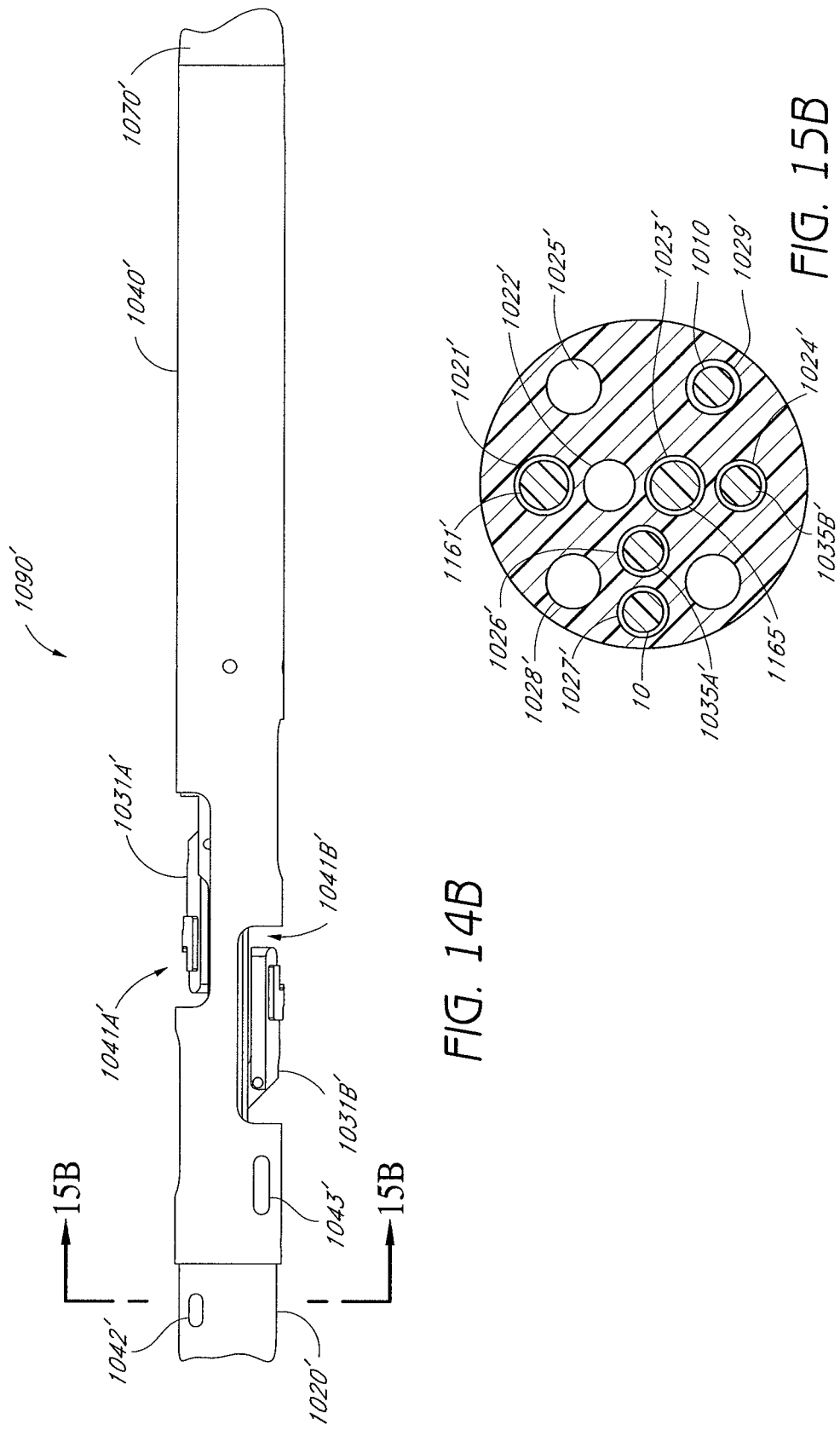
FIG. 15A illustrates a cross-sectional view of the elongate tubular member of an embodiment of the suturing device of FIGS. 13 and 14A, taken along the line 15A-15A of FIG. 14A.
FIG. 15B illustrates a cross-sectional view of the elongate tubular member of an embodiment of the suturing device of FIG. 14B, taken along the line 15B-15B of FIG. 14B.

For example, an elongate tubular member 1020', shown in FIGS. 14B and 15B, includes lumens for injection of die and an additional guidewire. The elongate tubular member 1020' is similar to the elongate tubular member 20 in some respects. Thus, similar features of the elongate tubular member 1020' are indicated with numerals similar to those of elongate tubular member 1020 followed by a prime ('). Additionally, elongate tubular member 1020' comprises a lumen 1028' through which die can be injected into the treatment site, and a lumen 1029' for a second guidewire 1010. In additional embodiments, further lumens may be used for other purposes, such as for injection of die to an additional location or to house yet another guidewire.

The elongate tubular member 1020' can comprise one or more openings near the spreader assembly 1090 between the lumen 1028' and the treatment site to permit expulsion of die from the lumen 1028'. Alternatively or additionally, die may pass from the lumen 1028' through a spreader assembly 1090' to the treatment site.

Similarly, the second guidwire 1010 can pass through the lumen 1029' into the spreader assembly 1090', which can have a guide, ramp or other feature to direct the second guidewire 1010 through an opening 1043' and away from the spreader assembly 1090'. Alternatively or additionally, the elongate tubular member 1020' can comprise an opening proximal to and near the spreader assembly 1090' between the lumen 1029' and the treatment site for passage of the second guidewire 1010.

Referring again to FIG. 14A, the spreader assembly 1090 is bonded, or otherwise joined, to the distal end of the elongated tubular member 1020, for example, with epoxy or by any other suitable technique known to those skilled in the art. The spreader assembly 1090 can comprise a spreader 1030 (FIG. 18), one or more suture clasp arms 1031, a casing 1040, and a distal tip 1070.

Figure 16:
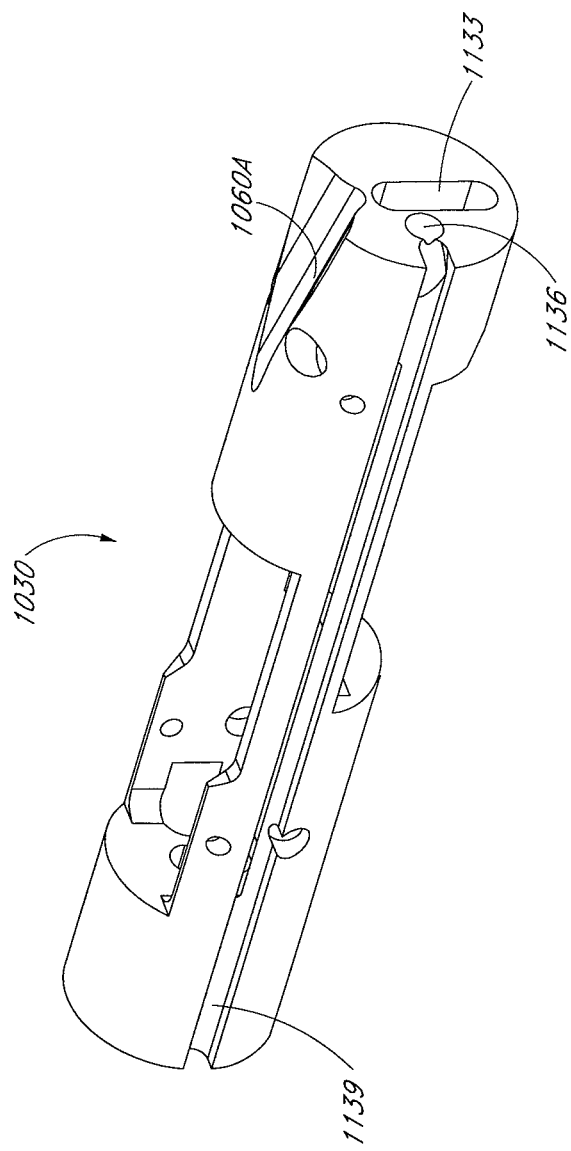
FIG. 16 illustrates a perspective view of a spreader assembly of an embodiment of the suturing device.
Figure 17:
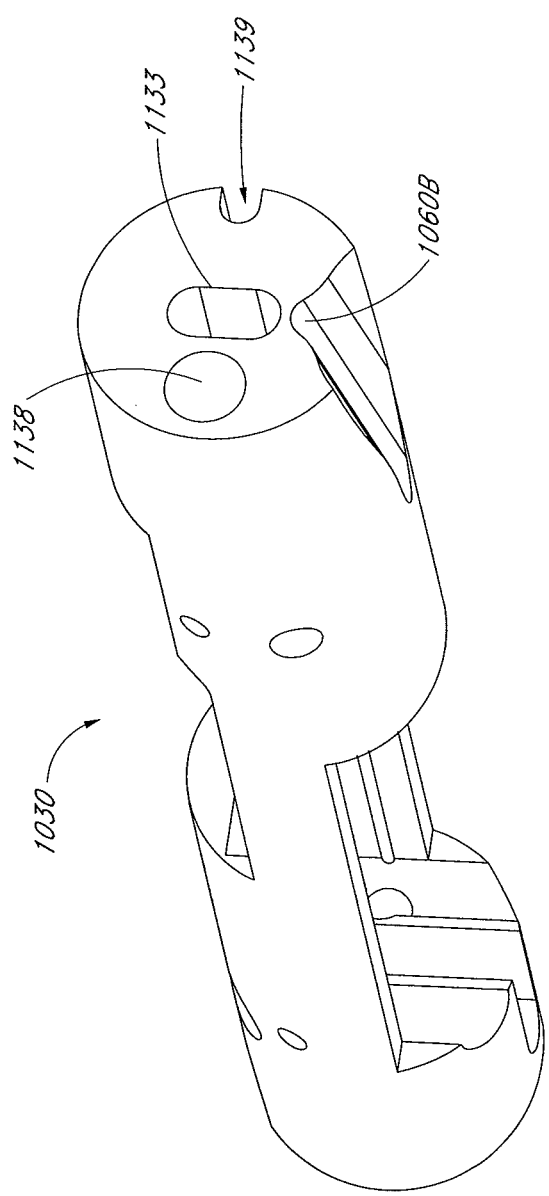
FIG. 17 illustrates another perspective view of the spreader assembly of FIG. 16.

Referring to FIGS. 16-18, the spreader 1030 comprises one or more lumens. The spreader 1030 has lumens 1133 and 1136 that extend generally parallel to a longitudinal axis of the spreader assembly 1090, as shown in FIG. 16. When the spreader 1030 and the elongate tubular member 1020 are properly connected, the lumens 1022, 1023, and 1024 of the member 1020 are preferably substantially aligned with the lumen 1133 of the spreader 1030, and the lumen 1026 of the member 1020 is preferably substantially aligned with the lumen 1136 of the spreader 1030 to provide continuous passageways between the elongate tubular member 1020 and the spreader 1030.

Figure 18A:
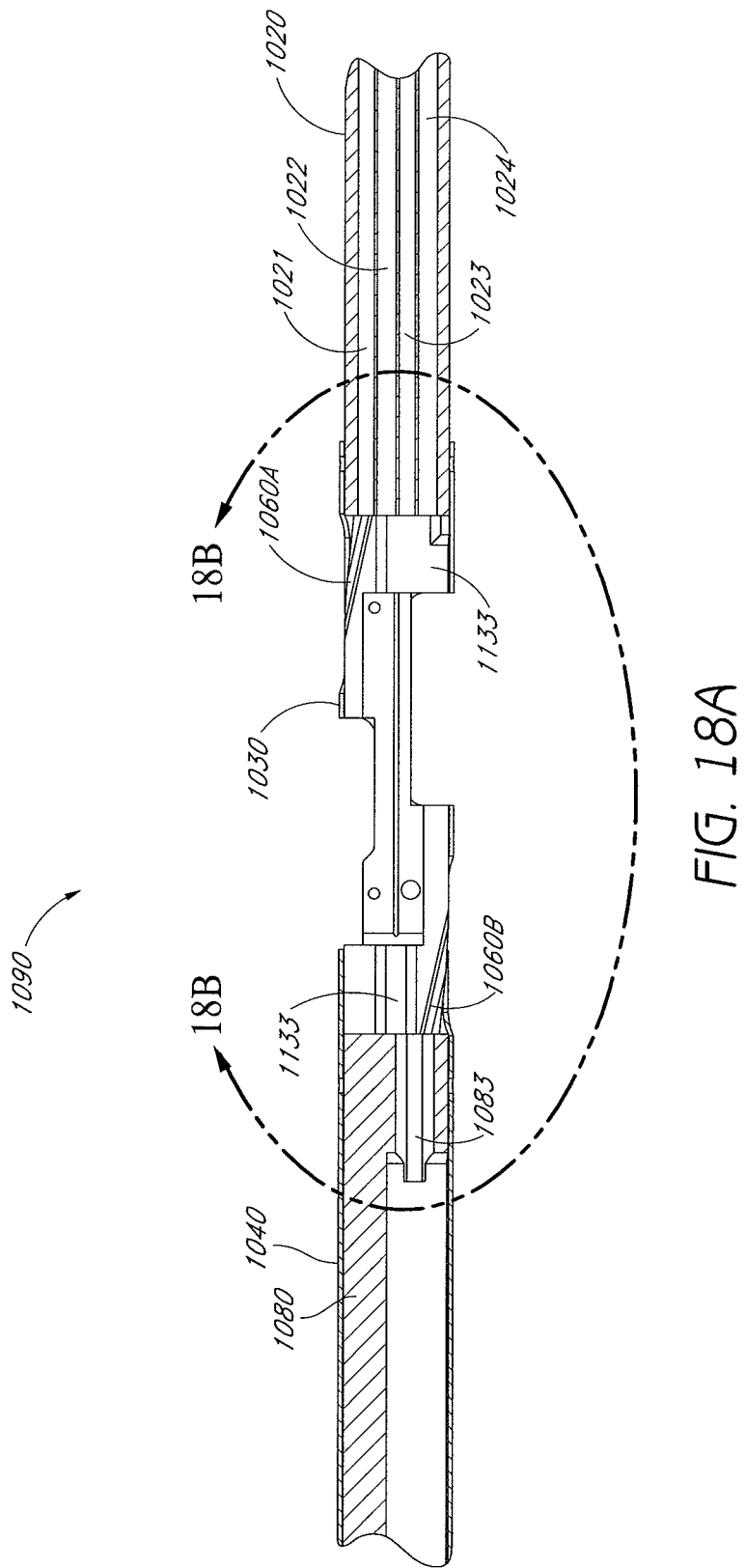
FIG. 18A illustrates a cross-sectional view of a distal end of an elongate tubular member, the spreader assembly of FIGS. 16 and 17, and a housing taken along the line 18-18 of FIG. 15A.

In some embodiments, a casing 1040 is placed over the connection between the elongate tubular member 1020 and the spreader 1030 to facilitate proper alignment of the internal lumens of the elongate tubular member 1020 and spreader 1030, as shown in FIG. 18A. The casing is preferably made of metal, but can also be made of other materials such as plastics.

As illustrated in FIG. 14A, the casing 1040 can comprise openings, or recesses, 1041A and 1041B located on the opposite sidewalls of the casing 1040 for allowing the release and deployment of a pair of suture clasp arms 1031A and 1031B housed within the spreader 1030. Accordingly, the openings 1041A and 1041B are sized and shaped to permit the suture clasp arms to fully extend from the spreader 1030.

In some embodiments, the casing 1040 has a length such that when the proximal end of the casing 1040 is positioned over the connection between the spreader 1030 and the elongate tubular member 1020, the distal end of the casing 1040 extends beyond the distal end of the spreader 1030 and, in some embodiments, engages a distal tip 1070 and/or a housing, such as housing 1080 shown in FIGS. 18A and 19, that is positioned between the spreader 1030 and the tip 1070.

As shown in FIG. 14A, the pair of suture clasp arms 1031A and 1031B are housed in the recesses 1041A and 1041B in the spreader assembly 1090. During storage and delivery of the suturing device, the suture clasp arms 1031A and 1031B are situated substantially parallel to the longitudinal axis of the suturing device such that the outer walls of the suture clasp arms do not extend beyond the outer diameter of the spreader assembly 1090.

The suture clasp arms 1031A and 1031B are connected to actuating rods 1035A and 1035B which extend through the passageways formed by lumens 1133 and 1136 in the spreader assembly and lumens 1024 and 1026 in the elongate tubular member 1020, as shown in FIG. 15A. After insertion and positioning of the suturing device at the PFO or other opening, the arms 1031A and 1031B can be deployed to the position shown in FIG. 19 by movement of the actuating rods 1035A and 1035B relative to the spreader 1030.

In the embodiment illustrated in FIGS. 14A and 19, the distal suture clasp arm 1031A and the proximal suture clasp arm 1031B are manufactured as separate components. The distal suture clasp arm 1031A and the proximal suture clasp arm 1031B are shown in greater detail in FIGS. 20 and 21, respectively. Each of the arms 1031 may be pivotally connected to the spreader 1030 at a first connection point, such as pivot apertures 1091, and connected to the actuating rods 1035 at a second connection point, such as apertures 1092. The arms may be connected to the spreader 1030 and the actuating rods 1035 by pins or by other techniques, such as by integral construction employing one or more compliant hinges. Accordingly, movement of the actuating rods 1035 relative to the spreader 1030 results in movement of the arms 1031.

When deployed, the suture clasp arms 1031A and 1031B extend from the suturing device 1100 in opposite directions from the longitudinal axis of the device. Preferably, the arms 1031A and 1031B form an acute angle with the longitudinal axis of the spreader. In some embodiments, a first arm 1031A extends outward toward the proximal end of the spreader assembly 1090 at an angle of between about 35-55.degree., alternatively about 40-50.degree., alternatively about 45.degree. with respect to the longitudinal axis of the spreader assembly 1090. The second arm 1031B can extend outward toward the distal end of the spreader assembly 1090 at approximately the same angle as the first arm 1031A with respect to the longitudinal axis of the spreader assembly 1090. In other embodiments, the second arm 1031B can extend outward from the spreader assembly 1090 at angle larger or smaller than the angle of the first arm 1031A with respect to the longitudinal axis of the spreader assembly 1090.

Figure 29A:
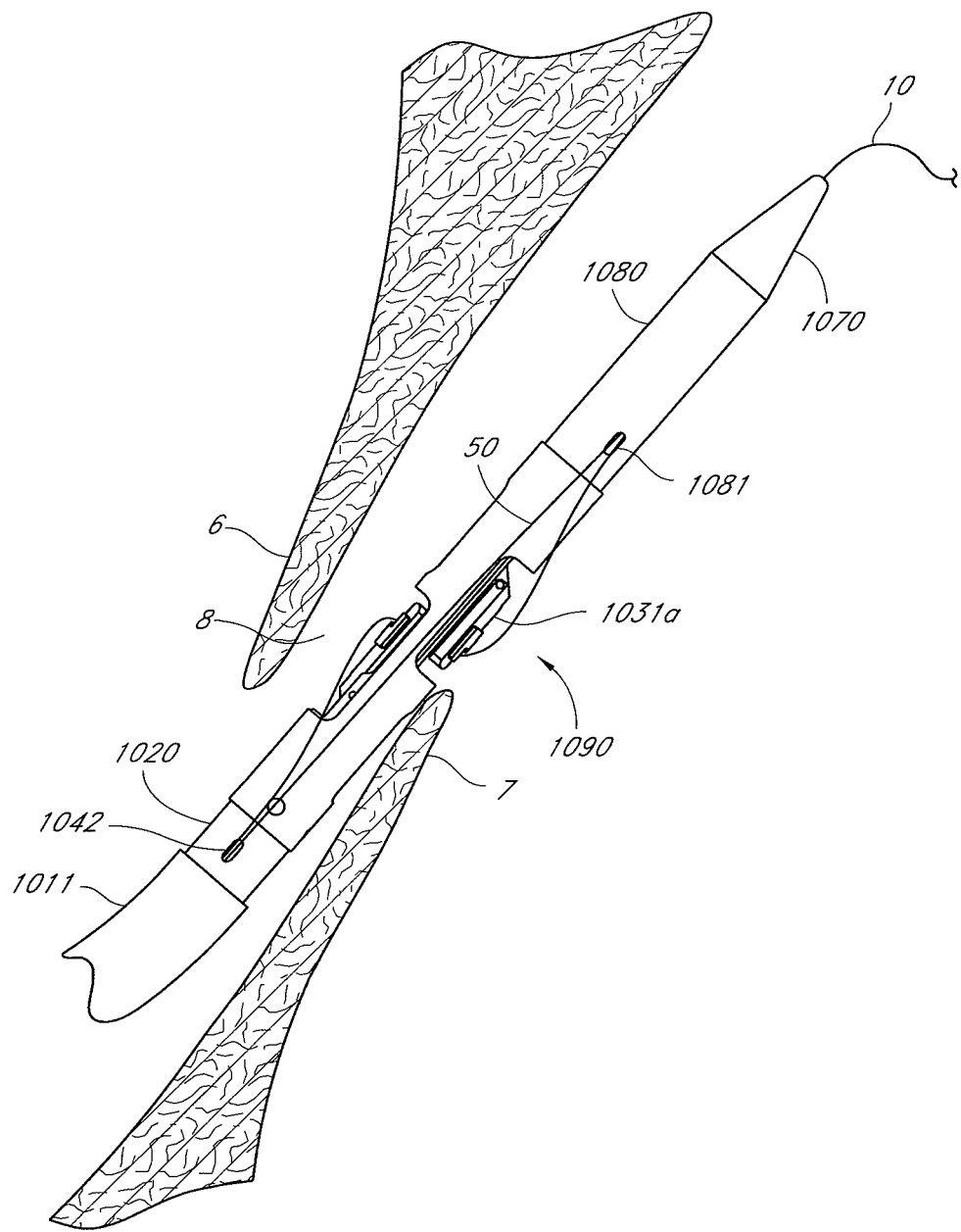
FIG. 29A is a schematic representation an embodiment of the suturing device deployed in a PFO.
Figure 29B:
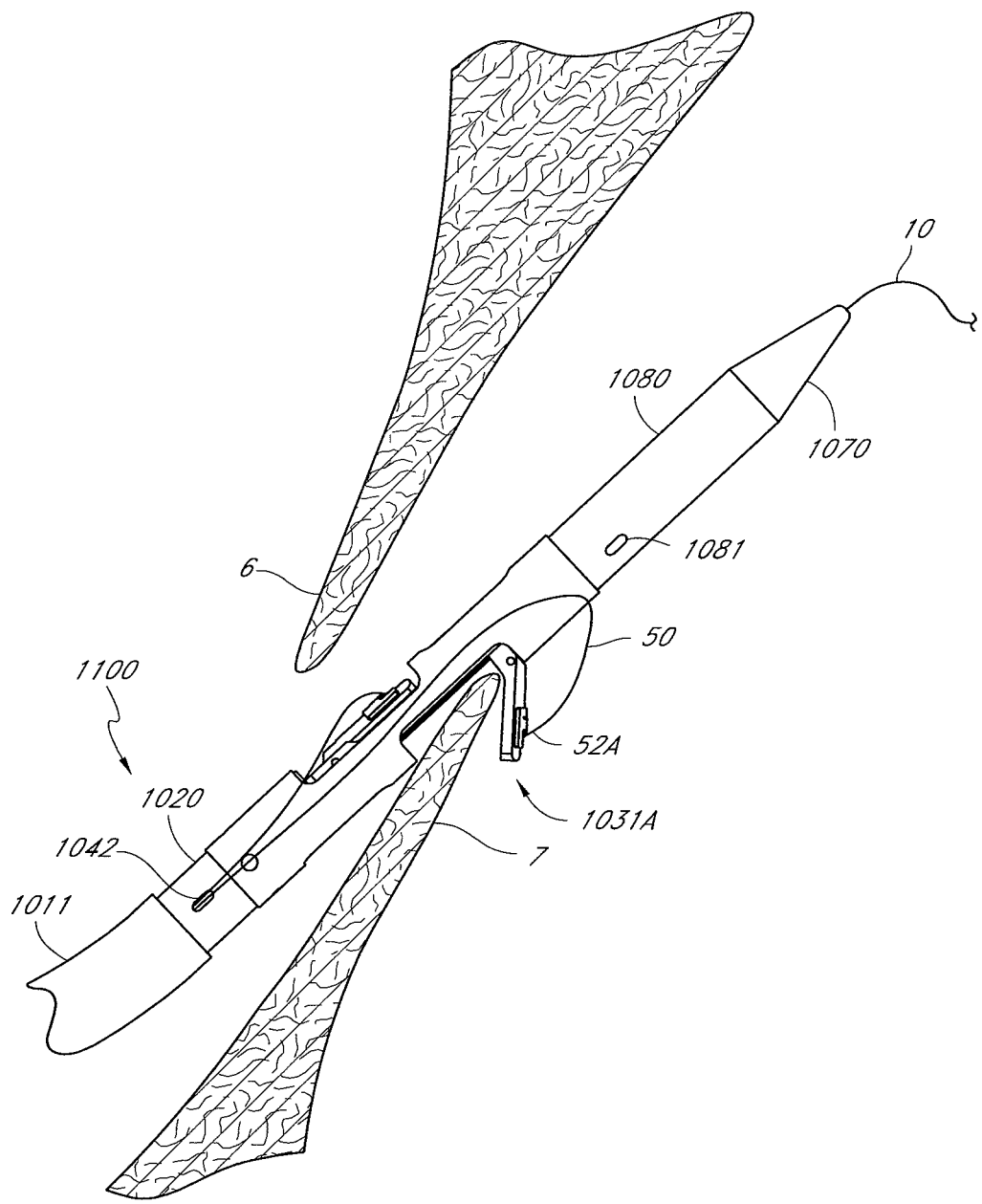
FIG. 29B is a schematic representation as in FIG. 29A with a distal suture clasp arm positioned around the septum primum.
Figure 29C:
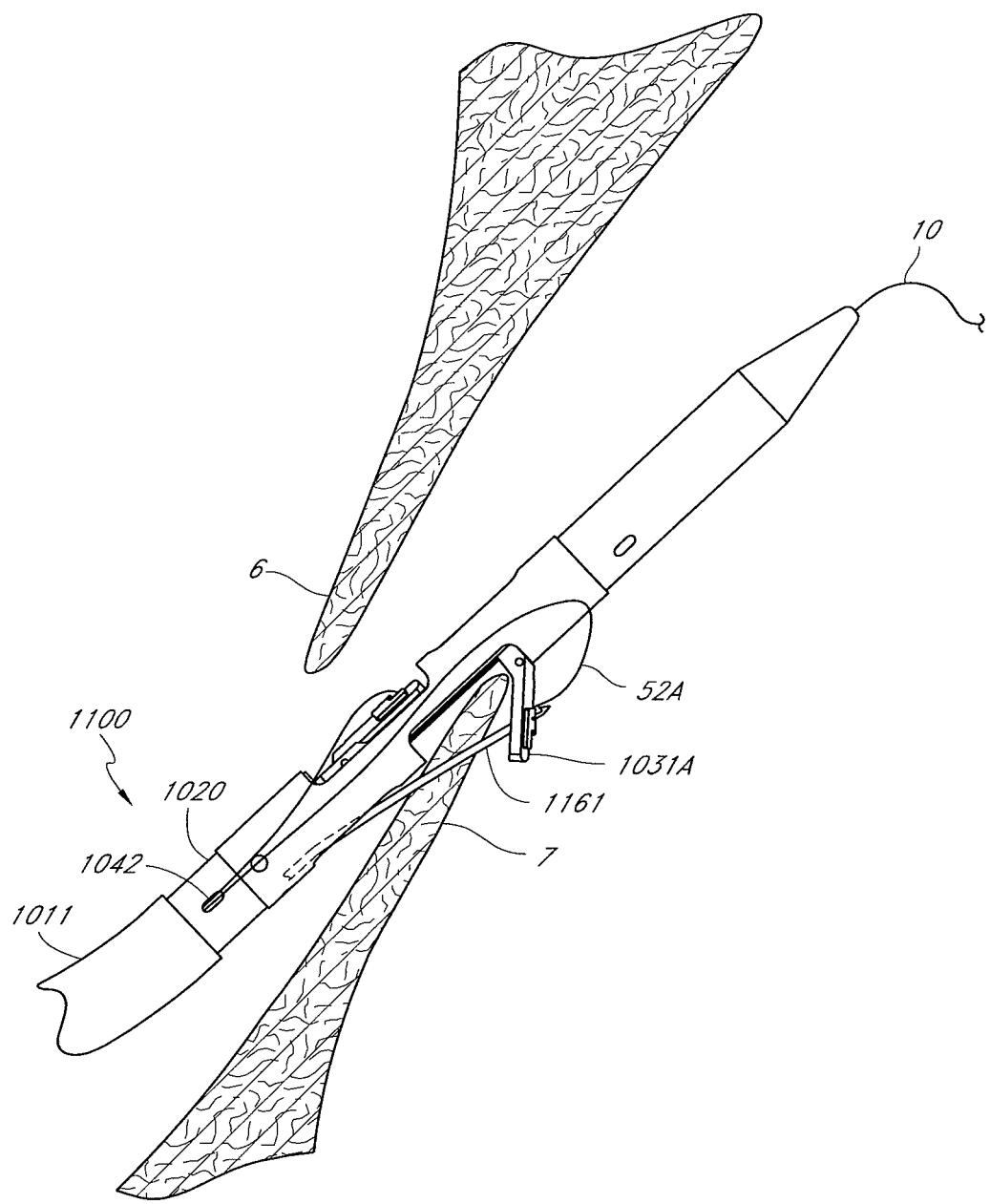
FIG. 29C is a schematic representation as in FIG. 29B showing the proximal needle engaging the distal suture clasp arm.
Figure 29D:
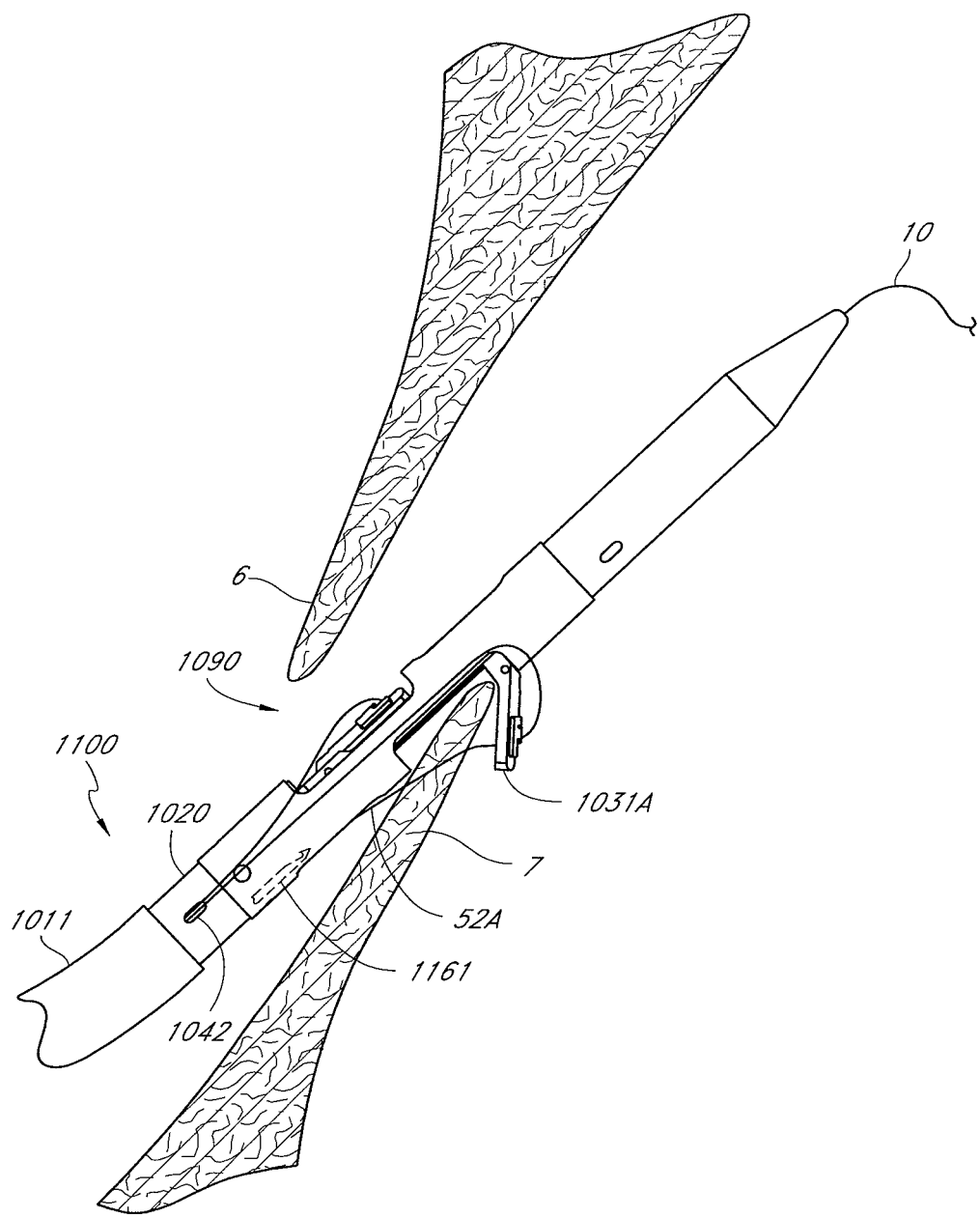
FIG. 29D is a schematic representation as in FIG. 29C showing the proximal needle and suture portion retracted through the septum primum.
Figure 29E:
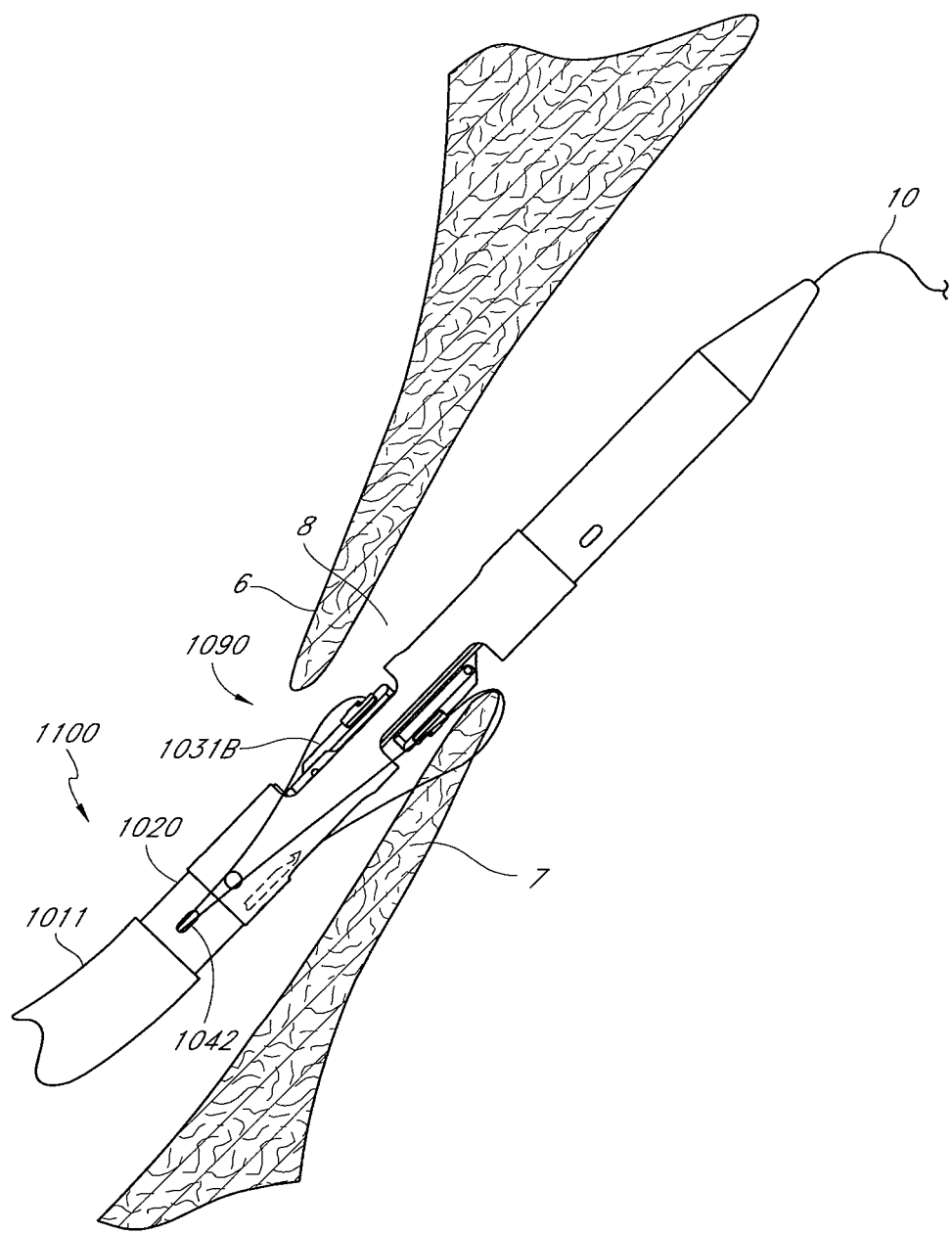
FIG. 29E is a schematic representation as in FIG. 29D showing the suturing device positioned to permit a proximal suture clasp arm to extend from the suturing device.
Figure 29F:
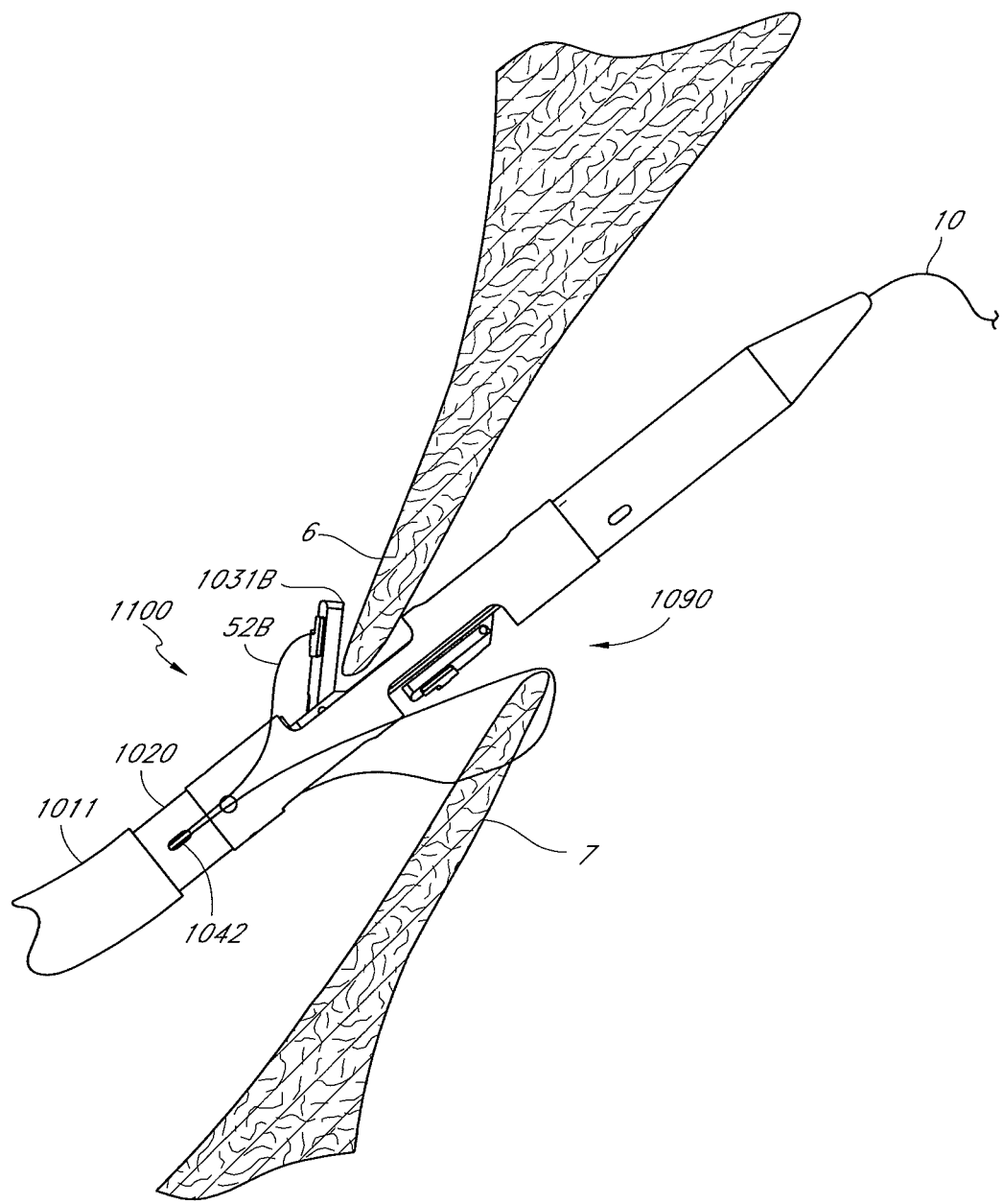
FIG. 29F is a schematic representation as in FIG. 29E with the proximal suture clasp arm positioned around the septum secundum.

As shown in FIGS. 29B and 29F, the suture clasp arms 1031A and 1031B can be independently actuated to be individually deployed depending upon the location of the tissue portion to be sutured. For example, in closing a PFO, the suturing device will first be positioned with respect to a first tissue portion to be sutured and then moved to a second position for suturing a second tissue portion. More specifically, as shown in FIG. 29B, when closing a PFO, the suturing device 1100 can be first positioned such that suture clasp arm 1031A extends around the septum primum 7 such that suture portion 52A may be engaged and pulled though the septum primum 7 to draw it toward the septum secundum 6. The non-engaged suture clasp arm 1031B can remain retracted in the spreader 1030, as shown in FIG. 29B.

The suture clasp arms 1031A, 1031B, like the suture clasp arms 31, have suture clasps 1033A, 1033B (see FIG. 19) for receiving and holding a suture 50. The suture clasps 1033A, 1033B of the suture clasp arms 1031A, 1031B may be configured in a manner similar to or the same as that described with respect to the suture clasps 33. For example, each clasp 1033 can be a circular opening with a diameter sized to securely receive and hold a loop of suture 50.

In use, the suture ends are positioned in the suture clasps 1033A and 1033B of the suture clasp arms 1031A and 1031B and held securely there until they are engaged and removed by suture catch mechanisms 1161 and 1165. As discussed above, the suture clasp arms 1031A and 1031B can comprise slots 1034A and 1034B (FIGS. 20 and 21) to guide the suture into the suture clasps 1033 at the proper angle and assist in maintaining the suture loops in the suture clasp until they are engaged by the suture catch mechanisms. When the suture catch mechanism engages the loops of the suture ends, the suture loops will slide out of the suture clasp 1033 and be released by the suture clasp arm 1031.

In some embodiments, the suture clasp arms 1031 can comprise legs 1093 that extend away from the clasps 1033, as illustrated in FIGS. 20 and 21. The legs 1093 can engage tissue portions at a location remote from a location where a suture catch mechanism is to penetrate a biological structure. The legs 1093 can gather the tissue toward the location where the suture catch mechanism is to penetrate the biological structure to facilitate secure suturing of the biological structure.

The suture 50 can be housed in the lumen 1025 (see FIG. 15A) of the elongate tubular member 1020. The suture lumen 1025 can have a port or opening 1042 near the distal end of the elongate tubular member 1020, as shown in FIG. 19. The suture 50 can be advanced through the opening 1042 such that the suture ends, or end portions 52A and 52B, extend outside of the suturing device 1100. One of the suture end portions 52B may extend from the opening 1042 to the suture clasp arm 1031B. The other suture end portion 52A may extend along the length of the casing and into a side opening 1081 in the housing 1080 (see FIGS. 19, 24, and 26). The suture portion 52A may loop back out of the opening 1081 to the suture clasp arm 1031A.

Figure 24:
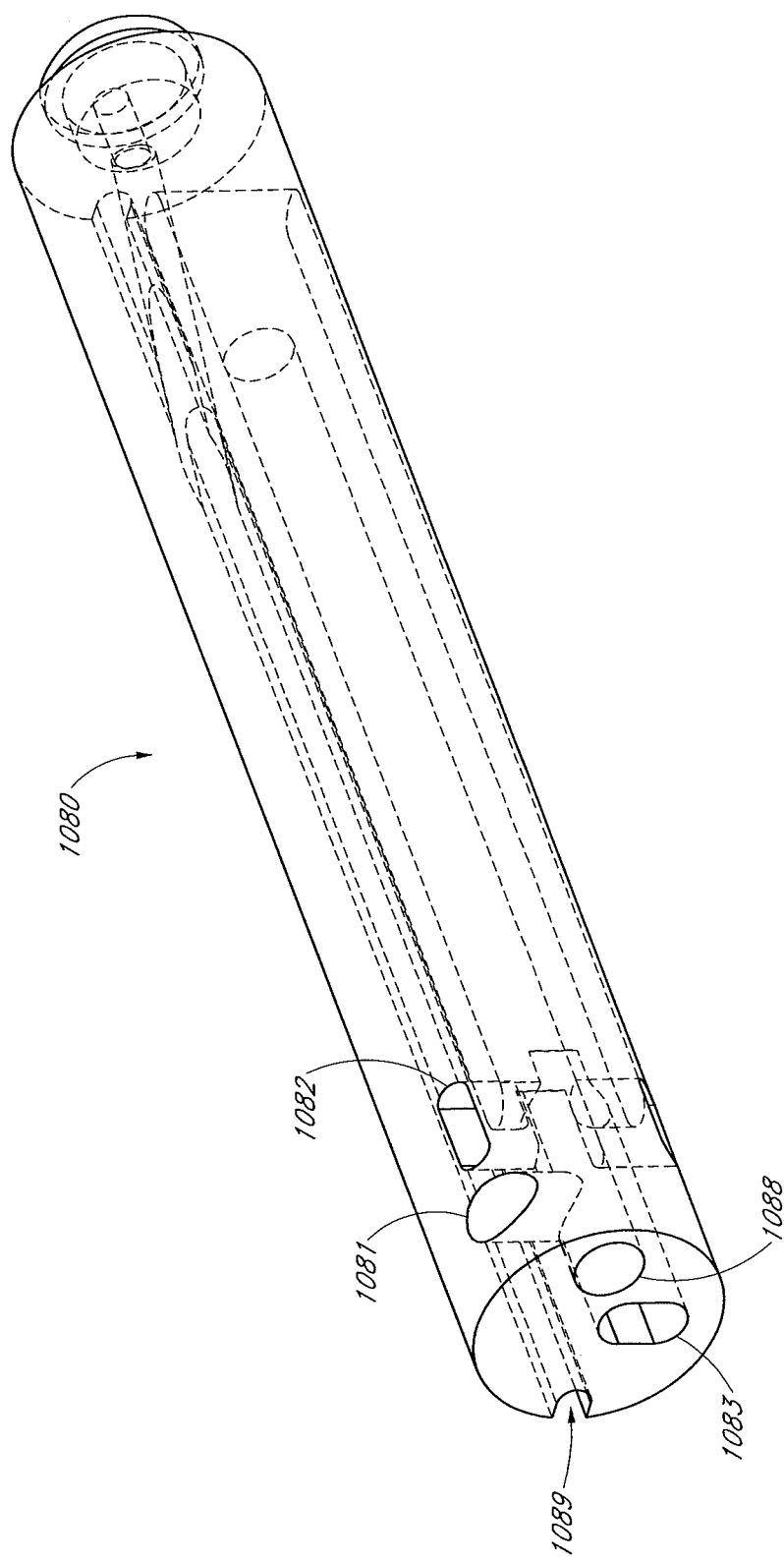
FIG. 24 illustrates a perspective view of a housing of an embodiment of the suturing device.
Figure 25:
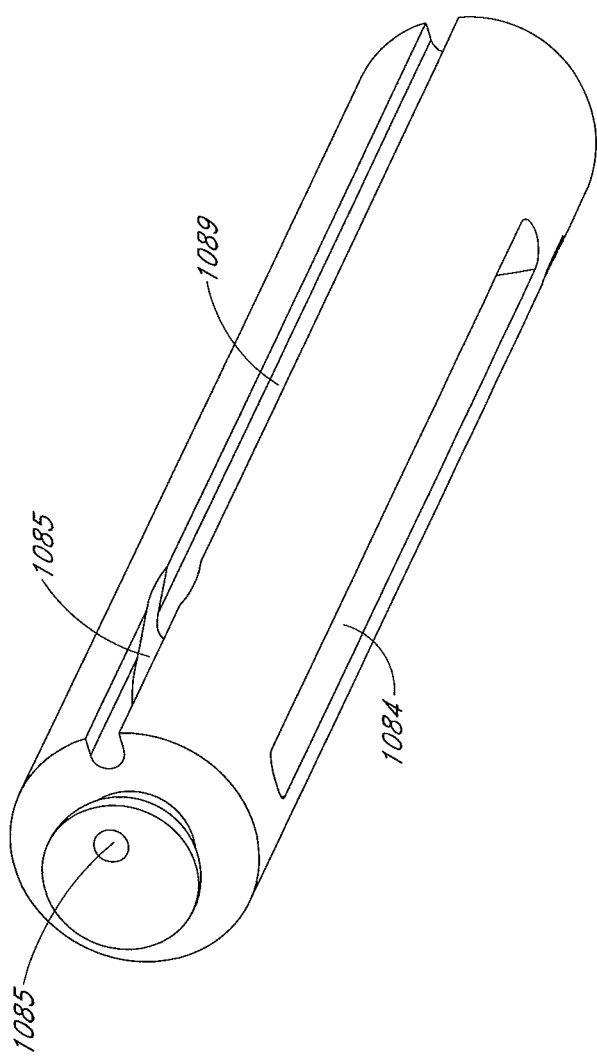
FIG. 25 illustrates another perspective view of the housing of FIG. 24.

The housing 1080 can have one or more openings that align with complementary openings in the spreader 1030. For example, the housing 1080 can comprise a groove, slot or lumen 1089 extends generally parallel to a longitudinal axis of the housing 1080, as shown in FIGS. 24 and 25. When the spreader 1030 and the housing 1080 are properly connected, the slot 1089 of the housing 1080 is preferably substantially aligned with a groove, slot, or lumen 1139 (see FIGS. 16-17) of the spreader 1030 to provide continuous passageways between the housing 1080 and the spreader 1030. In some embodiments, the housing 1080 can comprise an aperture 1085 that intersects the slot 1089 and extends distally toward a central longitudinal axis of the housing 1080, as shown in FIG. 25.

Additionally or alternatively, the housing 1080 can comprise apertures 1083 and 1088, shown in FIG. 24, that extend generally parallel to a longitudinal axis of the spreader assembly 1090. When the spreader 1030 and the housing 1080 are properly connected, the apertures 1083 and 1088 of the housing 1080 are preferably substantially aligned with lumens 1133 and 1138 (see FIG. 17) of the spreader 1030 to provide continuous passageways between the housing 1080 and the spreader 1030.

The aperture 1088 can extend generally along the longitudinal axis of the housing 1080 and may extend entirely through the housing or may, as shown in FIG. 24, extend only partially through the housing 1080. The aperture 1080 can be intersected by the side opening 1081 and an opening 1082. In some embodiments, the aperture 1083 can be intersected by an aperture 1084.

In some embodiments, the housing can comprise a suture retention mechanism. For example, referring to FIG. 26, the aperture 1088 can accommodate a follower pin 1094 and a spring 1095 that urges the follower pin out of the opening 1088. A cross pin 1096 can extend through the opening 1082 and engage the follower pin 1094 to limit the range of travel of the follower pin 1094 and inhibit rotation of the follower pin 1094 within the aperture 1088.

A proximal end of the follower pin 1094 engages a cam leg 1097 of the arm 1031A, shown in FIG. 20 such that when the arm 1031A is in the retracted position (see FIG. 14A) the cam leg 1097 pushes the follower pin 1094 into the aperture 1088 compressing the spring 1095. As the arm 1031A is extended from the spreader 1030 the cam leg 1097 moves away from the housing 1080 allowing the follower pin 1094 to move proximally.

Figure 26:
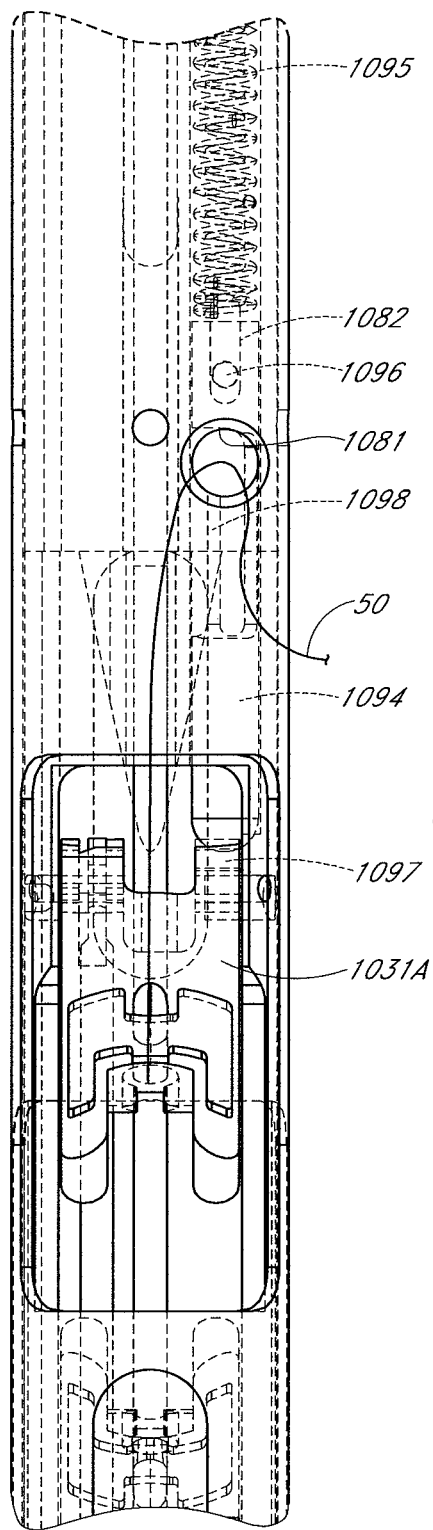
FIG. 26 illustrates a top view of a distal end of an embodiment of a suturing device with various features shown in phantom lines.

The follower pin 1094 can have a hook 1098, as illustrated in FIG. 26. A portion of the suture 50 that is looped through the opening 1081 extends around the hook 1098. When the arm 1031A is moved into the closed position, the follower pin 1094 moves distally such that the hook retains the suture 50 within the opening 1081. As the follower pin 1094 moves proximally when the arm 1031A is extended from the spreader 1030, the hook 1098 releases the suture 50 to permit the suture 50 to be pulled from the opening 1081.

The suture retention mechanism can allow the user of the device 1100 to control the release of the suture 50 from the opening 1081 in the housing 1080 to reduce the likelihood of the suture end portion 52A being pulled prematurely from the suture clasp 1033A, to provide slack in the suture 50 when the suture catch mechanism retrieves the suture end portion 52A, and to release the suture 50 to permit the suture catch mechanism pull the suture 50 through a biological structure.

In some embodiments, the suture catch mechanism 1161 can be similar to or the same as the suture catch mechanism 161, shown in FIG. 7A. The suture catch mechanism 1161 can be configured for engaging the suture clasp arm 1031A and can comprise an elongate, straight needle.

In some embodiments, the suture catch mechanism 1165 can be similar to or the same as the suture catch mechanism 165, shown in FIG. 7B. The suture catch mechanism 1165 is configured to engage a suture clasp arm 1031B and can comprise a bent needle.

In use, the needles 1161 and 1165, like the needles 161 and 165 shown in FIG. 8A, can be housed within passageways formed by lumens within the elongate tubular member 1020, spreader 1030, and the housing 1080. Referring to FIG. 18A, the suture catch mechanism 161 is slidably housed in the lumen 1021 of the elongate tubular member 1020, while suture catch mechanism 165 is slidably housed in the passageway formed by the lumen 1023 of the elongate tubular member, the lumen 1133 of the spreader 1030, and lumen 1083 of the housing 1080.

As shown in FIGS. 16-18, the spreader 1030 includes a plurality of needle guides 1060A and 1060B for guiding a plurality of suture catch mechanisms, such as a needle or other penetrating mechanism, towards the deployed suture clasp(s). In one embodiment, the spreader 1030 may comprise two needle guides 1060A and 1060B located on the distal and proximal ends of the spreader 1030 for guiding two needles toward deployed suture arms 1031A and 1031B illustrated in FIG. 19. Each of the needle guides 1060A and 1060B comprises an angled groove or channel in the sidewall of the spreader 1030 such that it will deflect a suture catch mechanism, or needle, exiting the suture assembly 1090 along a path that intercepts the suture clasps 1033A and 1033B of the suture clasp arms when the suture clasp arms 1031A and 1031B are in a deployed position. In some embodiments, the suture arms 1031A and 1031B may be similar to or the same as the suture arms 31A and 31B. For example, the suture arms 1031A and 1031B can be sized such that a groove having an angle of between about 10-35.degree., alternatively about 15-25.degree., alternatively about 19.degree. with respect to the longitudinal axis of the spreader assembly will spread the needles to the proper angle to engage the suture loops in the deployed suture clasps 1033.

In use, the proximal needle guide 1060A (FIGS. 16 and 18A) is aligned with the lumen 1021 of the elongate tubular member such that when a suture catch mechanism is advanced through the lumen 1021, the distal end of the needle will be deflected by the needle guide 1060A towards the deployed suture clasp arm 1031A. Once the needle 1161 penetrates the suture clasp 1033A on the suture clasp arm 1031A and engages the suture portion 52A held by the suture clasp 1033A, the needle 1161 may be retracted back into the lumen 1021 with the suture portion 52A held on the distal end of needle 1161, in a manner similar to that shown in FIG. 8C.

Likewise, distal needle guide 1060B (FIGS. 17 and 18A) is aligned with aperture 1083 of the housing 1080 such that when the distal tip of a needle housed in aperture 1083 is extended towards the suture clasp arm 1031B, the needle will be deflected toward the suture clasp 1033B. Before insertion, the needle 1165, similar to the needle 165, has been advanced through the lumen 1023 in the elongate tubular member 1020 beyond the spreader 1030 and positioned a slot or cavity 1083 within the housing 1080 of the suturing device that has been aligned with the lumen 1133 of the spreader 1030. The cavity 1083 is sized to receive the distal end of the needle 1165, including a turned portion similar to the turned portion 166 (see FIG. 7B). The turned portion is positioned in cavity 1083 such that the distal tip is aligned with the needle guide 1060B located on the distal end of the spreader 1030.

Thus, in use, when the proximal end of the needle 1165 is pulled back through the lumen 1023 of the elongate tubular member 1020, the turned portion of the needle will be advanced along the groove of the needle guide 1060B and deflected outward along the angle path of the groove to penetrate the deployed suture clasp 1033B on the suture clasp arm 1031B and engage suture portion 52B held therein. Once the needle 165 has engaged the suture portion 52B, the proximal end of the needle 165 may then be pushed forward through the lumen 1023 of the elongate tubular member which will cause the bent portion of the needle to be retracted along needle guide 1060B into cavity 1083 along with the suture portion 52B held on the needle 1165.

Under some circumstances, a suture catch mechanism, such as the needle 1161 or the needle 1165, when advanced may be oriented in direction toward a location slightly closer to or slightly farther from a longitudinal axis of the device 1100 than the center of the suture clasp 1033. A suture catch mechanism that is oriented in a direction that is toward a location slightly closer to or slightly farther from the longitudinal axis of the device 1100 than the center of the suture clasp 1033 may, in some instances, not properly engage the suture. As a result, the suture catch mechanism may not successfully retract the suture end portion.

Figure 22:
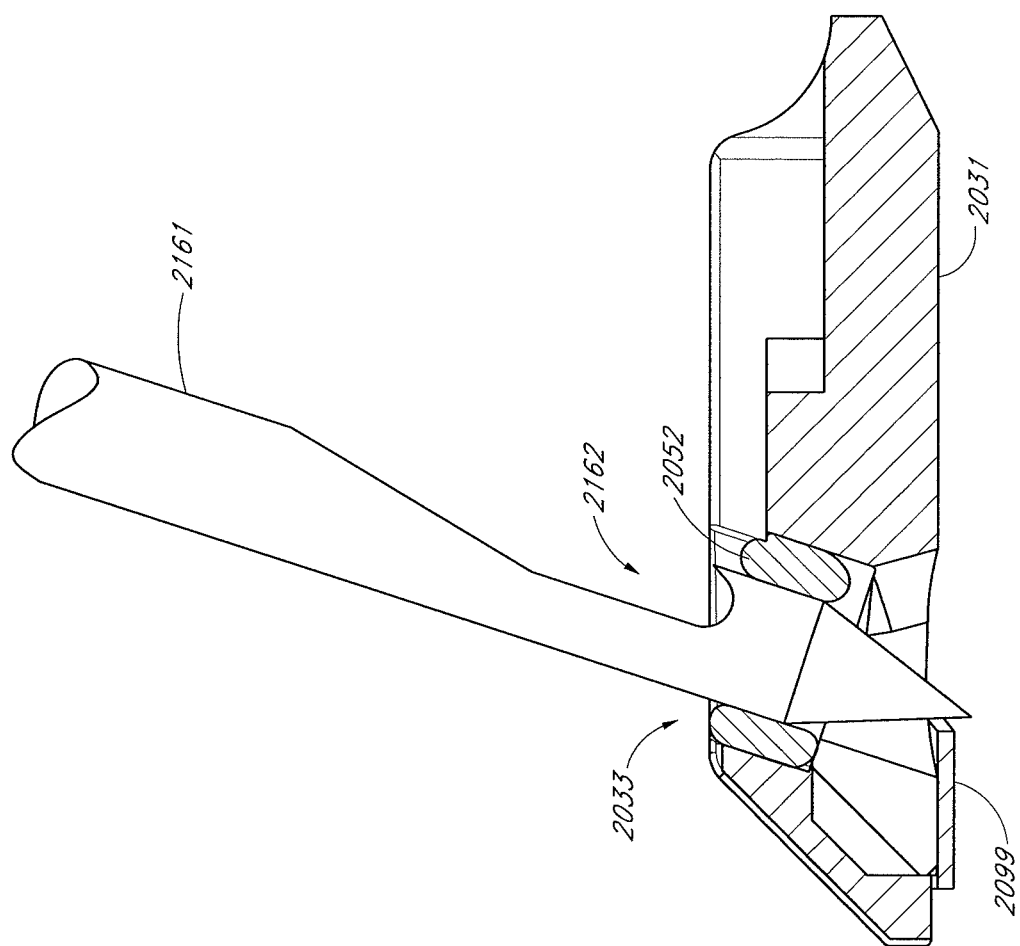
FIG. 22 illustrates a cross-sectional view of a suture clasp arm and a needle.

In some embodiments, the one or more of the suture clasp arms 1031 can have a deflector, such as deflecting plates 1099, 2099, shown in FIGS. 20-23. The deflecting plates 1099, 2099 are shown partially obscuring an opening on a back side of the suture clasp 1033 relative to the direction from which a suture catch mechanism, such as a needle 2161, penetrates the suture clasp 2033, as shown in FIG. 22. As the needle 2161 passes through the suture clasp 2033, the needle 2161 engages the deflector plate 2099, as shown in FIG. 22, and is diverted from its previous course toward a longitudinal axis of the device 1100. In an alternative embodiment, the suture catch mechanism can be diverted away from a longitudinal axis of the device. As the needle 2161 is diverted toward the longitudinal axis of the device, a suture engaging portion, such as a hook, recess, or groove 2161, moves toward a portion of a suture end 2052, shown schematically in FIG. 22.

The dimensions of the needle including the size and location of the suture engaging portion and the size and shape the needle tip, the size of the suture clasp, and the distance by which the deflectors obscure the back opening of the suture clasp should be relatively proportioned such that the deflectors 1099, 2099 cause the suture engaging portion of the needle to engage the portion of the suture end as the needle returns to its previous orientation. Thus, in the embodiment illustrated in FIG. 22, the hook 2162 would engage the suture portion 2052 as it retracted from the suture clasp 2033.

Figure 23:
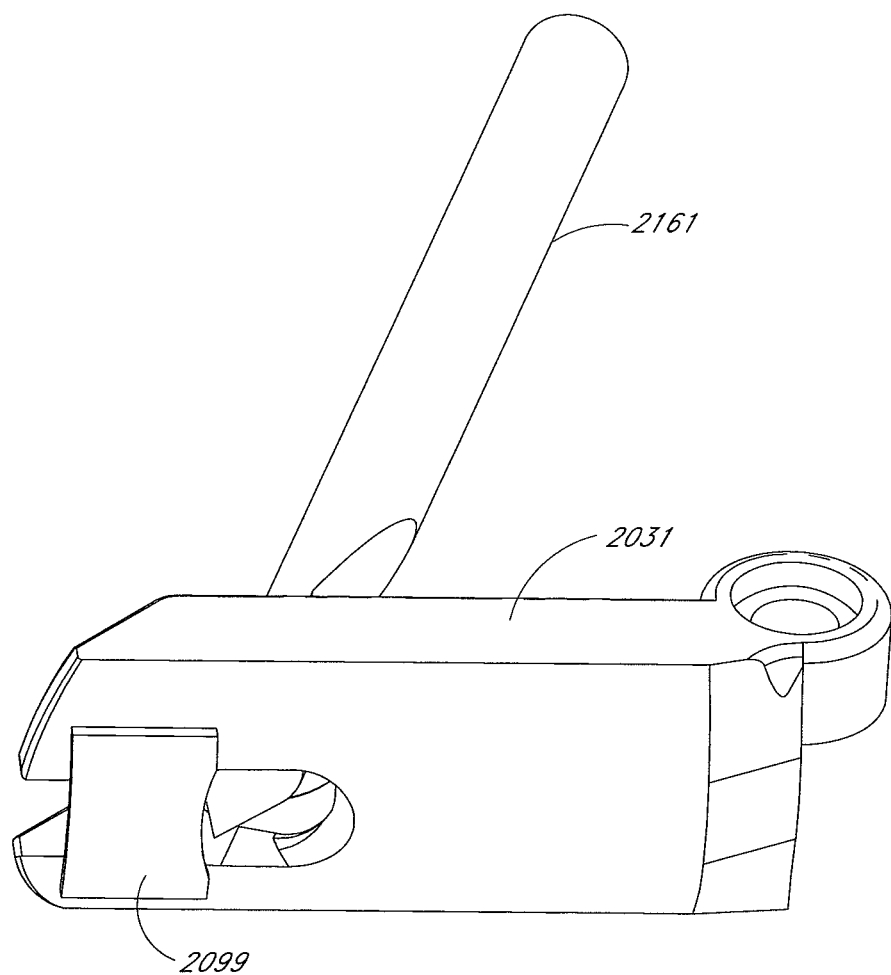
FIG. 23 illustrates a perspective view of the suture clasp arm and the needle of FIG. 22.

The deflector plates may be generally rectangular, as shown in FIG. 23, or may have other configurations, such as generally H-shaped as shown in FIG. 21. In some embodiments, the deflector plates can be made from metal, while in other embodiments the deflector plates can be made of plastics or other materials of sufficient rigid or resiliency to deflect a suture catch mechanism. The deflector plates may be joined to the suture clasp arms by welding, epoxy, adhesives or by other methods. In an alternative embodiment, the deflectors can be integrally formed with the suture clasp arm.

In some embodiments, the deflectors can compensate for misalignment of a suture catch mechanism with the center of a suture clasp relative to a longitudinal axis of the device to provide consistent capture of a suture end portion by the suture catch mechanism.

In some embodiments, bending of the elongate tubular member can affect the relative positions of the ends of the suture catch mechanisms to the spreader assembly. For example, if an elongate tubular member is bent then a distal end of a suture catch mechanism extending along the inside of the bend in the elongate member relative to the central axis of the elongate tubular member would be advanced relative to the spreader assembly. In such a circumstance, the suture catch mechanism may be advanced through a suture clasp farther than is desired, which may result in enlargement of a loop at an end of a suture that in turn inhibits the ability of the suture catch mechanism to retract the and of the suture.

On the other hand, if an elongate tubular member is bent then a distal end of a suture catch mechanism extending along the outside of the bend in the elongate member relative to the central axis of the elongate tubular member would be retracted relative to the spreader assembly. In such a circumstance, the suture catch mechanism may not be advanced through a suture clasp far enough to engage a suture end portion held by the suture clasp.

In some embodiments, the effects of bending of the elongate tubular member can be reduced or eliminated by using a suture catch mechanism that is sufficiently long to engage the corresponding suture clasp even if the suture catch mechanism extends along the outside of a bend in the elongate member relative to the central axis of the elongate member. Advancement of the suture catch mechanism may be limited by providing a stop mechanism in proximity to the spreader assembly where the effects of bending are small or absent.

Figure 18B:
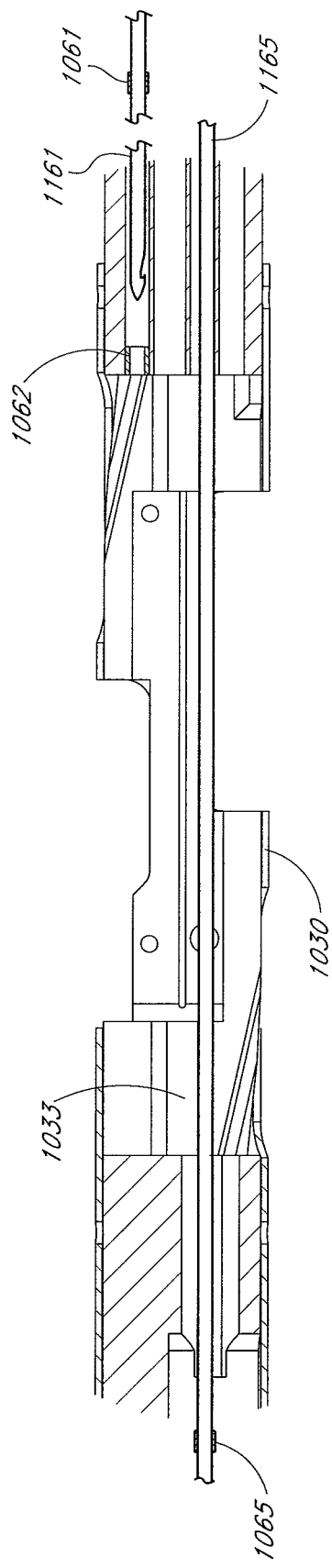
FIG. 18B illustrates a cross-sectional view of a distal end of an elongate tubular member, a spreader assembly, and a housing showing features for limiting the range of travel of suture catch mechanisms.

For example, as illustrated in FIG. 18B, a tube 1061 can be attached to the needle 1161 and another tube 1062 can be attached to the elongate tubular member 1020 within a counterbore in the lumen 1021. The inner diameter of tube 1062 is smaller than the outer diameter of tube 1061 such that tube 1061 cannot be advanced through tube 1062, thereby limiting the advancement of the needle 1161 relative to the spreader 1030.

Alternatively, the tube 1061 can be attached to the needle 1161 and extend over a portion of the length of the needle 1161 within the lumen 1021. In this configuration, the tube 1061 limits the movement of the suture catch mechanism by preventing movement of the suture catch mechanism along the guide 1060A by interference of the tube 1061 with the proximal end of the spreader 1030.

Similarly, movement of the bent needle 1165 toward the suture clasp arm 1031B can be limited by attachment of a tube 1065 to the needle 1165 at a location distal to the spreader 1030. The tube 1065 has an outer diameter that is larger than a dimension of the lumen 1133 such that the tube 1065 cannot be moved into the spreader 1030 as the needle 1165 is moved proximally, thereby limiting the movement of the needle 1161 relative to the spreader 1030 in a proximal direction.

In an alternative embodiment, the suture catch assembly may comprise four needles, for example two needles housed on each side of the elongate tubular member for engaging multiple suture portions in each of the suture clasp arms. Here, each of the needles may be independently actuated or alternatively both needles for engaging a single suture clasp arm may be jointly actuated such that they are deployed at the same time.

The distal tip 1070 is shown in FIGS. 14A, 19, and 29A as having a tapered configuration, but may alternatively be rounded or have other configurations. The distal tip 1070 is preferably atraumatic and can be bonded, adhered, or otherwise joined to the distal end of the spreader assembly 1090, for example, by insert molding or any other suitable technique known to those skilled in the art. The distal tip 1070 can have at least one lumen 1072 that forms a continuous passage with the aperture 1085 and the slot 1089 of the housing 1080 (FIG. 25) and the slot 1039 (FIG. 16) of the spreader 1030 and lumen 1027 of the elongate tubular member 1020 (FIG. 15A), which may accommodate, for example, a guidewire.

In addition, the distal tip 1070 may have one or more additional lumens 1173 that can be aligned with lumens in the spreader assembly 1030 and elongate tubular member 1020 to provide additional continuous passageways, for example for housing a suture catch mechanism. Here, as discussed above, the outer diameter of the distal tip is substantially the same size as the inner diameter of the casing 1040 such that when the distal end of the casing 1040 is positioned over the connection between the distal tip 1070, the housing 1080, and the spreader 1030, the casing maintains the proper alignment of the internal lumens of the distal tip 1070, the housing 1080, the spreader 1030, and the elongate member 1020.

Figure 27:
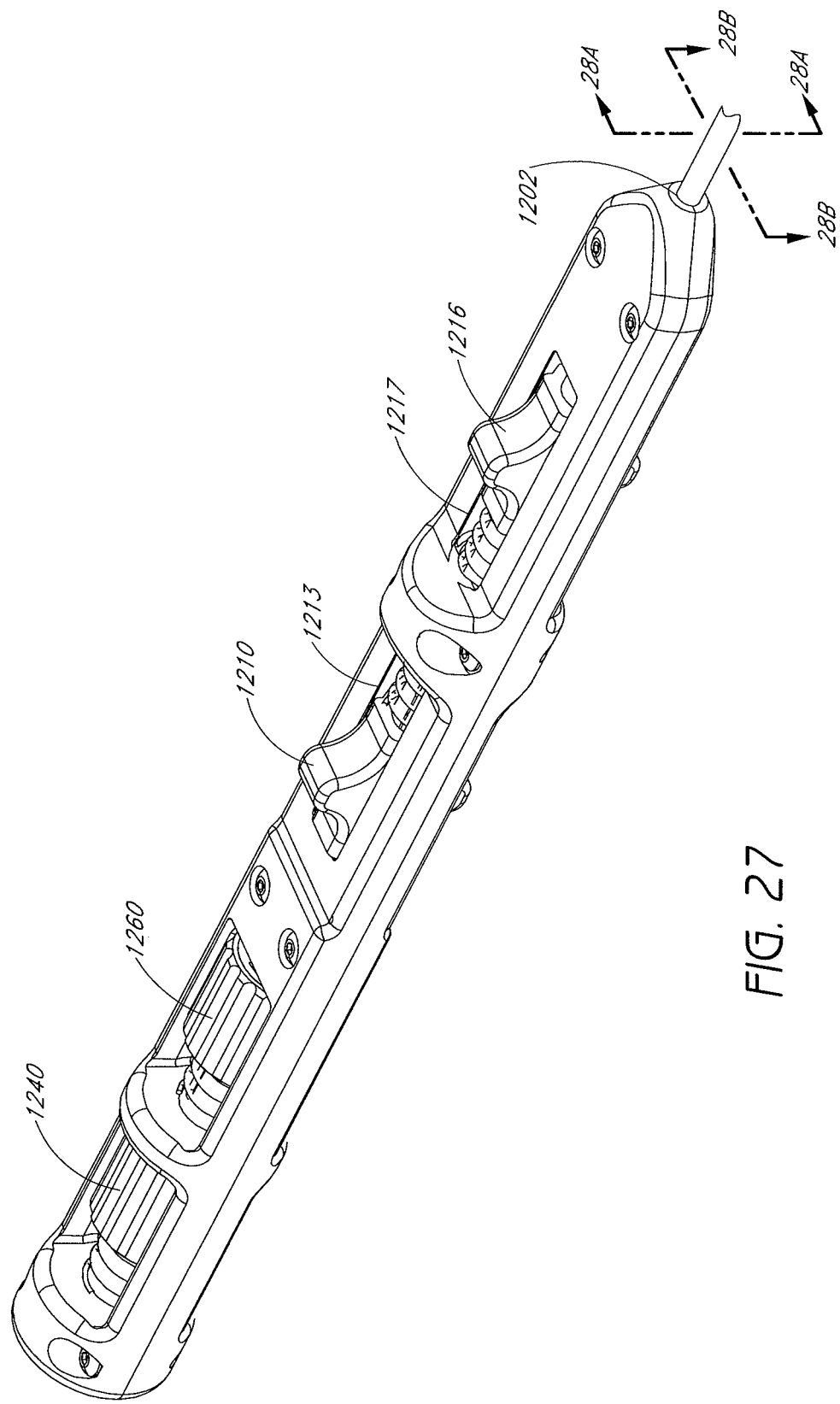
FIG. 27 is a perspective view of one embodiment of a handle of the suturing device.
Figure 28A:
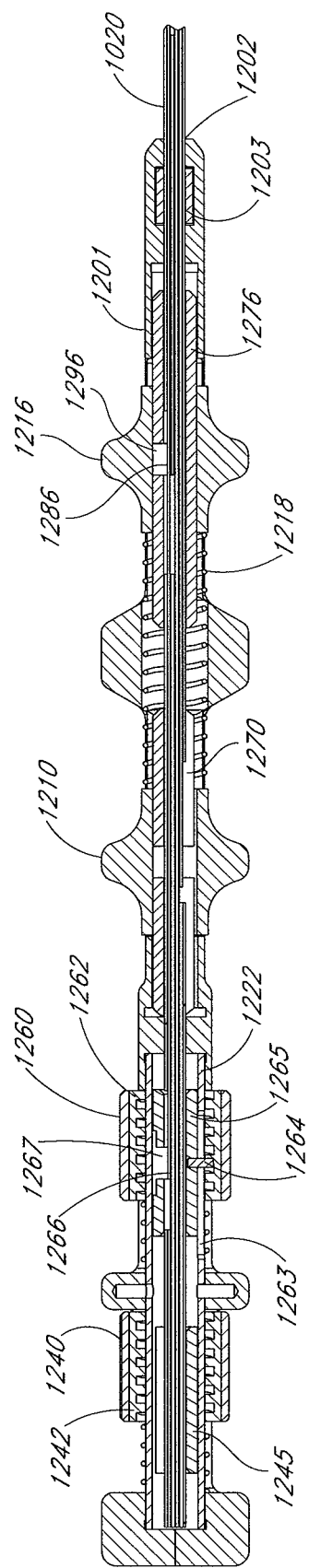
FIG. 28A is a cross-sectional view of the handle of FIG. 27 taken along the line 28A-28A shown in FIG. 27.
Figure 28B:
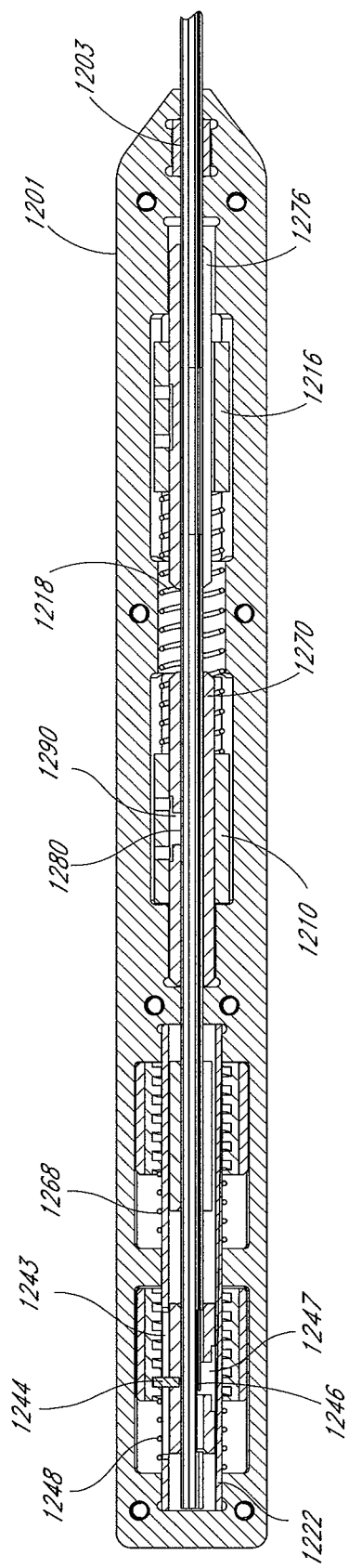
FIG. 28B is a cross-sectional view of the handle of FIG. 27 taken along the line 28B-28B shown in FIG. 27.

Referring now to FIGS. 27, 28A, and 28B, the proximal end of the needles 1161 and 1165 extend through the lumens 1021 and 1023 of the elongate tubular member and terminate at a connection to pulls 1210 and 1216 on the suturing device handle 1200. The handle 1200 includes a housing 1201 which is attached to the proximal end of the elongate tubular member 1020. The housing 1201 has an aperture 1202 providing a passageway between the handle 1200 and the multiple lumens of the elongate tubular member 1020. One or more actuators 1210, 1216, 1240 and 1260 may extend from the housing 1201. The pulls or knobs 1210, 1216, 1240 and 1260 can be connected to actuating rods or mechanisms for deploying and/or retracting the suture clasp arms and suture catch mechanisms moveably housed in the suturing device.

The elongate member 1020 is fixed to the housing 1201 in any suitable manner such as by welding, adhesion, or other bonding process to a collar 1203. The cylinder 1203 is engaged by the housing 1201. The cylinder 1203 can be rectangular or any other shape. The cylinder 1203 is connected to the housing 1201 in a manner that prevents limits rotation of the cylinder 1203 with the member 1020 relative to the housing 1201. The elongate member 1020 has a plurality of cutouts (not shown) that expose the actuator rods 1035 and the suture catch mechanisms 1161 and 1165 for connection to the actuators 1210, 1216, 1240, and 1260.

With reference to FIGS. 27, 28A, and 28B, in some embodiments, the handle 1200 can have two pulls 1210 and 1216 for deploying and retracting the suture catch mechanisms such as needles 1161 and 1165 of the suturing device. The pulls 1210 and 1216 can extend from the housing through openings 1213 and 1217, respectively, as shown in FIG. 27.

In one embodiment, the proximal end of needle 1165 extends from the proximal end of the lumen 1023 in the elongate tubular member through opening 1202 into the handle 1200 and is exposed by a cutout in the elongate tubular member 1020 for connection to a shaft 1276, shown in FIGS. 28A and 28B. The shaft 1276 can be generally U-shaped to permit the shaft to pass over the elongate member 1020 in a direction transfers to a longitudinal axis of the member 1020. The needle 1165 may be connected to the shaft 1276 directly by a suitable bonding process, or indirectly, such by connection to a small tube that is adhered to the needle 1165, for example, by epoxy, which is in turn connected to a tab 1286. The tab 1286 can be connected to the shaft 1276 at a notch 1296 in the shaft 1276. The pull 1216 can be connected to the shaft by a bonding process or by mechanical means, such as a set screw.

Similarly the proximal end of needle 1161 extends from the proximal end of the lumen 1021 in the elongate tubular member 1020 through opening 1202 into the handle 1200 and is exposed by a cutout in the elongate tubular member 1020 for connection to a shaft 1270, shown in FIGS. 28A and 28B. The shaft 1270 can be generally U-shaped to permit the shaft to pass over the elongate member 1020 in a direction transfers to a longitudinal axis of the member 1020. The needle 1161 may be connected to the shaft 1270 directly by a suitable bonding process, or indirectly, such as by connection to a small tube (not shown) that is adhered to the needle 1161, for example, by epoxy, which is in turn connected to a tab 1280. The tab 1280 can be connected to the shaft 1270 at a notch 1290 in the shaft 1270. The pull 1210 can be connected to the shaft by a bonding process or by mechanical means, such as a set screw.

In some embodiments, a spring 1218 can be positioned between the pulls 1210 and 1216. The spring 1218 can bias the needle 1161 proximally and the needle 1165 distally by biasing the pull 1210, which is connected to the needle 1161, from the pull 1216, which is connected to the needle 1165. A user can advance the needle 1161 by moving the pull 1210 to compress the spring 1218. The spring 1218 can assist in retraction of the needle 1161 as the spring 1218 decompresses. Similarly, a user can draw the needle 1165 proximally by moving the pull 1216 to compress the spring 1218. As the spring 1218 decompresses the needle 1165 is moved distally within the elongate member 1020.

The suture claps arms 1031A and 1031B can be deployed by rotation of actuators, or knobs, 1240 and 1260. For example, the knobs 1240, 1260 can be connected to threaded members 1242, 1262 in a manner that prevents the knobs 1240, 1260 from rotating with respect to the threaded members 1242, 1262. A tube 1222, which can be fixedly attached to the housing 1201, can extend through the threaded members 1242, 1262 such that the threaded members 1242, 1262 can both slide over and rotate with respect to the tube 1222.

The tube 1222 can have two slots 1243 and 1263 corresponding to the threaded members 1242, 1262. The two slots 1243 and 1263 are configured to allow two pins 1244 and 1264 to extend through the slots 1243, 1263 and operatively engage the threaded members 1242, 1262 such that rotation of the threaded members 1242, 1262 with respect to the tube 1222 causes the pins 1244, 1264 to move along the length of the slots 1243, 1263.

The pins 1244, 1264 are connected to shafts 1245, 1265 positioned within the tube 1222. The shafts 1245, 1265 can be connected to the actuator rods 1035A and 1035B by tabs, 1246, 1266. The tabs 1246, 1266 can be welded or otherwise attached to the actuator rods 1035A and 1035B and attached by any suitable bonding process to the shafts 1245, 1265 at notches 1247, 1267.

Accordingly, as a user rotates knobs 1240, 1260, the threaded members 1242, 1264 move the pins 1244, 1264 along the slots 1243, 1263. Movement of the pins 1244, 1264 in a direction along a longitudinal axis of the handle 1200 causes the shafts 1245, 1265 to move the actuator rods 1035A and 1035B either proximally or distally depending on the direction of rotation of the knobs 1240, 1260. As discussed above, proximal and distal movement of the actuator rods 1035A and 1035B causes the suture clasp arms 1031A and 1031B to move between a retracted position, shown in FIG. 14A, and an extended position, shown in FIG. 19. The knobs 1240, 1260 can be rotated individually to independently deploy and retract the suture clasp arms 1035A and 1035B.

In some embodiments, the handle 1200 can also comprise springs 1248, 1268 that bias the threaded members 1242, 1262 along the tube 1222. The springs 1248, 1268 can bias the threaded members 1242, 1262 either proximally or distally. In one embodiment, the springs 1248, 1268 bias the threaded members 1242, 1262 in directions that bias the suture clasp arms 1031A, 1031B toward in their extended positions such that rotation of the threaded member 1242, 1246 past the fully open position of the suture clasp arms 1031A, 1031B results in compression of the springs 1248, 1268. Alternatively, the springs 1248, 1268 can bias the threaded members 1242, 1262 in directions that bias the suture clasp arms 1031A, 1031B toward in their retracted positions.

The operation of the device 1100, described above, is illustrated according to one embodiment in FIGS. 29A-29I in conjunction with a procedure for closing a patent foramen ovale (PFO) in a patient's heart. As shown in FIG. 29A, the distal end of a suturing device 1100 is advanced through a venous access, such as the inferior vena cava, into the patient's left atrium and positioned in the tunnel 8 of the PFO between the septum primum 7 and the septum secundum 6. The suturing device 1100 may be advanced over a guidewire 10 or alternatively delivered through a catheter introducer sheath 1011 using techniques which are known in the art.

The suturing device 1100 is initially positioned with the distal tip 1070 extending beyond the tunnel of the PFO, such that the spreader assembly 1090 is near the tip of the secundum primum 7 and at least the suture clasp deployment arm 1031A is permitted to extend from the spreader assembly 1090. The suture clasp arm 1031A may then deployed from the spreader assembly 1090 and then the device 1100 is retracted until the suture clasp arm 1031A extends around the tip of the secundum primum 7, as shown in FIG. 29B, and gathers the tissue of the septum primum 7 between the arm 1031A and the spreader 1030. Referring to FIG. 26, as the arm 1031A is extended, the follower pin 1094 moves proximally to permit the suture 50 to be pulled from the opening 1081 in the housing 1080. With continued reference to FIG. 29B, the suture clasp arm 1031A holds a suture portion 52A, which may or may not still extend from opening 1081 of the housing 1080, in the suture clasp 1033A such that the suture portion 52A is positioned on the opposite side of the secundum primum 7 relative to the suturing device 1100.

Once the suture clasp arm 1031A has been properly positioned around the septum primum 7, needle 1161 may be deployed from the suturing device 1100 to penetrate the septum primum 7 and engage the suture clasp arm positioned on the opposite side of the septum primum 7. As discussed above, the needle 1161 is advanced through a passageway in the suturing device and deflected by needle guide 1060A (FIG. 18A) along an angle that intersects the deployed suture clasp arm 1031A as it exits the suturing device 1100. The needle has a sharp distal tip which penetrates the tissue of the septum primum 7 and engages suture clasp 1033A located on the tip of the suture clasp arm 1031A, as shown in FIG. 29C. The needle is initially advanced through the suture clasp 1033A which holds a suture portion 52A. When the needle is advanced through the suture clasp 1033A, a groove or hook on the needle tip engages the suture portion 52A.

As shown in FIG. 29D, once the suture loop has been engaged, the needle 1161 and engaged suture portion 52A are then retracted through the tissue of the septum primum 7 and into the lumen 1021 of the elongate member 1020 of the suturing device 1100. Once the suture has been engaged and pulled through the tissue of the septum primum 7, the device 1100 may be advanced slightly so that the suture clasp arm 1031A can be closed without pinching the septum primum 7. The device 1100 may then be repositioned such that the spreader assembly 1090 is adjacent the tip of the septum secundum 6.

As shown in FIG. 29E, the suturing device 1100 is withdrawn proximally through the tunnel of the PFO 8 until the suture clasp arm 1031B can be deployed. The suture clasp arm 1031B can then be extended then the device 1100 can be advanced such that the suture clasp arm 1031B extends around the tip of the septum secundum 6, as shown in FIG. 29F, and gathers the tissue of the septum secundum 6 between the arm 1031B and the spreader 1030. The suture clasp arm 1031B holds a suture portion 52B extending from opening 1042 in suture clasp 1033B such that the suture portion 52B is positioned on the opposite side of the septum secundum 6 relative to the PFO 8 and the suturing device 1100.

Figure 29G:
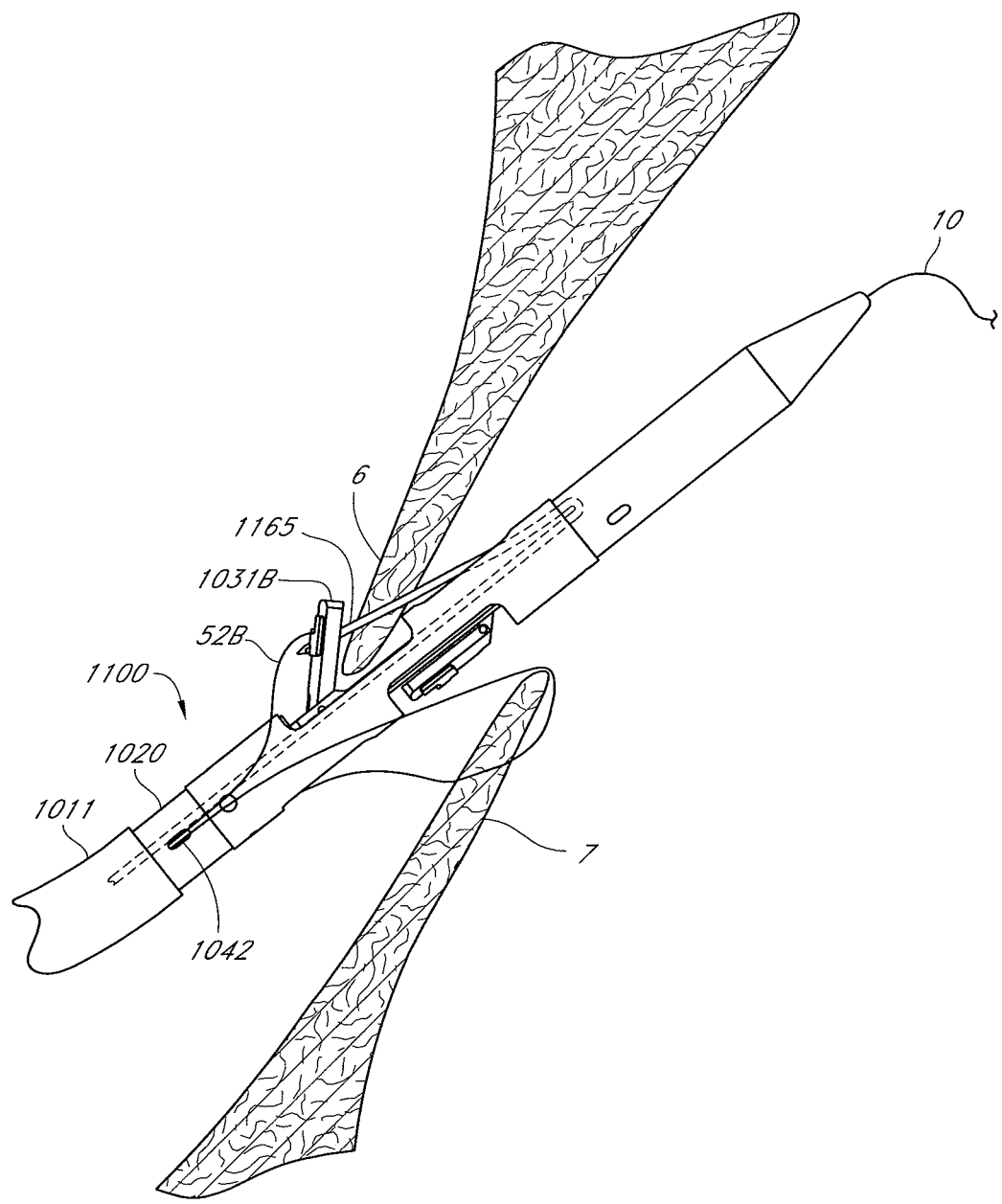
FIG. 29G is a schematic representation as in FIG. 29F showing the distal needle engaging the proximal suture clasp arm.

Once the suture clasp arm 1031B and suture portion 52B have been properly positioned around the septum secundum 6, the needle 1165 may be deployed from the distal end of the suturing device 1100 to penetrate the septum secundum 6 and engage the suture portion 52B. As shown in FIG. 29G, the tip of the needle 1165 is pulled proximally from a location distal the suture clasp arm 1031B through the tissue of the septum secundum 6 towards deployed suture clasp arm 1031B.

The needle 1165 is deflected outward by a needle guide 1060B (FIG. 18A) as the needle 1165 extends from the suturing device 1100 along an angle that intersects the suture clasp 1033B located on the tip of deployed suture arm 1031B. The needle 1165 has a sharp distal tip which penetrates the tissue of the septum secundum 6 and engages suture clasp 1033B located on the tip of the suture clasp arm 1031B. The needle 1165 is initially advanced through the suture clasp 1033B which holds a portion of suture 52B. When the needle 166 is advanced through the suture clasp 1033B, a groove or hook on the needle tip engages the suture portion 52B.

Figure 29H:
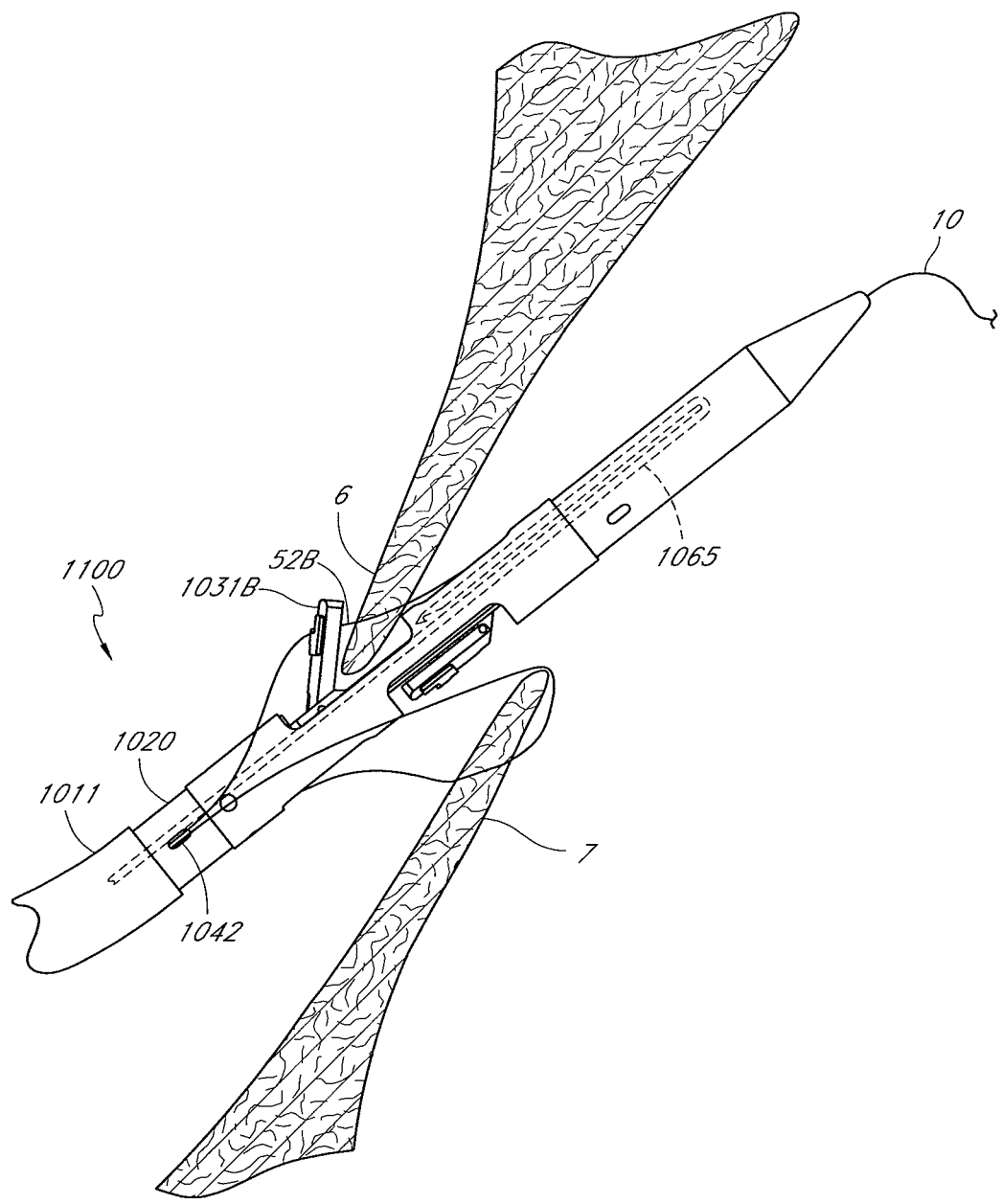
FIG. 29H is a schematic representation as in FIG. 29G following retraction of the distal needle and suture portion through the septum secundum.
Figure 291:
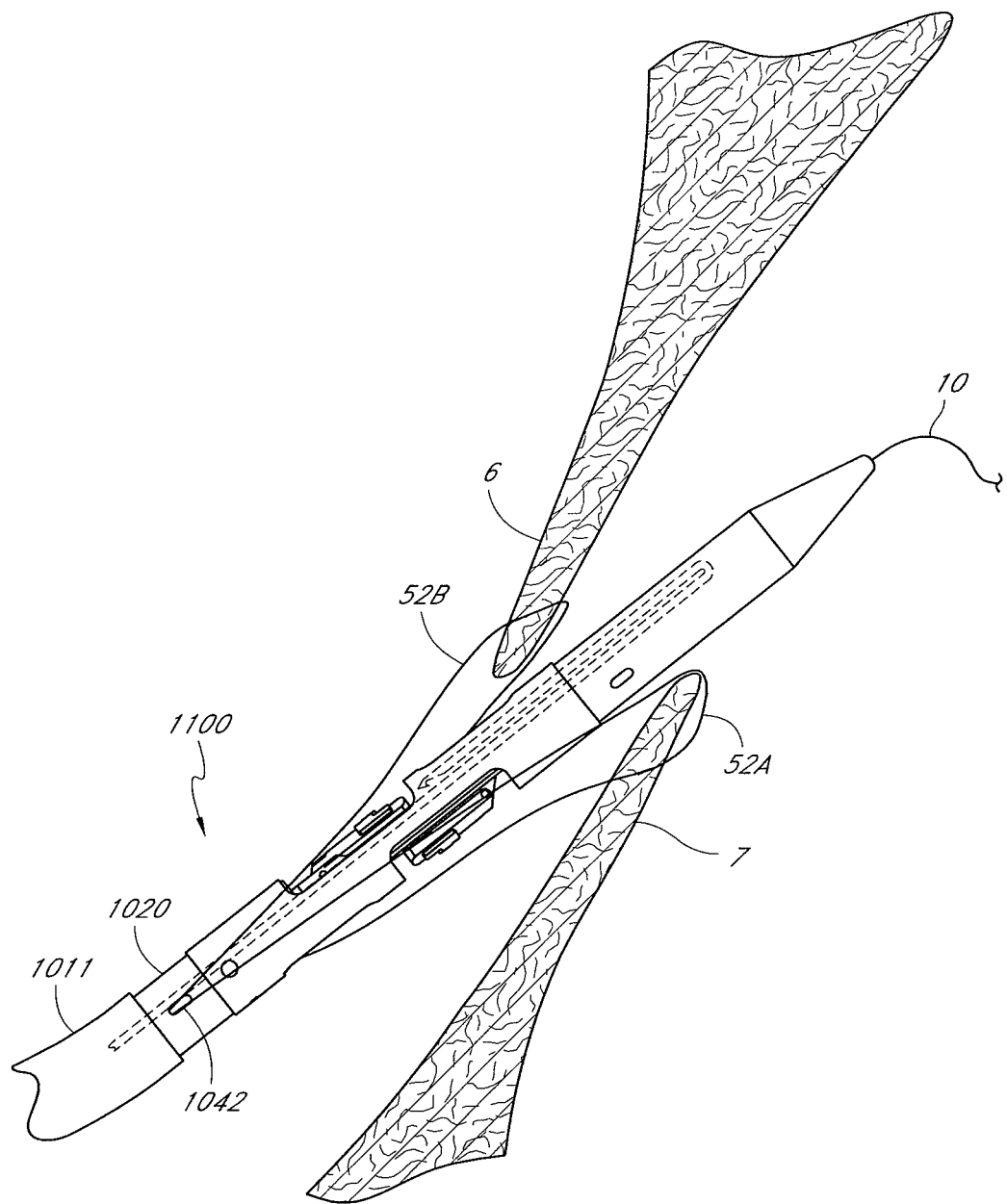

As shown in FIG. 29H, once the suture portion 52B has been engaged, the needle 1165 and engaged suture portion 52B are then retracted distally through the tissue of the septum secundum 6 and into the cavity 1083 of the suturing device 1100. The suture clasp arm 1031B may then be closed and the suturing device 1100 may be withdrawn from the patient's heart.

As shown in FIG. 29I, the suture portion 52A has been positioned through the septum primum 7 while suture portion 52B has been positioned through the septum secundum. After the suturing device 1100 has been withdrawn, the suture portions 52A and 52B will extend proximally from the PFO and can then be pulled to draw the septum secundum 6 and septum primum 7 towards one another to close the PFO, as shown in FIG. 10I, 10J, or 10K. As the suture 50 is pulled tight, the suture 50 preferably causes the septum secundum 6 and septum primum 7 to turns or folds so that the tip of the septum primum 7 extends in the opposite direction compared to the tip of the septum secundum 6, as illustrated in FIG. 10k.

With the suture portions 52A and 52B extending away from the PFO, a knot may be applied to the PFO to close the PFO. For example, a device for applying a knot may be used, such as described in U.S. Patent Publication No. 2007-0010829 A1, published Jan. 11, 2007, the entirety of which is hereby incorporated by reference. Alternatively, the method of securing the suture portions illustrated in FIG. 10L by applying a patch 254 may be used. As noted above, further details regarding delivery of a patch, as well as other devices, structures and methods that may be incorporated with the above or below embodiments, may be found in U.S. Pat. Nos. 5,860,990, 6,117,144, and 6,562,052, the entirety of each which is hereby incorporated by reference.

The operation of the device 1100', described above and shown in FIGS. 14B and 15B, is illustrated according to one embodiment in FIGS. 29J-29M in conjunction with a procedure for closing a patent foramen ovale (PFO) in a patient's heart. The operation of the device 1100' can be similar to the operation of the device 1100 in some respects. For example, the distal end of a suturing device 1100' is advanced through a venous access, such as the inferior vena cava, into the patient's left atrium and positioned in the tunnel 8 of the PFO between the septum primum 7 and the septum secundum 6 then operated in the manner described above with reference to FIGS. 29A-D to pass a suture portion 52A through the septum primum 7.

The operation of the device 1100' can differ from the operation of the device 1100 in other respects. In particular, the device 1100' can be used in conjunction with the second guidewire 1010 to facilitate placement of a suture portion through the septum secundum 6 in a location at or near a center of the septum secundum 6. Such placement of the suture through the septum secundum 6 may improve the likelihood of successful closure of the PFO. If the suture is placed through the septum secundum 6 at a location too far removed from the center of the septum secundum 6, to one side or the other, blood may continue to flow through the PFO after placement of the suture and application of a knot to the suture. Thus, use of the device 1100' with the second guidewire 1010 can improve the likelihood of securely closing the PFO.

Figure 29J:
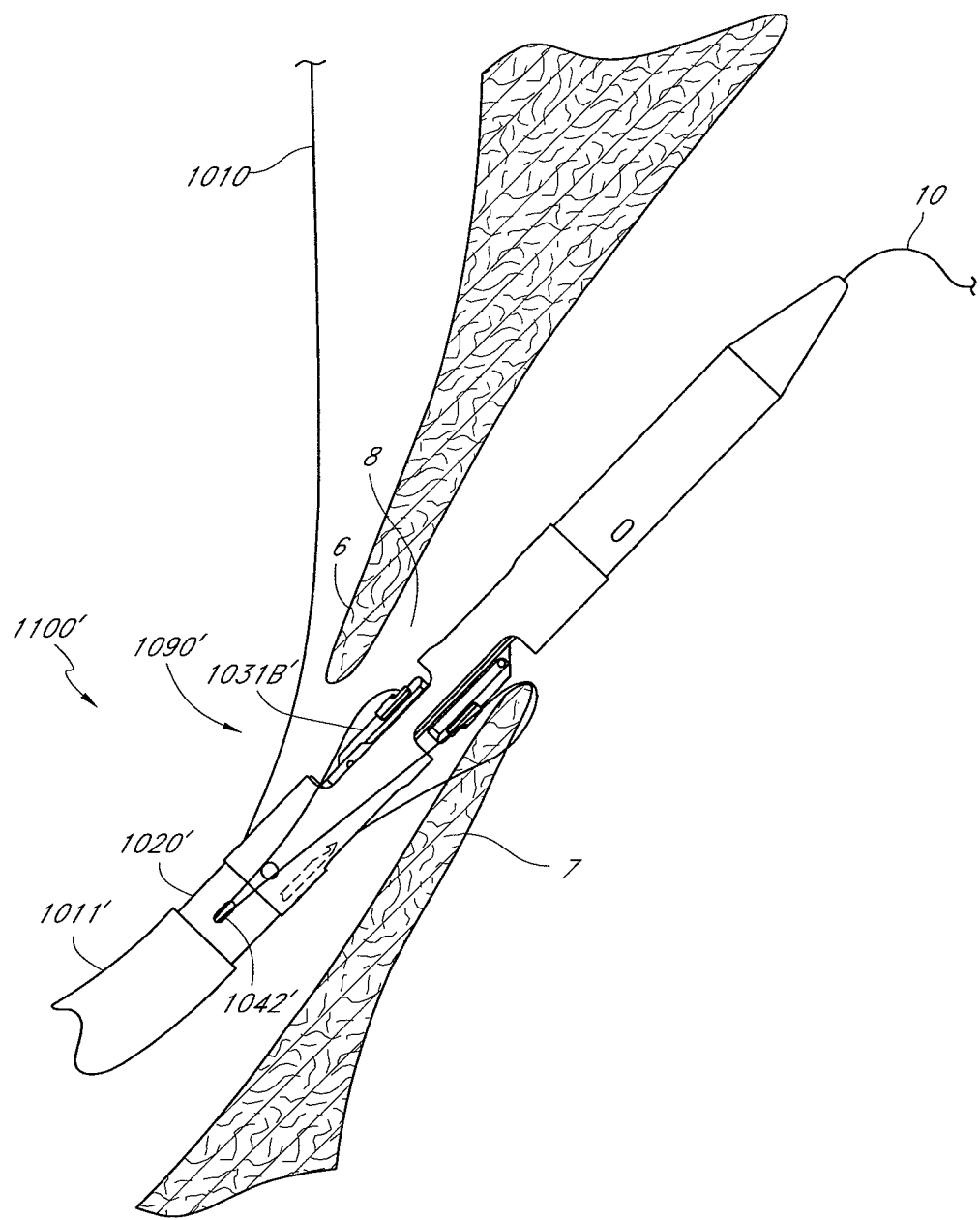
FIG. 29J is a schematic representation as in FIG. 29D showing the suturing device of FIGS. 14B and 15B positioned to permit the proximal suture clasp arm to extend from the suturing device and a second guide wire extended.

Once the suturing device 1100' has been operated in the manner described above with reference to FIGS. 29A-D, the suturing device 1100' may be withdrawn proximally through the tunnel of the PFO 8 until the suture clasp arm 1031B' can be deployed, as shown in FIG. 29J. The second guidewire 1010 can be advanced from the lumen 1029' (FIG. 15B) through the opening 1043' (FIG. 14B) into the superior vena cava (FIG. 1). The second guidewire 1010 may be preloaded in the device 1100' before introduction of the device 1100' into the body such that a distal end of the second guidewire is near the opening 1043'.

Figure 29K:
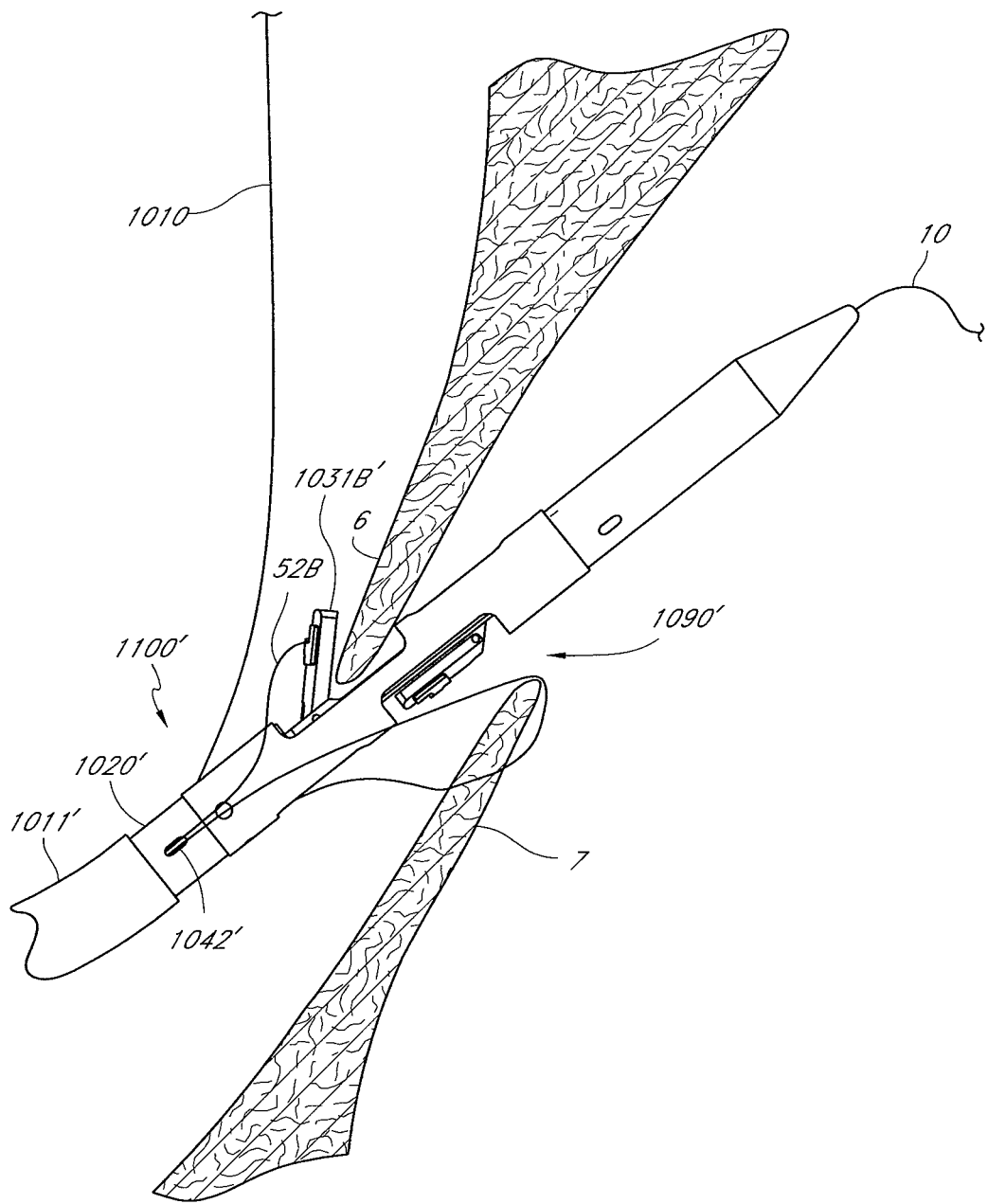
FIG. 29K is a schematic representation as in FIG. 29J with the proximal suture clasp arm positioned around the septum secundum.

The suture clasp arm 1031B' can then be extended and the device 1100' can be advanced such that the suture clasp arm 1031B' extends around the tip of the septum secundum 6, as shown in FIG. 29K, and gathers the tissue of the septum secundum 6 between the arm 1031B' and the spreader 1030'. Alternatively, the suture clasp arm 1031B' can be extended from the spreader assembly 1090' before the second guidewire 1010 is advanced into the superior vena cava. The suturing device 1100' can be configured such that when the second guidewire 1010 is advanced into the superior vena cava, the second guidewire 1010 directs the device 1100' toward the center of the septum segundum 6 as the device 1100' is advanced.

With the suturing device 1100' positioned with the suture clasp arm 1031B' extending around the tip of the septum secundum 6, as illustrated in FIG. 29K, the suture clasp arm 1031B' holds a suture portion 52B extending from opening 1042' in suture clasp 1033B' such that the suture portion 52B is positioned on the opposite side of the septum secundum 6 relative to the PFO 8 and the suturing device 1100'.

Figure 29L:
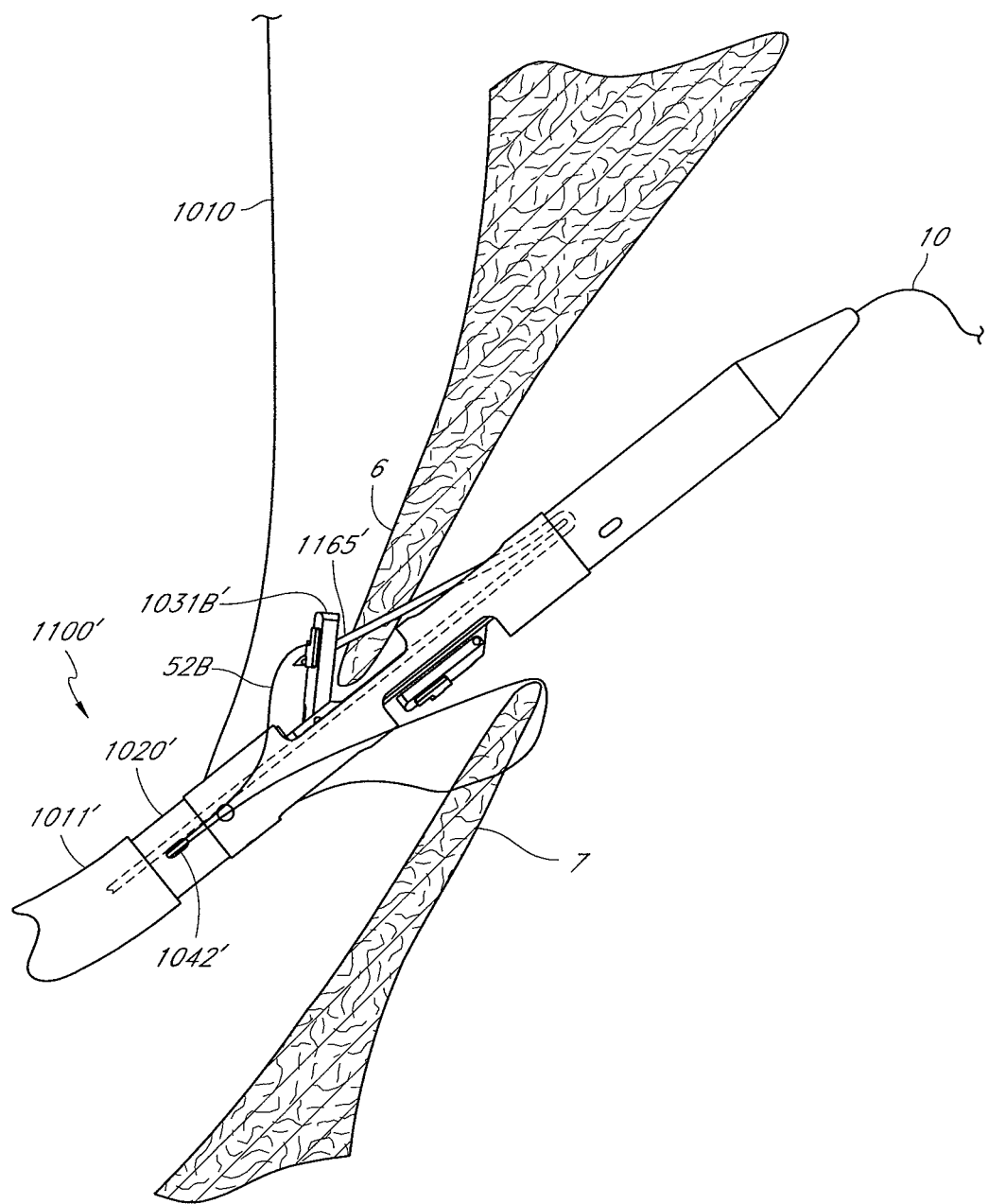
FIG. 29L is a schematic representation as in FIG. 29K showing the distal needle engaging the proximal suture clasp arm.

Once the suture clasp arm 1031B' and suture portion 52B have been properly positioned around the septum secundum 6, the needle 1165' may be deployed from the distal end of the suturing device 1100' to penetrate the septum secundum 6 and engage the suture portion 52B. As shown in FIG. 29L, the tip of the needle 1165' is pulled proximally from a location distal the suture clasp arm 1031B' through the tissue of the septum secundum 6 towards deployed suture clasp arm 1031B' to engage the suture portion 52B.

Figure 29M:
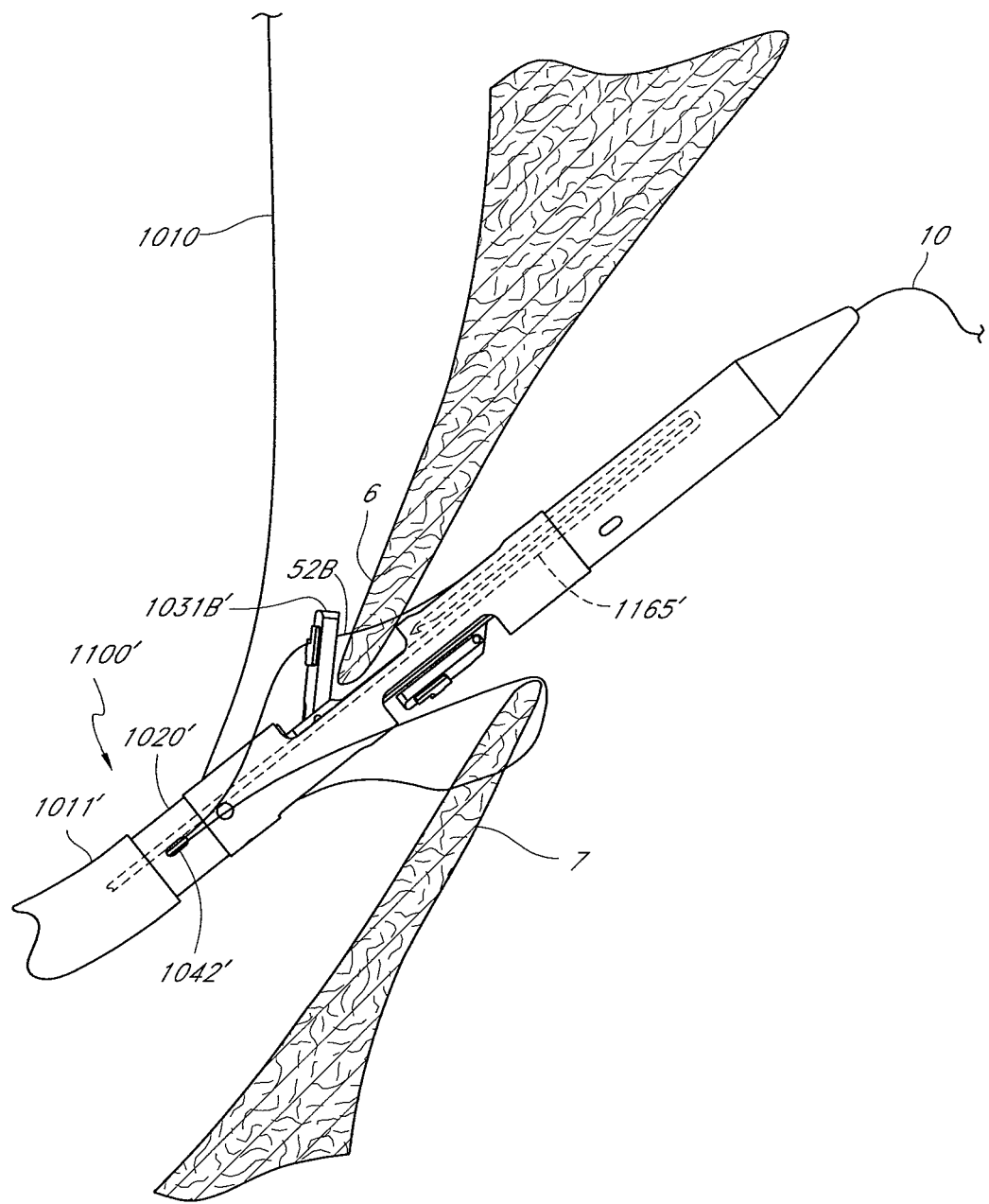
FIG. 29M is a schematic representation as in FIG. 29L following retraction of the distal needle and suture portion through the septum secundum.

Once the suture portion 52B has been engaged, the needle 1165' and engaged suture portion 52B are then retracted distally through the tissue of the septum secundum 6 and into the cavity 1083' of the suturing device 1100', as illustrated in FIG. 29M. The suture clasp arm 1031B' may then be closed and thereafter the second guidewire 1010 retracted into the suturing device 1100'. Alternatively, the second guidewire 1010 can be retracted into the suturing device 1100' before the suture clasp arm 1031B' is closed. Once the suture clasp arm 1031B' is closed, the suturing device 1100' may be withdrawn from the patient's heart and the PFO can be closed as described above.

Figure 30:
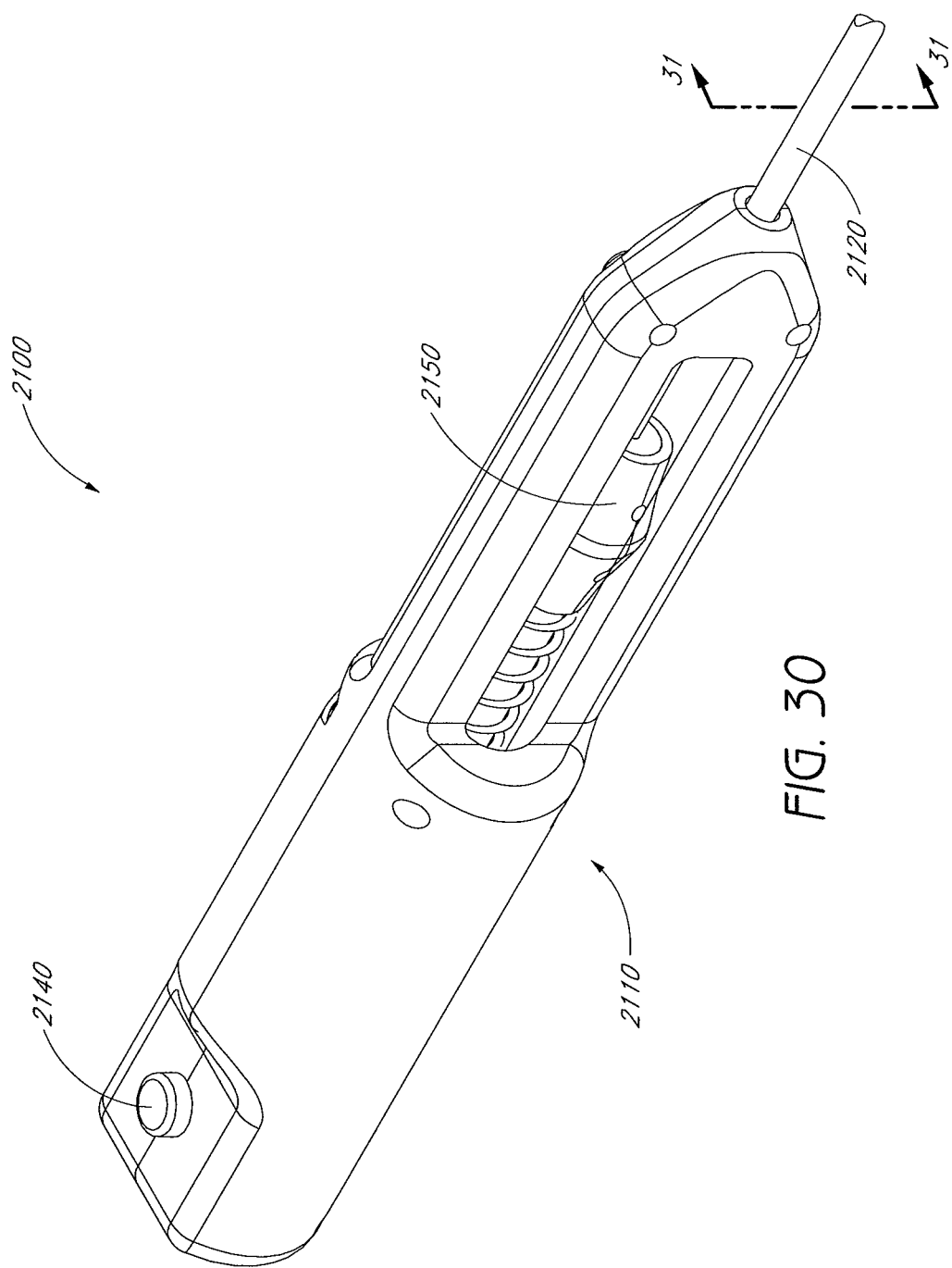
FIG. 30 is a perspective view of one embodiment of a handle of a knot placement device.
Figure 31:
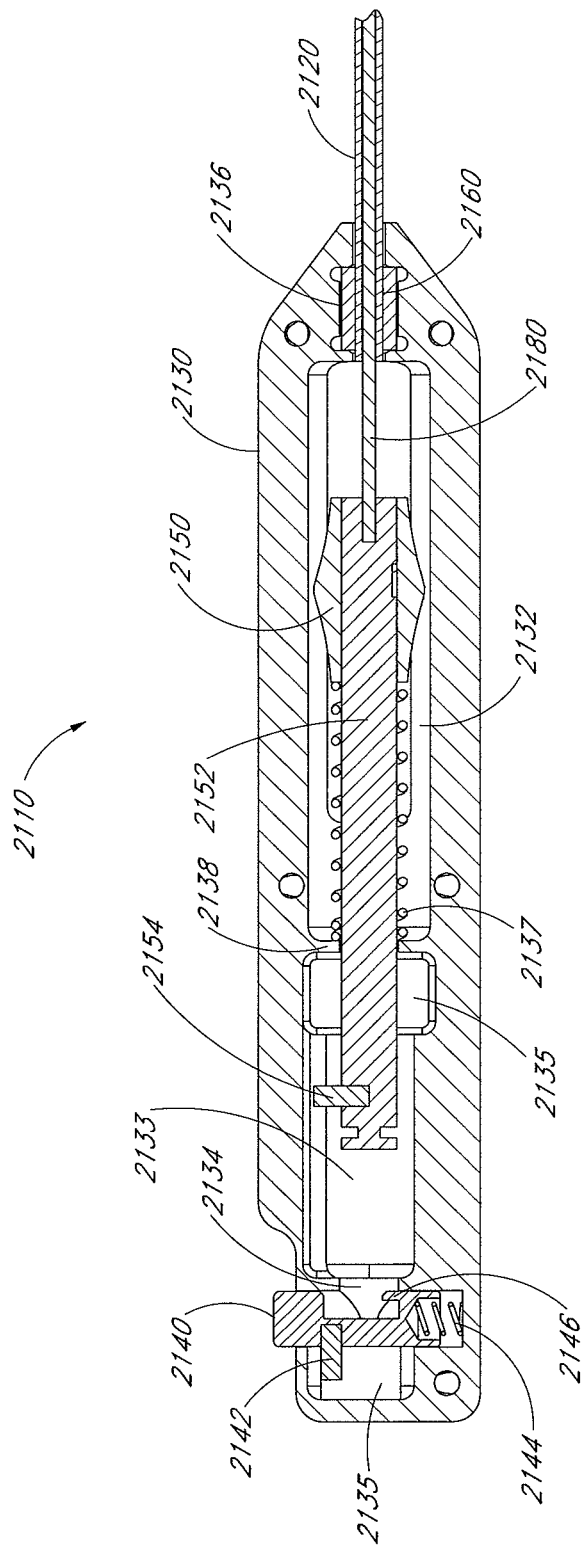
FIG. 31 is a cross-sectional view of the handle of FIG. 30 taken along the line 31-31 shown in FIG. 27.
Figure 32:
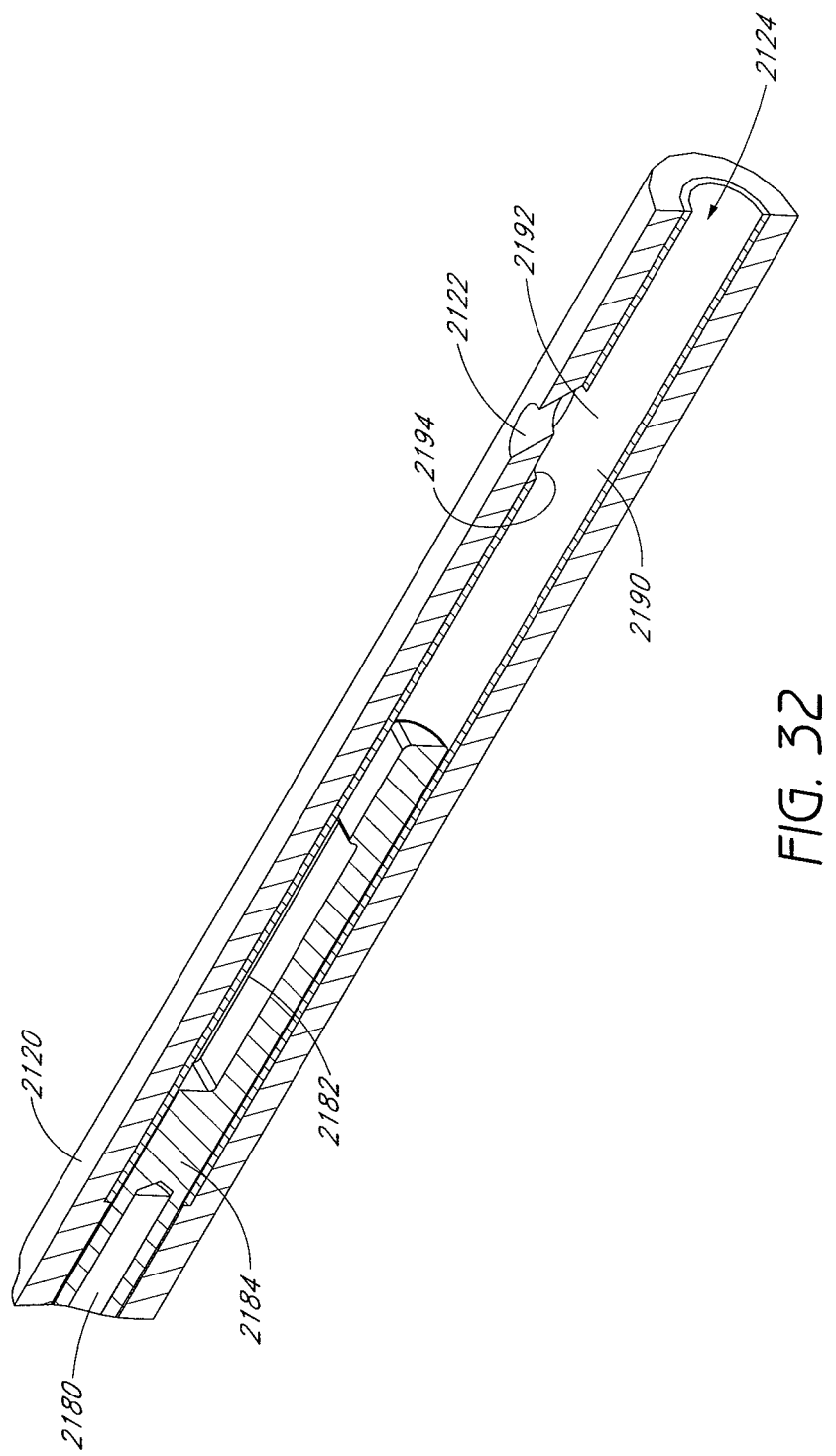
FIG. 32 is a cross-sectional view of a distal end of a knot placement device.

An embodiment of a device 2100 for applying a knot to a suture, comprising a handle 2110 and an elongate tubular member 2120, is illustrated in FIGS. 30-32, which is similar in some respects to the devices described in U.S. Patent Publication No. 2007-0010829 A1, published Jan. 11, 2007, but differs in some respects. The device 2100 can be used to apply a knot to a suture in any of the methods described above.

The handle 2110 of the device 2100 comprises a housing 2130, a button 2140, and a knob 2150. Referring to FIG. 31, the housing 2130 comprises an aperture 2132 configured to allow longitudinal and rotational movement of the knob 2150, a passage 2134 for movement of the button 2140 into and out of the housing 2130, and a mounting recess 2136.

The mounting recess 2136 can accommodate, support, and limit them movement of a mounting hub 2160. The mounting hub 2160 can be fixedly attached to the elongate member 2120. An actuating rod 2180 can extend through the elongate member 2120 to a shaft 2152 that is connected to the knob 2150. The shaft 2152 can be fixedly attached to the actuating rod 2180.

The button 2140 can comprise a pin 2142. When the button 2140 is positioned within the passage 2134, the pin 2142 can extends into a recess 2135 of the passage 2134. The recess 2135 can be dimensioned such that rotation and translation of the pin 2142 and button 2140 within the passage 2134 is constrained such that the button 2140 is not forced out of the passage 2134 by a spring 2144 that is positioned in the passage 2134 between the button 2140 and the housing 2130. In some embodiments, the button 2140 can have a hook, or projection, 2146 to engage the shaft 2152.

The aperture 2132 in the housing 2130 is configured to allow a user to manipulate at least a portion of the knob 2150 and can extend along the longitudinal axis of the device 2100 into the passage 2134. Within the aperture 2132, the housing 2130 can have a neck or ring 2138 that slidably and rotatably supports the shaft 2152. A spring 2137 biases the knob 2150 distally from the neck 2138.

In some embodiments, the aperture 2132 can have a narrow region 2133 and a wide region 2135. The narrow region 2133 can be dimensioned to inhibit rotation of the shaft 2152 when a pin 2154, which extends from the shaft 2152, is located within the narrow region 2133. As the shaft 2152 moves proximally within the aperture 2132, the pin 2154 moves from the narrow region 2133, in which rotation of the pin 2154 is limited, into the wide region 2135, which is large enough to allow the pin 2154 to rotate with the shaft 2152.

The shaft 2152 can also include a recess or groove 2156 for operative engagement with the hook 2146 of the button 2140 to retain the shaft 2152 in a proximally retracted position relative to the handle 2130. When the button 2140 is advanced into the housing 2130, the hook 2146 releases from the recess 2156 of the shaft 2152 and the spring 2138 biases the shaft 2152 distally within the handle 2130, which in turn advances the actuator rod 2180 distally.

As the shaft 2152 advances distally, the pin 2154 moves within the aperture 2132. Once the pin 2154 advances from the narrow region 2133 into the wide region 2135, the knob 2150 can be rotated.

FIG. 32 illustrates the distal end of the elongate tubular member 2120, the actuator rod 2180, a tip 2184, and a sleeve 2190. A suture (not shown) can extend through an opening 2122 in the elongate member 2120, an opening 2192 in the sleeve 2190, and out of an opening 2124 in the distal end of the elongate member 2120.

The sleeve 2190 can support a knot body (not shown) and a plug (not shown) of the type disclosed in U.S. Patent Publication No. 2007-0010829 A1 with the suture (not shown) extending between the knot body (not shown) and the plug (not shown). As the actuator rod 2180 advances, the plug is forced into the knot body by the tip 2184 to secure the suture (not shown) between the knot body and plug in the manner described in U.S. Patent Publication No. 2007-0010829 A1.

After the suture has been secured between the knot body and the plug, the actuator rod 2180 can be rotated by the user by rotating the knob 2150. While the actuator rod 2180 is in the advanced position, rotation of the rod 2180 can cause a cutting edge 2182 of the tip 2184 to rotate toward the opening 2192 in the sleeve 2190. The opening 2192 can have a cutting edge 2194 that cooperates with the cutting edge 2182 of the actuator rod 2180 to cut the suture.

FIGS. 33, 34A, 34B and 35 illustrate one embodiment of a handle 2200 that can be used in conjunction with a suturing device. For example, the handle 2200 can be connected to the elongate tubular member 1020 and spreader assembly 1090, shown in FIGS. 14A and 15A, or the elongate tubular member 1020' and spreader assembly 1090', shown in FIGS. 14B and 15B. While the handle 2200 will be described in reference to suturing devices, the handle 2200 could be used in conjunction with devices for other purposes.

As discussed above, in some embodiments, bending of the elongate tubular member can affect the relative positions of the ends of the suture catch mechanisms and the spreader assembly. For example, if an elongate tubular member is bent then a distal end of a suture catch mechanism extending along the inside of the bend in the elongate member relative to the central axis of the elongate tubular member would be advanced relative to the spreader assembly. In such a circumstance, the suture catch mechanism may be advanced through a suture clasp farther than is desired, which may result in enlargement of a loop at an end of a suture that in turn inhibits the ability of the suture catch mechanism to retract the and of the suture.

On the other hand, if an elongate tubular member is bent then a distal end of a suture catch mechanism extending along the outside of the bend in the elongate member relative to the central axis of the elongate tubular member would be retracted relative to the spreader assembly. In such a circumstance, the suture catch mechanism may not be advanced through a suture clasp far enough to engage a suture end portion held by the suture clasp.

As discussed above, in some embodiments, the effects of bending of the elongate tubular member can be reduced or eliminated by using a suture catch mechanism that is sufficiently long, providing a stop mechanism, or both. Additionally or alternatively, the handle 2200 can reduce or eliminate the effects of bending of the elongate tubular member.

Figure 33:
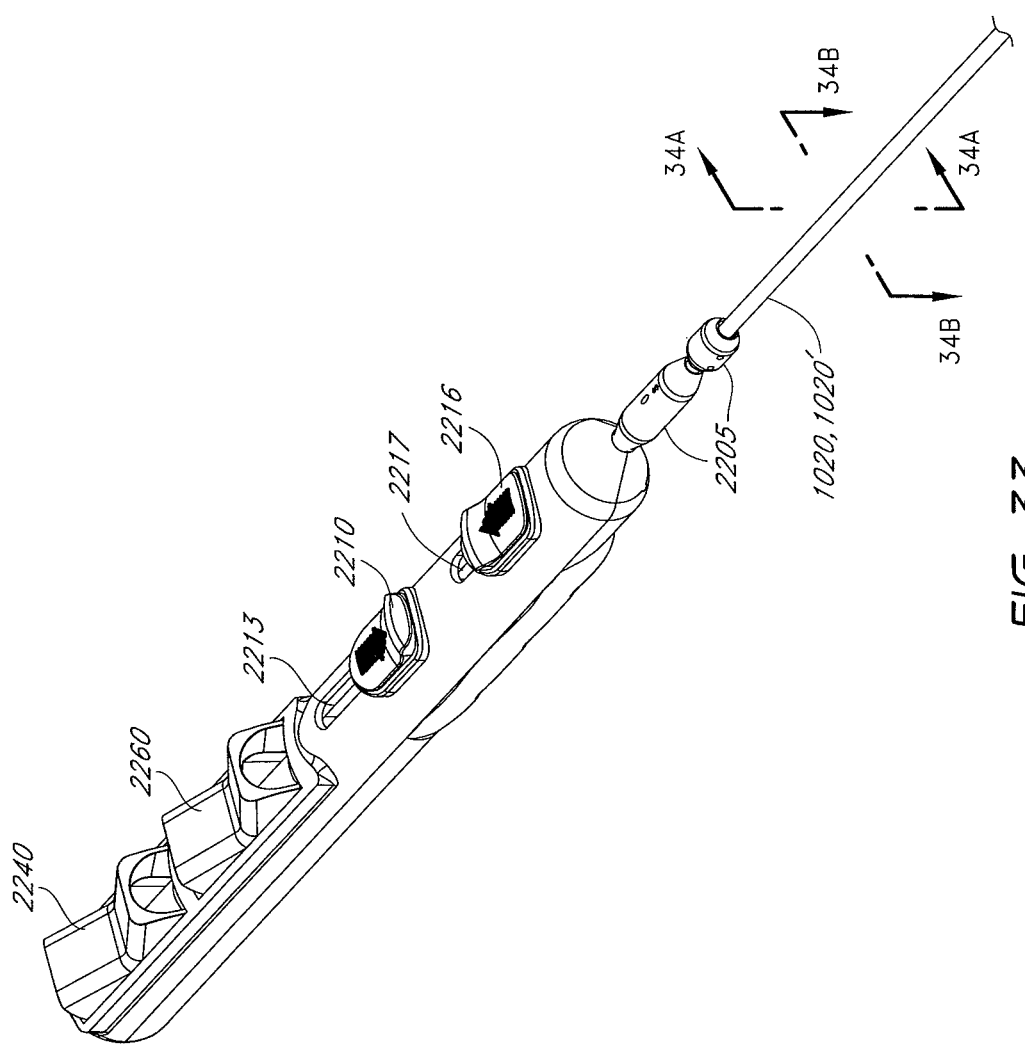
FIG. 33 is a perspective view of one embodiment of a handle of a suturing device.
Figure 34A:
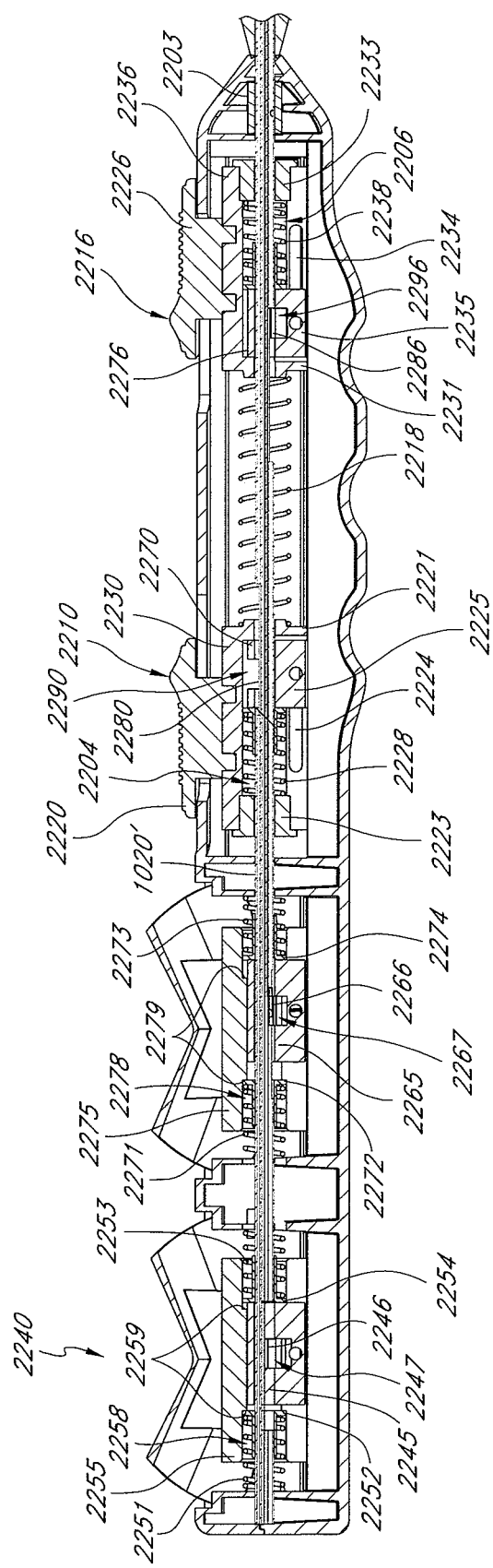
FIG. 34A is a cross-sectional view of the handle of FIG. 33 taken along the line 34A-34A shown in FIG. 33.

The handle 2200 can have a housing 2201, and one or more actuators 2210, 2216, 2240, and 2260 that extend from the housing 2201, as illustrated in FIGS. 33 and 34A. One or more pulls 2210 and 2216 can be actuated to deploy and retract the suture catch mechanisms, such as, needles 1161, 1165 of the suturing device. One or more switches 2240, 2260 can be actuated to deploy and retract the suture claps arms 1031A and 1031B.

With reference to FIG. 33, the housing 2201 can be attached to the proximal end of the elongate tubular member 1020. The housing 2201 can have an aperture 2202 providing a passageway between the handle 2200 and the multiple lumens of the elongate tubular member 1020.

In some embodiments, the handle 2200 can comprise one or more ports 2205 located distal to the housing 2201. The ports 2205 can comprise lumens configured to provide access to one or more lumens of the elongate tubular member 1020 for one or more of sutures, guidewires, or die.

Referring to FIG. 34A, the elongate member 1020 is fixed to the housing 2201 in any suitable manner such as by welding, adhesion, or other bonding process to a collar or cylinder 2203. The cylinder 2203 is engaged by the housing 2201. The cylinder 2203 can be rectangular or any other shape. The cylinder 2203 is connected to the housing 2201 in a manner that prevents limits rotation of the cylinder 2203 with the member 1020 relative to the housing 2201.

The elongate member 1020 has a plurality of cutouts (not shown) that expose the actuator rods 1035 and the suture catch mechanisms 1161 and 1165 to permit connection to the actuators 2210, 2216, 2240, and 2260. Referring to FIG. 15A, the proximal ends of the needles 1161 and 1165 extend through the lumens 1021 and 1023 of the elongate tubular member and terminate at a connection to pulls 2210 and 2216 on the suturing device handle 2200.

Figure 34B:
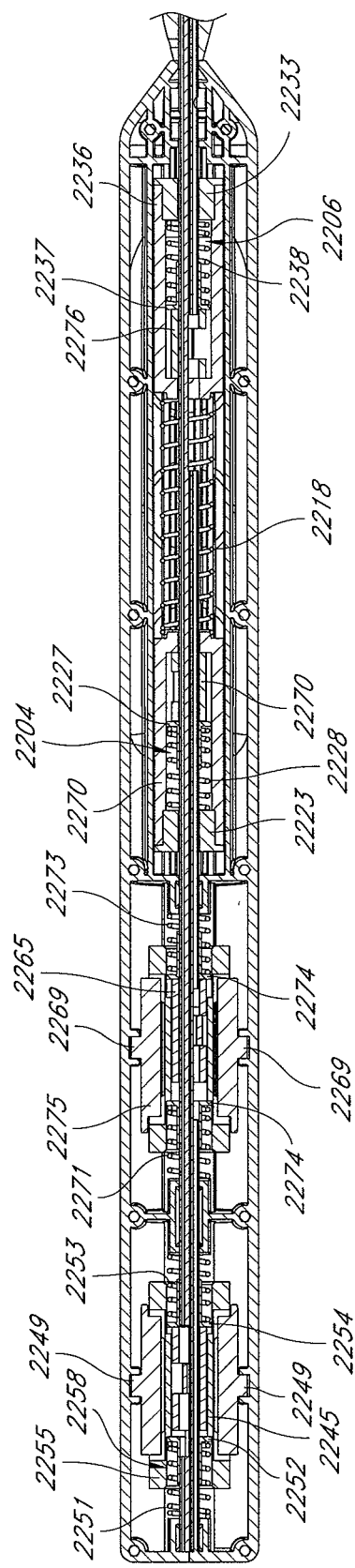
FIG. 34B is a cross-sectional view of the handle of FIG. 33 taken along the line 34B-34B shown in FIG. 33.

In one embodiment, the needles 1161, 1165 are connected to shafts, 2270, 2276, respectively. The proximal ends of needles 1161, 1165 can extend from the proximal end of the lumens 1021, 1023, respectively, in the elongate tubular member 1020 through opening 2202 into the handle 2200 (FIG. 33). The needles 1161, 1165 can be exposed by cutouts in the elongate tubular member 1020 for connection to the shafts, 2270, 2276, respectively. Referring to FIGS. 34A and 34B, the shafts 2270, 2276 can each have a passage to permit the elongate member 1020 to pass through the shafts 2270, 2276. The needles 1161, 1165 can be connected to the shafts 2270, 2276 directly by a suitable bonding process, or indirectly, such as by connection to small tubes that are adhered to the needles 1161, 1165, for example, by epoxy, which are in turn connected to tabs 2280, 2286. The tabs 2280, 2286 can be connected to the shafts 2270, 2276, respectively, at notches 2290, 2296 in the shafts 2270, 2276.

The shafts 2270, 2276 can be moved by the pulls 2210, 2216 in cooperation with springs 2228, 2238. The pulls 2210, 2216 can extend from the housing through openings 2213 and 2217, respectively, as shown in FIG. 33. Referring to FIG. 34A, the pulls 2210, 2216 can each comprise an external portion 2220, 2226 and an internal portion 2230, 2236, which can be integrally formed or can be connected by any bonding process. The external portions 2220, 2226 can be engaged by a user to move the pulls 2210, 2216, respectively.

The internal portions 2230, 2236 of the pulls 2210, 2216 can each have a passage 2204, 2206, a first end portion 2221, 2231, and a second end portion 2223, 2233. The passages 2204, 2206 can be configured to allow the shafts 2270, 2276 to move therein and the elongate tubular member 1020 to extend through the pulls 2210, 2216. The first end portions 2221, 2231 and second end portions 2223, 2233 can limit the movement of the shafts 2270, 2276 within the passage.

The first end portions 2221, 2231 and second end portions 2223, 2233 can be integrally formed with the internal portions 2230, 2236, or can be separate components. For example, in the embodiment of FIGS. 34A and 34B, the first end portions 2221, 2231 are integrally formed with the internal portions and second end portions 2223, 2233 are illustrated as separate components which can be mechanically connected, such as by threads, or can be connected by adhesive, or other bonding process to the internal portions.

The springs 2228, 2238 can be positioned between the second end portions 2223, 2233 and the shafts 2270, 2276, thereby biasing the shafts 2270, 2276 toward the first end portions 2221, 2231. In some embodiments, collars 2227, 2237 can be positioned between the springs 2228, 2238 and the shafts 2270, 2276. The collars 2227, 2237 may slidably move over the elongate tubular member 1020 and provide an interface between the springs 2228, 2238 and the shafts 2270, 2276. In some embodiments, a spring 2218 can be positioned between the pulls 2210 and 2216. The spring 2218 can bias the needle 1161 proximally and the needle 1165 distally by biasing the pull 2210, which is connected to the needle 1161, from the pull 2216, which is connected to the needle 1165.

In the embodiment illustrated in FIGS. 34A and 34B, a user can advance the needle 1161 by moving the pull 2210 to compress the spring 2218. As the pull 2210 is advanced distally, the second end portion 2223 pushes against the spring 2228, which in turn pushes the shaft 2270 distally along with the needle 1161. However, distal advancement of the shaft 2270 is limited by the first end portion 2221. Thus, a user is able to advance the needle 1161 at a controlled rate and is able to retract the needle 1161 by moving the pull 2210 proximally.

On the other hand, should the needle 1161 encounter resistance as the pull 2210 is advanced, such as from a stop mechanism, described above, the shaft 2270 will move away from the first end portion 2221 toward the second end 2223. Thus, the internal spring 2228 is compressed to avoid over-extension of the needle 1161.

Likewise, with continued reference to FIGS. 34A and 34B, a user can draw the needle 1165 proximally by moving the pull 2216 to compress the spring 2218. As the pull 2216 is drawn proximally, the second end portion 2233 pushes against the spring 2238, which in turn pushes the shaft 2276 proximally along with the needle 1165. However, proximal movement of the shaft 2276 is limited by the first end portion 2231. Thus, a user is able draw the needle 1165 proximally at a controlled rate and is able to retract the needle 1165 by moving the pull 2210 distally.

Should the needle 1165 encounter resistance as the pull 2216 is advanced, such as from a stop mechanism, described above, the shaft 2276 will move away from the first end portion 2231 toward the second end 2233. Thus, the internal spring 2238 is compressed to avoid over-extension of the needle 1165.

In some embodiments, the pulls 2210, 2216 can comprise slots 2224, 2234, while the shafts 2270, 2276 can comprise tabs 2225, 2235 that have holes therein. Thus, a user may place a tool through the hole in the tab 2225, 2235 to move the needle 1161, 1165 directly, without the aid of the pulls 2210, 2216 or the springs 2228, 2238.

Referring to FIGS. 33, 34A, 34B, the suture claps arms 1031A and 1031B can be deployed and retracted by movement of actuators 2240 and 2260. The actuators 2240, 2260 can be levers, switches, or rockers. In other embodiments the actuators 2240, 2260 can have other configurations.

As noted above, the elongate member 1020 can have a plurality of cutouts (not shown) that expose the actuator rods 1035 to permit connection to the actuators 2240, 2260. Referring to FIG. 15A, the proximal ends of the actuator rods 1035A, 1035B extend through the lumens 1026, 1024 of the elongate tubular member and terminate at connections to the pulls 2240 and 2260 on the suturing device handle 2200 (FIG. 33).

In one embodiment, the actuator rods 1035A, 1035B, which are connected to the suture claps arms 1031A and 1031B, are also connected to shafts 2245, 2265 (FIGS. 34A, 34B), respectively. The proximal ends of the actuator rods 1035A, 1035B can extend from the proximal end of the lumens 1026, 1024, respectively, in the elongate tubular member 1020 through opening 2202 into the handle 2200. The actuator rods 1035A, 1035B can be exposed by cutouts (not shown) in the elongate tubular member 1020 for connection to the shafts 2245, 2265, respectively. Referring to FIGS. 34A and 34B, the shafts 2245, 2265 can each have a passage to permit the elongate member 1020 to pass through the shafts 2245, 2265. The actuator rods 1035A, 1035B can be connected to the shafts 2245, 2265 directly by a suitable bonding process, or indirectly, such as by connection to small tubes that are adhered to the actuator rods 1035A, 1035B, for example, by epoxy, which are in turn connected to tabs 2246, 2266. The tabs 2246, 2266 can be connected to the shafts 2245, 2265, respectively, at notches 2247, 2267 in the shafts 2245, 2265. Thus, the actuator rods 1035A, 1035B move according to the movement of the shafts 2245, 2265.

With continued reference to FIGS. 34A and 34B, the handle 2200 can comprise springs 2251, 2253, 2271, 2273, collars 2252, 2254, 2272, 2274, and followers 2255, 2275. The springs 2251, 2271 can located proximal to the shafts 2245, 2265 between the housing 2201 the shafts 2245, 2265. The distal springs 2253, 2273 can be located distal to the shafts 2245, 2265 between the housing 2201 and the shafts 2245, 2265.

The collars 2252, 2272 can be located proximal to the shafts 2245, 2265, between the proximal springs 2251, 2271 and the shafts 2245, 2265. Thus, the proximal springs 2251, 2271 tend to distally bias the proximal collars 2252, 2272 against the shafts 2245, 2265.

The collars 2254, 2274 can be located distal to the shafts 2245, 2265 between the distal springs 2253, 2273 and the shafts 2245, 2265. Thus, the distal springs 2253, 2273 tend to proximally bias the distal collars 2254, 2274 against the shafts 2245, 2265.

Figure 35:
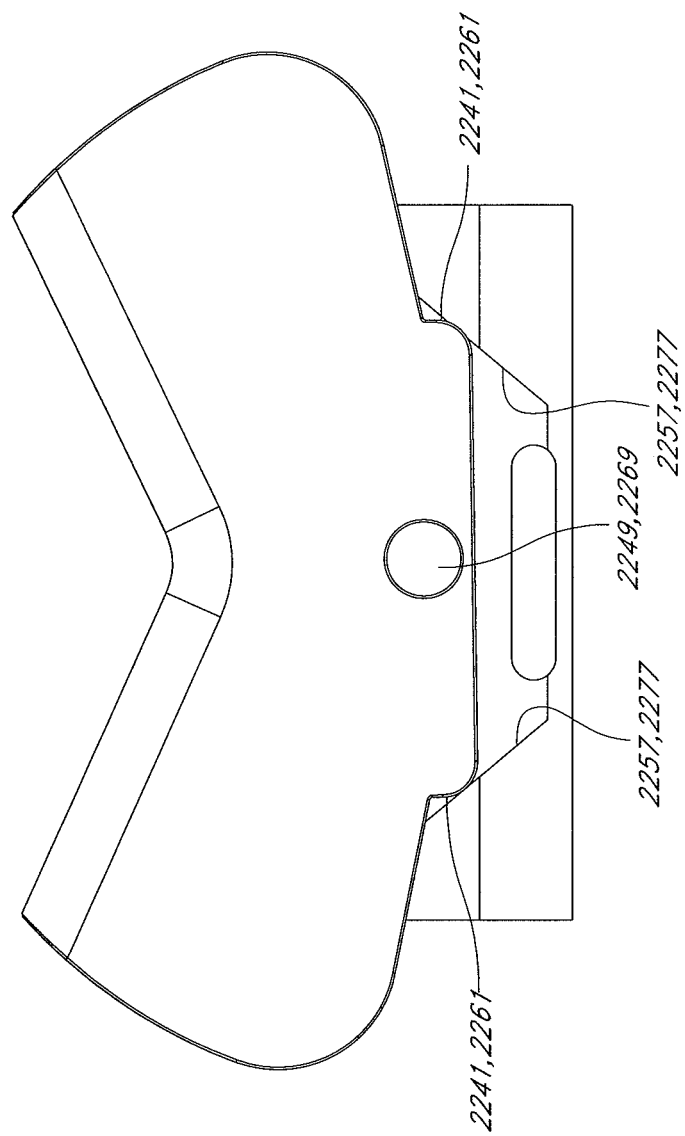
FIG. 35 is a side view of an actuator and a follower of the handle of FIG. 33.

With reference to FIG. 34A, the followers 2255, 2275 can each comprise a passage 2258, 2278, shoulders 2259, 2279, and ramps 2257, 2277 (FIG. 35). The passages 2258, 2278 can be configured to allow the shafts 2245, 2265 to move through the passages 2258, 2278, and the elongate tubular member 1020 to extend through the followers 2255, 2275. The shoulders 2259, 2279 and collars 2252, 2254, 2272, 2274 can be configured such that the collars engage the shoulders to prevent the collars from passing completely through the followers 2255, 2275.

Referring to FIG. 35, the actuators 2240, 2260 can each comprise cams 2241, 2261 and pivot pins 2249, 2269. The pivot pins 2249, 2269 cooperate with the housing 2201 for pivoting movement of the actuators 2240, 2260. The cams 2241, 2261 and the ramps 2257, 2277 of the followers 2255, 2275 can be configured such that cams engage the ramps to move the followers as the actuators pivot relative to the housing.

In use, movement of the actuators 2240, 2260 allows the springs 2251, 2253, 2271, 2273 to move shafts 2245, 2265 proximally and distally. For example, with reference to FIG. 34A, as the actuators 2240, 2260 pivot counterclockwise about the pivot pins 2249, 2269 (FIG. 34B), the followers 2255, 2275 are pushed proximally. As the followers 2255, 2275 move proximally, the proximal collars 2252, 2272 are likewise moved proximally to compress the proximal springs 2251, 2271. Proximal movement of the followers 2255, 2275 also allows the distal springs 2253, 2273 to proximally advance the distal collars 2254, 2274. In turn, the distal collars 2254, 2274 proximally advance the shafts 2245, 2265. As described above, the suture clasp arms 1031A, 1031B move with the shafts 2245, 2265. Thus, the suture clasp arms 1031A, 1031B are moved to their extended positions.

The distal springs 2253, 2273 can be configured such that they will not proximally move the actuator rods 1035A, 1035B beyond the location where the suture clasp arms 1031A, 1031B are fully extended, even if the actuators 2240, 2260 move the followers 2255, 2275 far enough to allow further decompression of the distal springs. For example, the force exerted by the distal springs can be insufficient to extend the suture clasp arms 1031A, 1031B beyond their fully-extended positions. On the contrary, the springs 2253, 2273 can have sufficient length and apply sufficient force to fully extend the suture clasp arms 1031A, 1031B, even if the elongate member 1020 is bent.

With continued reference to FIG. 34A, as the actuators 2240, 2260 pivot clockwise about the pivot pins 2249, 2269 (FIG. 34B), the followers 2255, 2275 are pushed distally. As the followers 2255, 2275 move distally, the distal collars 2254, 2274 are likewise moved distally to compress the distal springs 2253, 2273. Distal movement of the followers 2255, 2275 also allows the proximal springs 2251, 2271 to distally advance the proximal collars 2252, 2272. In turn, the proximal collars 2252, 2272 distally advance the shafts 2245, 2265. As described above, the suture clasp arms 1031A, 1031B move with the shafts 2245, 2265. Thus, the suture clasp arms 1031A, 1031B are moved to their retracted positions.

The proximal springs 2251, 2271 can be configured such that they will not distally advance actuator rods 1035A, 1035B beyond the location where the suture clasp arms 1031A, 1031B are fully retracted, even if the actuators 2240, 2260 move the followers 2255, 2275 far enough to allow further decompression of the proximal springs. For example, the force exerted by the proximal springs can be insufficient to damage the actuator rods 1035A, 1035B or the suture clasp arms 1031A, 1031B once the suture clasp arms have reached their fully-retracted positions. On the contrary, the proximal springs 2251, 2271 can have sufficient length and apply sufficient force to fully retract the suture clasp arms 1031A, 1031B, even if the elongate member 1020 is bent.

Figure 36:
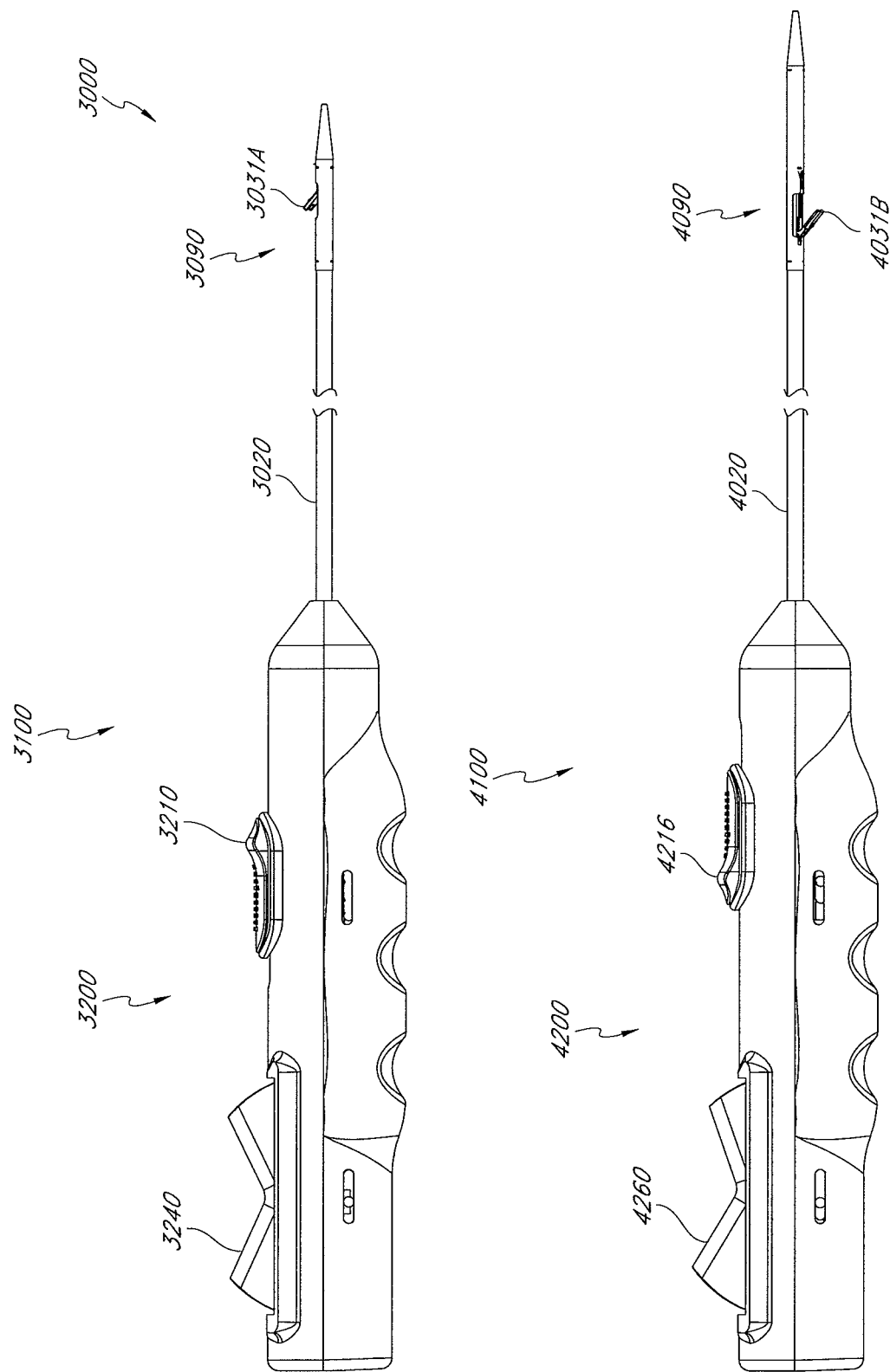
FIG. 36 is a side view of one embodiment of a system of suturing devices.

FIG. 36 illustrates one embodiment of a system for suturing an opening in a vessel wall or other biological tissue, or for performing other procedures as described above. The system 3000 can comprise a first suturing device 3100 and a second suturing device 4100. While the system and suturing devices 3100, 4100 will be described in reference to suturing an opening in the heart wall, such as a patent foramen ovale (PFO), the first suturing device 3100 and the second suturing device 4100, either alone or in combination, could be used, like the devices 100, 1100, 1100', to close other openings in the heart wall, such as a patent ductus arteriosus (PDA) or an atrial septal defect (ASD), other openings in bodily tissue, or the like. The device 1100 could also be used to suture adjacent biological structures or any other time it may be desired to apply a suture to a biological structure.

The first suturing device 3100 and the second suturing device 4100 can be similar to the suturing devices 1100, 1100' in some respects. Accordingly, components of the first suturing device 3100 and component of the second suturing device 41000 that are similar to those of the suturing devices 1100, 1100' are indicated by similar reference numerals 31XX and 41XX, respectively, rather than 11XX. For example, the suturing devices 3100, 4100 can each comprise an elongate tubular member 3020, 4020 having a spreader assembly 3090, 4090 connected to the distal end of the elongate tubular member 3020, 4020. The elongate tubular members 3020, 4020 can be similar to the elongate tubular members 1020, 1020'. Likewise, the spreader assemblies 3090, 4090 can be similar to the spreader assemblies 1090, 1090'. A handle 3200, 4200 can be provided at the proximal end of each tubular member 3020, 4020. The handles 3200, 4200 can be similar to the handle 1200 or the handle 2200.

The first suturing device 3100 and the second suturing device 4100 can differ from the suturing devices 1100, 1100' in some respects. For example, in contrast to the devices 1100, 1100', the devices 3100, 4100 can comprise a single suture clasp arm and a single suture catch mechanism. Accordingly, the elongate tubular members 3020, 4020, spreader assemblies 3090, 4090, and handles 3200, 4200 can be configured to operate the single suture clasp arm and the single suture catch mechanism, rather than plural suture clasp arms and plural suture catch mechanisms, by omission of those components associated with more than a single suture clasp arm and a single suture catch mechanism.

The spreader assemblies 3090, 4090 of the devices 3100, 4100 can be shorter than the spreader assemblies 1090, 1090' because the spreader assemblies 3090, 4090 may comprise fewer components the spreader assemblies 1090, 1090'. Therefore, the spreader assemblies 3090, 4090 may extend into left atrium less than the spreader assemblies 1090, 1090' when positioned in a PFO.

Figure 37:
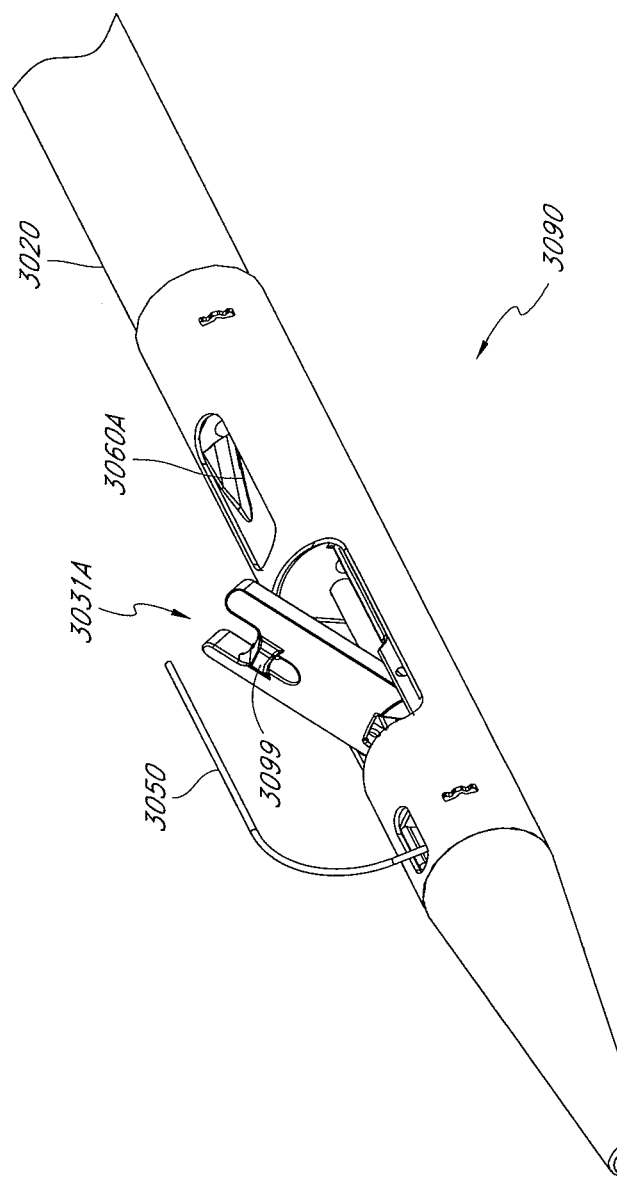
FIG. 37 is a perspective view of a distal end of a first suturing device of the system of FIG. 36.

The first suturing device 3100 can comprise a suture clasp arm 3031A and a suture catch mechanism 3161 (FIG. 39C) operated by a handle 3200 having a pull 3210 and an actuator 3240. Referring to FIG. 37, the suture clasp arm 3031A can comprise a deflecting plate 3099 that is integrally formed with the suture clasp arm 3031A.

The second suturing device 4100 can comprise a suture clasp arm 4031B and a suture catch mechanism 4165 (FIG. 39G) operated by a handle 4200 having a pull 4216 and an actuator 4260. The elongate tubular member 4020 and the spreader assembly 4090 can be configured for use of two guidewires similar to the elongate tubular member 1020' and the spreader assembly 1090'. Thus, the spreader assembly 4090 can comprise an opening 4043, shown in FIG. 38) through which a second guidewire can extend.

The suture clasp arm 4031B can comprise a guide section 4032, as shown in FIG. 38. The guide section 4032 can assist in maintaining a desired rotational orientation between the second guidewire and the spreader assembly 4090. The guide section 4032 can thus assist a user in directing the second guidewire to a desired location, such as the superior vena cava, as the second guidewire is extended from the device 4100. Additionally or alternatively, the guide section 4032 can assist a user in positioning the device 4100 in a desired located, such as substantially centered relative to the septum secundum 6 of the PFO.

Figure 39A:
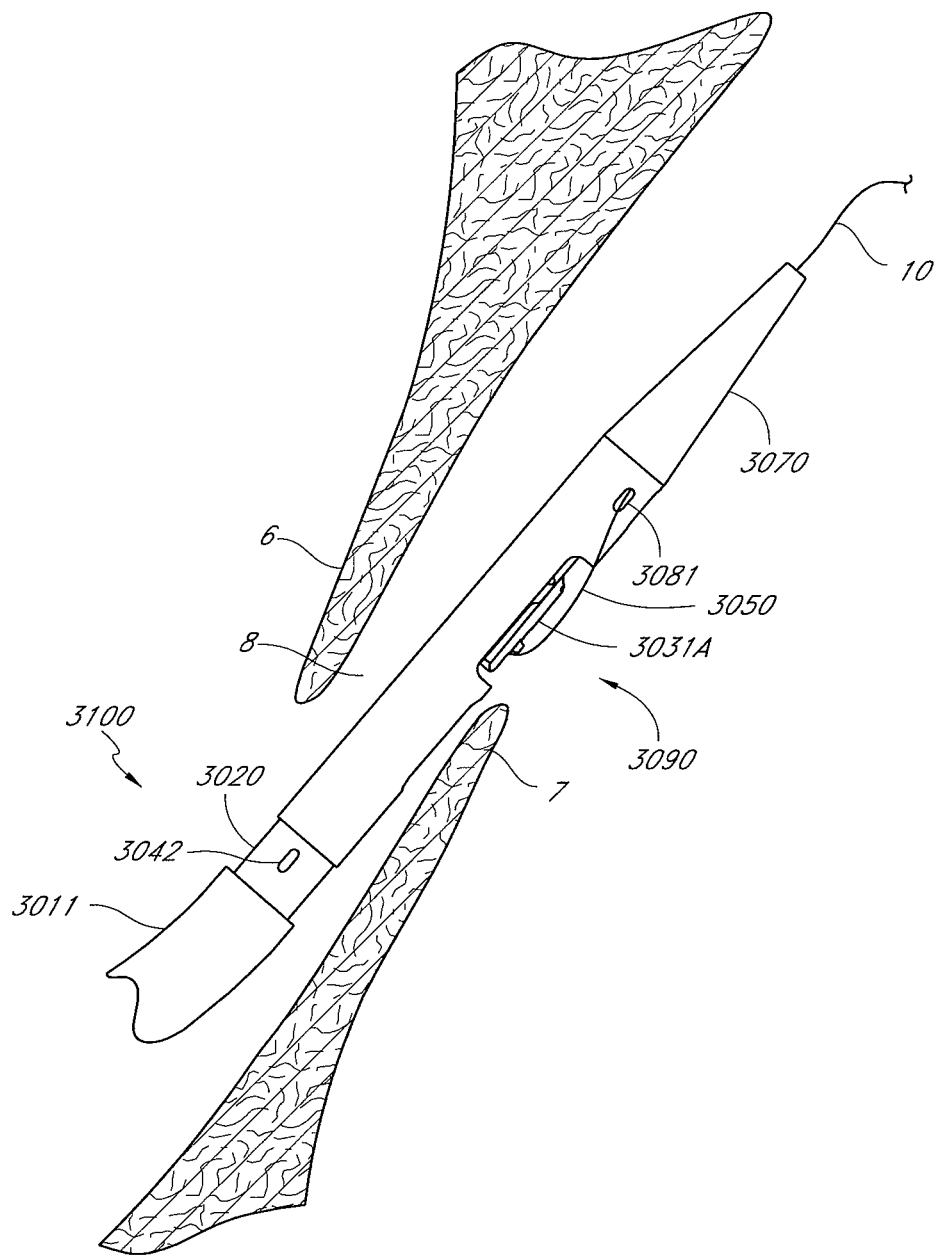
FIG. 39A is a schematic representation an embodiment of the first suturing device of the FIG. 37 deployed in a PFO.

The operation of the system 3000 comprising the first suturing device 3100 and the second suturing device 4100, described above, is illustrated according to one embodiment in FIGS. 39A-39L in conjunction with a procedure for closing a PFO. As shown in FIG. 39A, the distal end of a suturing device 3100 is advanced through the vasculature and positioned in the tunnel 8 of the PFO between the septum primum 7 and the septum secundum 6. The suturing device 3100 may be advanced over a guidewire 10 or alternatively delivered through a catheter introducer sheath 1011 using techniques which are known in the art.

Figure 39B:
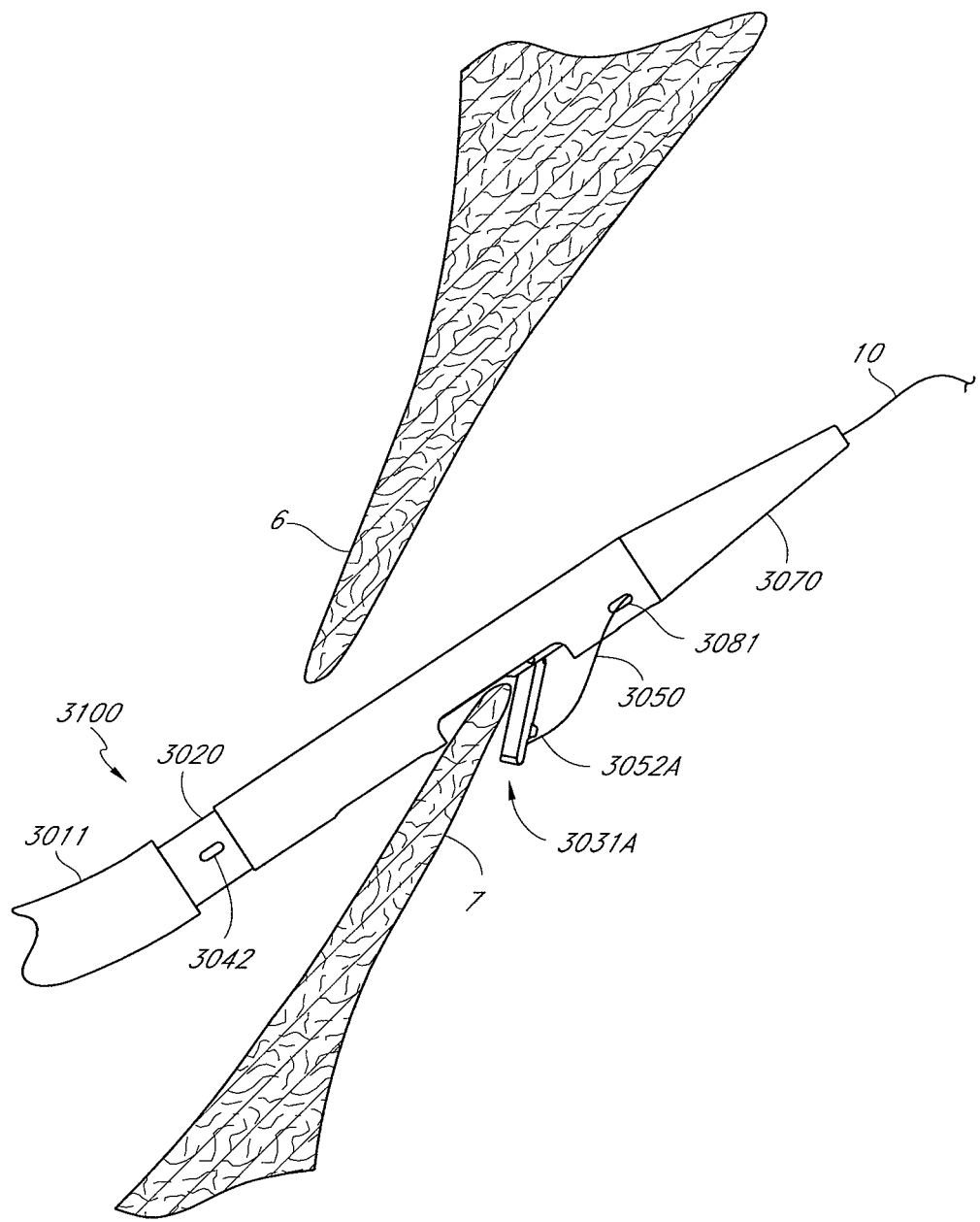
FIG. 39B is a schematic representation as in FIG. 39A with a suture clasp arm positioned around the septum primum.

The suturing device 3100 is initially positioned such that the spreader assembly 3090 is near the tip of the secundum primum 7 and the suture clasp deployment arm 3031A is permitted to extend from the spreader assembly 3090. The suture clasp arm 3031A may then deployed from the spreader assembly 3090 and then the device 3100 is retracted until the suture clasp arm 3031A extends around the tip of the secundum primum 7, as shown in FIG. 39B, and gathers the tissue of the septum primum 7 between the arm 3031A and the spreader 3030.

Figure 39C:
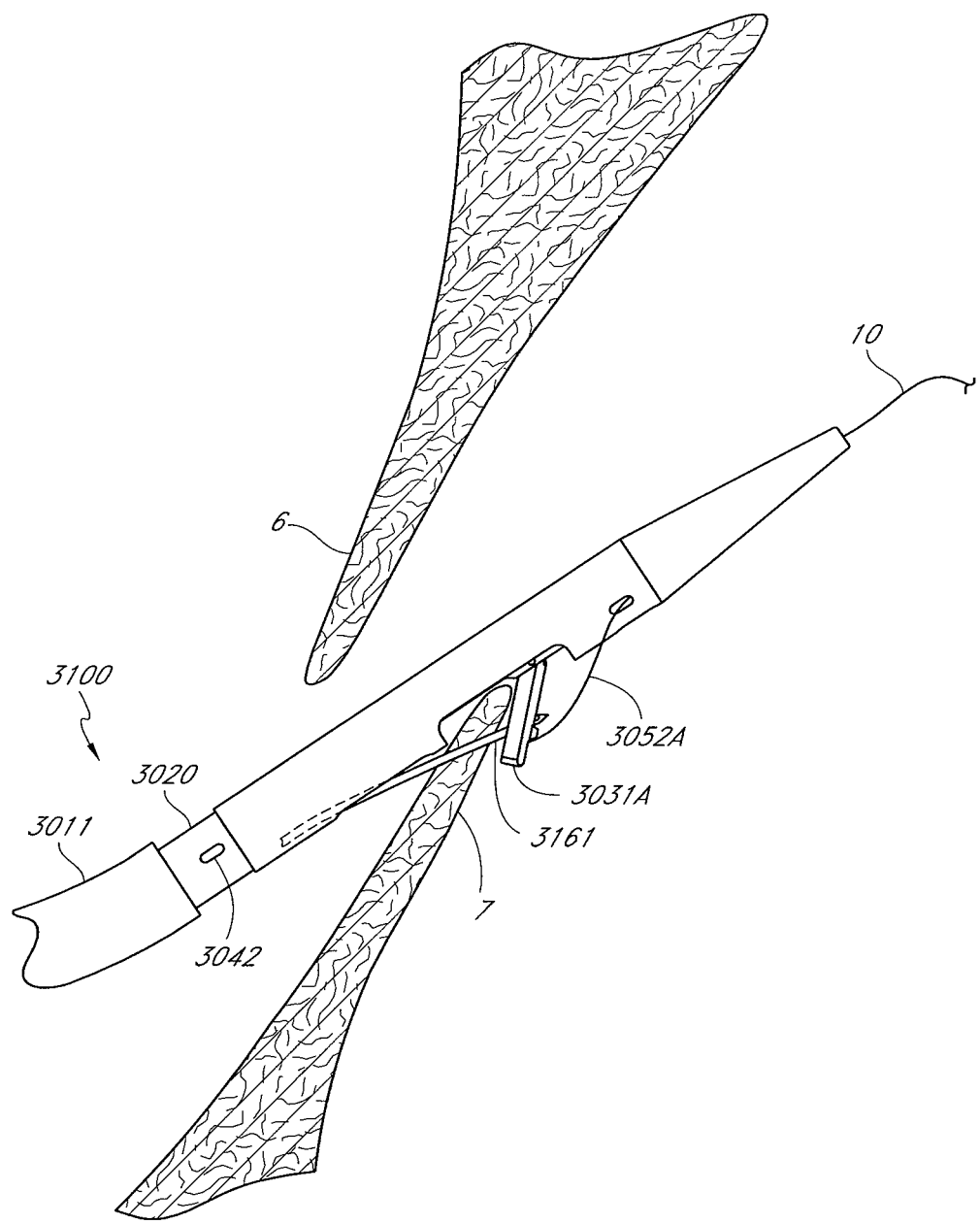
FIG. 39C is a schematic representation as in FIG. 39B showing a needle engaging the suture clasp arm.

Once the suture clasp arm 3031A has been properly positioned around the septum primum 7, needle 3161 may be deployed from the suturing device 3100 to penetrate the septum primum 7 and engage the suture clasp arm. The needle 3161 is advanced through a passageway in the suturing device and deflected by needle guide 3060A along an angle that intersects the deployed suture clasp arm 3031A as it exits the suturing device 3100. The needle engages the suture clasp arm 3031A, as shown in FIG. 39C, to engage the suture portion 3052A.

Figure 39D:
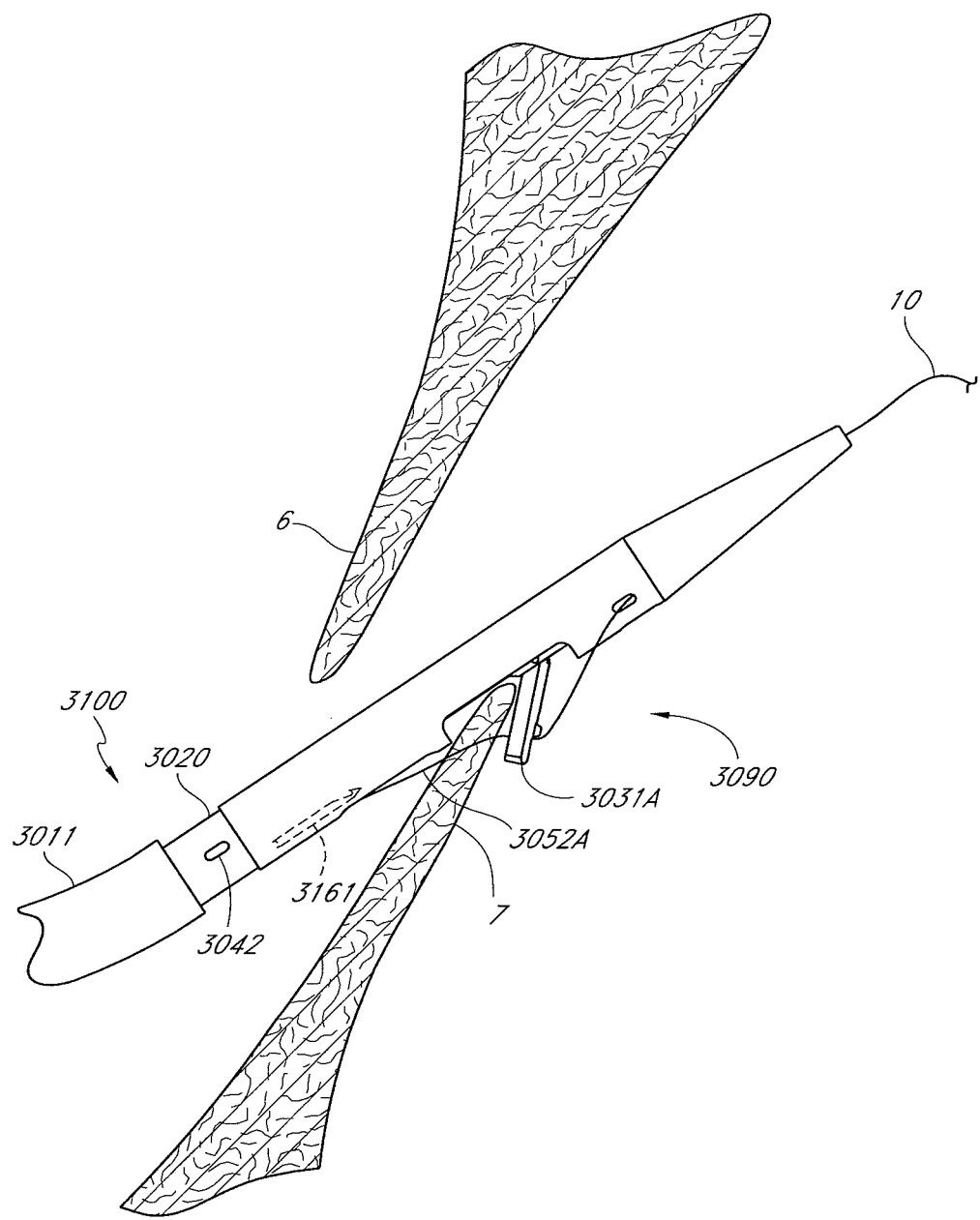
FIG. 39D is a schematic representation as in FIG. 39C showing the needle and suture portion retracted through the septum primum.

As shown in FIG. 39D, once the suture portion 3052A has been engaged, the needle 3161 and engaged suture portion 3052A are then retracted through the tissue of the septum primum 7 into the elongate member 3020 of the suturing device 3100. The device 3100 may be advanced slightly so that the suture clasp arm 3031A can be closed without pinching the septum primum 7. The first suturing device 3100 may then be withdrawn from the vasculature over the guidewire 10.

Figure 39E:
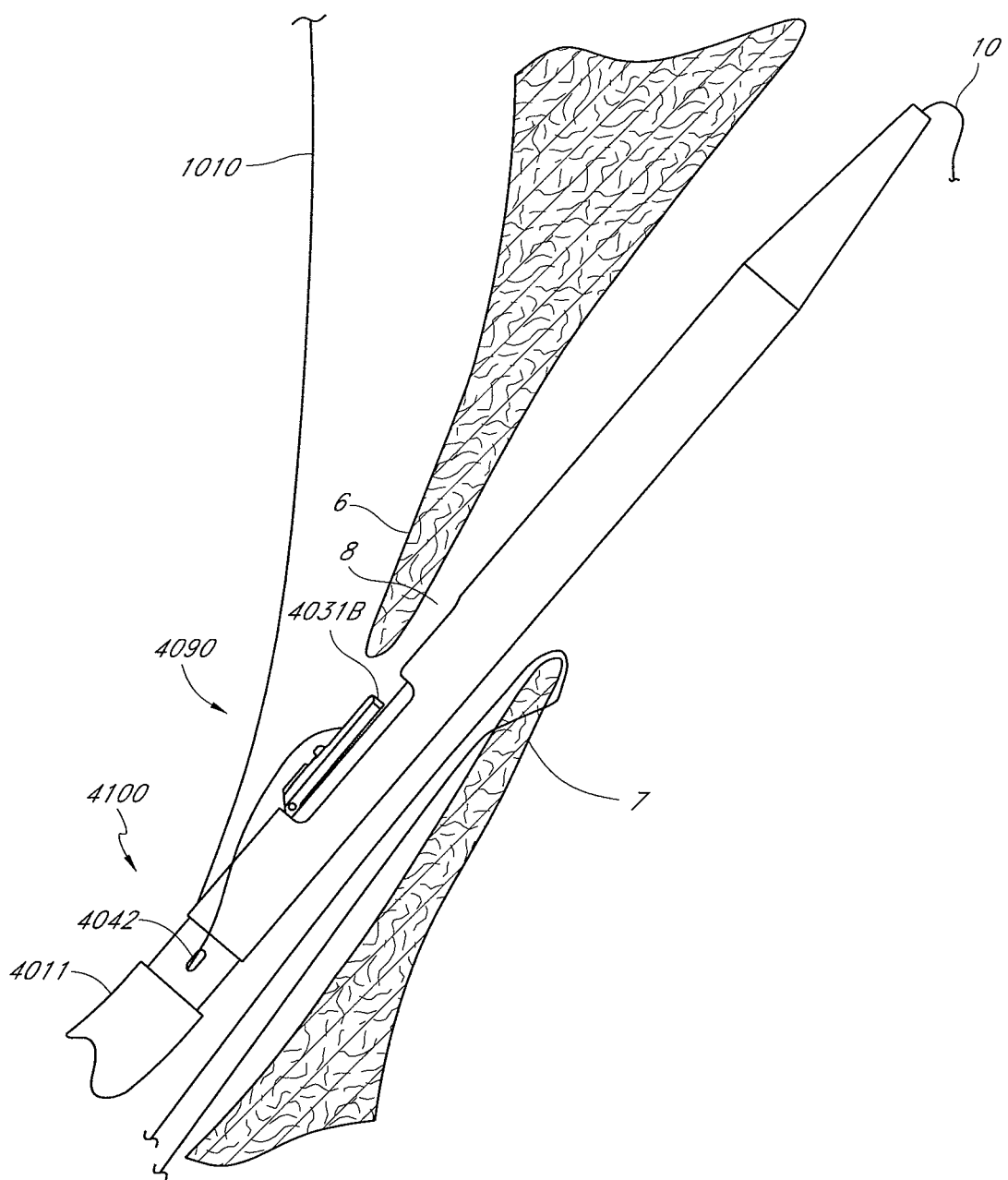
FIG. 39E is a schematic representation as in FIG. 39D showing the second suturing device of FIG. 38 positioned to permit a suture clasp arm to extend from the second suturing device and a second guidewire extended.

The second suturing device 4100 may then be advanced through the venous access into the tunnel 8 of the PFO between the septum primum 7 and the septum secundum 6, as shown in FIG. 39E. The second guidewire 1010 can be advanced through the opening 4043 (FIG. 38) into the superior vena cava (FIG. 1). The second guidewire 1010 may be preloaded in the device 4100 before introduction of the device 4100 into the body such that a distal end of the second guidewire is near the opening 4043.

Figure 39F:
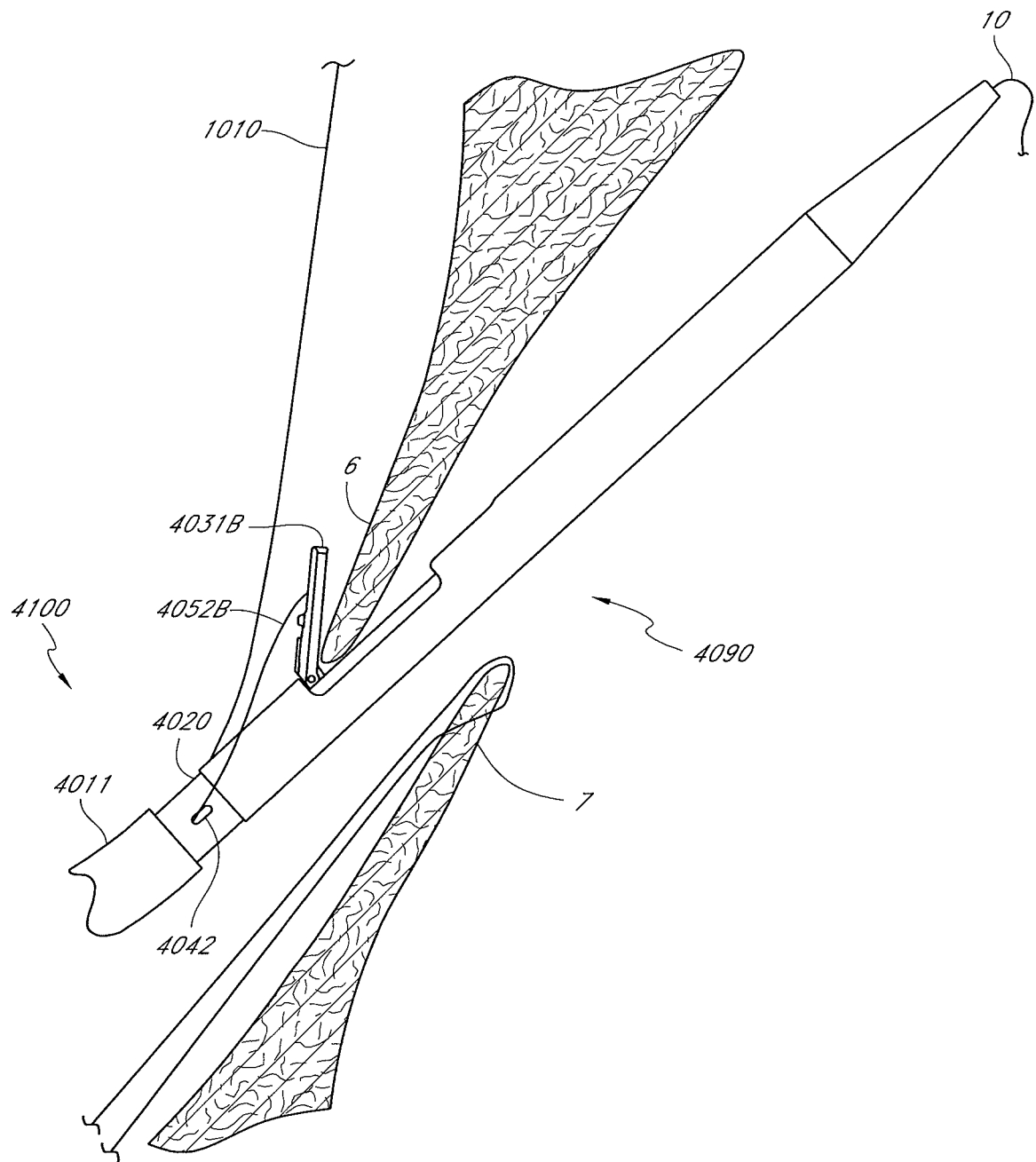
FIG. 39F is a schematic representation as in FIG. 39E with the suture clasp arm positioned around the septum secundum.

The suture clasp arm 4031B can then be extended and the device 4100 can be advanced such that the suture clasp arm 4031B extends around the tip of the septum secundum 6, as shown in FIG. 39F, and gathers the tissue of the septum secundum 6 between the arm 4031B and the spreader 4030. Alternatively, the suture clasp arm 4031B can be extended from the spreader assembly 4090 before the second guidewire 1010 is advanced into the superior vena cava. The suturing device 4100 can be configured such that when the second guidewire 1010 is advanced into the superior vena cava, the second guidewire 1010 directs the device 4100 toward the center of the septum segundum 6 as the device 4100 is advanced.

Figure 39G:
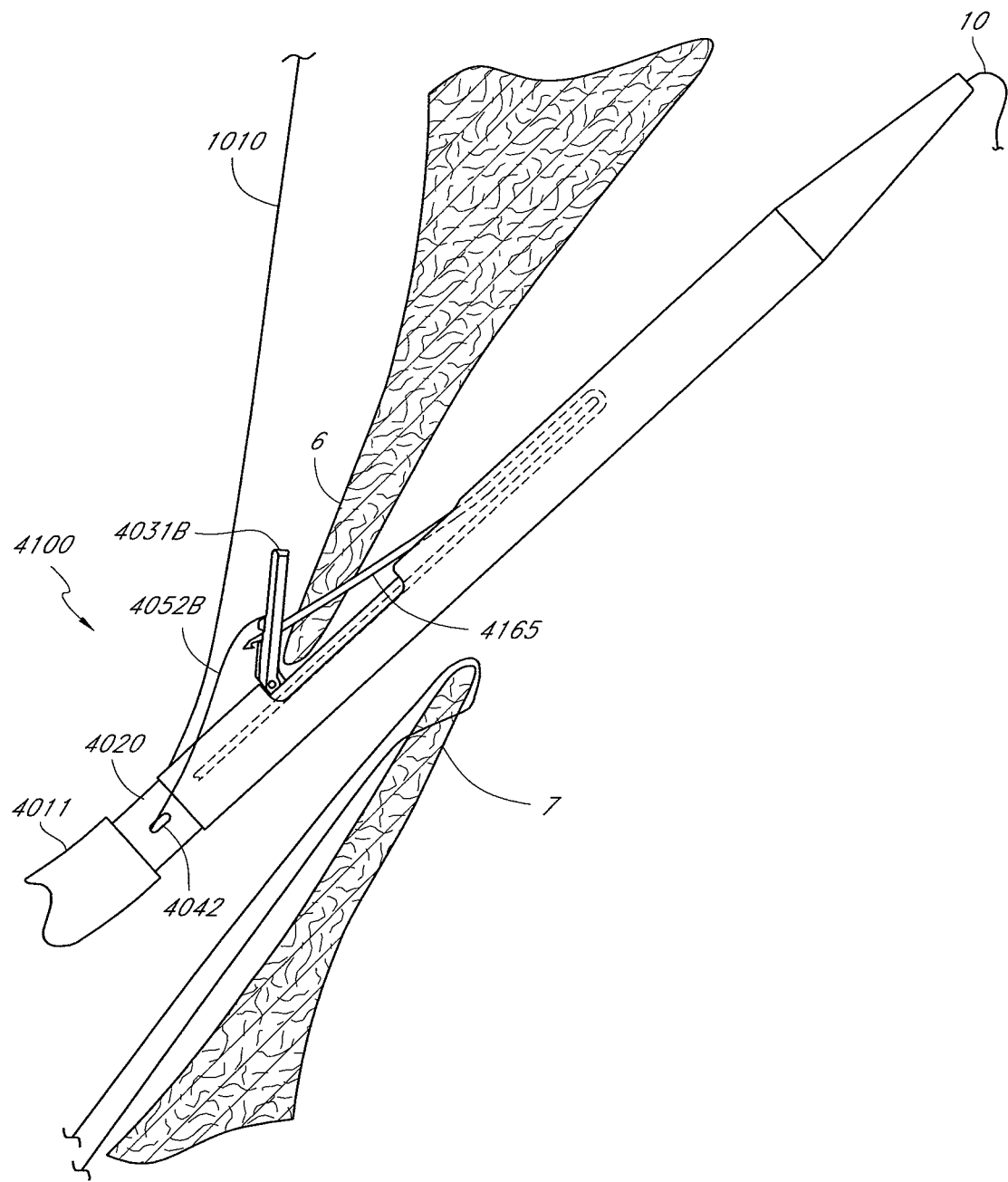
FIG. 39G is a schematic representation as in FIG. 39F showing a needle engaging the suture clasp arm.
Figure 39H:
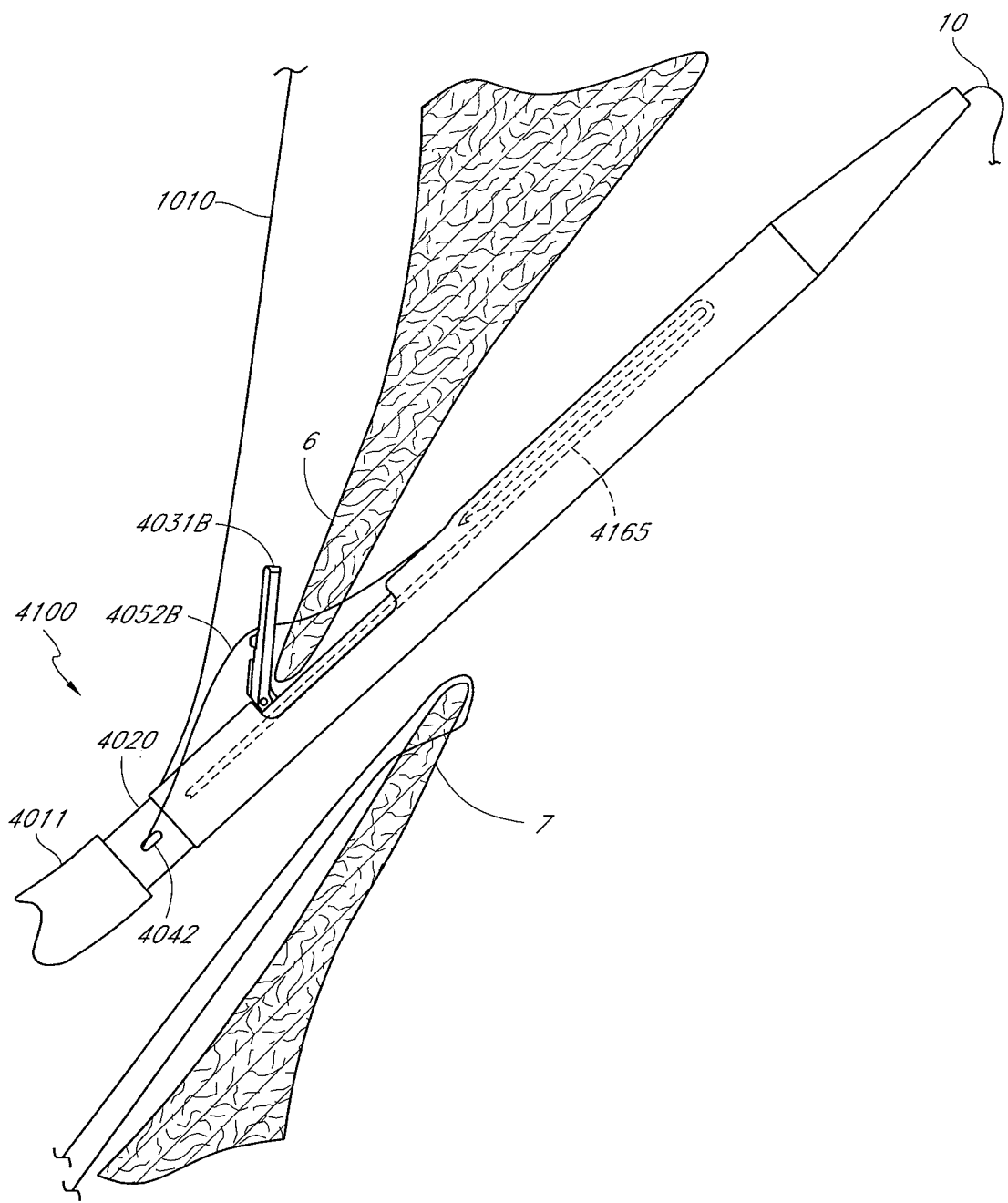
FIG. 39H is a schematic representation as in FIG. 39G following retraction of the needle and suture portion through the septum secundum.
Figure 391:
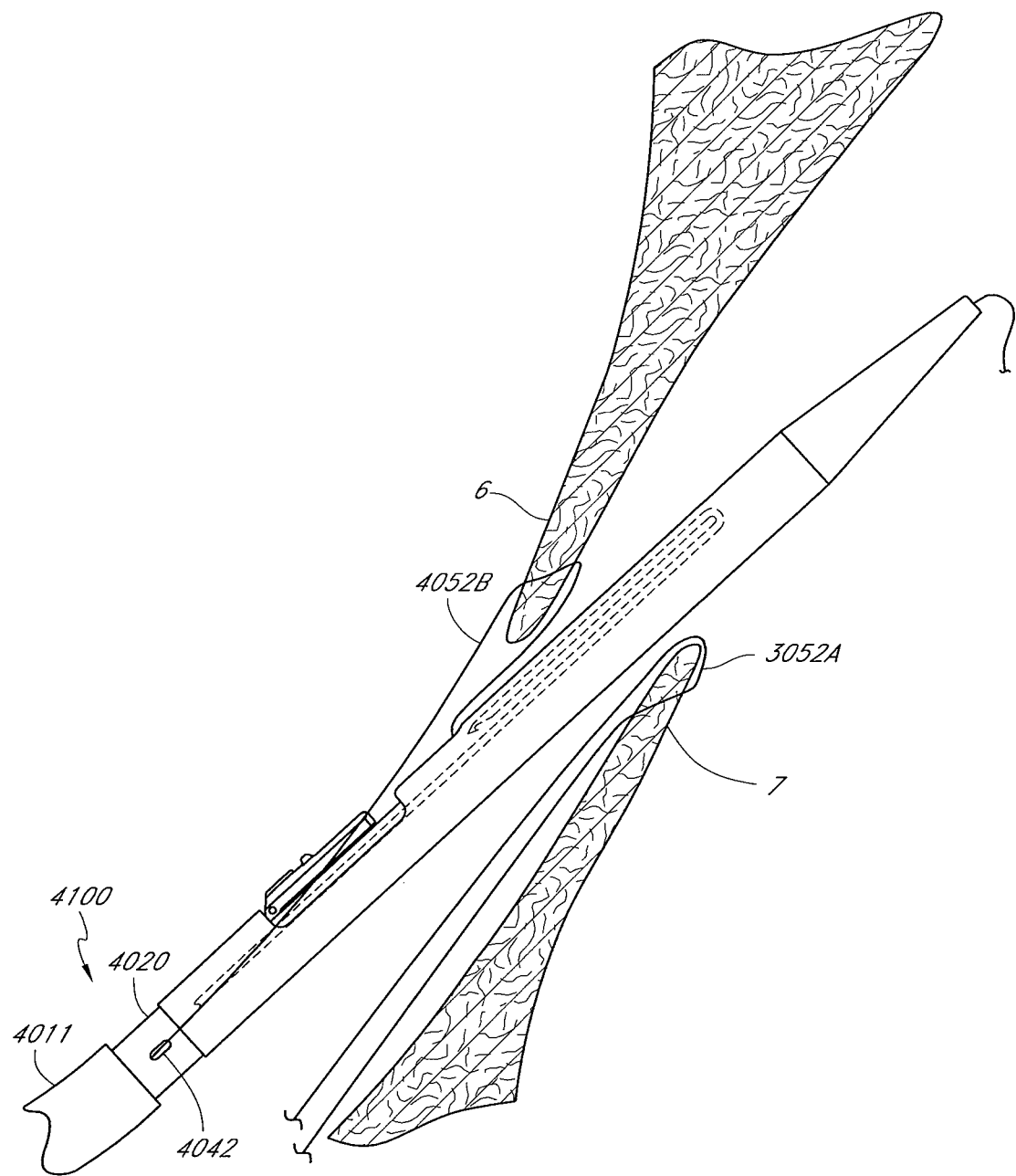

Once the suture clasp arm 4031B and suture portion 4052B have been properly positioned around the septum secundum 6, the needle 4165 may be deployed from the distal end of the suturing device 4100 to penetrate the septum secundum 6 and engage the suture portion 4052B. As shown in FIG. 39G, the tip of the needle 4165 is pulled proximally from a location distal the suture clasp arm 4031B through the tissue of the septum secundum 6 towards deployed suture clasp arm 4031B to engage the suture portion 4052B, as shown in FIG. 39G.

the suture portion 4052B has been engaged, the needle 4165 and engaged suture portion 4052B are then retracted distally through the tissue of the septum secundum 6 and into the suturing device 4100, as illustrated in FIG. 39H. The suture clasp arm 4031B may then be closed and thereafter the second guidewire 1010 retracted into the suturing device 4100. Alternatively, the second guidewire 1010 can be retracted into the suturing device 4100 before the suture clasp arm 4031B is closed. Once the suture clasp arm 4031B is closed, the suturing device 4100 may be withdrawn from the patient's heart.

Figure 39J:
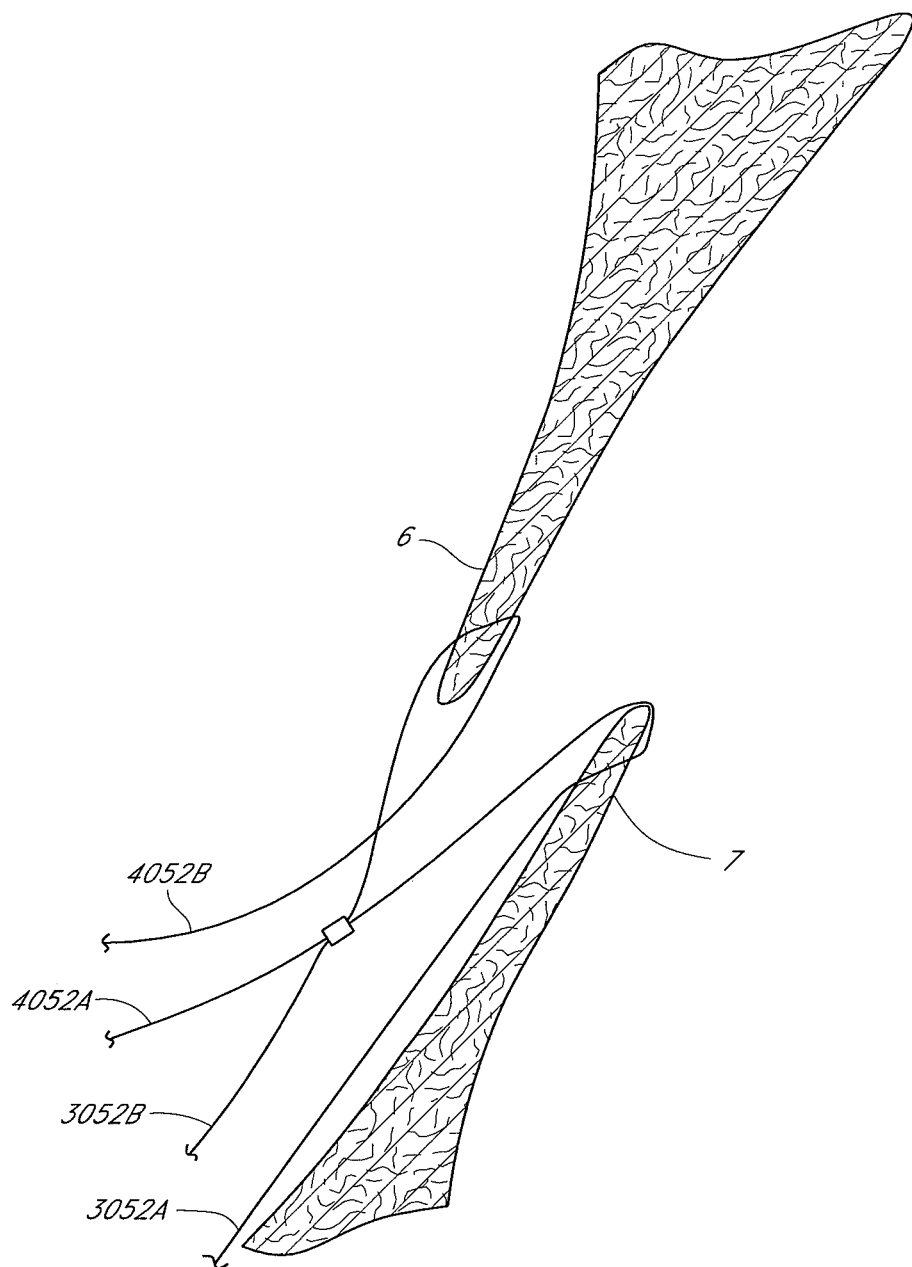
FIG. 39J is a schematic representation as in FIG. 39I showing the suture portions being joined by a first knot following withdrawal of the suturing device.

As shown in FIG. 39I, the suture portion 3052A has been positioned through the septum primum 7 while suture portion 4052B has been positioned through the septum secundum. After the suturing device 4100 has been withdrawn, the suture portions 3052A, 3052B, 4052A and 4052B will extend proximally from the PFO. The suture portions 3052B and 4052A can then be secured together, as illustrated in FIG. 39J, by tying a knot according to any known method or by applying a knot by any method or device that is described or referenced herein. The suture portions 3052B and 4052A can be secured together exterior to the body or within the body. Any excess portion of sutures 3050 and 4050 can be trimmed.

Figure 39K:
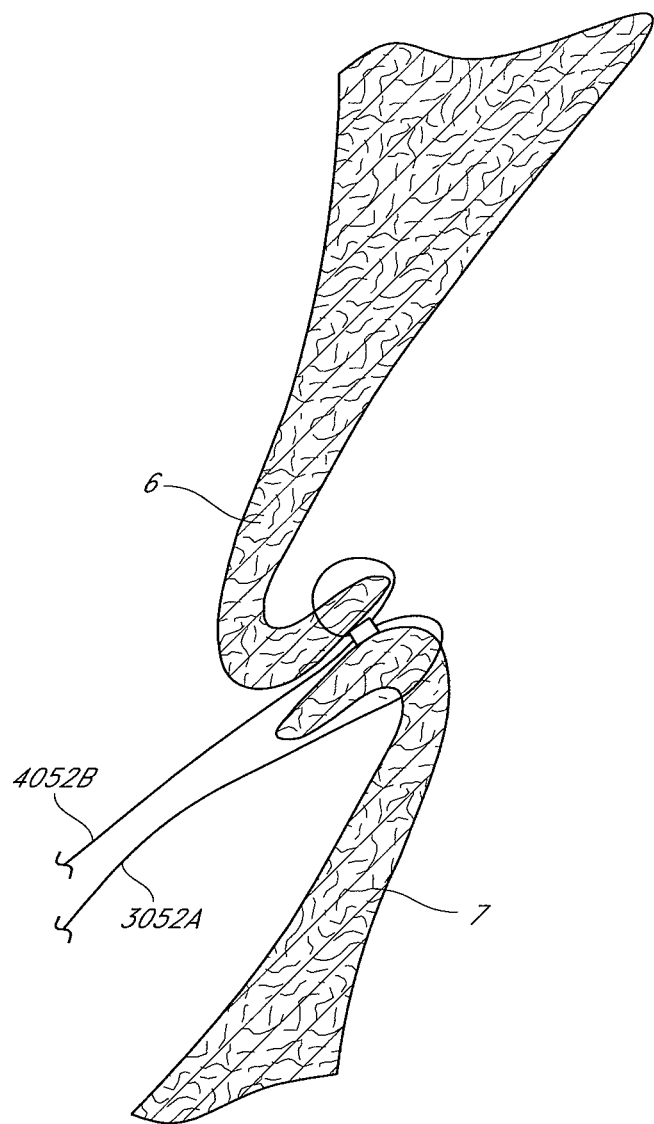
FIG. 39K is a schematic representation as in FIG. 39J showing the first knot being positioned between the septum secundum and septum primum.

The suture portions 3052A and 4052B can and can then be pulled to draw the septum secundum 6 and septum primum 7 towards one another to close the PFO, as described above. As the sutures 3050, 4050 are pulled tight, the sutures 3050, 4050 preferably cause the septum secundum 6 and septum primum 7 to turns or folds so that the tip of the septum primum 7 extends in the opposite direction compared to the tip of the septum secundum 6, as shown in FIG. 39K. The knot can be positioned between the septum primum 7 and the septum secundum 6, as illustrated in FIG. 39K. Such placement of the knot may agitate the tissue and promote healing between the septum primum 7 and the septum secundum 6. In one embodiment, the knot is positioned between the septum primum 7 and the septum secundum 6, as illustrated in FIG. 39K, by pulling the suture portion 4052B until the knot is pulled against the septum secundum 6 then pulling the suture portion 3052A to those the PFO.

Figure 40A:
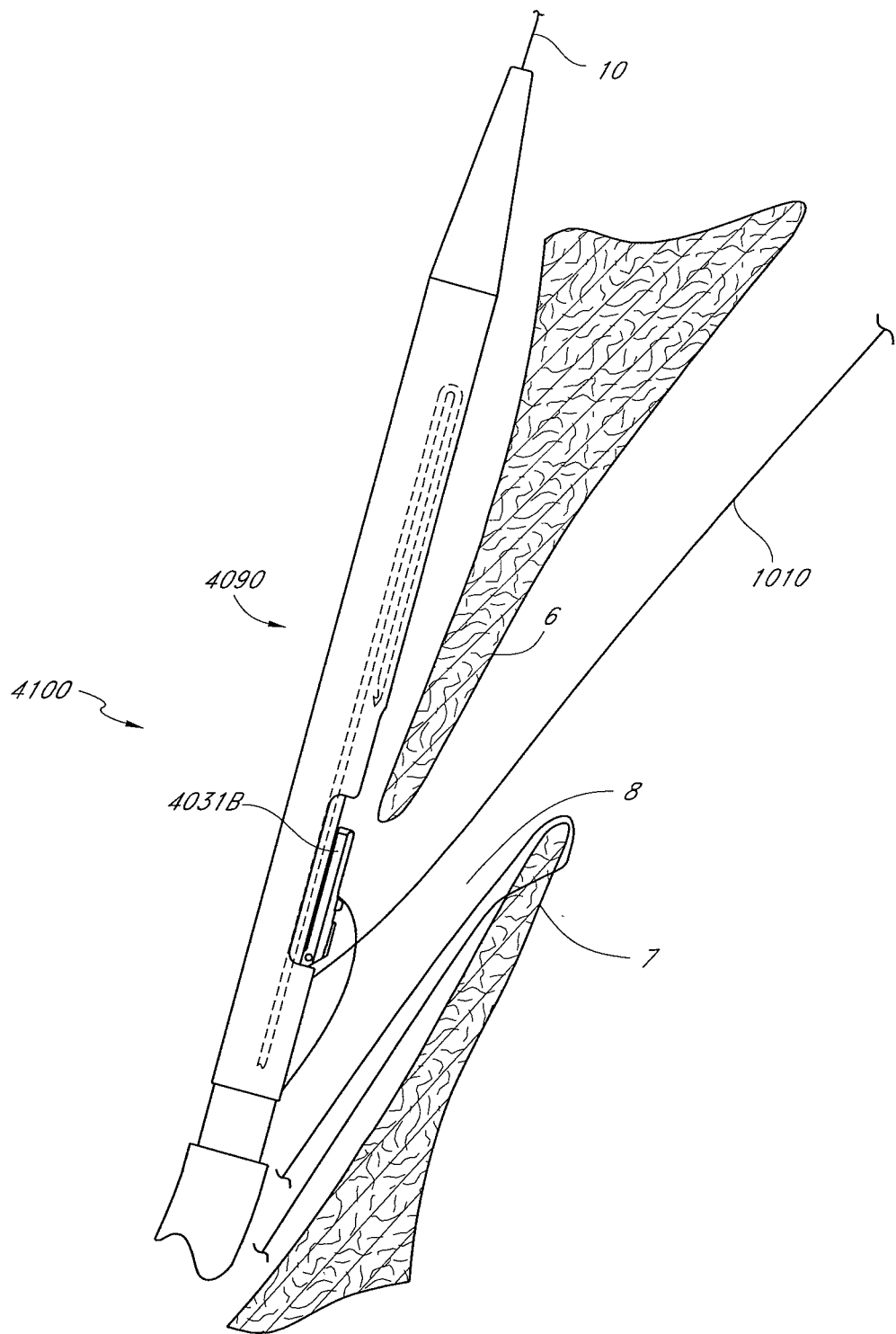
FIG. 40A is a schematic representation as in FIG. 39D showing the second suturing device positioned to permit the suture clasp arm to extend from the second suturing device and the second guide wire extended through the PFO.

An alternative method of operation of the second suturing device 4100 is illustrated according to one embodiment in FIGS. 40A-40E. After operating the first suturing device 3100 according to the above description of FIGS. 39A-D and withdrawn, the second suturing device 4100 may then be advanced through the venous access into the right atrium 2 of the heart adjacent to the PFO, as shown in FIG. 40A. The first guidewire 10 can be withdrawn from the PFO and advanced into the superior vena cava (FIG. 1) before or after introduction of the second suturing device 4100. Additionally or alternatively, a portion of the device 4100 can be advanced into the superior vena cava.

Figure 40B:
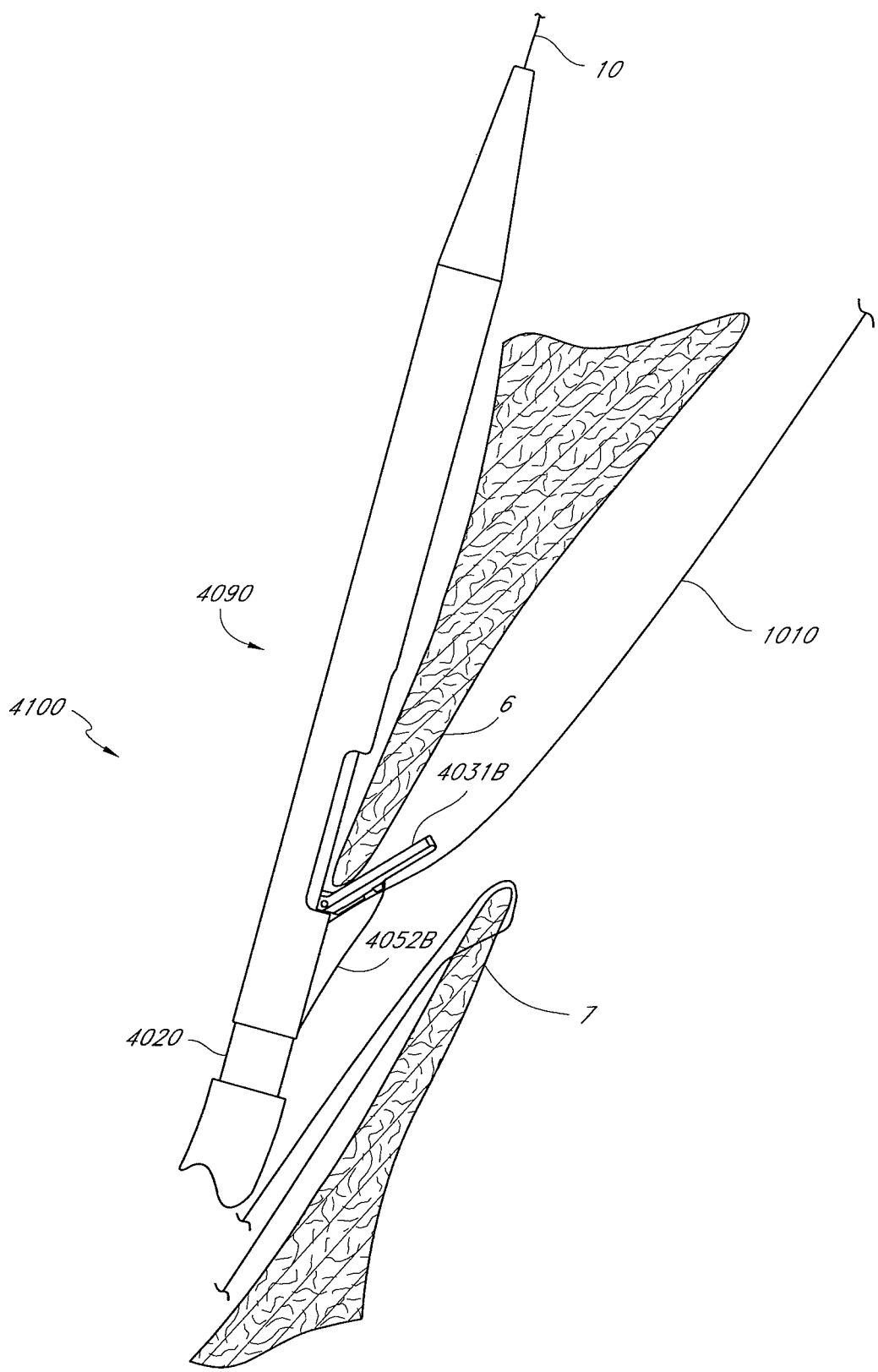
FIG. 40B is a schematic representation as in FIG. 40A with the suture clasp arm positioned in the PFO around the septum secundum.

The second guidewire 1010 can be advanced from the opening 4043 (FIG. 38) through the PFO between the septum primum 7 and the septum secundum 6. The suture clasp arm 4031B can then be extended and the device 4100 can be advanced such that the suture clasp arm 4031B extends around the tip of the septum secundum 6, as shown in FIG. 40B, and gathers the tissue of the septum secundum 6 between the arm 4031B and the spreader 4030. Alternatively, the suture clasp arm 4031B can be extended from the spreader assembly 4090 before the second guidewire 1010 is advanced into the PFO. The suturing device 4100 can be configured such that when the first guidewire 10 is advanced into the superior vena cava and the second guidewire 1010 is positioned through the PFO, the first guidewire 10 and the second guidewire 1010 direct the device 4100 toward the center of the septum secundum 6 as the device 4100 is advanced.

Figure 40C:
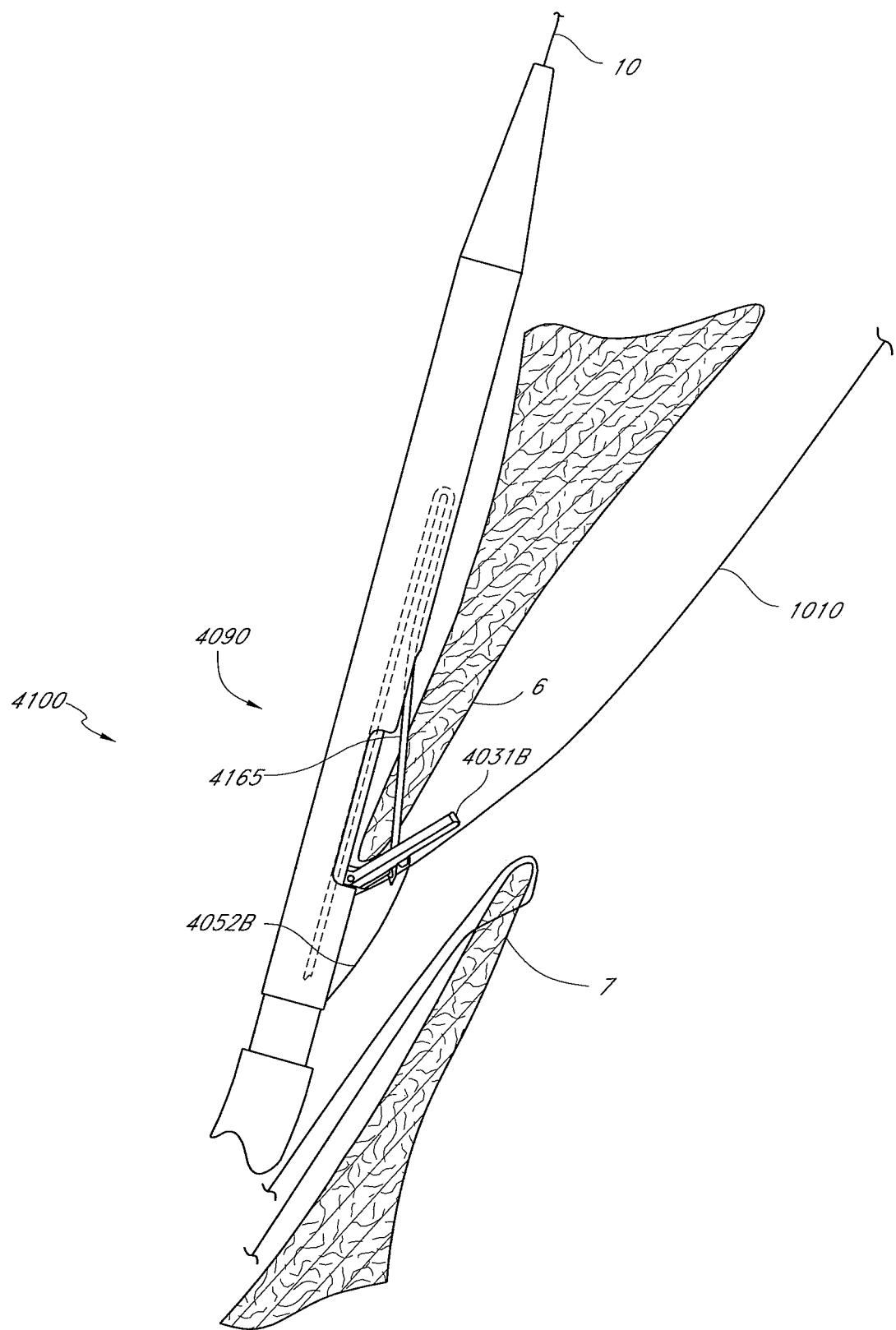
FIG. 40C is a schematic representation as in FIG. 40B showing the needle engaging the suture clasp arm.

Once the suture clasp arm 4031B and suture portion 4052B have been properly positioned around the septum secundum 6, the needle 4165 may be deployed from the distal end of the suturing device 4100 to penetrate the septum secundum 6 and engage the suture portion 4052B. As shown in FIG. 40C, the tip of the needle 4165 is pulled proximally from a location distal the suture clasp arm 4031B through the tissue of the septum secundum 6 towards deployed suture clasp arm 4031B to engage the suture portion 4052B.

Figure 40D:
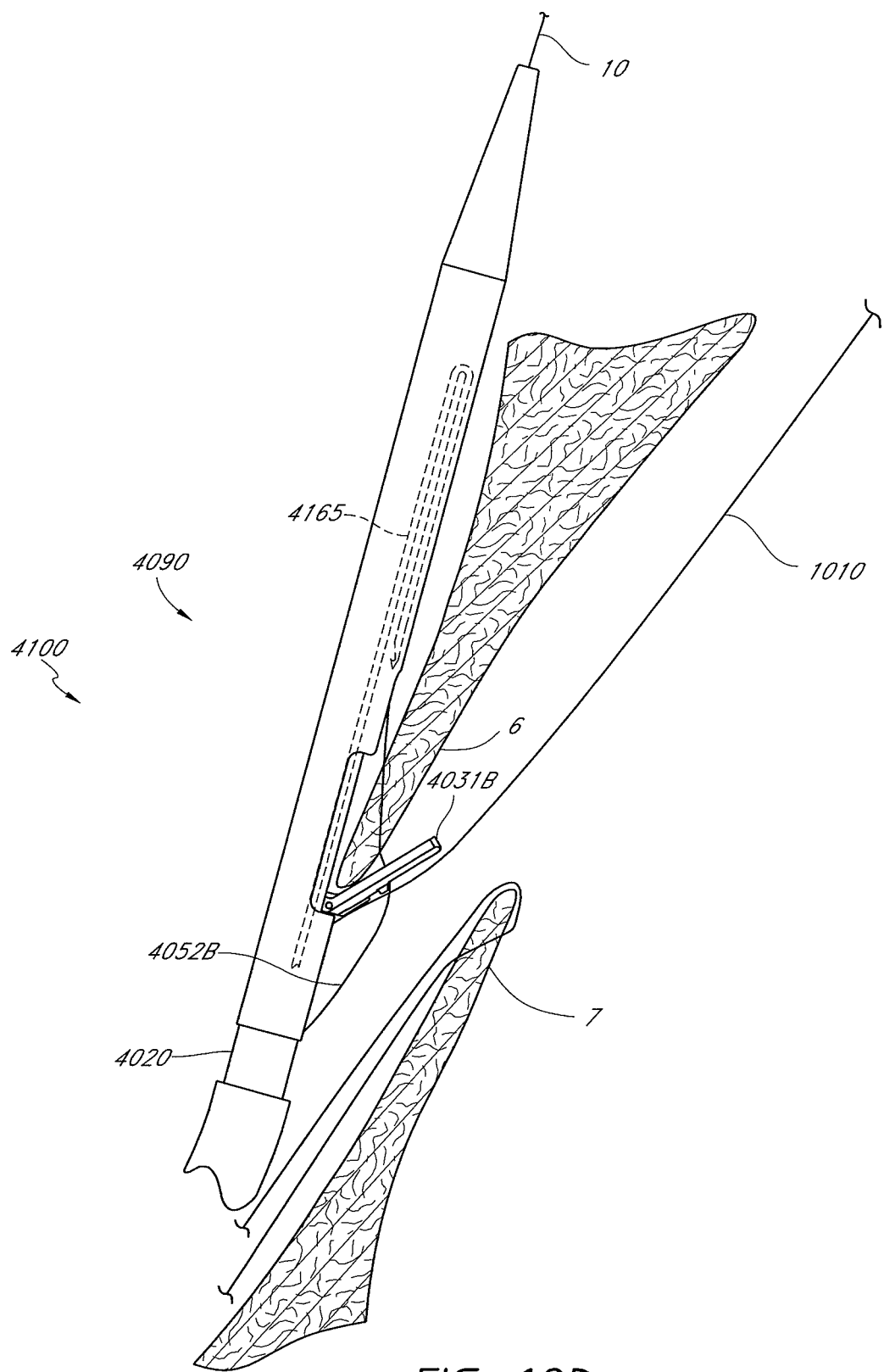
FIG. 40D is a schematic representation as in FIG. 40C following retraction of the needle and suture portion through the septum secundum.

As shown in FIG. 40D, once the suture portion 4052B has been engaged, the needle 4165 and engaged suture portion 4052B are then retracted distally through the tissue of the septum secundum 6 and into the suturing device 4100. The device 4100 can then be retracted slightly to permit the suture clasp arm 4031B to closed. Thereafter, the second guidewire 1010 can be retracted into the suturing device 4100. Alternatively, the second guidewire 1010 can be retracted into the suturing device 4100 before the suture clasp arm 4031B is closed. Once the suture clasp arm 4031B is closed, the suturing device 4100 may be withdrawn from the patient's heart.

Figure 40E:
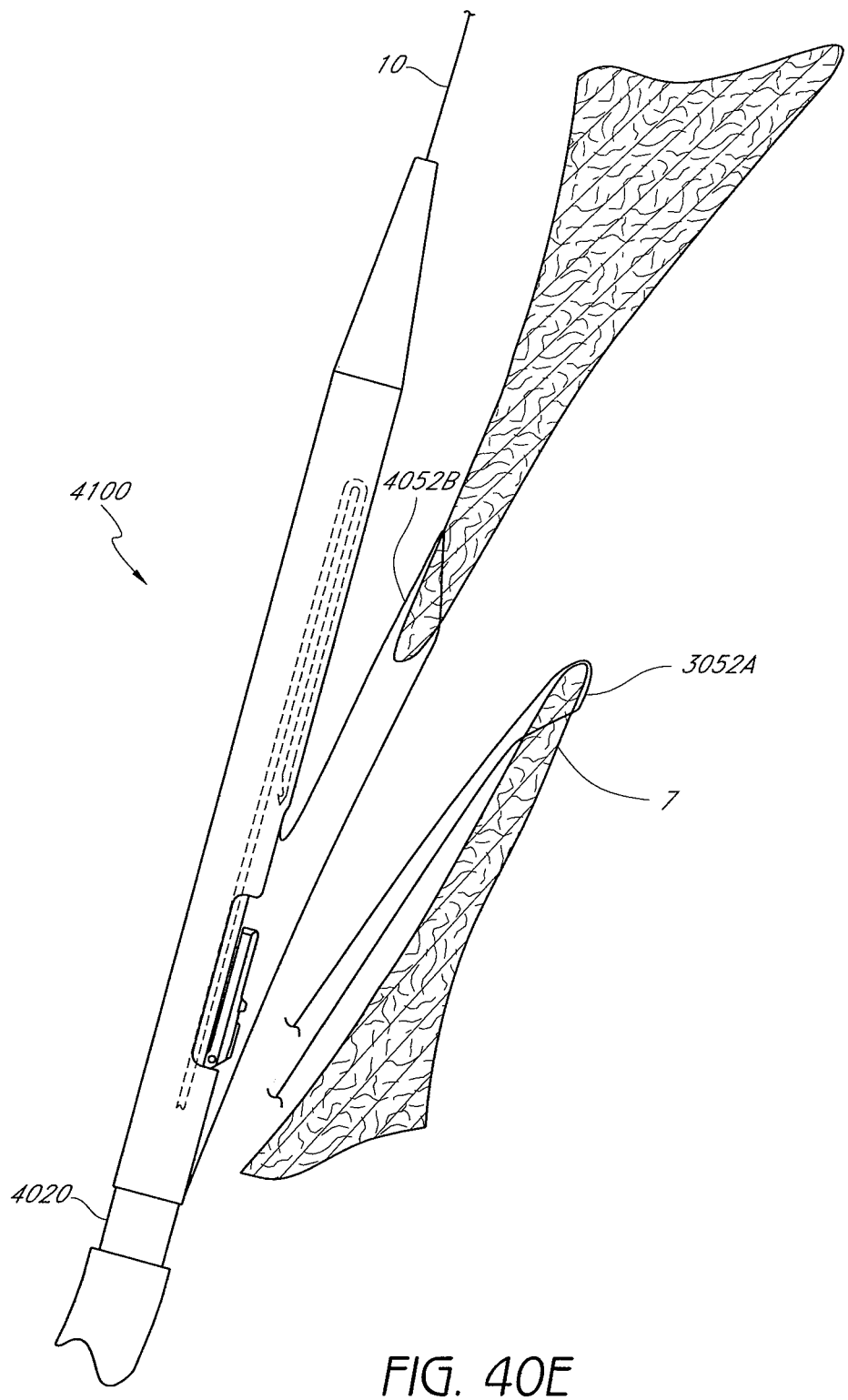
FIG. 40E is a schematic representation as in FIG. 40D showing the suture portions positioned through the septum secundum and septum primum, and the second suturing device being withdrawn.

As shown in FIG. 40E, the suture portion 3052A has been positioned through the septum primum 7 while suture portion 4052B has been positioned through the septum secundum. After the suturing device 4100 has been withdrawn, the sutures 3050 and 4050 can be used to draw the septum secundum 6 and septum primum 7 together to close the PFO, as described above.

Although the operation of the devices 3100 and 4100 has been described with reference to two sutures 3050, 4050, the devices 3100, 4100 can be used in some embodiments to place a single suture through both the septum primum 7 and the septum secundum 6, or to place multiple sutures through each of the septum primum 7 and the septum secundum 6. In some embodiments, plural devices 3100, plural devices 4100, or both can be used to place multiple sutures through one or both of the septum primum 7, the septum secundum 6, or other biological tissue, biological structure, prosthetic, or synthetic material or implantable device in the body. For example, plural devices may be used to suture a prosthetic heart valve to the heart or to affix a balloon, umbrella, or other device that is not properly positioned to the surrounding tissue.

Although the foregoing description of the preferred embodiments of the present invention has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention. For example, while the suturing device is described with respect to closing a patent foramen ovale in a patient's heart, it is further envisioned that the suturing device could used to close or reduce a variety of other tissue openings, lumens, hollow organs or natural or surgically created passageways in the body. The suturing device may have any suitable number of arms, such as two or four or more, and any given arm may have one or more suture clasps or openings.

We claim:

1. A device for applying a knot to a suture, the device comprising:
    a handle;
    an elongate tubular member having a proximal end and a distal end, wherein the proximal end of the elongate tubular member is coupled to the handle, and wherein the elongate tubular member comprises a first opening at the distal end and a second opening on a side wall of the elongate tubular member near the distal end, wherein the first opening and the second opening are configured to receive a suture such that the suture extends through the second opening and out the first opening;
    an actuator rod having a proximal end and a distal end that extends through and is translatable longitudinally within the elongate tubular member, the actuator rod further comprising a tip at the distal end of the actuator rod and a cutting edge that is rotatable about a longitudinal axis of the elongate tubular member; and
    a knot body and a plug for positioning within the distal end of the elongate tubular member;
    wherein the handle is usable to distally advance the actuator rod to cause the tip to force the plug into the knot body to secure the suture between the knot body and the plug when the knot body and the plug are positioned within the distal end of the elongate tubular member and the suture extends through the second opening and out the first opening; and
    wherein the handle is usable to rotate the actuator rod to rotate the cutting edge to cut the suture.

2. The device of claim 1, wherein when the actuator rod is in a proximal position, the handle is configured to resist rotation and when the actuator rod is in a distal position, the handle is configured to allow rotation of the actuator rod to rotate the cutting edge to cut the suture.

3. The device of claim 1, wherein the handle comprises a housing, a button and a knob.

4. The device of claim 3, wherein advancing the button into the housing causes the actuator rod to advance distally.

5. The device of claim 3, wherein the knob is rotatable to rotate the actuator rod and rotate the cutting edge to cut the suture.

6. The device of claim 1, further comprising a sleeve in the distal end of the elongate tubular member, the sleeve having a side opening configured to receive the suture, wherein the sleeve is configured to support the knot body and the plug.

7. The device of claim 6, wherein the side opening in the sleeve has a cutting edge that is configured to cooperate with the cutting edge of the actuator rod to cut the suture.

8. A device for applying a knot to a suture, the device comprising:
    a handle comprising a housing, a button and a knob;
    an elongate tubular member having a proximal end and a distal end, wherein the proximal end of the elongate tubular member is coupled to the handle and the distal end of the elongate tubular member is configured to couple to a suture;
    an actuator rod having a proximal end and a distal end that extends through and is translatable longitudinally within the elongate tubular member, wherein the proximal end of the actuator rod is coupled to the handle and the distal end of the actuator rod includes a cutting edge; and
    a knot body and a plug for positioning within the distal end of the elongate tubular member;
    wherein depressing the button is configured to advance the actuator rod to cause the distal end of the actuator rod to force the plug into the knot body to secure the suture between the knot body and the plug when the knot body and the plug are positioned within the distal end of the elongate tubular member and the distal end of the elongate tubular member is coupled to the suture; and
    wherein the knob is actuatable to cut the suture with the cutting edge.

9. The device of claim 8, wherein the cutting edge is rotatable about a longitudinal axis of the elongate tubular member by rotating the knob.

10. The device of claim 8, further comprising a sleeve inside the elongate tubular member near or at the distal end of the elongate tubular member, the sleeve having a side opening configured to receive the suture, wherein the sleeve is configured to support the knot body and the plug.

11. The device of claim 10, wherein the side opening in the sleeve has a cutting edge that is configured to cooperate with the cutting edge of the actuator rod to cut the suture.

12. A device for applying a knot to a suture, the device comprising:
    a handle comprising a housing, a button and a knob;
    an elongate tubular member having a proximal end and a distal end, wherein the proximal end of the elongate tubular member is coupled to the handle, and wherein the elongate tubular member comprises a first opening at the distal end and a second opening on a side wall of the elongate tubular member near the distal end, wherein the first opening and the second opening are configured to receive a suture such that the suture extends through the second opening and out the first opening;
    an actuator rod having a proximal end and a distal end that extends through and is translatable longitudinally within the elongate tubular member, the actuator rod comprising a tip at the distal end of the actuator rod and a cutting edge that is rotatable about a longitudinal axis of the elongate tubular member; and
    a knot body and a plug for positioning within the distal end of the elongate tubular member;
    wherein depressing the button is configured to distally advance the actuator rod to cause the tip to force the plug into the knot body to secure the suture between the knot body and the plug when the knot body and the plug are positioned within the distal end of the elongate tubular member and the suture extends through the second opening and out the first opening; and
    wherein the knob is usable to rotate the actuator rod to rotate the cutting edge to cut the suture.

13. The device of claim 12, further comprising a sleeve inside the elongate tubular member at or near the distal end of the elongate tubular member, the sleeve having a side opening configured to receive the suture, wherein the sleeve is configured to support the knot body and the plug.

14. The device of claim 13, wherein the side opening in the sleeve has a cutting edge that is configured to cooperate with the cutting edge of the actuator rod to cut the suture.

15. A device for applying a knot to a suture, the device comprising:
    a handle;
    an elongate tubular member having a proximal end and a distal end, wherein the proximal end of the elongate tubular member is coupled to the handle, and wherein the elongate tubular member comprises a first opening at the distal end and a second opening on a side wall of the elongate tubular member near the distal end, wherein the first opening and the second opening are configured to receive a suture such that the suture extends through the second opening and out the first opening;
    an actuator rod having a proximal end and a distal end that extends through and is translatable longitudinally within the elongate tubular member, the actuator rod further comprising a tip at the distal end of the actuator rod and a cutting edge that is rotatable about a longitudinal axis of the elongate tubular member; and
    a sleeve in the distal end of the elongate tubular member, the sleeve having a side opening configured to receive the suture, wherein the sleeve is configured to support a knot body and a plug, wherein the side opening in the sleeve has a cutting edge that is configured to cooperate with the cutting edge of the actuator rod to cut the suture;
    wherein the handle is usable to distally advance the actuator rod to secure the suture between the knot body and the plug when the knot body and the plug are positioned within the distal end of the elongate tubular member and the suture extends through the second opening and out the first opening; and
    wherein the handle is usable to rotate the actuator rod to rotate the cutting edge of the actuator rod to cut the suture.

16. A device for applying a knot to a suture, the device comprising:
    a handle comprising a housing, a button and a knob;
    an elongate tubular member having a proximal end and a distal end, wherein the proximal end of the elongate tubular member is coupled to the handle and the distal end of the elongate tubular member is configured to couple to a suture;
    an actuator rod having a proximal end and a distal end that extends through and is translatable longitudinally within the elongate tubular member, wherein the proximal end of the actuator rod is coupled to the handle and the distal end of the actuator rod includes a cutting edge; and
    a sleeve inside the elongate tubular member near or at the distal end of the elongate tubular member, the sleeve having a side opening configured to receive the suture, wherein the sleeve is configured to support a knot body and a plug, wherein the side opening in the sleeve has a cutting edge that is configured to cooperate with the cutting edge of the actuator rod to cut the suture;
    wherein the button is actuatable to distally advance the actuator rod to secure the suture between the knot body and the plug when the knot body and the plug are positioned within the distal end of the elongate tubular member and the distal end of the elongate tubular member is coupled to the suture; and
    wherein the knob is actuatable to cut the suture with the cutting edge of the actuator rod.

17. A device for applying a knot to a suture, the device comprising:
    a handle comprising a housing, a button and a knob;
    an elongate tubular member having a proximal end and a distal end, wherein the proximal end of the elongate tubular member is coupled to the handle, and wherein the elongate tubular member comprises a first opening at the distal end and a second opening on a side wall of the elongate tubular member near the distal end, wherein the first opening and the second opening are configured to receive a suture such that the suture extends through the second opening and out the first opening;
    an actuator rod having a proximal end and a distal end that extends through and is translatable longitudinally within the elongate tubular member, the actuator rod comprising a tip at the distal end of the actuator rod and a cutting edge that is rotatable about a longitudinal axis of the elongate tubular member; and
    a sleeve inside the elongate tubular member at or near the distal end of the elongate tubular member, the sleeve having a side opening configured to receive the suture, wherein the sleeve is configured to support a knot body and a plug, wherein the side opening in the sleeve has a cutting edge that is configured to cooperate with the cutting edge of the actuator rod to cut the suture;
    wherein the button is usable to distally advance the actuator rod to secure the suture between the knot body and the plug when the knot body and the plug are positioned within the distal end of the elongate tubular member and the suture extends through the second opening and out the first opening; and
    wherein the knob is usable to rotate the actuator rod to rotate the cutting edge of the actuator rod to cut the suture.

* * * * *

UNITED STATES PATENT AND TRADEMARK OFFICE
CERTIFICATE OF CORRECTION

PATENT NO. : 11,197,661 B2  
APPLICATION NO. : 16/161610  
DATED : December 14, 2021  
INVENTOR(S) : Anthony A. Nobles Page 1 of 2

It is certified that error appears in the above-identified patent and that said Letters Patent is hereby corrected as shown below:

On the Title Page

Page 2, Column 2 (U.S. Patent Documents), Line 34, delete "Slice" and insert --Stice--.

Page 3, Column 1 (U.S. Patent Documents), Line 75, delete "Burst" and insert --Hayburst--.

Page 3, Column 2 (U.S. Patent Documents), Line 72, delete "Weegen" and insert --Van Der Weegen--.

Page 6, Column 2 (Other Publications), Line 19, delete "byJohn Wright &Sons," and insert --by John Wright & Sons,--.

Page 6, Column 2 (Other Publications), Line 38, delete "SaundersCo.," and insert --Saunders Co.,--.

In the Specification

Column 1, Line 7, delete "continuation of" and insert --continuation of U.S. application Ser. No. 14/850,210, filed Sept. 10, 2015, now U.S. Pat. No. 10,182,802, which is a divisional of U.S. application Ser. No. 13/761,683, filed Feb. 7, 2013, now U.S. Pat. No. 9,131,938, which is a continuation of--.

Column 9, Line 15, delete "391" and insert --39I--.

Column 9, Line 49, delete "arteriosis" and insert --arteriosus--.

Column 10, Line 52, delete "polyethelyne," and insert --polyethylene,--.

Column 10, Line 52, delete "polymide," and insert --polyimide,--.

Column 16, Line 15, delete "know" and insert --known--.

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*

Column 20, Line 61, delete "arrangment." and insert --arrangement.--.

Column 21, Line 38, delete "guidwire" and insert --guidewire--.

Column 27, Line 12, delete "and" and insert --end--.

Column 30, Line 20, delete "29A-291" and insert --29A-29I--.

Column 32, Line 62, delete "segundum" and insert --secundum--.

Column 34, Line 63, delete "and" and insert --end--.

Column 39, Line 66, delete "FIG." and insert --(FIG.--.

Column 41, Line 5, delete "segundum" and insert --secundum--.

Column 41, Line 17, delete "the" and insert --The--.